US007192762B2

(12) United States Patent
Macool et al.

(10) Patent No.: US 7,192,762 B2
(45) Date of Patent: Mar. 20, 2007

(54) MORTIERELLA ALPINA GLYCEROL-3-PHOSPHATE O-ACYLTRANSFERASE FOR ALTERATION OF POLYUNSATURATED FATTY ACIDS AND OIL CONTENT IN OLEAGINOUS ORGANISMS

(75) Inventors: Daniel Joseph Macool, Philadelphia, PA (US); Zhixiong Xue, Chadds Ford, PA (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 14 days.

(21) Appl. No.: 11/254,173

(22) Filed: Oct. 19, 2005

(65) Prior Publication Data

US 2006/0094091 A1 May 4, 2006

Related U.S. Application Data

(60) Provisional application No. 60/624,812, filed on Nov. 4, 2004.

(51) Int. Cl.

| | |
|---|---|
| ***C12N 1/18*** | (2006.01) |
| ***C12N 15/70*** | (2006.01) |
| ***C12N 9/10*** | (2006.01) |
| ***C12N 1/13*** | (2006.01) |
| ***C12Q 1/68*** | (2006.01) |
| ***C12P 21/06*** | (2006.01) |
| ***C07H 21/04*** | (2006.01) |
| *C12N 1/19* | (2006.01) |
| *C12N 1/16* | (2006.01) |

(52) U.S. Cl. ............... 435/252.3; 435/69.1; 435/257.2; 435/254.11; 435/254.2; 435/320.1; 435/254.22; 435/193; 536/23.2

(58) Field of Classification Search ............. 435/252.3, 435/69.1, 320.1, 193; 536/23.2
See application file for complete search history.

(56) References Cited

FOREIGN PATENT DOCUMENTS

| | | | |
|---|---|---|---|
| WO | WO 00/78974 | A2 | 12/2000 |
| WO | WO 02/08391 | A2 | 1/2002 |
| WO | WO 2004/087902 | A2 | 10/2004 |
| WO | WO 2004/101757 | A2 | 11/2004 |

OTHER PUBLICATIONS

National Center for Biotechnology Information General Identifier No. 50257380, Accession No. EAL20089, Jul. 13, 2004, E. Fung et al., Cryptococcus Neoformans Serotype D Sequencing.
National Center for Biotechnology Information General Identifier No. 46099004. Accession No. EAK84237, Apr. 2, 2004, B. Birren et al.
Sanjay Mishra et al., Purification and Characterization of Thiol-Reagent-Sensitive Glycerol-3-Phosphate Acyltransferase from the Membrane Fraction of an Oleaginous Fungus. Biochem. J., vol. 355:315-322, 2001.
James O. Hill et al., Environmental Contributions to the Obesity Epidemic, Science, vol. 280:1371-1374, 1998.
Robert M. Bell et al., Enzymes of Triacylglycerol Formation in Mammals, the Enzymes, vol. 26:87-111, 1983.
Lori Dircks et al., Acytransferases of De Novo Glycerophospholipid Biosynthesis. Progress in Lipid Research, vol. 38:461-479, 1999.
U.S. Appl. No. 60/624,812, filed, Nov. 4, 2004, Damude, et al.
U.S. Appl. No. 11/265,761, filed, Nov. 2, 2005, Damude et al.
National Center for Biotechnology Information General Identifier No. 50257380, Accession No. EAL20089, Jul. 13, 2004, E. Fung et al., Cryptococcus Neoformans Serotype D Sequencing.
National Center for Biotechnology Information General Identifier No. 46099004, Accession No. EAK84237, Apr. 2, 2004, B. Birren et al.
Sanjay Mishra et al., Purification and Characterization of Thiol-Reagent-Sensitive Glycerol-3-Phosphate Acyltransferase From the Membrane Fraction of an Oleaginous Fungus, Biochem. J., vol. 355:315-322, 2001.
James O. Hill et al., Environmental Contributions to the Obesity Epidemic, Science, vol. 280:1371-1374, 1998.
Robert M. Bell et al., Enzymes of Triacylglycerol Formation in Mammals, the Enzymes. vol. 26:87-111, 1983.
Lori Dircks et al., Acyltransferases of De Novo Glycerophospholipid Biosynthesis. Progress in Lipid Research. vol. 38:461-479. 1999.

*Primary Examiner*—Rebecca E. Prouty
*Assistant Examiner*—Iqbal Chowdhury

(57) ABSTRACT

Glycerol-3-phosphate o-acyltransferase (GPAT) participates in the first step of oil biosynthesis and is expected to play a key role in altering the quantity of long-chain polyunsaturated fatty acids (PUFAs) produced in oils of oleaginous organisms. The present application provides a nucleic acid fragment isolated from *Mortierella alpina* encoding a GPAT that is suitable for use in the manufacture of oils enriched in omega fatty acids in oleaginous organisms. Most desirably, the substrate specificity of the instant GPAT will be particularly useful to enable accumulation of long-chain PUFAs having chain lengths equal to or greater than $C_{20}$ in oleaginous yeast, such as *Yarrowia lipolytica*.

8 Claims, 6 Drawing Sheets

Figure 1:
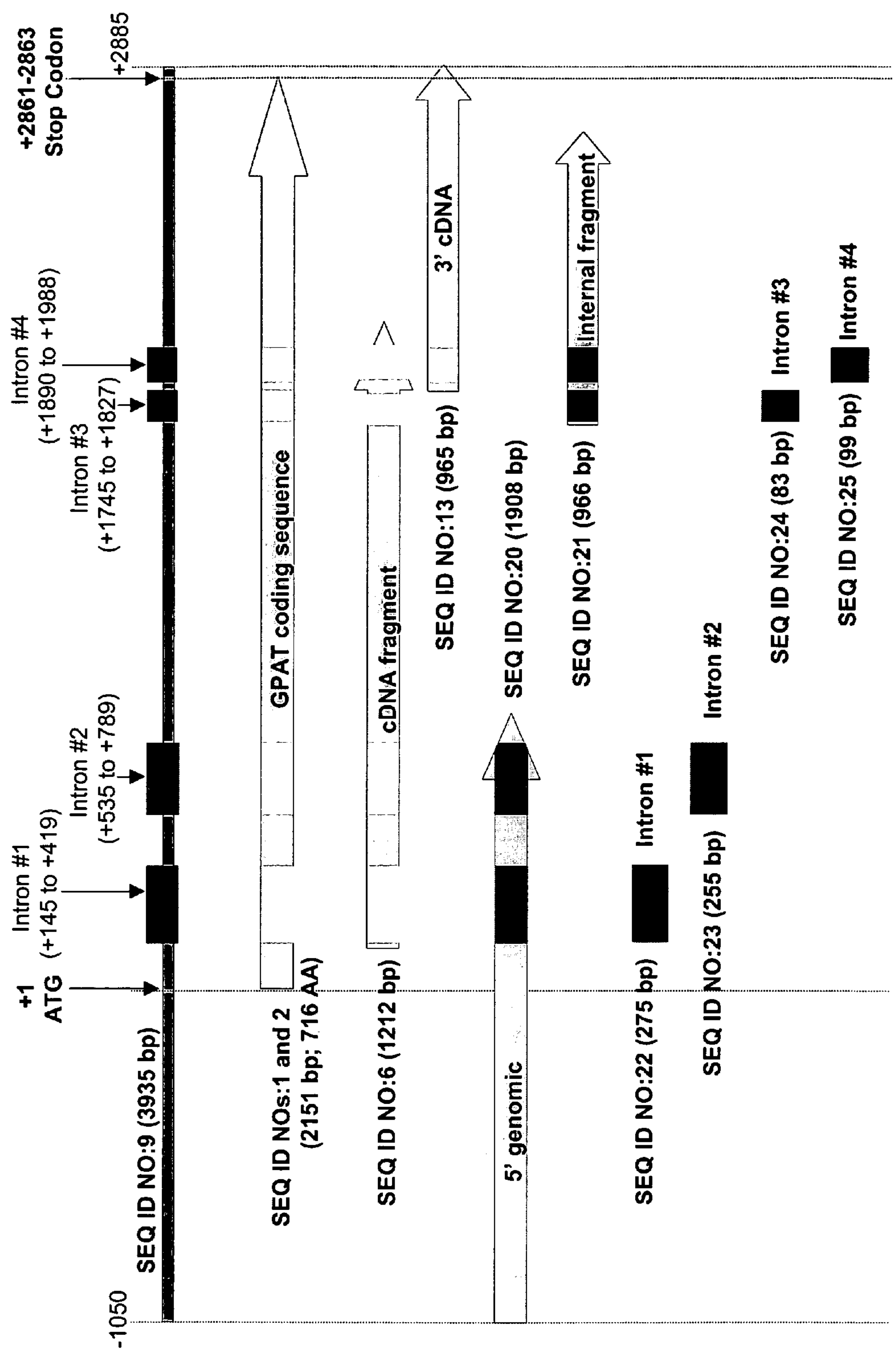

+2861-2863
Stop Codon
+2885
Intron #4
(+1890 to +1988)
Intron #3
(+1745 to +1827)
Intron #2
(+535 to +789)
Intron #1
(+145 to +419)
+1
ATG
-1050
SEQ ID NO:9 (3935 bp)
GPAT coding sequence
SEQ ID NOs:1 and 2
(2151 bp; 716 AA)
cDNA fragment
SEQ ID NO:6 (1212 bp)
3' cDNA
SEQ ID NO:13 (965 bp)
5' genomic
SEQ ID NO:20 (1908 bp)
Internal fragment
SEQ ID NO:21 (966 bp)
SEQ ID NO:22 (275 bp)
Intron #1
SEQ ID NO:23 (255 bp)
Intron #2
SEQ ID NO:24 (83 bp)
Intron #3
SEQ ID NO:25 (99 bp)
Intron #4

A
pKUNF12T6E
12649 bp
B
pDMW271
13034 bp
C
pZP3L37
12690 bp
D
pZKUT16
5833 bp

Figure 4
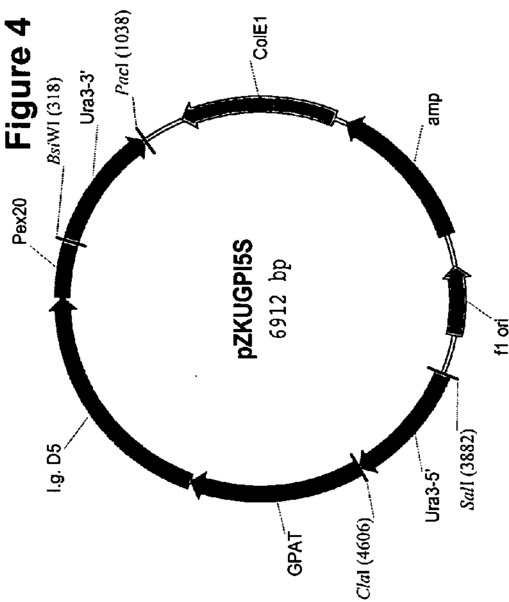
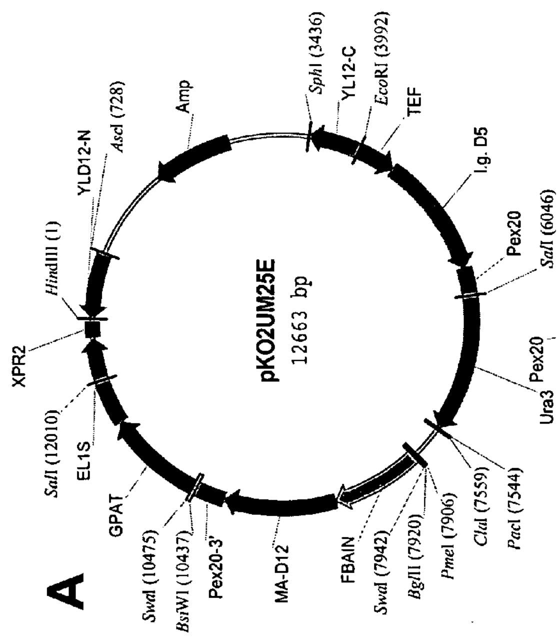
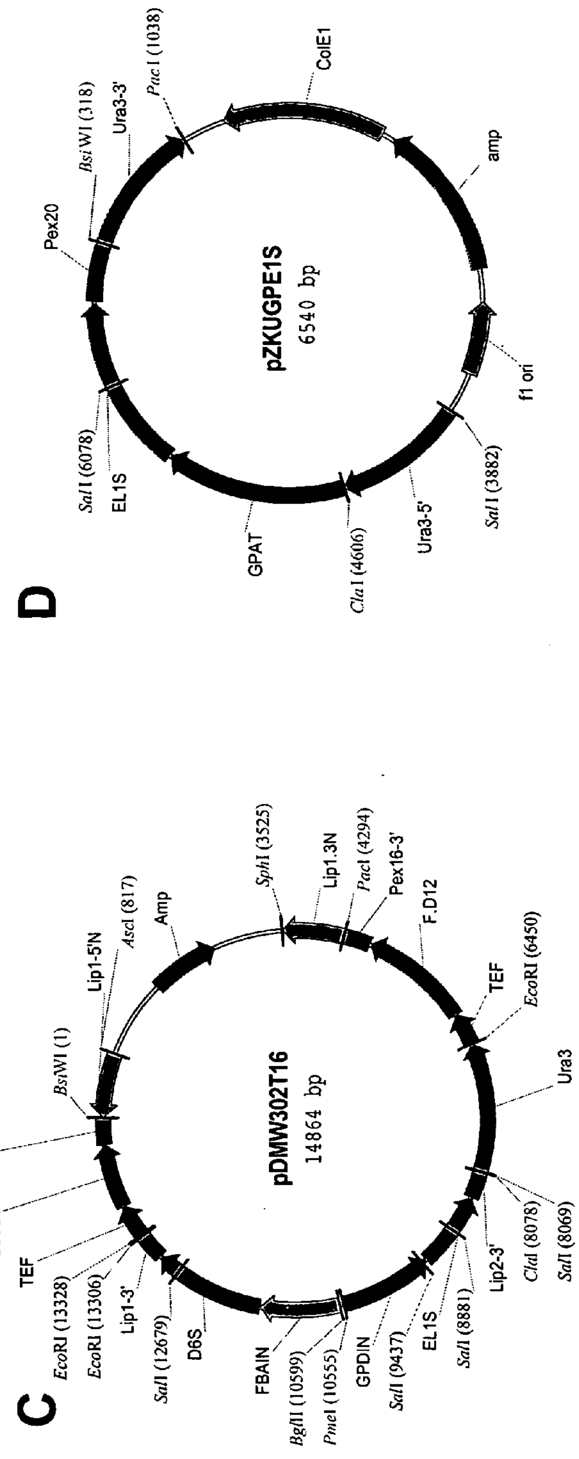

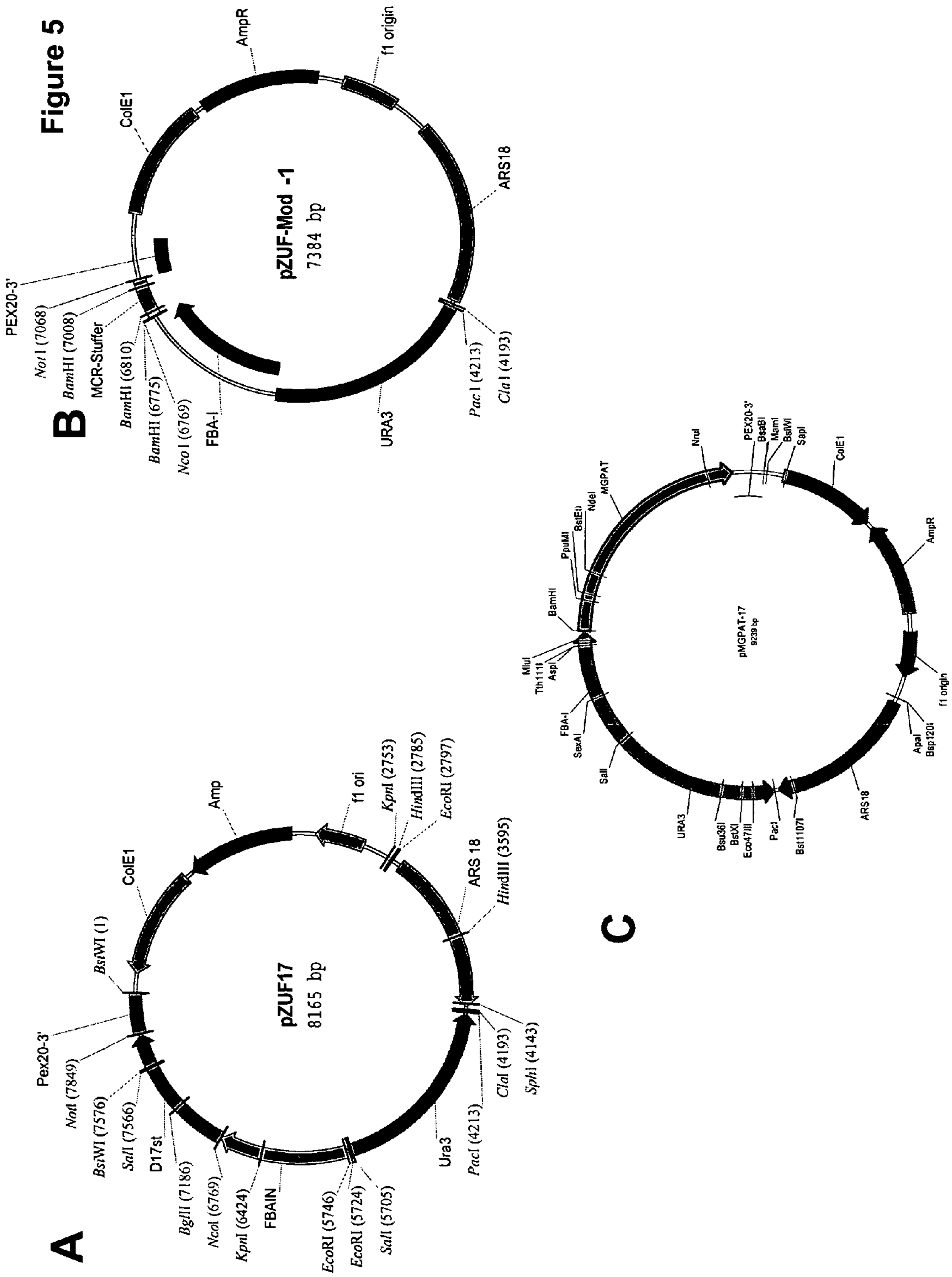

Figure 5
A
pZUF17
8165 bp
BsiWI (1)
ColE1
Amp
f1 ori
KpnI (2753)
HindIII (2785)
EcoRI (2797)
ARS 18
HindIII (3595)
ClaI (4193)
SphI (4143)
PacI (4213)
Ura3
SalI (5705)
EcoRI (5724)
EcoRI (5746)
FBAIN
KpnI (6424)
NcoI (6769)
BglII (7186)
D17st
SalI (7566)
BsiWI (7576)
NotI (7849)
Pex20-3'
B
pZUF-Mod -1
7384 bp
ColE1
AmpR
f1 origin
ARS18
PacI (4213)
ClaI (4193)
URA3
FBA-I
NcoI (6769)
BamHI (6775)
BamHI (6810)
MCR-Stuffer
BamHI (7008)
NotI (7068)
PEX20-3'
C
pMGPAT-17
9239 bp
NruI
PEX20-3'
BsaBI
MamI
BsiWI
SapI
ColE1
AmpR
f1 origin
ApaI
Bsp120I
ARS18
Bst1107I
PacI
Eco47III
BstXI
Bsu36I
URA3
SalI
SexAI
FBA-I
AspI
Tth111I
MluI
BamHI
PpuMI
BstEII
NdeI
MGPAT

SEQUENCE LISTING

```
<160> NUMBER OF SEQ ID NOS: 68

<210> SEQ ID NO 1
<211> LENGTH: 2151
<212> TYPE: DNA
<213> ORGANISM: Mortierella alpina

<400> SEQUENCE: 1

atggcccttc agatctacga ctttgtgtcg ttcttcttca ctatcctgct cgacatcttc     60

ttcagggaga ttcgtcccag aggcgcacac aagattccac aaaaaggccc cgtgatcttt    120

gtcgccgctc ctcatgccaa tcagtttgtc gatcctctcg tcttgatgcg agagtgcggc    180

cgcagagtct cattccttgc agccaaaaag tccatggacc gccggtggat tggtgcaatg    240

gcacgctcga tgaatgcgat tcctgttgag cgcccccagg accttgctaa agccggctcg    300

ggaatcatca aacttctgga tcgttatggc gaccctcttc gggtcaccgg tgtcggcact    360

aaattcacaa aggagctgct tgtgggcgac cagatctccc ttccaaagga cgtcggtgtc    420

ycagctgtgg gcgagatcat atctgatacc gagctgattg tcaagaagga attcaaagag    480

ctcaaggccc ttgagttgct gaccagtgct gaaggaacca agtacaaatg cctaccccat    540

atggaccaga cgaacgtcta caaaactgtc tttgagcgcc ttaacgcagg acattgcgtt    600

ggcattttcc ccgagggagg ctcccacgat cgtgctgaaa tgctgccatt gaaagctgga    660

gtcaccatca tggccctggg cgcattagcc gccaaccctt ccttggatct caagattgtc    720

acctgcggcc tcaactactt tcacccgcat cgcttccgct cgcgtgcagt agtcgagttt    780

ggcgagccat tgacggtttc gcctgagctg gtcgaaatgt acaagcgagg cggggcggaa    840

aagcgagagg cttgcggaaa actgctcgac acgatctatg aagctctccg cggtgtcact    900

ctcaacgcgc ctgattacga gacattgatg gtcattcaag cggcccgtcg cctttacaag    960

cctactcatc gcaagctgca gatctcgcag gtcgttgagt tgaaccgtag gttcgtcgca   1020

ggatacatgc acttcaagga caatccaaaa gtcattgaag ccaaggataa agtcatgcat   1080

tacaacactc agctgcggta ccatggattg cgggatcacc aagtgaatat tcgcaccacc   1140

aggaagcacg ctatcggcat gctcatctct cggctgatcc agatgatctt tttgagttgt   1200

ctggcgctac ctggaactct gatgaatctt ccggtcgcca ttgtcgctcg tgtcatcagc   1260
```

-continued

```
aacaaaaagg ccaaagaggc gctggctgcc tcgacagtca aaattgctgg aagggacgtc   1320

ttggctacgt ggaagttgct ggtcgctcta ggattgatgc ctgttctgta cttcacgtac   1380

tccgtcatgg tcttcatcta ttgcagccgc ttcgacctat cgttcaagtc gcgtcttttg   1440

gttgcttggg cagcatgggc gcttattcct tttgtaacct acgcaagcat ccgctttggt   1500

gaagttggta tcgatatctt caagtctatt cgcccattgt tcctgtccat catcccgggc   1560

gaggagagca cgatcaacga cctgcgcaag gcgcgcgcag aacttcaaaa gaccatcacc   1620

aatctcatca atgagctagc gccgcagata tatcccgact ttgattcaaa gcgcatcctc   1680

gatccatccc ctgcagatcg tcccagccgc tcagcatcag gcaccaacct tgcacagacg   1740

attttcaaca cggctgctca gcccttgaac caatggctag gcaaggatgg ccgctttgaa   1800

tgggagcgta ccgaggactc tgatgcagat gacgtgttct tctttttgga cccagcgaga   1860

ggaattatgg ggcggtctag ggcgtcgtct tggggaggtg gagcatttac gcctgctgtt   1920

gatgggtcgc gatcccggaa tcggagcagg acaagcagct tcacgtcggg ccagatccag   1980

ctgggcgagg gcttcaaact cgaggcactg acggagctgc cgcgggacaa cccttttgca   2040

gaagtgacca ggcggttgag tgtgagccga atgcagagat atgggctgga gggtatgacg   2100

cgctcggata cggatgaaaa cgaaggcccc gccaagtcaa aagacattta g            2151
```

```
<210> SEQ ID NO 2
<211> LENGTH: 716
<212> TYPE: PRT
<213> ORGANISM: Mortierella alpina
<220> FEATURE:
<221> NAME/KEY: misc_feature
<222> LOCATION: (141)..(141)
<223> OTHER INFORMATION: Xaa can be any naturally occurring amino acid

<400> SEQUENCE: 2

Met Ala Leu Gln Ile Tyr Asp Phe Val Ser Phe Phe Phe Thr Ile Leu
1               5                   10                  15

Leu Asp Ile Phe Phe Arg Glu Ile Arg Pro Arg Gly Ala His Lys Ile
            20                  25                  30

Pro Gln Lys Gly Pro Val Ile Phe Val Ala Ala Pro His Ala Asn Gln
        35                  40                  45

Phe Val Asp Pro Leu Val Leu Met Arg Glu Cys Gly Arg Arg Val Ser
    50                  55                  60

Phe Leu Ala Ala Lys Lys Ser Met Asp Arg Arg Trp Ile Gly Ala Met
65                  70                  75                  80

Ala Arg Ser Met Asn Ala Ile Pro Val Glu Arg Pro Gln Asp Leu Ala
                85                  90                  95

Lys Ala Gly Ser Gly Ile Ile Lys Leu Leu Asp Arg Tyr Gly Asp Pro
            100                 105                 110

Leu Arg Val Thr Gly Val Gly Thr Lys Phe Thr Lys Glu Leu Leu Val
        115                 120                 125

Gly Asp Gln Ile Ser Leu Pro Lys Asp Val Gly Val Xaa Ala Val Gly
    130                 135                 140

Glu Ile Ile Ser Asp Thr Glu Leu Ile Val Lys Lys Glu Phe Lys Glu
145                 150                 155                 160

Leu Lys Ala Leu Glu Leu Leu Thr Ser Ala Glu Gly Thr Lys Tyr Lys
                165                 170                 175

Cys Leu Pro His Met Asp Gln Thr Asn Val Tyr Lys Thr Val Phe Glu
            180                 185                 190

Arg Leu Asn Ala Gly His Cys Val Gly Ile Phe Pro Glu Gly Gly Ser
```

-continued

```
        195                 200                 205

His Asp Arg Ala Glu Met Leu Pro Leu Lys Ala Gly Val Thr Ile Met
    210                 215                 220

Ala Leu Gly Ala Leu Ala Ala Asn Pro Ser Leu Asp Leu Lys Ile Val
225                 230                 235                 240

Thr Cys Gly Leu Asn Tyr Phe His Pro His Arg Phe Arg Ser Arg Ala
                245                 250                 255

Val Val Glu Phe Gly Glu Pro Leu Thr Val Ser Pro Glu Leu Val Glu
            260                 265                 270

Met Tyr Lys Arg Gly Gly Ala Glu Lys Arg Glu Ala Cys Gly Lys Leu
        275                 280                 285

Leu Asp Thr Ile Tyr Glu Ala Leu Arg Gly Val Thr Leu Asn Ala Pro
    290                 295                 300

Asp Tyr Glu Thr Leu Met Val Ile Gln Ala Ala Arg Arg Leu Tyr Lys
305                 310                 315                 320

Pro Thr His Arg Lys Leu Gln Ile Ser Gln Val Val Glu Leu Asn Arg
                325                 330                 335

Arg Phe Val Ala Gly Tyr Met His Phe Lys Asp Asn Pro Lys Val Ile
            340                 345                 350

Glu Ala Lys Asp Lys Val Met His Tyr Asn Thr Gln Leu Arg Tyr His
        355                 360                 365

Gly Leu Arg Asp His Gln Val Asn Ile Arg Thr Thr Arg Lys His Ala
    370                 375                 380

Ile Gly Met Leu Ile Ser Arg Leu Ile Gln Met Ile Phe Leu Ser Cys
385                 390                 395                 400

Leu Ala Leu Pro Gly Thr Leu Met Asn Leu Pro Val Ala Ile Val Ala
                405                 410                 415

Arg Val Ile Ser Asn Lys Lys Ala Lys Glu Ala Leu Ala Ala Ser Thr
            420                 425                 430

Val Lys Ile Ala Gly Arg Asp Val Leu Ala Thr Trp Lys Leu Leu Val
        435                 440                 445

Ala Leu Gly Leu Met Pro Val Leu Tyr Phe Thr Tyr Ser Val Met Val
    450                 455                 460

Phe Ile Tyr Cys Ser Arg Phe Asp Leu Ser Phe Lys Ser Arg Leu Leu
465                 470                 475                 480

Val Ala Trp Ala Ala Trp Ala Leu Ile Pro Phe Val Thr Tyr Ala Ser
                485                 490                 495

Ile Arg Phe Gly Glu Val Gly Ile Asp Ile Phe Lys Ser Ile Arg Pro
            500                 505                 510

Leu Phe Leu Ser Ile Ile Pro Gly Glu Glu Ser Thr Ile Asn Asp Leu
        515                 520                 525

Arg Lys Ala Arg Ala Glu Leu Gln Lys Thr Ile Thr Asn Leu Ile Asn
    530                 535                 540

Glu Leu Ala Pro Gln Ile Tyr Pro Asp Phe Asp Ser Lys Arg Ile Leu
545                 550                 555                 560

Asp Pro Ser Pro Ala Asp Arg Pro Ser Arg Ser Ala Ser Gly Thr Asn
                565                 570                 575

Leu Ala Gln Thr Ile Phe Asn Thr Ala Ala Gln Pro Leu Asn Gln Trp
            580                 585                 590

Leu Gly Lys Asp Gly Arg Phe Glu Trp Glu Arg Thr Glu Asp Ser Asp
        595                 600                 605

Ala Gly Asp Val Phe Phe Phe Leu Asp Pro Ala Arg Gly Ile Met Gly
    610                 615                 620
```

-continued

```
Arg Ser Arg Ala Ser Ser Trp Gly Gly Gly Ala Phe Thr Pro Ala Val
625                 630                 635                 640

Asp Gly Ser Arg Ser Arg Asn Arg Ser Arg Thr Ser Ser Phe Thr Ser
                645                 650                 655

Gly Gln Ile Gln Leu Gly Glu Gly Phe Lys Leu Glu Ala Leu Thr Glu
            660                 665                 670

Leu Pro Arg Asp Asn Pro Phe Ala Glu Val Thr Arg Arg Leu Ser Val
        675                 680                 685

Ser Arg Met Gln Arg Tyr Gly Leu Glu Gly Met Thr Arg Ser Asp Thr
    690                 695                 700

Asp Glu Asn Glu Gly Pro Ala Lys Ser Lys Asp Ile
705                 710                 715
```

<210> SEQ ID NO 3
<211> LENGTH: 39
<212> TYPE: DNA
<213> ORGANISM: Artificial Sequence
<220> FEATURE:
<223> OTHER INFORMATION: SMART IV oligonucleotide

<400> SEQUENCE: 3
aagcagtggt atcaacgcag agtggccatt acggccggg 39

<210> SEQ ID NO 4
<211> LENGTH: 59
<212> TYPE: DNA
<213> ORGANISM: Artificial Sequence
<220> FEATURE:
<223> OTHER INFORMATION: CDSIII/3'PCR primer
<220> FEATURE:
<221> NAME/KEY: misc_feature
<222> LOCATION: (28)..(57)
<223> OTHER INFORMATION: thymidine (dT); see BD Biosciences Clontech's SMART cDNA technology
<220> FEATURE:
<221> NAME/KEY: misc_feature
<222> LOCATION: (59)..(59)
<223> OTHER INFORMATION: n is a, c, g, or t

<400> SEQUENCE: 4
attctagagg ccgaggcggc cgacatgttt tttttttttt tttttttttt tttttttvn 59

<210> SEQ ID NO 5
<211> LENGTH: 23
<212> TYPE: DNA
<213> ORGANISM: Artificial Sequence
<220> FEATURE:
<223> OTHER INFORMATION: 5'-PCR primer

<400> SEQUENCE: 5
aagcagtggt atcaacgcag agt 23

<210> SEQ ID NO 6
<211> LENGTH: 1212
<212> TYPE: DNA
<213> ORGANISM: Mortierella alpina

<400> SEQUENCE: 6
ccgcatgcca atcagtttgt cgatcctctc gtcttgatgc gagagtgcgg ccgcagagtc 60
tcattccttg cagccaaaaa gtccatggac cgccggtgga ttggtgcaat ggcacgctcg 120
atgaatgcga ttcctgttga gcgtccccag gaccttgcta aagccggctc gggaatcatc 180
aaacttctgg atcgttatgg cgaccctctt cgggtcaccg gtgtcggcac taaattcaca 240

-continued

```
aaggagctgc ttgtgggcga ccagatctcc cttccaaagg acgtcggtgt cycagctgtg    300

ggcgagatca tatctgatac cgagctgatt gtcaagaagg aattcaaaga gctcaaggcc    360

cttgagttgc tgaccagtgc tgaaggaacc aagtacaaat gcctacccca tatggaccag    420

acgaacgtct acaaaactgt ctttgagcgc cttaacgcag gacattgcgt tggcattttc    480

cccgagggag gctcccacga tcgtgctgaa atgctgccat tgaaagctgg agtcaccatc    540

atggccctgg gcgcattagc cgccaaccct tccttggatc tcaagattgt cacctgcggc    600

ctcaactact ttcacccgca tcgcttccgc tcgcgtgcag tagtcgagtt tggcgagcca    660

ttgacggttt cgcctgagct ggtcgaaatg tacaagcgag gcggggcgga aaagcgagag    720

gcttgcggaa aactgctcga cacgatctat gaagctctcc gcggtgtcac tctcaacgcg    780

cctgattacg agacattgat ggtcattcaa gcggcccgtc gcctttacaa gcctactcat    840

cgcaagctgc agatctcgca ggtcgttgag ttgaaccgta ggttcgtcgc aggatacatg    900

cacttcaagg acaatccaaa agtcattgaa gccaaggata aagtcatgca ttacaacact    960

cagctgcggt accatggatt gcgggatcac caagtgaata ttcgcaccac caggaagcac   1020

gctatcggca tgctcatctc tcggctgatc cagatgatct ttttgagttg tctggcgcta   1080

cctggaacyc tgatgaatct tccggtcgcc attgtcgctc gtgtcatcag caacaaaaag   1140

gccaaagagg cgctggctgc ctcgacagtc aaaattgctg gaagggacga catggcyaca   1200

tggaaaaggg cg                                                       1212


<210> SEQ ID NO 7
<211> LENGTH: 20
<212> TYPE: DNA
<213> ORGANISM: Artificial Sequence
<220> FEATURE:
<223> OTHER INFORMATION: Primer MGPAT-N1
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (9)..(9)
<223> OTHER INFORMATION: n is a, c, g, or t

<400> SEQUENCE: 7

ccncaygcna aycarttygt                                                 20


<210> SEQ ID NO 8
<211> LENGTH: 20
<212> TYPE: DNA
<213> ORGANISM: Artificial Sequence
<220> FEATURE:
<223> OTHER INFORMATION: Primer MGPAT-NR5
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (15)..(15)
<223> OTHER INFORMATION: n is a, c, g, or t

<400> SEQUENCE: 8

ttccangtng ccatntcrtc                                                 20
```

<210> SEQ ID NO 9
<211> LENGTH: 3935
<212> TYPE: DNA
<213> ORGANISM: Mortierella alpina
<220> FEATURE:
<221> NAME/KEY: misc_feature
<222> LOCATION: (1051)..(1053)
<223> OTHER INFORMATION: ATG translation initiation codon
<220> FEATURE:
<221> NAME/KEY: Intron
<222> LOCATION: (1195)..(1469)
<220> FEATURE:
<221> NAME/KEY: misc_feature
<222> LOCATION: (1379)..(1379)
<223> OTHER INFORMATION: n is a, c, g, or t
<220> FEATURE:
<221> NAME/KEY: misc_feature
<222> LOCATION: (1381)..(1381)
<223> OTHER INFORMATION: n is a, c, g, or t
<220> FEATURE:
<221> NAME/KEY: Intron
<222> LOCATION: (1585)..(1839)
<220> FEATURE:
<221> NAME/KEY: Intron
<222> LOCATION: (2795)..(2877)
<220> FEATURE:
<221> NAME/KEY: Intron
<222> LOCATION: (2940)..(3038)
<220> FEATURE:
<221> NAME/KEY: misc_feature
<222> LOCATION: (3911)..(3913)
<223> OTHER INFORMATION: TAG stop codon

<400> SEQUENCE: 9
actatagggc acgcgtggtc gacggcccgg gctggtcctt gaccctcgtt ctatgaatat 60
gcattacgac aaaagaaaat gaaaaaaaaa gagcacgcga gcaggagcgc ggttgtcaat 120
tttcaagcct acctcactcc tgtcatgtcg cgccattttc tttctttttc tcgtctcacg 180
atctctttga tcgaccagag tcgaatagaa tatgaacatg atcaacctaa ttgcgcgaga 240
gtgagccatt attgactatc agaccgggga gcatgcagcc tgatgcagca aaaatttgag 300
ctgtgcacaa tatttgtcat acataaaagt cggcccacat gtccaacagg gcggggtggc 360
ctgaacaccc aacgtgagaa tatggacctg actgctcaca ccatcgatac cgaggattgc 420
cgcatgcact cagctgccgt agacacgcac catataccat gtgataacgg atctggctgt 480
ggtgtaccca ggggcgatat acgcgcgcgt ccctgcggac ttgacgtgtt aacgactctg 540
tatgtggctc tgatgatgca tcgggtgcat tgaggctacg gccgaggcgg caatcgagac 600
gatgccattc tctcttttgg acggagaaag agaaggagga aggaaagcga ggccgaggga 660
cggaggaacg aggaagagag agcgagaggw agcgagagcg aaggcgacgg gctgtccaat 720
ggagcgcgta gagggtgatt tgggttcgct ctgccatact ttattcgcct gcatattcac 780
cacccgctgc atctttgcag tgtttgccct cttccttttc cttttccttt tctttttttct 840 tttttcgtct ttctgcccct catccgcatc tcccctgtcg cccattacct gctcgctttc 900
cacccctgtt tgcacaccta ccccagccca atcctgtcct agcgcactct ctctgcccgt 960
ccgcacgttt cttctatggc cctctaggcg cctttttgct gcccattctc tattgtccac 1020
ttacccacgc aggcacggcc gagtccagtc atggcccttc agatctacga ctttgtgtcg 1080
ttcttcttca ctatcctgct cgacatcttc ttcagggaga ttcgtcccag aggcgcacac 1140
aagattccac aaaaaggccc cgtgatcttt gtcgccgctc ctcatgccaa tcaggtacgt 1200
gcacgcaggc gttgttttct cggaccctac ctcgtcaaat agctgtacac gctggaatga 1260
gagcgcataa tcgcctggac acgggtgcag agttcatgca cgataagccg aacagcggga 1320

```
gccgacactc caaaagacct caggactagg ggaaaaaaaa aaaaaaaaaa aaaaaaaaana   1380
nctggactcg attagcccta ttcccaaggg tgggggttcg tcattggttg tcgcaaacat   1440
cccaacttac agcactcttg tcctcatagt ttgtcgatcc tctcgtcttg atgcgagagt   1500
gcggccgcag agtctcattc cttgcagcca aaaagtccat ggaccgccgg tggattggtg   1560
caatggcacg ctcgatgaat gcgagtaagt tgctaggatt cccaccctcc cggctttatt   1620
ttgcagctct ctcatacacg tacacacaca cacacaaaga agattctcga tggtcactgg   1680
atgctttggt ggtgctgtcg aaagggctgc agactcttgc tgtgtggtga tagagtgccg   1740
gctttgatcc cccatcgacc gtttgggtcc ctcaccaaga catcagccct gagagcagat   1800
taattgatct gatactgttg aatcgttttc tacccatagt tcctgttgag cgccccccagg   1860
accttgctaa agccggctcg ggaatcatca aacttctgga tcgttatggc gaccctcttc   1920
gggtcaccgg tgtcggcact aaattcacaa aggagctgct tgtgggcgac cagatctccc   1980
ttccaaagga cgtcggtgtc ycagctgtgg gcgagatcat atctgatacc gagctgattg   2040
tcaagaagga attcaaagag ctcaaggccc ttgagttgct gaccagtgct gaaggaacca   2100
agtacaaatg cctaccccat atggaccaga cgaacgtcta caaaactgtc tttgagcgcc   2160
ttaacgcagg acattgcgtt ggcattttcc ccgagggagg ctcccacgat cgtgctgaaa   2220
tgctgccatt gaaagctgga gtcaccatca tggccctggg cgcattagcc gccaaccctt   2280
ccttggatct caagattgtc acctgcggcc tcaactactt tcacccgcat cgcttccgct   2340
cgcgtgcagt agtcgagttt ggcgagccat tgacggtttc gcctgagctg gtcgaaatgt   2400
acaagcgagg cggggcggaa aagcgagagg cttgcggaaa actgctcgac acgatctatg   2460
aagctctccg cggtgtcact ctcaacgcgc ctgattacga gacattgatg gtcattcaag   2520
cggcccgtcg cctttacaag cctactcatc gcaagctgca gatctcgcag gtcgttgagt   2580
tgaaccgtag gttcgtcgca ggatacatgc acttcaagga caatccaaaa gtcattgaag   2640
ccaaggataa agtcatgcat tacaacactc agctgcggta ccatggattg cgggatcacc   2700
aagtgaatat tcgcaccacc aggaagcacg ctatcggcat gctcatctct cggctgatcc   2760
agatgatctt tttgagttgt ctggcgctac ctgggtaaga gcatttttct atatcgacaa   2820
gggtctctag tgagttggct acggaatggt cactaacgca tgcttttgcc aatacagaac   2880
tctgatgaat cttccggtcg ccattgtcgc tcgtgtcatc agcaacaaaa aggccaaagg   2940
tatacttttt tttttttttt tttttttttt tcgcctttgt gttttgtgct cgacctgtga   3000
aaactaattt atttcttcct tcgttctgcc accggtagag gcgctggctg cctcgacagt   3060
caaaattgct ggaagggacg tcttggctac gtggaagttg ctggtcgctc taggattgat   3120
gcctgttctg tacttcacgt actccgtcat ggtcttcatc tattgcagcc gcttcgacct   3180
atcgttcaag tcgcgtcttt tggttgcttg ggcagcatgg gcgcttattc cttttgtaac   3240
ctacgcaagc atccgctttg gtgaagttgg tatcgatatc ttcaagtcta ttcgcccatt   3300
gttcctgtcc atcatcccgg gcgaggagag cacgatcaac gacctgcgca aggcgcgcgc   3360
agaacttcaa aagaccatca ccaatctcat caatgagcta gcgccgcaga tatatcccga   3420
ctttgattca aagcgcatcc tcgatccatc ccctgcagat cgtcccagcc gctcagcatc   3480
aggcaccaac cttgcacaga cgattttcaa cacggctgct cagcccttga accaatggct   3540
aggcaaggat ggccgctttg aatgggagcg taccgaggac tctgatgcag atgacgtgtt   3600
cttctttttg gacccagcga gaggaattat ggggcggtct agggcgtcgt cttggggagg   3660
```

-continued

```
tggagcattt acgcctgctg ttgatgggtc gcgatcccgg aatcggagca ggacaagcag   3720

cttcacgtcg ggccagatcc agctgggcga gggcttcaaa ctcgaggcac tgacggagct   3780

gccgcgggac aacccttttg cagaagtgac caggcggttg agtgtgagcc gaatgcagag   3840

atatgggctg gagggtatga cgcgctcgga tacggatgaa aacgaaggcc ccgccaagtc   3900

aaaagacatt taggaataaa cgcccgtatt tcccc                              3935


<210> SEQ ID NO 10
<211> LENGTH: 22
<212> TYPE: DNA
<213> ORGANISM: Artificial Sequence
<220> FEATURE:
<223> OTHER INFORMATION: Primer MGPAT-5N1

<400> SEQUENCE: 10

catctctcgg ctgatccaga tg                                              22


<210> SEQ ID NO 11
<211> LENGTH: 21
<212> TYPE: DNA
<213> ORGANISM: Artificial Sequence
<220> FEATURE:
<223> OTHER INFORMATION: Primer MGPAT-5N2

<400> SEQUENCE: 11

ttgtctggcg ctacctggaa c                                               21


<210> SEQ ID NO 12
<211> LENGTH: 22
<212> TYPE: DNA
<213> ORGANISM: Artificial Sequence
<220> FEATURE:
<223> OTHER INFORMATION: Primer MGPAT-5N3

<400> SEQUENCE: 12

cattgtcgct cgtgtcatca gc                                              22


<210> SEQ ID NO 13
<211> LENGTH: 965
<212> TYPE: DNA
<213> ORGANISM: Mortierella alpina

<400> SEQUENCE: 13

cattgtcgct cgtgtcatca gcaacaaaaa ggccaaagag gcgctggctg cctcgacagt     60

caaaattgct ggaagggacg tcttggctac gtggaagttg ctggtcgctc taggattgat    120

gcctgttctg tacttcacgt actccgtcat ggtcttcatc tattgcagcc gcttcgacct    180

atcgttcaag tcgcgtcttt tggttgcttg ggcagcatgg gcgcttattc cttttgtaac    240

ctacgcaagc atccgctttg gtgaagttgg tatcgatatc ttcaagtcta ttcgcccatt    300

gttcctgtcc atcatcccgg gcgaggagag cacgattaac gacctgcgca aggcgcgcgc    360

agaacttcaa aagaccatca ccaatctcat caatgagcta gcgccgcaga tatatcccga    420

ctttgattca aagcgcatcc tcgatccatc ccctgcagat cgtcccagcc gctcagcatc    480

aggcaccaac cttgcacaga cgattttcaa cacggctgct cagcccttga accaatggct    540

aggcaaggat ggccgctttg aatgggagcg taccgaggac tctgatgcag gtgacgtgtt    600

cttctttttg gacccagcga gaggaattat ggggcggtct agggcgtcgt cttggggagg    660

tggagcattt acccctgctg ttgatgggtc gcgatcccgg aatcggagca ggacaagcag    720

cttcacgtcg ggccagatcc agctgggcga gggcttcaaa ctcgaggcac tgacggagct    780
```

gccgcgggac aacccttttg cagaagtgac caggcggttg agtgtgagcc gaatgcagag 840
atatgggctg gagggtatga cgcgctcgga tacggatgaa aacgaaggcc ccgccaagtc 900
aaaagacatt taggaataaa cgcccgtatt tccccaaaaa aaaaaaaaaa aaaaaaaaaa 960
aaaaa 965

<210> SEQ ID NO 14
<211> LENGTH: 44
<212> TYPE: DNA
<213> ORGANISM: Artificial Sequence
<220> FEATURE:
<223> OTHER INFORMATION: Genome Walker adaptor-1

<400> SEQUENCE: 14
gtaatacgac tatagggcac gcgtggtcga cggcccgggc tggt 44

<210> SEQ ID NO 15
<211> LENGTH: 8
<212> TYPE: DNA
<213> ORGANISM: Artificial Sequence
<220> FEATURE:
<223> OTHER INFORMATION: Genome Walker adaptor-2
<220> FEATURE:
<221> NAME/KEY: misc_feature
<222> LOCATION: (1)..(1)
<223> OTHER INFORMATION: 5' end is associated with a -PO4 group
<220> FEATURE:
<221> NAME/KEY: misc_feature
<222> LOCATION: (8)..(8)
<223> OTHER INFORMATION: 3' end is associated with a -H2N group

<400> SEQUENCE: 15 accagccc 8

<210> SEQ ID NO 16
<211> LENGTH: 22
<212> TYPE: DNA
<213> ORGANISM: Artificial Sequence
<220> FEATURE:
<223> OTHER INFORMATION: Primer MGPAT-5-1A

<400> SEQUENCE: 16
cagctccttt gtgaatttag tg 22

<210> SEQ ID NO 17
<211> LENGTH: 22
<212> TYPE: DNA
<213> ORGANISM: Artificial Sequence
<220> FEATURE:
<223> OTHER INFORMATION: Primer AP1

<400> SEQUENCE: 17
gtaatacgac tcactatagg gc 22

<210> SEQ ID NO 18
<211> LENGTH: 23
<212> TYPE: DNA
<213> ORGANISM: Artificial Sequence
<220> FEATURE:
<223> OTHER INFORMATION: Primer MGPAT-3N1

<400> SEQUENCE: 18
cataacgatc cagaagtttg atg 23

<210> SEQ ID NO 19

<211> LENGTH: 19
<212> TYPE: DNA
<213> ORGANISM: Artificial Sequence
<220> FEATURE:
<223> OTHER INFORMATION: Primer AP2

<400> SEQUENCE: 19
actatagggc acgcgtggt 19

<210> SEQ ID NO 20
<211> LENGTH: 1908
<212> TYPE: DNA
<213> ORGANISM: Mortierella alpina
<220> FEATURE:
<221> NAME/KEY: misc_feature
<222> LOCATION: (1051)..(1053)
<223> OTHER INFORMATION: ATG translation initiation codon
<220> FEATURE:
<221> NAME/KEY: Intron
<222> LOCATION: (1195)..(1469)
<220> FEATURE:
<221> NAME/KEY: misc_feature
<222> LOCATION: (1379)..(1379)
<223> OTHER INFORMATION: n is a, c, g, or t
<220> FEATURE:
<221> NAME/KEY: misc_feature
<222> LOCATION: (1381)..(1381)
<223> OTHER INFORMATION: n is a, c, g, or t
<220> FEATURE:
<221> NAME/KEY: Intron
<222> LOCATION: (1585)..(1839)

<400> SEQUENCE: 20
actatagggc acgcgtggtc gacggcccgg gctggtcctt gaccctcgtt ctatgaatat 60
gcattacgac aaaagaaaat gaaaaaaaaa gagcacgcga gcaggagcgc ggttgtcaat 120
tttcaagcct acctcactcc tgtcatgtcg cgccattttc tttctttttc tcgtctcacg 180
atctctttga tcgaccagag tcgaatagaa tatgaacatg atcaacctaa ttgcgcgaga 240
gtgagccatt attgactatc agaccgggga gcatgcagcc tgatgcagca aaaatttgag 300
ctgtgcacaa tatttgtcat acataaaagt cggcccacat gtccaacagg gcggggtggc 360
ctgaacaccc aacgtgagaa tatggacctg actgctcaca ccatcgatac cgaggattgc 420
cgcatgcact cagctgccgt agacacgcac catataccat gtgataacgg atctggctgt 480
ggtgtaccca ggggcgatat acgcgcgcgt ccctgcggac ttgacgtgtt aacgactctg 540
tatgtggctc tgatgatgca tcgggtgcat tgaggctacg gccgaggcgg caatcgagac 600
gatgccattc tctcttttgg acggagaaag agaaggagga aggaaagcga ggccgaggga 660
cggaggaacg aggaagagag agcgagaggw agcgagagcg aaggcgacgg gctgtccaat 720
ggagcgcgta gagggtgatt tgggttcgct ctgccatact ttattcgcct gcatattcac 780
cacccgctgc atctttgcag tgtttgccct cttcctttc cttttccttt tcttttttct 840
tttttcgtct ttctgcccct catccgcatc tcccctgtcg cccattacct gctcgctttc 900
cacccctgtt tgcacaccta ccccagccca atcctgtcct agcgcactct ctctgcccgt 960
ccgcacgttt cttctatggc cctctaggcg cctttttgct gcccattctc tattgtccac 1020
ttacccacgc aggcacggcc gagtccagtc atggcccttc agatctacga ctttgtgtcg 1080
ttcttcttca ctatcctgct cgacatcttc ttcagggaga ttcgtcccag aggcgcacac 1140
aagattccac aaaaaggccc cgtgatcttt gtcgccgctc ctcatgccaa tcaggtacgt 1200
gcacgcaggc gttgttttct cggaccctac ctcgtcaaat agctgtacac gctggaatga 1260
gagcgcataa tcgcctggac acgggtgcag agttcatgca cgataagccg aacagcggga 1320

-continued

```
gccgacactc caaaagacct caggactagg ggaaaaaaaa aaaaaaaaaa aaaaaaaana   1380

nctggactcg attagcccta ttcccaaggg tgggggttcg tcattggttg tcgcaaacat   1440

cccaacttac agcactcttg tcctcatagt ttgtcgatcc tctcgtcttg atgcgagagt   1500

gcggccgcag agtctcattc cttgcagcca aaaagtccat ggaccgccgg tggattggtg   1560

caatggcacg ctcgatgaat gcgagtaagt tgctaggatt cccaccctcc cggctttatt   1620

ttgcagctct ctcatacacg tacacacaca cacacaaaga agattctcga tggtcactgg   1680

atgctttggt ggtgctgtcg aaagggctgc agactcttgc tgtgtggtga tagagtgccg   1740

gctttgatcc cccatcgacc gtttgggtcc ctcaccaaga catcagccct gagagcagat   1800

taattgatct gatactgttg aatcgttttc tacccatagt tcctgttgag cgcccccagg   1860

accttgctaa agccggctcg ggaatcatca aacttctgga tcgttatg                1908
```

<210> SEQ ID NO 21
<211> LENGTH: 966
<212> TYPE: DNA
<213> ORGANISM: Mortierella alpina
<220> FEATURE:
<221> NAME/KEY: Intron
<222> LOCATION: (19)..(101)
<220> FEATURE:
<221> NAME/KEY: Intron
<222> LOCATION: (164)..(262)

<400> SEQUENCE: 21

```
ttgtctggcg ctacctgggt aagagcattt ttctatatcg acaagggtct ctagtgagtt     60

ggctacggaa tggtcactaa cgcatgcttt tgccaataca gaactctgat gaatcttccg    120

gtcgccattg tcgctcgtgt catcagcaac aaaaaggcca aaggtatact tttttttttt    180

tttttttttt tttttcgcct ttgtgttttg tgctcgacct gtgaaaacta atttatttct    240

tccttcgttc tgccaccggt agaggcgctg gctgcctcga cagtcaaaat tgctggaagg    300

gacgtcttgg ctacgtggaa gttgctggtc gctctaggat tgatgcctgt tctgtacttc    360

acgtactccg tcatggtctt catctattgc agccgcttcg acctatcgtt caagtcgcgt    420

cttttggttg cttgggcagc atgggcgctt attccttttg taacctacgc aagcatccgc    480

tttggtgaag ttggtatcga tatcttcaag tctattcgcc cattgttcct gtccatcatc    540

ccgggcgagg agagcacgat caacgacctg cgcaaggcgc gcgcagaact tcaaaagacc    600

atcaccaatc tcatcaatga gctagcgccg cagatatatc ccgactttga ttcaaagcgc    660

atcctcgatc catcccctgc agatcgtccc agccgctcag catcaggcac caaccttgca    720

cagacgattt tcaacacggc tgctcagccc ttgaaccaat ggctaggcaa ggatggccgc    780

tttgaatggg agcgtaccga ggactctgat gcagatgacg tgttcttctt tttggaccca    840

gcgagaggaa ttatggggcg gtctagggcg tcgtcttggg gaggtggagc atttacgcct    900

gctgttgatg ggtcgcgatc ccggaatcgg agcaggacaa gcagcttcac gtcgggccag    960

atccag                                                               966
```

<210> SEQ ID NO 22
<211> LENGTH: 275
<212> TYPE: DNA
<213> ORGANISM: Mortierella alpina
<220> FEATURE:
<221> NAME/KEY: Intron
<222> LOCATION: (1)..(275)
<220> FEATURE:
<221> NAME/KEY: Intron
<222> LOCATION: (1)..(275)
<220> FEATURE:
<221> NAME/KEY: misc_feature
<222> LOCATION: (185)..(185)
<223> OTHER INFORMATION: n is a, c, g, or t
<220> FEATURE:
<221> NAME/KEY: misc_feature
<222> LOCATION: (187)..(187)
<223> OTHER INFORMATION: n is a, c, g, or t

<400> SEQUENCE: 22

```
gtacgtgcac gcaggcgttg ttttctcgga ccctacctcg tcaaatagct gtacacgctg     60

gaatgagagc gcataatcgc ctggacacgg gtgcagagtt catgcacgat aagccgaaca    120

gcgggagccg acactccaaa agacctcagg actaggggaa aaaaaaaaaa aaaaaaaaaa    180

aaaananctg gactcgatta gccctattcc caagggtggg ggttcgtcat tggttgtcgc    240

aaacatccca acttacagca ctcttgtcct catag                              275
```

<210> SEQ ID NO 23
<211> LENGTH: 255
<212> TYPE: DNA
<213> ORGANISM: Mortierella alpina
<220> FEATURE:
<221> NAME/KEY: Intron
<222> LOCATION: (1)..(255)
<220> FEATURE:
<221> NAME/KEY: Intron
<222> LOCATION: (1)..(255)

<400> SEQUENCE: 23

```
gtaagttgct aggattccca ccctcccggc tttattttgc agctctctca tacacgtaca     60

cacacacaca caaagaagat tctcgatggt cactggatgc tttggtggtg ctgtcgaaag    120

ggctgcagac tcttgctgtg tggtgataga gtgccggctt tgatccccca tcgaccgttt    180

gggtccctca ccaagacatc agccctgaga gcagattaat tgatctgata ctgttgaatc    240

gttttctacc catag                                                    255
```

<210> SEQ ID NO 24
<211> LENGTH: 83
<212> TYPE: DNA
<213> ORGANISM: Mortierella alpina
<220> FEATURE:
<221> NAME/KEY: Intron
<222> LOCATION: (1)..(83)
<220> FEATURE:
<221> NAME/KEY: Intron
<222> LOCATION: (1)..(83)

<400> SEQUENCE: 24

```
gtaagagcat ttttctatat cgacaagggt ctctagtgag ttggctacgg aatggtcact     60

aacgcatgct tttgccaata cag                                            83
```

<210> SEQ ID NO 25
<211> LENGTH: 99
<212> TYPE: DNA
<213> ORGANISM: Mortierella alpina
<220> FEATURE:
<221> NAME/KEY: Intron
<222> LOCATION: (1)..(99)
<220> FEATURE:
<221> NAME/KEY: Intron
<222> LOCATION: (1)..(99)

<400> SEQUENCE: 25

```
gtatactttt tttttttttt tttttttttt ttcgcctttg tgttttgtgc tcgacctgtg     60
```

aaaactaatt tatttcttcc ttcgttctgc caccggtag 99

<210> SEQ ID NO 26
<211> LENGTH: 12649
<212> TYPE: DNA
<213> ORGANISM: Artificial Sequence
<220> FEATURE:
<223> OTHER INFORMATION: Plasmid pKUNF12T6E
<220> FEATURE:
<221> NAME/KEY: misc_feature
<222> LOCATION: (2507)..(2507)
<223> OTHER INFORMATION: n is a, c, g, or t
<220> FEATURE:
<221> NAME/KEY: misc_feature
<222> LOCATION: (2512)..(2515)
<223> OTHER INFORMATION: n is a, c, g, or t

<400> SEQUENCE: 26
taaccctcac taaagggaac aaaagctgga gctccaccgc ggacacaata tctggtcaaa 60
tttcagtttc gttacataaa tcgttatgtc aaaggagtgt gggaggttaa gagaattatc 120
accggcaaac tatctgttaa ttgctaggta cctctagacg tccacccggg tcgcttggcg 180
gccgaagagg ccggaatctc gggccgcggt ggcggccgct tagttggtct tggacttctt 240
gggcttcttc aggtaggact ggacaaagaa gttgccgaac agagcgagca gggtgatcat 300
gtacacgccg agcagctgga ccagagcctg agggtagtcg caggggaaga ggtagtcgta 360
cagggactgc accagcatag ccatgaactg ggtcatctgc agagtggtga tgtagggctt 420
gatgggcttg acgaagccga agccctgaga ggaaaagaag tagtaggcgt acatgacggt 480
gtggacgaag gagttgagga tgacggagaa gtaggcgtcg ccaccaggag cgtacttggc 540
aatagcccac cagatggcga agatggtggc atggtggtac acgtgcagga aggagacctg 600
gttgaacttc ttgcacagga tcatgatagc ggtgtccagg aactcgtagg ccttggagac 660
gtagaacacg tagacgattc gggacatgcc ctgagcgtgg gactcgttgc ccttctccat 720
gtcgttgccg aagaccttgt agccacccag gatagcctgt cggatggtct cgacgcacat 780
gtagagggac agtccgaaga ggaacaggtt gtggagcagc ttgatggtct tcagctcgaa 840
gggcttctcc atctgcttca tgatgggaat gccgaagagc agcatggcca tgtagccgac 900
ctcgaaggcg agcatggtgg agacgtccat catgggcaga ccgtcggtca gagcgtaggg 960
cttagctccg tccatccact ggtcgacacc ggtctcgact cgtccgacca cgtcgtccca 1020
gacagaggag ttggccatgg tgaatgattc ttatactcag aaggaaatgc ttaacgattt 1080
cgggtgtgag ttgacaagga gagagagaaa agaagaggaa aggtaattcg gggacggtgg 1140
tcttttatac ccttggctaa agtcccaacc acaaagcaaa aaaattttca gtagtctatt 1200
ttgcgtccgg catgggttac ccggatggcc agacaaagaa actagtacaa agtctgaaca 1260
agcgtagatt ccagactgca gtaccctacg cccttaacgg caagtgtggg aaccggggga 1320
ggtttgatat gtggggtgaa gggggctctc gccggggttg ggcccgctac tgggtcaatt 1380
tggggtcaat tggggcaatt ggggctgttt tttgggacac aaatacgccg ccaacccggt 1440
ctctcctgaa ttctgcatcg atcgaggaag aggacaagcg gctgcttctt aagtttgtga 1500
catcagtatc caaggcacca ttgcaaggat tcaaggcttt gaacccgtca tttgccattc 1560
gtaacgctgg tagacaggtt gatcggttcc ctacggcctc cacctgtgtc aatcttctca 1620
agctgcctga ctatcaggac attgatcaac ttcggaagaa acttttgtat gccattcgat 1680
cacatgctgg tttcgatttg tcttagagga acgcatatac agtaatcata gagaataaac 1740

-continued

```
gatattcatt tattaaagta gatagttgag gtagaagttg taaagagtga taaatagcgg   1800
ccgcgcctac ttaagcaacg ggcttgataa cagcgggggg ggtgcccacg ttgttgcggt   1860
tgcggaagaa cagaacaccc ttaccagcac cctcggcacc agcgctgggc tcaacccact   1920
ggcacatacg cgcactgcgg tacatggcgc ggatgaagcc acgaggacca tcctggacat   1980
cagcccggta gtgcttgccc atgatgggct taatggcctc ggtggcctcg tccgcgttgt   2040
agaaggggat gctgctgacg tagtggtgga ggacatgagt ctcgatgatg ccgtggagaa   2100
ggtggcggcc gatgaagccc atctcacggt caatggtagc agcggcacca cggacgaagt   2160
tccactcgtc gttggtgtag tggggaaggg tagggtcggt gtgctggagg aaggtgatgg   2220
caacgagcca gtggttaacc cagaggtagg gaacaaagta ccagatggcc atgttgtaga   2280
aaccgaactt ctgaacgagg aagtacagag cagtggccat cagaccgata ccaatatcgc   2340
tgaggacgat gagcttagcg tcactgttct cgtacagagg gctgcgggga tcgaagtggt   2400
taacaccacc gccgaggccg ttatgcttgc ccttgccgcg accctcacgc tggcgctcgt   2460
ggtagttgtg gccggtaaca ttggtgatga ggtagttggg ccagccnacg annnnctcag   2520
taagatgagc gagctcgtgg gtcatctttc cgagacgagt agcctgctgc tcgcgggttc   2580
ggggaacgaa gaccatgtca cgctccatgt tgccagtggc cttgtggtgc tttcggtggg   2640
agatttgcca gctgaagtag gggacaagga gggaagagtg aagaacccag ccagtaatgt   2700
cgttgatgat gcgagaatcg gagaaagcac cgtgaccgca ctcatgggca ataacccaga   2760
gaccagtacc gaaaagaccc tgaagaacgg tgtacacggc ccacagacca gcgcgggcgg   2820
gggtggaggg gatatattcg ggggtcacaa agttgtacca gatgctgaaa gtggtagtca   2880
ggaggacaat gtcgcggagg atataaccgt atcccttgag agcggagcgc ttgaagcagt   2940
gcttagggat ggcattgtag atgtccttga tggtaaagtc gggaacctcg aactggttgc   3000
cgtaggtgtc gagcatgaca ccatactcgg acttgggctt ggcgatatca acctcggaca   3060
tggacgagag cgatgtggaa gaggccgagt ggcggggaga gtctgaagga gagacggcgg   3120
cagactcaga atccgtcaca gtagttgagg tgacggtgcg tctaagcgca gggttctgct   3180
tgggcagagc cgaagtggac gccatggaga gctgggttag tttgtgtaga gagtgtgtgt   3240
tgctagcgac tttcggattg tgtcattaca caaaacgcgt cgtctcgaca ctgatcttgt   3300
cgtggatact cacggctcgg acatcgtcgc cgacgatgac accggacttt cgcttaagga   3360
cgtcagtaac aggcattgtg tgatgtgtag tttagatttc gaatctgtgg ggaaagaaag   3420
gaaaaaagag actggcaacc gattgggaga gccactgttt atatataccc tagacaagcc   3480
ccccgcttgt aagatgttgg tcaatgtaaa ccagtattaa ggttggcaag tgcaggagaa   3540
gcaaggtgtg ggtaccgagc aatggaaatg tgcggaaggc aaaaaaatga ggccacggcc   3600
tattgtcggg gctatatcca gggggcgatt gaagtacact aacatgacat gtgtccacag   3660
accctcaatc tggcctgatg agccaaatcc atacgcgctt tcgcagctct aaaggctata   3720
acaagtcaca ccaccctgct cgacctcagc gccctcactt tttgttaaga caaactgtac   3780
acgctgttcc agcgttttct gcctgcacct ggtgggacat ttggtgcaac ctaaagtgct   3840
cggaacctct gtggtgtcca gatcagcgca gcagttccga ggtagttttg aggcccttag   3900
atgatgcaat ggtgtcagtc gctggatcac gagtcttaat ggcagtattc gttcttattt   3960
gtgccattga gccccgttat cctcgtatct tctacccccc atcccatccc tttgttggtg   4020
caaccctacc catttattgt tgggtgcagc ccaaccgacg tggagagctt ggcttggcca   4080
tataaaaagg cccccccta gtggcaatgg cagaaagtca gctgtgagtt gttgaatttg   4140
```

-continued

```
tcatctaggc ggcctggccg tcttctccgg ggcaattgtt cctctatagt actgcgtaca   4200
ctgtttaaac agtgtacgca gatctgcgac gacggaattc ctgcagccca tctgcagaat   4260
tcaggagaga ccgggttggc ggcgtatttg tgtcccaaaa aacagcccca attgccccaa   4320
ttgaccccaa attgacccag tagcgggccc aaccccggcg agagcccccct tcaccccaca   4380
tatcaaacct cccccggttc ccacacttgc cgttaagggc gtagggtact gcagtctgga   4440
atctacgctt gttcagactt tgtactagtt tctttgtctg gccatccggg taacccatgc   4500
cggacgcaaa atagactact gaaaattttt ttgctttgtg gttgggactt tagccaaggg   4560
tataaaagac caccgtcccc gaattacctt tcctcttctt ttctctctct ccttgtcaac   4620
tcacacccga aatcgttaag catttccttc tgagtataag aatcattcac catggctgcc   4680
gctccctctg tgcgaacctt tacccgagcc gaggttctga acgctgaggc tctgaacgag   4740
ggcaagaagg acgctgaggc tcccttcctg atgatcatcg acaacaaggt gtacgacgtc   4800
cgagagttcg tccctgacca tcctggaggc tccgtgattc tcacccacgt tggcaaggac   4860
ggcaccgacg tctttgacac ctttcatccc gaggctgctt gggagactct cgccaacttc   4920
tacgttggag acattgacga gtccgaccga gacatcaaga acgatgactt tgccgctgag   4980
gtccgaaagc tgcgaaccct gttccagtct ctcggctact acgactcctc taaggcctac   5040
tacgccttca aggtctcctt caacctctgc atctggggac tgtccaccgt cattgtggcc   5100
aagtggggtc agacctccac cctcgccaac gtgctctctg ctgccctgct cggcctgttc   5160
tggcagcagt gcggatggct ggctcacgac tttctgcacc accaggtctt ccaggaccga   5220
ttctggggtg atctcttcgg agccttcctg ggaggtgtct gccagggctt ctcctcttcc   5280
tggtggaagg acaagcacaa cactcaccat gccgctccca acgtgcatgg cgaggatcct   5340
gacattgaca cccaccctct cctgacctgg tccgagcacg ctctggagat gttctccgac   5400
gtccccgatg aggagctgac ccgaatgtgg tctcgattca tggtcctgaa ccagacctgg   5460
ttctacttcc ccattctctc cttcgctcga ctgtcttggt gcctccagtc cattctcttt   5520
gtgctgccca acggtcaggc tcacaagccc tccggagctc gagtgcccat ctccctggtc   5580
gagcagctgt ccctcgccat gcactggacc tggtacctcg ctaccatgtt cctgttcatc   5640
aaggatcctg tcaacatgct cgtgtacttc ctggtgtctc aggctgtgtg cggaaacctg   5700
ctcgccatcg tgttctccct caaccacaac ggtatgcctg tgatctccaa ggaggaggct   5760
gtcgacatgg atttctttac caagcagatc atcactggtc gagatgtcca tcctggactg   5820
ttcgccaact ggttcaccgg tggcctgaac taccagatcg agcatcacct gttcccttcc   5880
atgcctcgac acaacttctc caagatccag cctgccgtcg agaccctgtg caagaagtac   5940
aacgtccgat accacaccac tggtatgatc gagggaactg ccgaggtctt ctcccgactg   6000
aacgaggtct ccaaggccac ctccaagatg ggcaaggctc agtaagcggc cgcatgagaa   6060
gataaatata taaatacatt gagatattaa atgcgctaga ttagagagcc tcatactgct   6120
cggagagaag ccaagacgag tactcaaagg ggattacacc atccatatcc acagacacaa   6180
gctggggaaa ggttctatat acactttccg gaataccgta gtttccgatg ttatcaatgg   6240
gggcagccag gatttcaggc acttcggtgt ctcggggtga aatggcgttc ttggcctcca   6300
tcaagtcgta ccatgtcttc atttgcctgt caaagtaaaa cagaagcaga tgaagaatga   6360
acttgaagtg aaggaattta aattgccccg gagaagacgg ccaggccgcc tagatgacaa   6420
attcaacaac tcacagctga ctttctgcca ttgccactag gggggggcct tttatatgg    6480
```

-continued

```
ccaagccaag ctctccacgt cggttgggct gcacccaaca ataaatgggt agggttgcac   6540
caacaaaggg atgggatggg gggtagaaga tacgaggata acggggctca atggcacaaa   6600
taagaacgaa tactgccatt aagactcgtg atccagcgac tgacaccatt gcatcatcta   6660
agggcctcaa aactacctcg gaactgctgc gctgatctgg acaccacaga ggttccgagc   6720
actttaggtt gcaccaaatg tcccaccagg tgcaggcaga aaacgctgga acagcgtgta   6780
cagtttgtct taacaaaaag tgagggcgct gaggtcgagc agggtggtgt gacttgttat   6840
agcctttaga gctgcgaaag cgcgtatgga tttggctcat caggccagat tgagggtctg   6900
tggacacatg tcatgttagt gtacttcaat cgccccctgg atatagcccc gacaataggc   6960
cgtggcctca tttttttgcc ttccgcacat ttccattgct cggtacccac accttgcttc   7020
tcctgcactt gccaacctta atactggttt acattgacca acatcttaca agcggggggc   7080
ttgtctaggg tatatataaa cagtggctct cccaatcggt tgccagtctc tttttccctt   7140
tctttcccca cagattcgaa atctaaacta cacatcacac aatgcctgtt actgacgtcc   7200
ttaagcgaaa gtccggtgtc atcgtcggcg acgatgtccg agccgtgagt atccacgaca   7260
agatcagtgt cgagacgacg cgttttgtgt aatgacacaa tccgaaagtc gctagcaaca   7320
cacactctct acacaaacta acccagctct ccatggagtc cattgctccc ttcctgccct   7380
ccaagatgcc tcaggacctg ttcatggacc tcgccagcgc tatcggtgtc cgagctgctc   7440
cctacgtcga tcccctggag gctgccctgg ttgcccaggc cgagaagtac attcccacca   7500
ttgtccatca cactcgaggc ttcctggttg ccgtggagtc tcccctggct cgagagctgc   7560
ctctgatgaa ccccttccac gtgctcctga tcgtgctcgc ctacctggtc accgtgtttg   7620
tgggtatgca gatcatgaag aactttgaac gattcgaggt caagaccttc tccctcctgc   7680
acaacttctg tctggtctcc atctccgcct acatgtgcgg tggcatcctg tacgaggctt   7740
atcaggccaa ctatggactg tttgagaacg ctgccgatca caccttcaag ggtctcccta   7800
tggctaagat gatctggctc ttctacttct ccaagatcat ggagtttgtc gacaccatga   7860
tcatggtcct caagaagaac aaccgacaga tttcctttct gcacgtgtac caccactctt   7920
ccatcttcac catctggtgg ctggtcacct tcgttgctcc caacggtgaa gcctacttct   7980
ctgctgccct gaactccttc atccacgtca tcatgtacgg ctactacttt ctgtctgccc   8040
tgggcttcaa gcaggtgtcg ttcatcaagt tctacatcac tcgatcccag atgacccagt   8100
tctgcatgat gtctgtccag tcttcctggg acatgtacgc catgaaggtc cttggccgac   8160
ctggataccc cttcttcatc accgctctgc tctggttcta catgtggacc atgctcggtc   8220
tcttctacaa cttttaccga aagaacgcca agctcgccaa gcaggccaag gctgacgctg   8280
ccaaggagaa ggccagaaag ctccagtaag cggccgcaag tgtggatggg gaagtgagtg   8340
cccggttctg tgtgcacaat tggcaatcca agatggatgg attcaacaca gggatatagc   8400
gagctacgtg gtggtgcgag gatatagcaa cggatattta tgtttgacac ttgagaatgt   8460
acgatacaag cactgtccaa gtacaatact aaacatactg tacatactca tactcgtacc   8520
cgggcaacgg tttcacttga gtgcagtggc tagtgctctt actcgtacag tgtgcaatac   8580
tgcgtatcat agtctttgat gtatatcgta ttcattcatg ttagttgcgt acgaagtcgt   8640
caatgatgtc gatatgggtt ttgatcatgc acacataagg tccgacctta tcggcaagct   8700
caatgagctc cttggtggtg gtaacatcca gagaagcaca caggttggtt ttcttggctg   8760
ccacgagctt gagcactcga gcggcaaagg cggacttgtg gacgttagct cgagcttcgt   8820
aggagggcat tttggtggtg aagaggagac tgaaataaat ttagtctgca gaacttttta   8880
```

-continued

```
tcggaacctt atctggggca gtgaagtata tgttatggta atagttacga gttagttgaa    8940
cttatagata gactggacta tacggctatc ggtccaaatt agaaagaacg tcaatggctc    9000
tctgggcgtc gcctttgccg acaaaaatgt gatcatgatg aaagccagca atgacgttgc    9060
agctgatatt gttgtcggcc aaccgcgccg aaaacgcagc tgtcagaccc acagcctcca    9120
acgaagaatg tatcgtcaaa gtgatccaag cacactcata gttggagtcg tactccaaag    9180
gcggcaatga cgagtcagac agatactcgt cgaccttttc cttgggaacc accaccgtca    9240
gcccttctga ctcacgtatt gtagccaccg acacaggcaa cagtccgtgg atagcagaat    9300
atgtcttgtc ggtccatttc tcaccaactt taggcgtcaa gtgaatgttg cagaagaagt    9360
atgtgccttc attgagaatc ggtgttgctg atttcaataa agtcttgaga tcagtttggc    9420
gcgccagctg cattaatgaa tcggccaacg cgcggggaga ggcggtttgc gtattgggcg    9480
ctcttccgct tcctcgctca ctgactcgct gcgctcggtc gttcggctgc ggcgagcggt    9540
atcagctcac tcaaaggcgg taatacggtt atccacagaa tcaggggata acgcaggaaa    9600
gaacatgtga gcaaaaggcc agcaaaaggc caggaaccgt aaaaaggccg cgttgctggc    9660
gtttttccat aggctccgcc cccctgacga gcatcacaaa aatcgacgct caagtcagag    9720
gtggcgaaac ccgacaggac tataaagata ccaggcgttt ccccctggaa gctccctcgt    9780
gcgctctcct gttccgaccc tgccgcttac cggatacctg tccgcctttc tcccttcggg    9840
aagcgtggcg ctttctcata gctcacgctg taggtatctc agttcggtgt aggtcgttcg    9900
ctccaagctg ggctgtgtgc acgaaccccc cgttcagccc gaccgctgcg ccttatccgg    9960
taactatcgt cttgagtcca acccggtaag acacgactta tcgccactgg cagcagccac   10020
tggtaacagg attagcagag cgaggtatgt aggcggtgct acagagttct tgaagtggtg   10080
gcctaactac ggctacacta gaagaacagt atttggtatc tgcgctctgc tgaagccagt   10140
taccttcgga aaaagagttg gtagctcttg atccggcaaa caaaccaccg ctggtagcgg   10200
tggttttttt gtttgcaagc agcagattac gcgcagaaaa aaaggatctc aagaagatcc   10260
tttgatcttt tctacggggt ctgacgctca gtggaacgaa aactcacgtt aagggatttt   10320
ggtcatgaga ttatcaaaaa ggatcttcac ctagatcctt ttaaattaaa aatgaagttt   10380
taaatcaatc taaagtatat atgagtaaac ttggtctgac agttaccaat gcttaatcag   10440
tgaggcacct atctcagcga tctgtctatt tcgttcatcc atagttgcct gactccccgt   10500
cgtgtagata actacgatac gggagggctt accatctggc cccagtgctg caatgatacc   10560
gcgagaccca cgctcaccgg ctccagattt atcagcaata aaccagccag ccggaagggc   10620
cgagcgcaga agtggtcctg caactttatc cgcctccatc cagtctatta attgttgccg   10680
ggaagctaga gtaagtagtt cgccagttaa tagtttgcgc aacgttgttg ccattgctac   10740
aggcatcgtg gtgtcacgct cgtcgtttgg tatggcttca ttcagctccg gttcccaacg   10800
atcaaggcga gttacatgat cccccatgtt gtgcaaaaaa gcggttagct ccttcggtcc   10860
tccgatcgtt gtcagaagta agttggccgc agtgttatca ctcatggtta tggcagcact   10920
gcataattct cttactgtca tgccatccgt aagatgcttt tctgtgactg gtgagtactc   10980
aaccaagtca ttctgagaat agtgtatgcg gcgaccgagt tgctcttgcc cggcgtcaat   11040
acgggataat accgcgccac atagcagaac tttaaaagtg ctcatcattg gaaaacgttc   11100
ttcggggcga aaactctcaa ggatcttacc gctgttgaga tccagttcga tgtaacccac   11160
tcgtgcaccc aactgatctt cagcatcttt tactttcacc agcgtttctg ggtgagcaaa   11220
```

```
aacaggaagg caaaatgccg caaaaaaggg aataagggcg acacggaaat gttgaatact  11280

catactcttc ctttttcaat attattgaag catttatcag ggttattgtc tcatgagcgg  11340

atacatattt gaatgtattt agaaaaataa acaaataggg gttccgcgca catttccccg  11400

aaaagtgcca cctgatgcgg tgtgaaatac cgcacagatg cgtaaggaga aaataccgca  11460

tcaggaaatt gtaagcgtta atattttgtt aaaattcgcg ttaaattttt gttaaatcag  11520

ctcatttttt aaccaatagg ccgaaatcgg caaaatccct tataaatcaa aagaatagac  11580

cgagataggg ttgagtgttg ttccagtttg gaacaagagt ccactattaa agaacgtgga  11640

ctccaacgtc aaagggcgaa aaaccgtcta tcagggcgat ggcccactac gtgaaccatc  11700

accctaatca agttttttgg ggtcgaggtg ccgtaaagca ctaaatcgga accctaaagg  11760

gagcccccga tttagagctt gacggggaaa gccggcgaac gtggcgagaa aggaagggaa  11820

gaaagcgaaa ggagcgggcg ctagggcgct ggcaagtgta gcggtcacgc tgcgcgtaac  11880

caccacaccc gccgcgctta atgcgccgct acagggcgcg tccattcgcc attcaggctg  11940

cgcaactgtt gggaagggcg atcggtgcgg gcctcttcgc tattacgcca gctggcgaaa  12000

gggggatgtg ctgcaaggcg attaagttgg gtaacgccag ggttttccca gtcacgacgt  12060

tgtaaaacga cggccagtga attgtaatac gactcactat agggcgaatt gggcccgacg  12120

tcgcatgcag tggtggtatt gtgactgggg atgtagttga gaataagtca tacacaagtc  12180

agctttcttc gagcctcata taagtataag tagttcaacg tattagcact gtacccagca  12240

tctccgtatc gagaaacaca acaacatgcc ccattggaca gatcatgcgg atacacaggt  12300

tgtgcagtat catacatact cgatcagaca ggtcgtctga ccatcataca agctgaacaa  12360

gcgctccata cttgcacgct ctctatatac acagttaaat tacatatcca tagtctaacc  12420

tctaacagtt aatcttctgg taagcctccc agccagcctt ctggtatcgc ttggcctcct  12480

caataggatc tcggttctgg ccgtacagac ctcggccgac aattatgata tccgttccgg  12540

tagacatgac atcctcaaca gttcggtact gctgtccgag agcgtctccc ttgtcgtcaa  12600

gacccacccc gggggtcaga ataagccagt cctcagagtc gcccttaat             12649
```

```
<210> SEQ ID NO 27
<211> LENGTH: 973
<212> TYPE: DNA
<213> ORGANISM: Yarrowia lipolytica
<220> FEATURE:
<221> NAME/KEY: misc_feature
<223> OTHER INFORMATION: Promoter FBAIN

<400> SEQUENCE: 27

aaattgcccc ggagaagacg gccaggccgc ctagatgaca aattcaacaa ctcacagctg     60

actttctgcc attgccacta gggggggcc tttttatatg gccaagccaa gctctccacg    120

tcggttgggc tgcacccaac aataaatggg tagggttgca ccaacaaagg gatgggatgg    180

ggggtagaag atacgaggat aacggggctc aatggcacaa ataagaacga atactgccat    240

taagactcgt gatccagcga ctgacaccat tgcatcatct aagggcctca aaactacctc    300

ggaactgctg cgctgatctg gacaccacag aggttccgag cactttaggt tgcaccaaat    360

gtcccaccag gtgcaggcag aaaacgctgg aacagcgtgt acagtttgtc ttaacaaaaa    420

gtgagggcgc tgaggtcgag cagggtggtg tgacttgtta tagcctttag agctgcgaaa    480

gcgcgtatgg atttggctca tcaggccaga ttgagggtct gtggacacat gtcatgttag    540

tgtacttcaa tcgccccctg gatatagccc cgacaatagg ccgtggcctc attttttttgc    600
```

-continued

```
cttccgcaca tttccattgc tcggtaccca caccttgctt ctcctgcact tgccaacctt    660

aatactggtt tacattgacc aacatcttac aagcgggggg cttgtctagg gtatatataa    720

acagtggctc tcccaatcgg ttgccagtct ctttttttcct ttctttcccc acagattcga    780

aatctaaact acacatcaca caatgcctgt tactgacgtc cttaagcgaa agtccggtgt    840

catcgtcggc gacgatgtcc gagccgtgag tatccacgac aagatcagtg tcgagacgac    900

gcgttttgtg taatgacaca atccgaaagt cgctagcaac acacactctc tacacaaact    960

aacccagctc tcc                                                       973
```

<210> SEQ ID NO 28
<211> LENGTH: 957
<212> TYPE: DNA
<213> ORGANISM: Mortierella alpina
<220> FEATURE:
<221> NAME/KEY: misc_feature
<223> OTHER INFORMATION: synthetic elongase 1 (codon-optimized)

<400> SEQUENCE: 28

```
atggagtcca ttgctccctt cctgccctcc aagatgcctc aggacctgtt catggacctc     60

gccagcgcta tcggtgtccg agctgctccc tacgtcgatc cctggaggc tgccctggtt    120

gcccaggccg agaagtacat tcccaccatt gtccatcaca ctcgaggctt cctggttgcc    180

gtggagtctc ccctggctcg agagctgcct ctgatgaacc ccttccacgt gctcctgatc    240

gtgctcgcct acctggtcac cgtgtttgtg ggtatgcaga tcatgaagaa ctttgaacga    300

ttcgaggtca agaccttctc cctcctgcac aacttctgtc tggtctccat ctccgcctac    360

atgtgcggtg gcatcctgta cgaggcttat caggccaact atggactgtt tgagaacgct    420

gccgatcaca ccttcaaggg tctccctatg gctaagatga tctggctctt ctacttctcc    480

aagatcatgg agtttgtcga caccatgatc atggtcctca agaagaacaa ccgacagatt    540

tcctttctgc acgtgtacca ccactcttcc atcttcacca tctggtggct ggtcaccttc    600

gttgctccca acggtgaagc ctacttctct gctgccctga actccttcat ccacgtcatc    660

atgtacggct actactttct gtctgccctg ggcttcaagc aggtgtcgtt catcaagttc    720

tacatcactc gatcccagat gacccagttc tgcatgatgt ctgtccagtc ttcctgggac    780

atgtacgcca tgaaggtcct tggccgacct ggatacccct tcttcatcac cgctctgctc    840

tggttctaca tgtggaccat gctcggtctc ttctacaact tttaccgaaa gaacgccaag    900

ctcgccaagc aggccaaggc tgacgctgcc aaggagaagg ccagaaagct ccagtaa       957
```

<210> SEQ ID NO 29
<211> LENGTH: 318
<212> TYPE: PRT
<213> ORGANISM: Mortierella alpina AX464731

<400> SEQUENCE: 29

```
Met Glu Ser Ile Ala Pro Phe Leu Pro Ser Lys Met Pro Gln Asp Leu
1               5                   10                  15

Phe Met Asp Leu Ala Thr Ala Ile Gly Val Arg Ala Ala Pro Tyr Val
            20                  25                  30

Asp Pro Leu Glu Ala Ala Leu Val Ala Gln Ala Glu Lys Tyr Ile Pro
        35                  40                  45

Thr Ile Val His His Thr Arg Gly Phe Leu Val Ala Val Glu Ser Pro
    50                  55                  60

Leu Ala Arg Glu Leu Pro Leu Met Asn Pro Phe His Val Leu Leu Ile
65                  70                  75                  80
```

-continued

```
Val Leu Ala Tyr Leu Val Thr Val Phe Val Gly Met Gln Ile Met Lys
                85                  90                  95

Asn Phe Glu Arg Phe Glu Val Lys Thr Phe Ser Leu Leu His Asn Phe
            100                 105                 110

Cys Leu Val Ser Ile Ser Ala Tyr Met Cys Gly Gly Ile Leu Tyr Glu
        115                 120                 125

Ala Tyr Gln Ala Asn Tyr Gly Leu Phe Glu Asn Ala Ala Asp His Thr
    130                 135                 140

Phe Lys Gly Leu Pro Met Ala Lys Met Ile Trp Leu Phe Tyr Phe Ser
145                 150                 155                 160

Lys Ile Met Glu Phe Val Asp Thr Met Ile Met Val Leu Lys Lys Asn
                165                 170                 175

Asn Arg Gln Ile Ser Phe Leu His Val Tyr His His Ser Ser Ile Phe
            180                 185                 190

Thr Ile Trp Trp Leu Val Thr Phe Val Ala Pro Asn Gly Glu Ala Tyr
        195                 200                 205

Phe Ser Ala Ala Leu Asn Ser Phe Ile His Val Ile Met Tyr Gly Tyr
    210                 215                 220

Tyr Phe Leu Ser Ala Leu Gly Phe Lys Gln Val Ser Phe Ile Lys Phe
225                 230                 235                 240

Tyr Ile Thr Arg Ser Gln Met Thr Gln Phe Cys Met Met Ser Val Gln
                245                 250                 255

Ser Ser Trp Asp Met Tyr Ala Met Lys Val Leu Gly Arg Pro Gly Tyr
            260                 265                 270

Pro Phe Phe Ile Thr Ala Leu Leu Trp Phe Tyr Met Trp Thr Met Leu
        275                 280                 285

Gly Leu Phe Tyr Asn Phe Tyr Arg Lys Asn Ala Lys Leu Ala Lys Gln
    290                 295                 300

Ala Lys Ala Asp Ala Ala Lys Glu Lys Ala Arg Lys Leu Gln
305                 310                 315
```

<210> SEQ ID NO 30
<211> LENGTH: 1374
<212> TYPE: DNA
<213> ORGANISM: Mortierella alpina
<220> FEATURE:
<221> NAME/KEY: misc_feature
<223> OTHER INFORMATION: synthetic delta-6 desaturase (codon-optimized)

<400> SEQUENCE: 30

```
atggctgccg ctccctctgt gcgaaccttt acccgagccg aggttctgaa cgctgaggct     60

ctgaacgagg gcaagaagga cgctgaggct cccttcctga tgatcatcga caacaaggtg    120

tacgacgtcc gagagttcgt ccctgaccat cctggaggct ccgtgattct cacccacgtt    180

ggcaaggacg gcaccgacgt ctttgacacc tttcatcccg aggctgcttg ggagactctc    240

gccaacttct acgttggaga cattgacgag tccgaccgag acatcaagaa cgatgacttt    300

gccgctgagg tccgaaagct gcgaaccctg ttccagtctc tcggctacta cgactcctct    360

aaggcctact acgccttcaa ggtctccttc aacctctgca tctggggact gtccaccgtc    420

attgtggcca agtggggtca gacctccacc ctcgccaacg tgctctctgc tgccctgctc    480

ggcctgttct ggcagcagtg cggatggctg gctcacgact ttctgcacca ccaggtcttc    540

caggaccgat tctggggtga tctcttcgga gccttcctgg gaggtgtctg ccagggcttc    600

tcctcttcct ggtggaagga caagcacaac actcaccatg ccgctcccaa cgtgcatggc    660
```

-continued

```
gaggatcctg acattgacac ccaccctctc ctgacctggt ccgagcacgc tctggagatg    720

ttctccgacg tccccgatga ggagctgacc cgaatgtggt ctcgattcat ggtcctgaac    780

cagacctggt tctacttccc cattctctcc ttcgctcgac tgtcttggtg cctccagtcc    840

attctctttg tgctgcccaa cggtcaggct cacaagccct ccggagctcg agtgcccatc    900

tccctggtcg agcagctgtc cctcgccatg cactggacct ggtacctcgc taccatgttc    960

ctgttcatca aggatcctgt caacatgctc gtgtacttcc tggtgtctca ggctgtgtgc   1020

ggaaacctgc tcgccatcgt gttctccctc aaccacaacg gtatgcctgt gatctccaag   1080

gaggaggctg tcgacatgga tttctttacc aagcagatca tcactggtcg agatgtccat   1140

cctggactgt tcgccaactg gttcaccggt ggcctgaact accagatcga gcatcacctg   1200

ttcccttcca tgcctcgaca caacttctcc aagatccagc ctgccgtcga gaccctgtgc   1260

aagaagtaca acgtccgata ccacaccact ggtatgatcg agggaactgc cgaggtcttc   1320

tcccgactga acgaggtctc caaggccacc tccaagatgg gcaaggctca gtaa         1374


<210> SEQ ID NO 31
<211> LENGTH: 457
<212> TYPE: PRT
<213> ORGANISM: Mortierella alpina AF465281

<400> SEQUENCE: 31

Met Ala Ala Ala Pro Ser Val Arg Thr Phe Thr Arg Ala Glu Val Leu
1               5                   10                  15

Asn Ala Glu Ala Leu Asn Glu Gly Lys Lys Asp Ala Glu Ala Pro Phe
            20                  25                  30

Leu Met Ile Ile Asp Asn Lys Val Tyr Asp Val Arg Glu Phe Val Pro
        35                  40                  45

Asp His Pro Gly Gly Ser Val Ile Leu Thr His Val Gly Lys Asp Gly
    50                  55                  60

Thr Asp Val Phe Asp Thr Phe His Pro Glu Ala Ala Trp Glu Thr Leu
65                  70                  75                  80

Ala Asn Phe Tyr Val Gly Asp Ile Asp Glu Ser Asp Arg Asp Ile Lys
                85                  90                  95

Asn Asp Asp Phe Ala Ala Glu Val Arg Lys Leu Arg Thr Leu Phe Gln
            100                 105                 110

Ser Leu Gly Tyr Tyr Asp Ser Ser Lys Ala Tyr Tyr Ala Phe Lys Val
        115                 120                 125

Ser Phe Asn Leu Cys Ile Trp Gly Leu Ser Thr Val Ile Val Ala Lys
    130                 135                 140

Trp Gly Gln Thr Ser Thr Leu Ala Asn Val Leu Ser Ala Ala Leu Leu
145                 150                 155                 160

Gly Leu Phe Trp Gln Gln Cys Gly Trp Leu Ala His Asp Phe Leu His
                165                 170                 175

His Gln Val Phe Gln Asp Arg Phe Trp Gly Asp Leu Phe Gly Ala Phe
            180                 185                 190

Leu Gly Gly Val Cys Gln Gly Phe Ser Ser Ser Trp Trp Lys Asp Lys
        195                 200                 205

His Asn Thr His His Ala Ala Pro Asn Val His Gly Glu Asp Pro Asp
    210                 215                 220

Ile Asp Thr His Pro Leu Leu Thr Trp Ser Glu His Ala Leu Glu Met
225                 230                 235                 240

Phe Ser Asp Val Pro Asp Glu Glu Leu Thr Arg Met Trp Ser Arg Phe
                245                 250                 255
```

-continued

```
Met Val Leu Asn Gln Thr Trp Phe Tyr Phe Pro Ile Leu Ser Phe Ala
            260                 265                 270

Arg Leu Ser Trp Cys Leu Gln Ser Ile Leu Phe Val Leu Pro Asn Gly
        275                 280                 285

Gln Ala His Lys Pro Ser Gly Ala Arg Val Pro Ile Ser Leu Val Glu
    290                 295                 300

Gln Leu Ser Leu Ala Met His Trp Thr Trp Tyr Leu Ala Thr Met Phe
305                 310                 315                 320

Leu Phe Ile Lys Asp Pro Val Asn Met Leu Val Tyr Phe Leu Val Ser
                325                 330                 335

Gln Ala Val Cys Gly Asn Leu Leu Ala Ile Val Phe Ser Leu Asn His
            340                 345                 350

Asn Gly Met Pro Val Ile Ser Lys Glu Glu Ala Val Asp Met Asp Phe
        355                 360                 365

Phe Thr Lys Gln Ile Ile Thr Gly Arg Asp Val His Pro Gly Leu Phe
    370                 375                 380

Ala Asn Trp Phe Thr Gly Gly Leu Asn Tyr Gln Ile Glu His His Leu
385                 390                 395                 400

Phe Pro Ser Met Pro Arg His Asn Phe Ser Lys Ile Gln Pro Ala Val
                405                 410                 415

Glu Thr Leu Cys Lys Lys Tyr Asn Val Arg Tyr His Thr Thr Gly Met
            420                 425                 430

Ile Glu Gly Thr Ala Glu Val Phe Ser Arg Leu Asn Glu Val Ser Lys
        435                 440                 445

Ala Thr Ser Lys Met Gly Lys Ala Gln
    450                 455
```

<210> SEQ ID NO 32
<211> LENGTH: 1001
<212> TYPE: DNA
<213> ORGANISM: Yarrowia lipolytica
<220> FEATURE:
<221> NAME/KEY: misc_feature
<223> OTHER INFORMATION: Promoter FBA

<400> SEQUENCE: 32

```
taaacagtgt acgcagtact atagaggaac aattgccccg gagaagacgg ccaggccgcc     60

tagatgacaa attcaacaac tcacagctga ctttctgcca ttgccactag gggggggcctt    120

tttatatggc caagccaagc tctccacgtc ggttgggctg cacccaacaa taaatgggta    180

gggttgcacc aacaaaggga tgggatgggg ggtagaagat acgaggataa cggggctcaa    240

tggcacaaat aagaacgaat actgccatta agactcgtga tccagcgact gacaccattg    300

catcatctaa gggcctcaaa actacctcgg aactgctgcg ctgatctgga caccacagag    360

gttccgagca ctttaggttg caccaaatgt cccaccaggt gcaggcagaa aacgctggaa    420

cagcgtgtac agtttgtctt aacaaaaagt gagggcgctg aggtcgagca gggtggtgtg    480

acttgttata gcctttagag ctgcgaaagc gcgtatggat ttggctcatc aggccagatt    540

gagggtctgt ggacacatgt catgttagtg tacttcaatc gccccctgga tatagccccg    600

acaataggcc gtggcctcat ttttttgcct tccgcacatt tccattgctc ggtacccaca    660

ccttgcttct cctgcacttg ccaaccttaa tactggttta cattgaccaa catcttacaa    720

gcggggggct tgtctagggt atatataaac agtggctctc ccaatcggtt gccagtctct    780

tttttccttt ctttccccac agattcgaaa tctaaactac acatcacaca atgcctgtta    840
```

-continued

```
ctgacgtcct taagcgaaag tccggtgtca tcgtcggcga cgatgtccga gccgtgagta    900

tccacgacaa gatcagtgtc gagacgacgc gttttgtgta atgacacaat ccgaaagtcg    960

ctagcaacac acactctcta cacaaactaa cccagctctc c                       1001
```

<210> SEQ ID NO 33
<211> LENGTH: 1434
<212> TYPE: DNA
<213> ORGANISM: Fusarium monoliforme
<220> FEATURE:
<221> NAME/KEY: misc_feature
<223> OTHER INFORMATION: delta-12 desaturase

<400> SEQUENCE: 33

```
atggcgtcca cttcggctct gcccaagcag aaccctgcgc ttagacgcac cgtcacctca     60

actactgtga cggattctga gtctgccgcc gtctctcctt cagactctcc ccgccactcg    120

gcctcttcca catcgctctc gtccatgtcc gaggttgata tcgccaagcc caagtccgag    180

tatggtgtca tgctcgacac ctacggcaac cagttcgagg ttcccgactt taccatcaag    240

gacatctaca atgccatccc taagcactgc ttcaagcgct ccgctctcaa gggatacggt    300

tatatcctcc gcgacattgt cctcctgact accactttca gcatctggta caactttgtg    360

acccccgaat atatcccctc cacccccgcc cgcgctggtc tgtgggccgt gtacaccgtt    420

cttcagggtc ttttcggtac tggtctctgg gttattgccc atgagtgcgg tcacggtgct    480

ttctccgatt ctcgcatcat caacgacatt actggctggg ttcttcactc ttccctcctt    540

gtcccctact tcagctggca aatctcccac cgaaagcacc acaaggccac tggcaacatg    600

gagcgtgaca tggtcttcgt tccccgaacc cgcgagcagc aggctactcg tctcggaaag    660

atgacccacg agctcgctca tcttactgag gagacccccg ctttcactct tctcatgctc    720

gtccttcagc agctcgttgg ctggcccaac tacctcatca ccaatgttac cggccacaac    780

taccacgagc gccagcgtga gggtcgcggc aagggcaagc ataacggcct cggcggtggt    840

gttaaccact tcgatccccg cagccctctg tacgagaaca gtgacgctaa gctcatcgtc    900

ctcagcgata ttggtatcgg tctgatggcc actgctctgt acttcctcgt tcagaagttc    960

ggtttctaca acatggccat ctggtacttt gttccctacc tctgggttaa ccactggctc   1020

gttgccatca ccttcctcca gcacaccgac cctacccttc cccactacac caacgacgag   1080

tggaacttcg tccgtggtgc cgctgctacc attgaccgtg agatgggctt catcggccgc   1140

caccttctcc acggcatcat cgagactcat gtcctccacc actacgtcag cagcatcccc   1200

ttctacaacg cggacgaggc caccgaggcc attaagccca tcatgggcaa gcactaccgg   1260

gctgatgtcc aggatggtcc tcgtggcttc atccgcgcca tgtaccgcag tgcgcgtatg   1320

tgccagtggg ttgagcccag cgctggtgcc gagggtgctg gtaagggtgt tctgttcttc   1380

cgcaaccgca acaacgtggg caccccccc gctgttatca agcccgttgc ttaa          1434
```

<210> SEQ ID NO 34
<211> LENGTH: 477
<212> TYPE: PRT
<213> ORGANISM: Fusarium monoliforme

<400> SEQUENCE: 34

```
Met Ala Ser Thr Ser Ala Leu Pro Lys Gln Asn Pro Ala Leu Arg Arg
1               5                   10                  15

Thr Val Thr Ser Thr Thr Val Thr Asp Ser Glu Ser Ala Ala Val Ser
            20                  25                  30
```

-continued

```
Pro Ser Asp Ser Pro Arg His Ser Ala Ser Ser Thr Ser Leu Ser Ser
        35                  40                  45

Met Ser Glu Val Asp Ile Ala Lys Pro Lys Ser Glu Tyr Gly Val Met
    50                  55                  60

Leu Asp Thr Tyr Gly Asn Gln Phe Glu Val Pro Asp Phe Thr Ile Lys
65                  70                  75                  80

Asp Ile Tyr Asn Ala Ile Pro Lys His Cys Phe Lys Arg Ser Ala Leu
                85                  90                  95

Lys Gly Tyr Gly Tyr Ile Leu Arg Asp Ile Val Leu Leu Thr Thr Thr
            100                 105                 110

Phe Ser Ile Trp Tyr Asn Phe Val Thr Pro Glu Tyr Ile Pro Ser Thr
        115                 120                 125

Pro Ala Arg Ala Gly Leu Trp Ala Val Tyr Thr Val Leu Gln Gly Leu
    130                 135                 140

Phe Gly Thr Gly Leu Trp Val Ile Ala His Glu Cys Gly His Gly Ala
145                 150                 155                 160

Phe Ser Asp Ser Arg Ile Ile Asn Asp Ile Thr Gly Trp Val Leu His
                165                 170                 175

Ser Ser Leu Leu Val Pro Tyr Phe Ser Trp Gln Ile Ser His Arg Lys
            180                 185                 190

His His Lys Ala Thr Gly Asn Met Glu Arg Asp Met Val Phe Val Pro
        195                 200                 205

Arg Thr Arg Glu Gln Gln Ala Thr Arg Leu Gly Lys Met Thr His Glu
    210                 215                 220

Leu Ala His Leu Thr Glu Glu Thr Pro Ala Phe Thr Leu Leu Met Leu
225                 230                 235                 240

Val Leu Gln Gln Leu Val Gly Trp Pro Asn Tyr Leu Ile Thr Asn Val
                245                 250                 255

Thr Gly His Asn Tyr His Glu Arg Gln Arg Glu Gly Arg Gly Lys Gly
            260                 265                 270

Lys His Asn Gly Leu Gly Gly Gly Val Asn His Phe Asp Pro Arg Ser
        275                 280                 285

Pro Leu Tyr Glu Asn Ser Asp Ala Lys Leu Ile Val Leu Ser Asp Ile
    290                 295                 300

Gly Ile Gly Leu Met Ala Thr Ala Leu Tyr Phe Leu Val Gln Lys Phe
305                 310                 315                 320

Gly Phe Tyr Asn Met Ala Ile Trp Tyr Phe Val Pro Tyr Leu Trp Val
                325                 330                 335

Asn His Trp Leu Val Ala Ile Thr Phe Leu Gln His Thr Asp Pro Thr
            340                 345                 350

Leu Pro His Tyr Thr Asn Asp Glu Trp Asn Phe Val Arg Gly Ala Ala
        355                 360                 365

Ala Thr Ile Asp Arg Glu Met Gly Phe Ile Gly Arg His Leu Leu His
    370                 375                 380

Gly Ile Ile Glu Thr His Val Leu His His Tyr Val Ser Ser Ile Pro
385                 390                 395                 400

Phe Tyr Asn Ala Asp Glu Ala Thr Glu Ala Ile Lys Pro Ile Met Gly
                405                 410                 415

Lys His Tyr Arg Ala Asp Val Gln Asp Gly Pro Arg Gly Phe Ile Arg
            420                 425                 430

Ala Met Tyr Arg Ser Ala Arg Met Cys Gln Trp Val Glu Pro Ser Ala
        435                 440                 445

Gly Ala Glu Gly Ala Gly Lys Gly Val Leu Phe Phe Arg Asn Arg Asn
```

-continued

```
    450                 455                 460

Asn Val Gly Thr Pro Pro Ala Val Ile Lys Pro Val Ala
465                 470                 475


<210> SEQ ID NO 35
<211> LENGTH: 819
<212> TYPE: DNA
<213> ORGANISM: Thraustochytrium aureum
<220> FEATURE:
<221> NAME/KEY: misc_feature
<223> OTHER INFORMATION: synthetic elongase (codon-optimized)

<400> SEQUENCE: 35

atggccaact cctctgtctg ggacgacgtg gtcggacgag tcgagaccgg tgtcgaccag      60

tggatggacg gagctaagcc ctacgctctg accgacggtc tgcccatgat ggacgtctcc     120

accatgctcg ccttcgaggt cggctacatg gccatgctgc tcttcggcat tcccatcatg     180

aagcagatgg agaagccctt cgagctgaag accatcaagc tgctccacaa cctgttcctc     240

ttcggactgt ccctctacat gtgcgtcgag accatccgac aggctatcct gggtggctac     300

aaggtcttcg gcaacgacat ggagaagggc aacgagtccc acgctcaggg catgtcccga     360

atcgtctacg tgttctacgt ctccaaggcc tacgagttcc tggacaccgc tatcatgatc     420

ctgtgcaaga agttcaacca ggtctccttc ctgcacgtgt accaccatgc caccatcttc     480

gccatctggt gggctattgc caagtacgct cctggtggcg acgcctactt ctccgtcatc     540

ctcaactcct tcgtccacac cgtcatgtac gcctactact tcttttcctc tcagggcttc     600

ggcttcgtca agcccatcaa gccctacatc accactctgc agatgaccca gttcatggct     660

atgctggtgc agtccctgta cgactacctc ttcccctgcg actaccctca ggctctggtc     720

cagctgctcg gcgtgtacat gatcaccctg ctcgctctgt tcggcaactt ctttgtccag     780

tcctacctga agaagcccaa gaagtccaag accaactaa                            819


<210> SEQ ID NO 36
<211> LENGTH: 272
<212> TYPE: PRT
<213> ORGANISM: Thraustochytrium aureum

<400> SEQUENCE: 36

Met Ala Asn Ser Ser Val Trp Asp Asp Val Val Gly Arg Val Glu Thr
1               5                   10                  15

Gly Val Asp Gln Trp Met Asp Gly Ala Lys Pro Tyr Ala Leu Thr Asp
            20                  25                  30

Gly Leu Pro Met Met Asp Val Ser Thr Met Leu Ala Phe Glu Val Gly
        35                  40                  45

Tyr Met Ala Met Leu Leu Phe Gly Ile Pro Ile Met Lys Gln Met Glu
    50                  55                  60

Lys Pro Phe Glu Leu Lys Thr Ile Lys Leu Leu His Asn Leu Phe Leu
65                  70                  75                  80

Phe Gly Leu Ser Leu Tyr Met Cys Val Glu Thr Ile Arg Gln Ala Ile
                85                  90                  95

Leu Gly Gly Tyr Lys Val Phe Gly Asn Asp Met Glu Lys Gly Asn Glu
            100                 105                 110

Ser His Ala Gln Gly Met Ser Arg Ile Val Tyr Val Phe Tyr Val Ser
        115                 120                 125

Lys Ala Tyr Glu Phe Leu Asp Thr Ala Ile Met Ile Leu Cys Lys Lys
    130                 135                 140
```

-continued

```
Phe Asn Gln Val Ser Phe Leu His Val Tyr His His Ala Thr Ile Phe
145                 150                 155                 160

Ala Ile Trp Trp Ala Ile Ala Lys Tyr Ala Pro Gly Gly Asp Ala Tyr
                165                 170                 175

Phe Ser Val Ile Leu Asn Ser Phe Val His Thr Val Met Tyr Ala Tyr
            180                 185                 190

Tyr Phe Phe Ser Ser Gln Gly Phe Gly Phe Val Lys Pro Ile Lys Pro
        195                 200                 205

Tyr Ile Thr Thr Leu Gln Met Thr Gln Phe Met Ala Met Leu Val Gln
    210                 215                 220

Ser Leu Tyr Asp Tyr Leu Phe Pro Cys Asp Tyr Pro Gln Ala Leu Val
225                 230                 235                 240

Gln Leu Leu Gly Val Tyr Met Ile Thr Leu Leu Ala Leu Phe Gly Asn
                245                 250                 255

Phe Phe Val Gln Ser Tyr Leu Lys Lys Pro Lys Lys Ser Lys Thr Asn
            260                 265                 270
```

<210> SEQ ID NO 37
<211> LENGTH: 13034
<212> TYPE: DNA
<213> ORGANISM: Artificial Sequence
<220> FEATURE:
<223> OTHER INFORMATION: Plasmid pDMW271

<400> SEQUENCE: 37

```
cgatgcagaa ttcaggagag accgggttgg cggcgtattt gtgtcccaaa aaacagcccc     60

aattgcccca attgacccca aattgaccca gtagcgggcc caaccccggc gagagccccc    120

ttcaccccac atatcaaacc tcccccggtt cccacacttg ccgttaaggg cgtagggtac    180

tgcagtctgg aatctacgct tgttcagact ttgtactagt ttctttgtct ggccatccgg    240

gtaacccatg ccggacgcaa aatagactac tgaaaatttt tttgctttgt ggttgggact    300

ttagccaagg gtataaaaga ccaccgtccc cgaattacct ttcctcttct tttctctctc    360

tccttgtcaa ctcacacccg aaatcgttaa gcatttcctt ctgagtataa gaatcattca    420

ccatggatgg ctcccgaccc tgtcgctgcc gagaccgctg cccagggtcc cactccccga    480

tacttcacct gggacgaggt cgcccagcga tccggttgcg aggaacgatg gctggtcatc    540

gaccgaaagg tgtacaacat ctctgagttc acccgacgac atcccggtgg ctcccgagtg    600

atctcgcact acgctggaca ggacgccact gaccccttcg ttgcctttca cattaacaag    660

ggcctggtta agaagtacat gaactccctg ctcattggag agctgtctcc cgaacagcct    720

tcgtttgagc ctaccaagaa caaggagctg accgacgagt ttcgagagct ccgagccacc    780

gttgagcgaa tgggactgat gaaggccaac catgtcttct ttctgctcta cctgctccac    840

attcttctcc ttgacggagc tgcctggctt accctgtggg tcttcggcac ttcctttctg    900

ccctttcttc tctgcgccgt cctgctctct gccgtgcagg ctcaggctgg ttggcttcag    960

catgactttg gtcacctttc cgtgttctct acctccaagt ggaaccacct gctccatcac   1020

ttcgtgatcg gccacctcaa gggtgctcct gcctcgtggt ggaaccacat gcatttccag   1080

caccatgcca agcccaactg ttttcgaaag gatcccgaca tcaacatgca ccccttcttt   1140

ttcgctcttg gcaagatcct gtccgtcgag ctcggaaagc agaagaagaa gtacatgccc   1200

tacaaccacc agcacaagta cttcttcctg attggacctc ccgctctcct gcctctttac   1260

tttcagtggt acatctttta ctttgttatt cagcgaaaga agtgggttga tcttgcctgg   1320

atgatcacct tctacgtccg attcttcctg acctacgtcc ctctccttgg actgaaggcc   1380
```

```
tttctcggtc tgttctttat cgtccgattc ctggagtcca actggttcgt gtgggtgacc   1440
cagatgaacc acattcccat gcacattgac catgatcgaa acatggactg ggtgtcgact   1500
cagctgcagg ccacctgcaa cgttcacaag tctgctttca acgactggtt ttccggtcac   1560
ctcaactttc agattgagca ccatctgttt cccaccatgc ctcgacacaa ctaccacaag   1620
gttgctcccc tggtccagtc gctctgtgcc aagcatggca tcgagtacca gtccaagccc   1680
ctgctctctg ccttcgctga catcattcac tcgctgaagg aatctggcca gctctggctc   1740
gatgcctacc tgcaccagta agcggccgca ttgatgattg gaaacacaca catgggttat   1800
atctaggtga gagttagttg gacagttata tattaaatca gctatgccaa cggtaacttc   1860
attcatgtca acgaggaacc agtgactgca agtaatatag aatttgacca ccttgccatt   1920
ctcttgcact cctttactat atctcattta tttcttatat acaaatcact tcttcttccc   1980
agcatcgagc tcggaaacct catgagcaat aacatcgtgg atctcgtcaa tagagggctt   2040
tttggactcc ttgctgttgg ccaccttgtc cttgctgtct ggctcattct gtttcaacgc   2100
cttttaatta acggagtagg tctcggtgtc ggaagcgacg ccagatccgt catcctcctt   2160
tcgctctcca aagtagatac ctccgacgag ctctcggaca atgatgaagt cggtgccctc   2220
aacgtttcgg atgggggaga gatcggcgag cttgggcgac agcagctggc agggtcgcag   2280
gttggcgtac aggttcaggt cctttcgcag cttgaggaga ccctgctcgg gtcgcacgtc   2340
ggttcgtccg tcgggagtgg tccatacggt gttggcagcg cctccgacag caccgagcat   2400
aatagagtca gcctttcggc agatgtcgag agtagcgtcg gtgatgggct cgccctcctt   2460
ctcaatggca gctcctccaa tgagtcggtc ctcaaacaca aactcggtgc cggaggcctc   2520
agcaacagac ttgagcacct tgacggcctc ggcaatcacc tcggggccac agaagtcgcc   2580
gccgagaaga acaatcttct tggagtcagt cttggtcttc ttagtttcgg gttccattgt   2640
ggatgtgtgt ggttgtatgt gtgatgtggt gtgtggagtg aaaatctgtg gctggcaaac   2700
gctcttgtat atatacgcac ttttgcccgt gctatgtgga agactaaacc tccgaagatt   2760
gtgactcagg tagtgcggta tcggctaggg acccaaacct tgtcgatgcc gatagcatgc   2820
gacgtcgggc ccaattcgcc ctatagtgag tcgtattaca attcactggc cgtcgtttta   2880
caacgtcgtg actgggaaaa ccctggcgtt acccaactta atcgccttgc agcacatccc   2940
cctttcgcca gctggcgtaa tagcgaagag gcccgcaccg atcgcccttc ccaacagttg   3000
cgcagcctga atggcgaatg gacgcgccct gtagcggcgc attaagcgcg gcgggtgtgg   3060
tggttacgcg cagcgtgacc gctacacttg ccagcgccct agcgcccgct cctttcgctt   3120
tcttcccttc ctttctcgcc acgttcgccg gctttccccg tcaagctcta aatcgggggc   3180
tccctttagg gttccgattt agtgctttac ggcacctcga ccccaaaaaa cttgattagg   3240
gtgatggttc acgtagtggg ccatcgccct gatagacggt ttttcgccct ttgacgttgg   3300
agtccacgtt ctttaatagt ggactcttgt tccaaactgg aacaacactc aaccctatct   3360
cggtctattc ttttgattta taagggattt tgccgatttc ggcctattgg ttaaaaaatg   3420
agctgattta acaaaaattt aacgcgaatt ttaacaaaat attaacgctt acaatttcct   3480
gatgcggtat tttctcctta cgcatctgtg cggtatttca caccgcatca ggtggcactt   3540
ttcggggaaa tgtgcgcgga acccctattt gtttattttt ctaaatacat tcaaatatgt   3600
atccgctcat gagacaataa ccctgataaa tgcttcaata atattgaaaa aggaagagta   3660
tgagtattca acatttccgt gtcgccctta ttcccttttt tgcggcattt tgccttcctg   3720
```

-continued

```
tttttgctca cccagaaacg ctggtgaaag taaaagatgc tgaagatcag ttgggtgcac   3780
gagtgggtta catcgaactg gatctcaaca gcggtaagat ccttgagagt tttcgccccg   3840
aagaacgttt tccaatgatg agcactttta aagttctgct atgtggcgcg gtattatccc   3900
gtattgacgc cgggcaagag caactcggtc gccgcataca ctattctcag aatgacttgg   3960
ttgagtactc accagtcaca gaaaagcatc ttacggatgg catgacagta agagaattat   4020
gcagtgctgc cataaccatg agtgataaca ctgcggccaa cttacttctg acaacgatcg   4080
gaggaccgaa ggagctaacc gcttttttgc acaacatggg ggatcatgta actcgccttg   4140
atcgttggga accggagctg aatgaagcca taccaaacga cgagcgtgac accacgatgc   4200
ctgtagcaat ggcaacaacg ttgcgcaaac tattaactgg cgaactactt actctagctt   4260
cccggcaaca attaatagac tggatggagg cggataaagt tgcaggacca cttctgcgct   4320
cggcccttcc ggctggctgg tttattgctg ataaatctgg agccggtgag cgtgggtctc   4380
gcggtatcat tgcagcactg gggccagatg gtaagccctc ccgtatcgta gttatctaca   4440
cgacggggag tcaggcaact atggatgaac gaaatagaca gatcgctgag ataggtgcct   4500
cactgattaa gcattggtaa ctgtcagacc aagtttactc atatatactt tagattgatt   4560
taaaacttca tttttaattt aaaaggatct aggtgaagat cctttttgat aatctcatga   4620
ccaaaatccc ttaacgtgag ttttcgttcc actgagcgtc agaccccgta gaaaagatca   4680
aaggatcttc ttgagatcct ttttttctgc gcgtaatctg ctgcttgcaa acaaaaaaac   4740
caccgctacc agcggtggtt tgtttgccgg atcaagagct accaactctt tttccgaagg   4800
taactggctt cagcagagcg cagataccaa atactgttct tctagtgtag ccgtagttag   4860
gccaccactt caagaactct gtagcaccgc ctacatacct cgctctgcta atcctgttac   4920
cagtggctgc tgccagtggc gataagtcgt gtcttaccgg gttggactca agacgatagt   4980
taccggataa ggcgcagcgg tcgggctgaa cggggggttc gtgcacacag cccagcttgg   5040
agcgaacgac ctacaccgaa ctgagatacc tacagcgtga gctatgagaa agcgccacgc   5100
ttcccgaagg gagaaaggcg gacaggtatc cggtaagcgg cagggtcgga acaggagagc   5160
gcacgaggga gcttccaggg ggaaacgcct ggtatcttta tagtcctgtc gggtttcgcc   5220
acctctgact tgagcgtcga tttttgtgat gctcgtcagg ggggcggagc ctatggaaaa   5280
acgccagcaa cgcggccttt ttacggttcc tggccttttg ctggcctttt gctcacatgt   5340
tctttcctgc gttatcccct gattctgtgg ataaccgtat taccgccttt gagtgagctg   5400
ataccgctcg ccgcagccga acgaccgagc gcagcgagtc agtgagcgag gaagcggaag   5460
agcgcccaat acgcaaaccg cctctccccg cgcgttggcc gattcattaa tgcagctggc   5520
gcgcccactg agctcgtcta acggacttga tatacaacca attaaaacaa atgaaaagaa   5580
atacagttct ttgtatcatt tgtaacaatt accctgtaca aactaaggta ttgaaatccc   5640
acaatattcc caaagtccac ccctttccaa attgtcatgc ctacaactca tataccaagc   5700
actaacctac caaacaccac taaaacccca caaaatatat cttaccgaat atacagtaac   5760
aagctaccac cacactcgtt gggtgcagtc gccagcttaa agatatctat ccacatcagc   5820
cacaactccc ttcctttaat aaaccgacta cacccttggc tattgaggtt atgagtgaat   5880
atactgtaga caagacactt tcaagaagac tgtttccaaa acgtaccact gtcctccact   5940
acaaacacac ccaatctgct tcttctagtc aaggttgcta caccggtaaa ttataaatca   6000
tcatttcatt agcagggcag ggcccttttt atagagtctt atacactagc ggaccctgcc   6060
ggtagaccaa cccgcaggcg cgtcagtttg ctccttccat caatgcgtcg tagaaacgac   6120
```

```
ttactccttc ttgagcagct ccttgacctt gttggcaaca agtctccgac ctcggaggtg   6180
gaggaagagc ctccgatatc ggcggtagtg ataccagcct cgacggactc cttgacggca   6240
gcctcaacag cgtcaccggc gggcttcatg ttaagagaga acttgagcat catggcggca   6300
gacagaatgg tggcgtacgc aactaacatg aatgaatacg atatacatca aagactatga   6360
tacgcagtat tgcacactgt acgagtaaga gcactagcca ctgcactcaa gtgaaaccgt   6420
tgcccgggta cgagtatgag tatgtacagt atgtttagta ttgtacttgg acagtgcttg   6480
tatcgtacat tctcaagtgt caaacataaa tatccgttgc tatatcctcg caccaccacg   6540
tagctcgcta tatccctgtg ttgaatccat ccatcttgga ttgccaattg tgcacacaga   6600
accgggcact cacttcccca tccacacttg cggccgctta gctgcctact cttccttggg   6660
acggagtcca agaacacgca agtgctccaa atgtgaagca aatgcttgcc aaaacgtatc   6720
cttgacaagg tatggaacct tgtactcgct gcaggtgttc ttgatgatgg ccagaatatc   6780
gggataatgg tgctgcgaca cgttggggaa cagatggtgc acagcctggt agttcaagct   6840
gccagtgatg ctggtccaga ggtgcgaatc gtgtgcgtaa tcctgcgtag tctcgacctg   6900
catagctgcc cagtcctttt ggatgatccc gttctcgtca ggcaacggcc actgaacttc   6960
ctcaacaacg tggttcgcct ggaaggtcag cgccagccag taagacgaca ccatgtccgc   7020
gaccgtgaac aagagcagca ccttgcccag gggcagatac tgcaggggaa caatcaggcg   7080
ataccagaca aagaaagcct tgccgcccca gaacatcaca gtgtgccatg tcgagatggg   7140
attgacacga atagcgtcat tggtcttgac aaagtacaaa atgttgatgt cctgaatgcg   7200
caccttgaac gccagcagtc cgtacaggaa aggaacaaac atgtgctggt tgatgtggtt   7260
gacaaaccac ttttggttgg gcttgatacg acgaacatcg ggctcagacg tcgacacgtc   7320
gggatctgct ccagcaatgt tggtgtaggg gtgatggccg agcatatgtt ggtacatcca   7380
caccaggtac gatgctccgt tgaaaaagtc gtgcgtggct cccagaatct tccagacagt   7440
ggggttgtgg gtcactgaaa agtgagacgc atcatgaaga gggttgagtc cgacttgtgc   7500
gcacgcaaat cccatgatga ttgcaaacac cacctgaagc catgtgcgtt cgacaacgaa   7560
aggcacaaag agctgcgcgt agtaggaagc gatcaaggat ccaaagataa gagcgtatcg   7620
tccccagatc tctggtctat tcttgggatc aatgttccga tccgtaaagt agccctcgac   7680
tctcgtcttg atggttttgt ggaacaccgt tggctccggg aagatgggca gctcattcga   7740
gaccagtgta ccgacatagt acttcttcat aatggcatct gcagccccaa acgcgtgata   7800
catctcaaag accggagtaa catctcggcc agctccgagc aggagagtgt ccactccacc   7860
aggatggcgg ctcaagaact ttgtgacatc gtacaccctg ccgcggatgg ccaagagtag   7920
gtcgtccttg gtgttatggg ccgccagctc ttcccaggtg aaggtttttc cttggtccgt   7980
tcccatggag agctgggtta gtttgtgtag agagtgtgtg ttgctagcga ctttcggatt   8040
gtgtcattac acaaaacgcg tcgtctcgac actgatcttg tcgtggatac tcacggctcg   8100
gacatcgtcg ccgacgatga caccggactt tcgcttaagg acgtcagtaa caggcattgt   8160
gtgatgtgta gtttagattt cgaatctgtg gggaaagaaa ggaaaaaaga gactggcaac   8220
cgattgggag agccactgtt tatatatacc ctagacaagc cccccgcttg taagatgttg   8280
gtcaatgtaa accagtatta aggttggcaa gtgcaggaga agcaaggtgt gggtaccgag   8340
caatggaaat gtgcggaagg caaaaaaatg aggccacggc ctattgtcgg ggctatatcc   8400
agggggcgat tgaagtacac taacatgaca tgtgtccaca gaccctcaat ctggcctgat   8460
```

-continued

```
gagccaaatc catacgcgct ttcgcagctc taaaggctat aacaagtcac accaccctgc   8520
tcgacctcag cgccctcact ttttgttaag acaaactgta cacgctgttc cagcgttttc   8580
tgcctgcacc tggtgggaca tttggtgcaa cctaaagtgc tcggaacctc tgtggtgtcc   8640
agatcagcgc agcagttccg aggtagtttt gaggccctta gatgatgcaa tggtgtcagt   8700
cgctggatca cgagtcttaa tggcagtatt cgttcttatt tgtgccattg agccccgtta   8760
tcctcgtatc ttctaccccc catcccatcc ctttgttggt gcaaccctac ccatttattg   8820
ttgggtgcag cccaaccgac gtggagagct tggcttggcc atataaaaag gcccccccct   8880
agtggcaatg gcagaaagtc agctgtgagt tgttgaattt gtcatctagg cggcctggcc   8940
gtcttctccg gggcaattta aattccttca cttcaagttc attcttcatc tgcttctgtt   9000
ttactttgac aggcaaatga agacatggta cgacttgatg gaggccaaga acgccatttc   9060
accccgagac accgaagtgc ctgaaatcct ggctgccccc attgataaca tcggaaacta   9120
cggtattccg gaaagtgtat atagaacctt tccccagctt gtgtctgtgg atatggatgg   9180
tgtaatcccc tttgagtact cgtcttggct tctctccgag cagtatgagg ctctctaatc   9240
tagcgcattt aatatctcaa tgtatttata tatttatctt ctcatgcggc cgcttagctg   9300
cctactcttc cttgggacgg agtccaagaa cacgcaagtg ctccaaatgt gaagcaaatg   9360
cttgccaaaa cgtatccttg acaaggtatg gaaccttgta ctcgctgcag gtgttcttga   9420
tgatggccag aatatcggga taatggtgct gcgacacgtt ggggaacaga tggtgcacag   9480
cctggtagtt caagctgcca gtgatgctgg tccagaggtg cgaatcgtgt gcgtaatcct   9540
gcgtagtctc gacctgcata gctgcccagt ccttttggat gatcccgttc tcgtcaggca   9600
acggccactg aacttcctca acaacgtggt tcgcctggaa ggtcagcgcc agccagtaag   9660
acgacaccat gtccgcgacc gtgaacaaga gcagcacctt gcccaggggc agatactgca   9720
ggggaacaat caggcgatac cagacaaaga aagccttgcc gccccagaac atcacagtgt   9780
gccatgtcga gatgggattg acacgaatag cgtcattggt cttgacaaag tacaaaatgt   9840
tgatgtcctg aatgcgcacc ttgaacgcca gcagtccgta caggaaagga acaaacatgt   9900
gctggttgat gtggttgaca aaccactttt ggttgggctt gatacgacga acatcgggct   9960
cagacgtcga cacgtcggga tctgctccag caatgttggt gtaggggtga tggccgagca  10020
tatgttggta catccacacc aggtacgatg ctccgttgaa aaagtcgtgc gtggctccca  10080
gaatcttcca gacagtgggg ttgtgggtca ctgaaaagtg agacgcatca tgaagagggt  10140
tgagtccgac ttgtgcgcac gcaaatccca tgatgattgc aaacaccacc tgaagccatg  10200
tgcgttcgac aacgaaaggc acaaagagct gcgcgtagta ggaagcgatc aaggatccaa  10260
agataagagc gtatcgtccc cagatctctg gtctattctt gggatcaatg ttccgatccg  10320
taaagtagcc ctcgactctc gtcttgatgg ttttgtggaa caccgttggc tccgggaaga  10380
tgggcagctc attcgagacc agtgtaccga catagtactt cttcataatg gcatctgcag  10440
ccccaaacgc gtgatacatc tcaaagaccg gagtaacatc tcggccagct ccgagcagga  10500
gagtgtccac tccaccagga tggcggctca agaactttgt gacatcgtac accctgccgc  10560
ggatggccaa gagtaggtcg tccttggtgt tatgggccgc cagctcttcc caggtgaagg  10620
tttttccttg gtccgttccc atggtgaatg attcttatac tcagaaggaa atgcttaacg  10680
atttcgggtg tgagttgaca aggagagaga gaaaagaaga ggaaaggtaa ttcggggacg  10740
gtggtctttt ataccettgg ctaaagtccc aaccacaaag caaaaaaatt ttcagtagtc  10800
tattttgcgt ccggcatggg ttacccggat ggccagacaa agaaactagt acaaagtctg  10860
```

```
aacaagcgta gattccagac tgcagtaccc tacgccctta acggcaagtg tgggaaccgg  10920
gggaggtttg atatgtgggg tgaagggggc tctcgccggg gttgggcccg ctactgggtc  10980
aatttggggt caattggggc aattggggct gttttttggg acacaaatac gccgccaacc  11040
cggtctctcc tgatcgatgg gctgcaggaa ttctacaata cgtgagtcag aagggctgac  11100
ggtggtggtt cccaaggaaa aggtcgacga gtatctgtct gactcgtcat tgccgccttt  11160
ggagtacgac tccaactatg agtgtgcttg gatcactttg acgatacatt cttcgttgga  11220
ggctgtgggt ctgacagctg cgttttcggc gcggttggcc gacaacaata tcagctgcaa  11280
cgtcattgct ggctttcatc atgatcacat ttttgtcggc aaaggcgacg cccagagagc  11340
cattgacgtt ctttctaatt tggaccgata gccgtatagt ccagtctatc tataagttca  11400
actaactcgt aactattacc ataacatata cttcactgcc ccagataagg ttccgataaa  11460
aagttctgca gactaaattt atttcagtct cctcttcacc accaaaatgc cctcctacga  11520
agctcgagct aacgtccaca agtccgcctt tgccgctcga gtgctcaagc tcgtggcagc  11580
caagaaaacc aacctgtgtg cttctctgga tgttaccacc accaaggagc tcattgagct  11640
tgccgataag gtcggacctt atgtgtgcat gatcaaaacc catatcgaca tcattgacga  11700
cttcacctac gccggcactg tgctccccct caaggaactt gctcttaagc acggtttctt  11760
cctgttcgag gacagaaagt tcgcagatat tggcaacact gtcaagcacc agtaccggtg  11820
tcaccgaatc gccgagtggt ccgatatcac caacgcccac ggtgtacccg gaaccggaat  11880
cattgctggc ctgcgagctg gtgccgagga aactgtctct gaacagaaga aggaggacgt  11940
ctctgactac gagaactccc agtacaagga gttcctagtc cctctcccca acgagaagct  12000
ggccagaggt ctgctcatgc tggccgagct gtcttgcaag ggctctctgg ccactggcga  12060
gtactccaag cagaccattg agcttgcccg atccgacccc gagtttgtgg ttggcttcat  12120
tgcccagaac cgacctaagg gcgactctga ggactggctt attctgaccc ccggggtggg  12180
tcttgacgac aagggagacg ctctcggaca gcagtaccga actgttgagg atgtcatgtc  12240
taccggaacg gatatcataa ttgtcggccg aggtctgtac ggccagaacc gagatcctat  12300
tgaggaggcc aagcgatacc agaaggctgg ctgggaggct taccagaaga ttaactgtta  12360
gaggttagac tatggatatg taatttaact gtgtatatag agagcgtgca agtatggagc  12420
gcttgttcag cttgtatgat ggtcagacga cctgtctgat cgagtatgta tgatactgca  12480
caacctgtgt atccgcatga tctgtccaat ggggcatgtt gttgtgtttc tcgatacgga  12540
gatgctgggt acagtgctaa tacgttgaac tacttatact tatatgaggc tcgaagaaag  12600
ctgacttgtg tatgacttat tctcaactac atccccagtc acaataccac cactgcacta  12660
ccactacacc agatctgcgt acactgttta aacggtaggt tagtgcttgg tatatgagtt  12720
gtaggcatga caatttggaa aggggtggac tttgggaata ttgtgggatt tcaatacctt  12780
agtttgtaca gggtaattgt tacaaatgat acaaagaact gtatttcttt tcatttgttt  12840
taattggttg tatatcaagt ccgttagacg agctcagtgc cttggctttt ggcactgtat  12900
ttcattttta gaggtacact acattcagtg aggtatggta aggttgaggg cataatgaag  12960
gcaccttgta ctgacagtca cagacctctc accgagaatt ttatgagata tactcgggtt  13020
cattttaggc tcat                                                    13034
```

<210> SEQ ID NO 38
<211> LENGTH: 1341
<212> TYPE: DNA

-continued

<213> ORGANISM: Mortierella alpina AF067654
<220> FEATURE:
<221> NAME/KEY: misc_feature
<223> OTHER INFORMATION: delta-5 desaturase

<400> SEQUENCE: 38

```
atgggaacgg accaaggaaa aaccttcacc tgggaagagc tggcggccca taacaccaag     60

gacgacctac tcttggccat ccgcggcagg gtgtacgatg tcacaaagtt cttgagccgc    120

catcctggtg gagtggacac tctcctgctc ggagctggcc gagatgttac tccggtcttt    180

gagatgtatc acgcgtttgg ggctgcagat gccattatga agaagtacta tgtcggtaca    240

ctggtctcga atgagctgcc catcttcccg gagccaacgg tgttccacaa aaccatcaag    300

acgagagtcg agggctactt tacggatcgg aacattgatc ccaagaatag accagagatc    360

tggggacgat acgctcttat ctttggatcc ttgatcgctt cctactacgc gcagctcttt    420

gtgcctttcg ttgtcgaacg cacatggctt caggtggtgt ttgcaatcat catgggattt    480

gcgtgcgcac aagtcggact caaccctctt catgatgcgt ctcacttttc agtgacccac    540

aaccccactg tctggaagat tctgggagcc acgcacgact tttcaacgg agcatcgtac     600

ctggtgtgga tgtaccaaca tatgctcggc catcacccct acaccaacat tgctggagca    660

gatcccgacg tgtcgacgtc tgagcccgat gttcgtcgta tcaagcccaa ccaaaagtgg    720

tttgtcaacc acatcaacca gcacatgttt gttcctttcc tgtacggact gctggcgttc    780

aaggtgcgca ttcaggacat caacattttg tactttgtca agaccaatga cgctattcgt    840

gtcaatccca tctcgacatg gcacactgtg atgttctggg gcggcaaggc tttctttgtc    900

tggtatcgcc tgattgttcc cctgcagtat ctgcccctgg gcaaggtgct gctcttgttc    960

acggtcgcgg acatggtgtc gtcttactgg ctggcgctga ccttccaggc gaaccacgtt   1020

gttgaggaag ttcagtggcc gttgcctgac gagaacggga tcatccaaaa ggactgggca   1080

gctatgcagg tcgagactac gcaggattac gcacacgatt cgcacctctg gaccagcatc   1140

actggcagct tgaactacca ggctgtgcac catctgttcc ccaacgtgtc gcagcaccat   1200

tatcccgata ttctggccat catcaagaac acctgcagcg agtacaaggt tccatacctt   1260

gtcaaggata cgttttggca agcatttgct tcacatttgg agcacttgcg tgttcttgga   1320

ctccgtccca aggaagagta g                                              1341
```

<210> SEQ ID NO 39
<211> LENGTH: 446
<212> TYPE: PRT
<213> ORGANISM: Mortierella alpina AF067654

<400> SEQUENCE: 39

```
Met Gly Thr Asp Gln Gly Lys Thr Phe Thr Trp Glu Glu Leu Ala Ala
1               5                   10                  15

His Asn Thr Lys Asp Asp Leu Leu Leu Ala Ile Arg Gly Arg Val Tyr
            20                  25                  30

Asp Val Thr Lys Phe Leu Ser Arg His Pro Gly Gly Val Asp Thr Leu
        35                  40                  45

Leu Leu Gly Ala Gly Arg Asp Val Thr Pro Val Phe Glu Met Tyr His
    50                  55                  60

Ala Phe Gly Ala Ala Asp Ala Ile Met Lys Lys Tyr Tyr Val Gly Thr
65                  70                  75                  80

Leu Val Ser Asn Glu Leu Pro Ile Phe Pro Glu Pro Thr Val Phe His
                85                  90                  95
```

-continued

```
Lys Thr Ile Lys Thr Arg Val Glu Gly Tyr Phe Thr Asp Arg Asn Ile
            100                 105                 110

Asp Pro Lys Asn Arg Pro Glu Ile Trp Gly Arg Tyr Ala Leu Ile Phe
        115                 120                 125

Gly Ser Leu Ile Ala Ser Tyr Tyr Ala Gln Leu Phe Val Pro Phe Val
    130                 135                 140

Val Glu Arg Thr Trp Leu Gln Val Val Phe Ala Ile Ile Met Gly Phe
145                 150                 155                 160

Ala Cys Ala Gln Val Gly Leu Asn Pro Leu His Asp Ala Ser His Phe
                165                 170                 175

Ser Val Thr His Asn Pro Thr Val Trp Lys Ile Leu Gly Ala Thr His
            180                 185                 190

Asp Phe Phe Asn Gly Ala Ser Tyr Leu Val Trp Met Tyr Gln His Met
        195                 200                 205

Leu Gly His His Pro Tyr Thr Asn Ile Ala Gly Ala Asp Pro Asp Val
    210                 215                 220

Ser Thr Ser Glu Pro Asp Val Arg Arg Ile Lys Pro Asn Gln Lys Trp
225                 230                 235                 240

Phe Val Asn His Ile Asn Gln His Met Phe Val Pro Phe Leu Tyr Gly
                245                 250                 255

Leu Leu Ala Phe Lys Val Arg Ile Gln Asp Ile Asn Ile Leu Tyr Phe
            260                 265                 270

Val Lys Thr Asn Asp Ala Ile Arg Val Asn Pro Ile Ser Thr Trp His
        275                 280                 285

Thr Val Met Phe Trp Gly Gly Lys Ala Phe Phe Val Trp Tyr Arg Leu
    290                 295                 300

Ile Val Pro Leu Gln Tyr Leu Pro Leu Gly Lys Val Leu Leu Leu Phe
305                 310                 315                 320

Thr Val Ala Asp Met Val Ser Ser Tyr Trp Leu Ala Leu Thr Phe Gln
                325                 330                 335

Ala Asn His Val Val Glu Glu Val Gln Trp Pro Leu Pro Asp Glu Asn
            340                 345                 350

Gly Ile Ile Gln Lys Asp Trp Ala Ala Met Gln Val Glu Thr Thr Gln
        355                 360                 365

Asp Tyr Ala His Asp Ser His Leu Trp Thr Ser Ile Thr Gly Ser Leu
    370                 375                 380

Asn Tyr Gln Ala Val His His Leu Phe Pro Asn Val Ser Gln His His
385                 390                 395                 400

Tyr Pro Asp Ile Leu Ala Ile Ile Lys Asn Thr Cys Ser Glu Tyr Lys
                405                 410                 415

Val Pro Tyr Leu Val Lys Asp Thr Phe Trp Gln Ala Phe Ala Ser His
            420                 425                 430

Leu Glu His Leu Arg Val Leu Gly Leu Arg Pro Lys Glu Glu
        435                 440                 445
```

```
<210> SEQ ID NO 40
<211> LENGTH: 1335
<212> TYPE: DNA
<213> ORGANISM: Homo sapiens
<220> FEATURE:
<221> NAME/KEY: misc_feature
<223> OTHER INFORMATION: synthetic delta-5 desaturase (codon-optimized)

<400> SEQUENCE: 40

atggctcccg accctgtcgc tgccgagacc gctgcccagg gtcccactcc ccgatacttc     60
```

-continued

```
acctgggacg aggtcgccca gcgatccggt tgcgaggaac gatggctggt catcgaccga    120

aaggtgtaca acatctctga gttcacccga cgacatcccg gtggctcccg agtgatctcg    180

cactacgctg gacaggacgc cactgacccc ttcgttgcct ttcacattaa caagggcctg    240

gttaagaagt acatgaactc cctgctcatt ggagagctgt ctcccgaaca gccttcgttt    300

gagcctacca agaacaagga gctgaccgac gagtttcgag agctccgagc caccgttgag    360

cgaatgggac tgatgaaggc caaccatgtc ttctttctgc tctacctgct ccacattctt    420

ctccttgacg gagctgcctg gcttaccctg tgggtcttcg gcacttcctt tctgcccttt    480

cttctctgcg ccgtcctgct ctctgccgtg caggctcagg ctggttggct tcagcatgac    540

tttggtcacc tttccgtgtt ctctacctcc aagtggaacc acctgctcca tcacttcgtg    600

atcggccacc tcaagggtgc tcctgcctcg tggtggaacc acatgcattt ccagcaccat    660

gccaagccca actgttttcg aaaggatccc gacatcaaca tgcacccctt ctttttcgct    720

cttggcaaga tcctgtccgt cgagctcgga aagcagaaga agaagtacat gccctacaac    780

caccagcaca agtacttctt cctgattgga cctcccgctc tcctgcctct ttactttcag    840

tggtacatct tttactttgt tattcagcga aagaagtggg ttgatcttgc ctggatgatc    900

accttctacg tccgattctt cctgacctac gtccctctcc ttggactgaa ggcctttctc    960

ggtctgttct ttatcgtccg attcctggag tccaactggt tcgtgtgggt gacccagatg   1020

aaccacattc ccatgcacat tgaccatgat cgaaacatgg actgggtgtc gactcagctg   1080

caggccacct gcaacgttca caagtctgct ttcaacgact ggttttccgg tcacctcaac   1140

tttcagattg agcaccatct gtttcccacc atgcctcgac acaactacca caaggttgct   1200

cccctggtcc agtcgctctg tgccaagcat ggcatcgagt accagtccaa gcccctgctc   1260

tctgccttcg ctgacatcat tcactcgctg aaggaatctg gccagctctg gctcgatgcc   1320

tacctgcacc agtaa                                                    1335
```

<210> SEQ ID NO 41
<211> LENGTH: 444
<212> TYPE: PRT
<213> ORGANISM: Homo sapiens

<400> SEQUENCE: 41

```
Met Ala Pro Asp Pro Val Ala Ala Glu Thr Ala Ala Gln Gly Pro Thr
1               5                   10                  15

Pro Arg Tyr Phe Thr Trp Asp Glu Val Ala Gln Arg Ser Gly Cys Glu
            20                  25                  30

Glu Arg Trp Leu Val Ile Asp Arg Lys Val Tyr Asn Ile Ser Glu Phe
        35                  40                  45

Thr Arg Arg His Pro Gly Gly Ser Arg Val Ile Ser His Tyr Ala Gly
    50                  55                  60

Gln Asp Ala Thr Asp Pro Phe Val Ala Phe His Ile Asn Lys Gly Leu
65                  70                  75                  80

Val Lys Lys Tyr Met Asn Ser Leu Leu Ile Gly Glu Leu Ser Pro Glu
                85                  90                  95

Gln Pro Ser Phe Glu Pro Thr Lys Asn Lys Glu Leu Thr Asp Glu Phe
            100                 105                 110

Arg Glu Leu Arg Ala Thr Val Glu Arg Met Gly Leu Met Lys Ala Asn
        115                 120                 125

His Val Phe Phe Leu Leu Tyr Leu Leu His Ile Leu Leu Leu Asp Gly
    130                 135                 140
```

-continued

```
Ala Ala Trp Leu Thr Leu Trp Val Phe Gly Thr Ser Phe Leu Pro Phe
145                 150                 155                 160

Leu Leu Cys Ala Val Leu Leu Ser Ala Val Gln Ala Gln Ala Gly Trp
                165                 170                 175

Leu Gln His Asp Phe Gly His Leu Ser Val Phe Ser Thr Ser Lys Trp
            180                 185                 190

Asn His Leu Leu His His Phe Val Ile Gly His Leu Lys Gly Ala Pro
        195                 200                 205

Ala Ser Trp Trp Asn His Met His Phe Gln His His Ala Lys Pro Asn
    210                 215                 220

Cys Phe Arg Lys Asp Pro Asp Ile Asn Met His Pro Phe Phe Phe Ala
225                 230                 235                 240

Leu Gly Lys Ile Leu Ser Val Glu Leu Gly Lys Gln Lys Lys Lys Tyr
                245                 250                 255

Met Pro Tyr Asn His Gln His Lys Tyr Phe Phe Leu Ile Gly Pro Pro
            260                 265                 270

Ala Leu Leu Pro Leu Tyr Phe Gln Trp Tyr Ile Phe Tyr Phe Val Ile
        275                 280                 285

Gln Arg Lys Lys Trp Val Asp Leu Ala Trp Met Ile Thr Phe Tyr Val
    290                 295                 300

Arg Phe Phe Leu Thr Tyr Val Pro Leu Leu Gly Leu Lys Ala Phe Leu
305                 310                 315                 320

Gly Leu Phe Phe Ile Val Arg Phe Leu Glu Ser Asn Trp Phe Val Trp
                325                 330                 335

Val Thr Gln Met Asn His Ile Pro Met His Ile Asp His Asp Arg Asn
            340                 345                 350

Met Asp Trp Val Ser Thr Gln Leu Gln Ala Thr Cys Asn Val His Lys
        355                 360                 365

Ser Ala Phe Asn Asp Trp Phe Ser Gly His Leu Asn Phe Gln Ile Glu
    370                 375                 380

His His Leu Phe Pro Thr Met Pro Arg His Asn Tyr His Lys Val Ala
385                 390                 395                 400

Pro Leu Val Gln Ser Leu Cys Ala Lys His Gly Ile Glu Tyr Gln Ser
                405                 410                 415

Lys Pro Leu Leu Ser Ala Phe Ala Asp Ile Ile His Ser Leu Lys Glu
            420                 425                 430

Ser Gly Gln Leu Trp Leu Asp Ala Tyr Leu His Gln
        435                 440
```

<210> SEQ ID NO 42
<211> LENGTH: 12690
<212> TYPE: DNA
<213> ORGANISM: Artificial Sequence
<220> FEATURE:
<223> OTHER INFORMATION: Plasmid pZP3L37

<400> SEQUENCE: 42

```
aaataccagt tggccacaaa cccttgacga tctcgtatgt cccctccgac atactcccgg     60

ccggctgggg tacgttcgat agcgctatcg gcatcgacaa ggtttgggtc cctagccgat    120

accgcactac ctgagtcaca atcttcggag gtttagtctt ccacatagca cgggcaaaag    180

tgcgtatata tacaagagcg tttgccagcc acagattttc actccacaca ccacatcaca    240

catacaacca cacacatcca caatggaacc cgaaactaag aagaccaaga ctgactccaa    300

gaagattgtt cttctcggcg gcgacttctg tggccccgag gtgattgccg aggccgtcaa    360
```

-continued

```
ggtgctcaag tctgttgctg aggcctccgg caccgagttt gtgtttgagg accgactcat    420
tggaggagct gccattgaga aggagggcga gcccatcacc gacgctactc tcgacatctg    480
ccgaaaggct gactctatta tgctcggtgc tgtcggaggc gctgccaaca ccgtatggac    540
cactcccgac ggacgaaccg acgtgcgacc cgagcagggt ctcctcaagc tgcgaaagga    600
cctgaacctg tacgccaacc tgcgaccctg ccagctgctg tcgcccaagc tcgccgatct    660
ctcccccatc cgaaacgttg agggcaccga cttcatcatt gtccgagagc tcgtcggagg    720
tatctacttt ggagagcgaa aggaggatga cggatctggc gtcgcttccg acaccgagac    780
ctactccgtt cctgaggttg agcgaattgc ccgaatggcc gccttcctgg cccttcagca    840
caaccccccct cttcccgtgt ggtctcttga caaggccaac gtgctggcct cctctcgact    900
ttggcgaaag actgtcactc gagtcctcaa ggacgaattc cccagctcg agctcaacca    960
ccagctgatc gactcggccg ccatgatcct catcaagcag ccctccaaga tgaatggtat   1020
catcatcacc accaacatgt ttggcgatat catctccgac gaggcctccg tcatccccgg   1080
ttctctgggt ctgctgccct ccgcctctct ggcttctctg cccgacacca acgaggcgtt   1140
cggtctgtac gagccctgtc acggatctgc ccccgatctc ggcaagcaga aggtcaaccc   1200
cattgccacc attctgtctg ccgccatgat gctcaagttc tctcttaaca tgaagcccgc   1260
cggtgacgct gttgaggctg ccgtcaagga gtccgtcgag gctggtatca ctaccgccga   1320
tatcggaggc tcttcctcca cctccgaggt cggagacttg ttgccaacaa ggtcaaggag   1380
ctgctcaaga aggagtaagt cgtttctacg acgcattgat ggaaggagca aactgacgcg   1440
cctgcgggtt ggtctaccgg cagggtccgc tagtgtataa gactctataa aaagggccct   1500
gccctgctaa tgaaatgatg atttataatt taccggtgta gcaaccttga ctagaagaag   1560
cagattgggt gtgtttgtag tggaggacag tggtacgttt tggaaacagt cttcttgaaa   1620
gtgtcttgtc tacagtatat tcactcataa cctcaatagc caagggtgta gtcggtttat   1680
taaaggaagg gagttgtggc tgatgtggat agatatcttt aagctggcga ctgcacccaa   1740
cgagtgtggt ggtagcttgt tagatctgta tattcggtaa gatatatttt gtggggtttt   1800
agtggtgttt aaacagtgta cgcagtacta tagaggaaca attgccccgg agaagacggc   1860
caggccgcct agatgacaaa ttcaacaact cacagctgac tttctgccat tgccactagg   1920
ggggggcctt tttatatggc caagccaagc tctccacgtc ggttgggctg cacccaacaa   1980
taaatgggta gggttgcacc aacaaaggga tgggatgggg ggtagaagat acgaggataa   2040
cggggctcaa tggcacaaat aagaacgaat actgccatta agactcgtga tccagcgact   2100
gacaccattg catcatctaa gggcctcaaa actacctcgg aactgctgcg ctgatctgga   2160
caccacagag gttccgagca ctttaggttg caccaaatgt cccaccaggt gcaggcagaa   2220
aacgctggaa cagcgtgtac agtttgtctt aacaaaaagt gagggcgctg aggtcgagca   2280
gggtggtgtg acttgttata gcctttagag ctgcgaaagc gcgtatggat ttggctcatc   2340
aggccagatt gagggtctgt ggacacatgt catgttagtg tacttcaatc gccccctgga   2400
tatagccccg acaataggcc gtggcctcat ttttttgcct tccgcacatt tccattgctc   2460
ggtacccaca ccttgcttct cctgcacttg ccaaccttaa tactggttta cattgaccaa   2520
catcttacaa gcggggggct tgtctagggt atatataaac agtggctctc ccaatcggtt   2580
gccagtctct tttttccttt ctttccccac agattcgaaa tctaaactac acatcacaca   2640
atgcctgtta ctgacgtcct taagcgaaag tccggtgtca tcgtcggcga cgatgtccga   2700
gccgtgagta tccacgacaa gatcagtgtc gagacgacgc gttttgtgta atgacacaat   2760
```

-continued

```
ccgaaagtcg ctagcaacac acactctcta cacaaactaa cccagctctc catggctgag   2820
gataagacca aggtcgagtt ccctaccctg actgagctga agcactctat ccctaacgct   2880
tgctttgagt ccaacctcgg actctcgctc tactacactg cccgagcgat cttcaacgca   2940
tctgcctctg ctgctctgct ctacgctgcc cgatctactc ccttcattgc cgataacgtt   3000
ctgctccacg ctctggtttg cgccacctac atctacgtgc agggtgtcat cttctggggt   3060
ttctttaccg tcggtcacga ctgtggtcac tctgccttct cccgatacca ctccgtcaac   3120
ttcatcattg gctgcatcat gcactctgcc attctgactc ccttcgagtc ctggcgagtg   3180
acccaccgac accatcacaa gaacactggc aacattgata aggacgagat cttctaccct   3240
catcggtccg tcaaggacct ccaggacgtg cgacaatggg tctacaccct cggaggtgct   3300
tggtttgtct acctgaaggt cggatatgct cctcgaacca tgtcccactt tgacccctgg   3360
gaccctctcc tgcttcgacg agcctccgct gtcatcgtgt ccctcggagt ctgggctgcc   3420
ttcttcgctg cctacgccta cctcacatac tcgctcggct ttgccgtcat gggcctctac   3480
tactatgctc ctctctttgt ctttgcttcg ttcctcgtca ttactacctt cttgcatcac   3540
aacgacgaag ctactccctg gtacggtgac tcggagtgga cctacgtcaa gggcaacctg   3600
agctccgtcg accgatcgta cggagctttc gtggacaacc tgtctcacca cattggcacc   3660
caccaggtcc atcacttgtt ccctatcatt ccccactaca agctcaacga agccaccaag   3720
cactttgctg ccgcttaccc tcacctcgtg agacgtaacg acgagcccat cattactgcc   3780
ttcttcaaga ccgctcacct ctttgtcaac tacggagctg tgcccgagac tgctcagatt   3840
ttcaccctca aagagtctgc cgctgcagcc aaggccaaga gcgactaagc ggccgctatt   3900
tatcactctt tacaacttct acctcaacta tctactttaa taaatgaata tcgtttattc   3960
tctatgatta ctgtatatgc gttcctctaa gacaaatcga aaccagcatg tgatcgaatg   4020
gcatacaaaa gtttcttccg aagttgatca atgtcctgat agtcaggcag cttgagaaga   4080
ttgacacagg tggaggccgt agggaaccga tcaacctgtc taccagcgtt acgaatggca   4140
aatgacgggt tcaaagcctt gaatccttgc aatggtgcct tggatactga tgtcacaaac   4200
ttaagaagca gccgcttgtc ctcttcctcg atcgatcagg agagaccggg ttggcggcgt   4260
atttgtgtcc caaaaaacag ccccaattgc cccaattgac cccaaattga cccagtagcg   4320
ggcccaaccc cggcgagagc ccccttcacc ccacatatca aacctccccc ggttcccaca   4380
cttgccgtta agggcgtagg gtactgcagt ctggaatcta cgcttgttca gactttgtac   4440
tagtttcttt gtctggccat ccgggtaacc catgccggac gcaaaataga ctactgaaaa   4500
tttttttgct ttgtggttgg gactttagcc aagggtataa aagaccaccg tccccgaatt   4560
acctttcctc ttcttttctc tctctccttg tcaactcaca cccgaaatcg ttaagcattt   4620
ccttctgagt ataagaatca ttcaccatgg ctgaggataa gaccaaggtc gagttcccta   4680
ccctgactga gctgaagcac tctatcccta acgcttgctt tgagtccaac ctcggactct   4740
cgctctacta cactgcccga gcgatcttca acgcatctgc ctctgctgct ctgctctacg   4800
ctgcccgatc tactcccttc attgccgata acgttctgct ccacgctctg gtttgcgcca   4860
cctacatcta cgtgcagggt gtcatcttct ggggtttctt taccgtcggt cacgactgtg   4920
gtcactctgc cttctcccga taccactccg tcaacttcat cattggctgc atcatgcact   4980
ctgccattct gactcccttc gagtcctggc gagtgaccca ccgacaccat cacaagaaca   5040
ctggcaacat tgataaggac gagatcttct accctcatcg gtccgtcaag gacctccagg   5100
```

-continued

```
acgtgcgaca atgggtctac accctcggag gtgcttggtt tgtctacctg aaggtcggat   5160
atgctcctcg aaccatgtcc cactttgacc cctgggaccc tctcctgctt cgacgagcct   5220
ccgctgtcat cgtgtccctc ggagtctggg ctgccttctt cgctgcctac gcctacctca   5280
catactcgct cggctttgcc gtcatgggcc tctactacta tgctcctctc tttgtctttg   5340
cttcgttcct cgtcattact accttcttgc atcacaacga cgaagctact ccctggtacg   5400
gtgactcgga gtggacctac gtcaagggca acctgagctc cgtcgaccga tcgtacggag   5460
ctttcgtgga caacctgtct caccacattg gcacccacca ggtccatcac ttgttcccta   5520
tcattcccca ctacaagctc aacgaagcca ccaagcactt tgctgccgct taccctcacc   5580
tcgtgagacg taacgacgag cccatcatta ctgccttctt caagaccgct cacctctttg   5640
tcaactacgg agctgtgccc gagactgctc agattttcac cctcaaagag tctgccgctg   5700
cagccaaggc caagagcgac taagcggccg caagtgtgga tggggaagtg agtgcccggt   5760
tctgtgtgca caattggcaa tccaagatgg atggattcaa cacagggata tagcgagcta   5820
cgtggtggtg cgaggatata gcaacggata tttatgtttg acacttgaga atgtacgata   5880
caagcactgt ccaagtacaa tactaaacat actgtacata ctcatactcg tacccgggca   5940
acggtttcac ttgagtgcag tggctagtgc tcttactcgt acagtgtgca atactgcgta   6000
tcatagtctt tgatgtatat cgtattcatt catgttagtt gcgtacggtg tgtatcgtag   6060
aggtagtgac gtgttgtcca cagggcgact gtgtccgtgt atatatatat tcctcggccc   6120
gagcttattt gtgtggggtt gaggaaatca aaccaaatcg gtagtcagag aaataaaaca   6180
aaaagaaata aaaagaaata gaggacgcac aacgccatca ccgtcggaga gacaggagaa   6240
gggaaaatgg gcaaaaatgc ccttatcaca cccgcccgct ttgtgctctc attcggctcc   6300
cacaagagcc tcttgtcctg gttccccccc cccacatttt aacaccccac acgacgttgc   6360
tgcacgtgga attttcggcc gaaaacctgt ggggtactta cttttggcac tggagagaag   6420
catctgggat tttgggaacc taggcagaag atgaggaaaa aaataagagg aaccgttgtg   6480
agcttgctta tcagtgtcat atactccccc ctccttgcgt tttgcgtctt tttcccccta   6540
tttttcaaat tttgcgattt tttttctctt tttttccgct tttttccgct tttttttttgg  6600
ccggctttta tccatttctc caagccgagg atcacatcta tgcagcccag tccgttggag   6660
catatctgcg gtagagtttc ggaacggcgt taagcactgt gtccgggtcg gtctggaacg   6720
agattgagcg ggaaattcgg gggaataaga ccaccgttgg actccccgca atgaggagat   6780
caagatgtgc ttttcagaat tctgattggt ggcgcgccag ctgcattaat gaatcggcca   6840
acgcgcgggg agaggcggtt tgcgtattgg gcgctcttcc gcttcctcgc tcactgactc   6900
gctgcgctcg gtcgttcggc tgcggcgagc ggtatcagct cactcaaagg cggtaatacg   6960
gttatccaca gaatcagggg ataacgcagg aaagaacatg tgagcaaaag gccagcaaaa   7020
ggccaggaac cgtaaaaagg ccgcgttgct ggcgtttttc cataggctcc gcccccctga   7080
cgagcatcac aaaaatcgac gctcaagtca gaggtggcga aacccgacag gactataaag   7140
ataccaggcg tttccccctg gaagctccct cgtgcgctct cctgttccga ccctgccgct   7200
taccggatac ctgtccgcct ttctcccttc gggaagcgtg gcgctttctc atagctcacg   7260
ctgtaggtat ctcagttcgg tgtaggtcgt tcgctccaag ctgggctgtg tgcacgaacc   7320
ccccgttcag cccgaccgct gcgccttatc cggtaactat cgtcttgagt ccaacccggt   7380
aagacacgac ttatcgccac tggcagcagc cactggtaac aggattagca gagcgaggta   7440
tgtaggcggt gctacagagt tcttgaagtg gtggcctaac tacggctaca ctagaagaac   7500
```

-continued

```
agtatttggt atctgcgctc tgctgaagcc agttaccttc ggaaaaagag ttggtagctc   7560
ttgatccggc aaacaaacca ccgctggtag cggtggtttt tttgtttgca agcagcagat   7620
tacgcgcaga aaaaaaggat ctcaagaaga tcctttgatc ttttctacgg ggtctgacgc   7680
tcagtggaac gaaaactcac gttaagggat tttggtcatg agattatcaa aaaggatctt   7740
cacctagatc cttttaaatt aaaaatgaag ttttaaatca atctaaagta tatatgagta   7800
aacttggtct gacagttacc aatgcttaat cagtgaggca cctatctcag cgatctgtct   7860
atttcgttca tccatagttg cctgactccc cgtcgtgtag ataactacga tacgggaggg   7920
cttaccatct ggccccagtg ctgcaatgat accgcgagac ccacgctcac cggctccaga   7980
tttatcagca ataaaccagc cagccggaag ggccgagcgc agaagtggtc ctgcaacttt   8040
atccgcctcc atccagtcta ttaattgttg ccgggaagct agagtaagta gttcgccagt   8100
taatagtttg cgcaacgttg ttgccattgc tacaggcatc gtggtgtcac gctcgtcgtt   8160
tggtatggct tcattcagct ccggttccca acgatcaagg cgagttacat gatcccccat   8220
gttgtgcaaa aaagcggtta gctccttcgg tcctccgatc gttgtcagaa gtaagttggc   8280
cgcagtgtta tcactcatgg ttatggcagc actgcataat tctcttactg tcatgccatc   8340
cgtaagatgc ttttctgtga ctggtgagta ctcaaccaag tcattctgag aatagtgtat   8400
gcggcgaccg agttgctctt gcccggcgtc aatacgggat aataccgcgc cacatagcag   8460
aactttaaaa gtgctcatca ttggaaaacg ttcttcgggg cgaaaactct caaggatctt   8520
accgctgttg agatccagtt cgatgtaacc cactcgtgca cccaactgat cttcagcatc   8580
ttttactttc accagcgttt ctgggtgagc aaaaacagga aggcaaaatg ccgcaaaaaa   8640
gggaataagg gcgacacgga aatgttgaat actcatactc ttcctttttc aatattattg   8700
aagcatttat cagggttatt gtctcatgag cggatacata tttgaatgta tttagaaaaa   8760
taaacaaata ggggttccgc gcacatttcc ccgaaaagtg ccacctgatg cggtgtgaaa   8820
taccgcacag atgcgtaagg agaaaatacc gcatcaggaa attgtaagcg ttaatatttt   8880
gttaaaattc gcgttaaatt tttgttaaat cagctcattt tttaaccaat aggccgaaat   8940
cggcaaaatc ccttataaat caaaagaata gaccgagata gggttgagtg ttgttccagt   9000
ttggaacaag agtccactat taaagaacgt ggactccaac gtcaaagggc gaaaaaccgt   9060
ctatcagggc gatggcccac tacgtgaacc atcaccctaa tcaagttttt tggggtcgag   9120
gtgccgtaaa gcactaaatc ggaaccctaa agggagcccc cgatttagag cttgacgggg   9180
aaagccggcg aacgtggcga gaaaggaagg gaagaaagcg aaaggagcgg gcgctagggc   9240
gctggcaagt gtagcggtca cgctgcgcgt aaccaccaca cccgccgcgc ttaatgcgcc   9300
gctacagggc gcgtccattc gccattcagg ctgcgcaact gttgggaagg gcgatcggtg   9360
cgggcctctt cgctattacg ccagctggcg aaagggggat gtgctgcaag gcgattaagt   9420
tgggtaacgc cagggttttc ccagtcacga cgttgtaaaa cgacggccag tgaattgtaa   9480
tacgactcac tatagggcga attgggcccg acgtcgcatg cgtcgagata tcgacattgt   9540
tccatctcca gtttaacccc aacttatcga gagtatttgt gagacacgca ataaatgaat   9600
ttataccaat caaatccata ttctacgctg tctacatata gatacttttt gtcatctctt   9660
gccctactat ttcgtcgata tatgaaggat acgccaaccg aacccatact ccacgctaca   9720
cacgcgcctt ttcacgcatt tctggggaaa atagacaccc ttggtgtcac ctgaagaata   9780
tgaaagaaga tattcattgt attgagctgt agatctgtgt atttcttgac ctcatcaatg   9840
```

-continued

```
acttctgggc tctttacctc gaatcatggt ggtactgtac cacatctcaa caccttgtag   9900
cacacctatg ggaaaattga gactatgaat ggattcccgt gcccgtatta ctctactaat   9960
ttgatcttgg aacgcgaaaa tacgtttcta ggactccaaa gaatctcaac tcttgtcctt  10020
actaaatata ctacccatag ttgatggttt acttgaacag agaggacatg ttcacttgac  10080
ccaaagtttc tcgcatctct tggatatttg aacaacggcg tccactgacc gtcagttatc  10140
cagtcacaaa acccccacat tcatacattc ccatgtacgt ttacaaagtt ctcaattcca  10200
tcgtgcaaat caaaatcaca tctattcatt catcatatat aaacccatca tgtctactaa  10260
cactcacaac tccatagaaa acatcgactc agaacacacg ctccatctat tcctcgtcca  10320
gctcgcaaat gtcgtcatct taattaaaag gcgttgaaac agaatgagcc agacagcaag  10380
gacaaggtgg ccaacagcaa ggagtccaaa aagccctcta ttgacgagat ccacgatgtt  10440
attgctcatg aggtttccga gctcgatgct gggaagaaga agtgatttgt atataagaaa  10500
taaatgagat atagtaaagg agtgcaagag aatggcaagg tggtcaaatt ctatattact  10560
tgcagtcact ggttcctcgt tgacatgaat gaagttaccg ttggcatagc tgatttaata  10620
tataactgtc caactaactc tcacctagat ataacccatg tgtgtgtttc caatcatcaa  10680
tgcggccgct tagtcgctct tggccttggc tgcagcggca gactctttga gggtgaaaat  10740
ctgagcagtc tcgggcacag ctccgtagtt gacaaagagg tgagcggtct tgaagaaggc  10800
agtaatgatg ggctcgtcgt tacgtctcac gaggtgaggg taagcggcag caaagtgctt  10860
ggtggcttcg ttgagcttgt agtggggaat gatagggaac aagtgatgga cctggtgggt  10920
gccaatgtgg tgagacaggt tgtccacgaa agctccgtac gatcggtcga cggagctcag  10980
gttgcccttg acgtaggtcc actccgagtc accgtaccag ggagtagctt cgtcgttgtg  11040
atgcaagaag gtagtaatga cgaggaacga agcaaagaca aagagaggag catagtagta  11100
gaggcccatg acggcaaagc cgagcgagta tgtgaggtag gcgtaggcag cgaagaaggc  11160
agcccagact ccgagggaca cgatgacagc ggaggctcgt cgaagcagga gagggtccca  11220
ggggtcaaag tgggacatgg ttcgaggagc atatccgacc ttcaggtaga caaaccaagc  11280
acctccgagg gtgtagaccc attgtcgcac gtcctggagg tccttgacgg accgatgagg  11340
gtagaagatc tcgtccttat caatgttgcc agtgttcttg tgatggtgtc ggtgggtcac  11400
tcgccaggac tcgaagggag tcagaatggc agagtgcatg atgcagccaa tgatgaagtt  11460
gacggagtgg tatcgggaga aggcagagtg accacagtcg tgaccgacgg taaagaaacc  11520
ccagaagatg acaccctgca cgtagatgta ggtggcgcaa accagagcgt ggagcagaac  11580
gttatcggca atgaagggag tagatcgggc agcgtagagc agagcagcag aggcagatgc  11640
gttgaagatc gctcgggcag tgtagtagag cgagagtccg aggttggact caaagcaagc  11700
gttagggata gagtgcttca gctcagtcag ggtagggaac tcgaccttgg tcttatcctc  11760
agccatggta ccagagctgg gttagtttgt gtagagagtg tgtgttgcta gcgactttcg  11820
gattgtgtca ttacacaaaa cgcgtcgtct cgacactgat cttgtcgtgg atactcacgg  11880
ctcggaattc tgtgatgtgt agtttagatt tcgaatctgt ggggaaagaa aggaaaaaag  11940
agactggcaa ccgattggga gagccactgt ttatatatac cctagacaag cccccccgctt  12000
gtaagatgtt ggtcaatgta aaccagtatt aaggttggca agtgcaggag aagcaaggtg  12060
tgggtaccga gcaatggaaa tgtgcggaag gcaaaaaaat gaggccacgg cctattgtcg  12120
gggctatatc caggggggcga ttgaagtaca ctaacatgac atgtgtccac agaccctcaa  12180
tctggcctga tgagccaaat ccatacgcgc tttcgcagct ctaaaggcta taacaagtca  12240
```

```
caccaccctg ctcgacctca gcgccctcac tttttgttaa gacaaactgt acacgctgtt  12300

ccagcgtttt ctgcctgcac ctggtgggac atttggtgca acctaaagtg ctcggaacct  12360

ctgtggtgtc cagatcagcg cagcagttcc gaggtagttt tgaggccctt agatgatgca  12420

atggtgtcag tcgctggatc acgagtctta atggcagtat tcgttcttat ttgtgccatt  12480

gagccccgtt atcctcgtat cttctacccc ccatcccatc cctttgttgg tgcaacccta  12540

cccatttatt gttgggtgca gcccaaccga cgtggagagc ttggcttggc catataaaaa  12600

ggcccccccc tagtggcaat ggcagaaagt cagctgtgag ttgttgaatt tgtcatctag  12660

gcggcctggc cgtcttctcc ggggcaattt                                   12690
```

```
<210> SEQ ID NO 43
<211> LENGTH: 1077
<212> TYPE: DNA
<213> ORGANISM: Saprolegnia diclina
<220> FEATURE:
<221> NAME/KEY: misc_feature
<223> OTHER INFORMATION: synthetic delta-17 desaturase (codon-optimized)

<400> SEQUENCE: 43

atggctgagg ataagaccaa ggtcgagttc cctaccctga ctgagctgaa gcactctatc     60

cctaacgctt gctttgagtc caacctcgga ctctcgctct actacactgc ccgagcgatc    120

ttcaacgcat ctgcctctgc tgctctgctc tacgctgccc gatctactcc cttcattgcc    180

gataacgttc tgctccacgc tctggtttgc gccacctaca tctacgtgca gggtgtcatc    240

ttctggggtt tctttaccgt cggtcacgac tgtggtcact ctgccttctc ccgataccac    300

tccgtcaact tcatcattgg ctgcatcatg cactctgcca ttctgactcc cttcgagtcc    360

tggcgagtga cccaccgaca ccatcacaag aacactggca acattgataa ggacgagatc    420

ttctaccctc atcggtccgt caaggacctc caggacgtgc gacaatgggt ctacaccctc    480

ggaggtgctt ggtttgtcta cctgaaggtc ggatatgctc ctcgaaccat gtcccacttt    540

gacccctggg accctctcct gcttcgacga gcctccgctg tcatcgtgtc cctcggagtc    600

tgggctgcct tcttcgctgc ctacgcctac ctcacatact cgctcggctt tgccgtcatg    660

ggcctctact actatgctcc tctctttgtc tttgcttcgt tcctcgtcat tactaccttc    720

ttgcatcaca acgacgaagc tactccctgg tacggtgact cggagtggac ctacgtcaag    780

ggcaacctga gctccgtcga ccgatcgtac ggagctttcg tggacaacct gtctcaccac    840

attggcaccc accaggtcca tcacttgttc cctatcattc cccactacaa gctcaacgaa    900

gccaccaagc actttgctgc cgcttaccct cacctcgtga gacgtaacga cgagcccatc    960

attactgcct tcttcaagac cgctcacctc tttgtcaact acggagctgt gcccgagact   1020

gctcagattt tcaccctcaa agagtctgcc gctgcagcca aggccaagag cgactaa      1077
```

```
<210> SEQ ID NO 44
<211> LENGTH: 358
<212> TYPE: PRT
<213> ORGANISM: Saprolegnia diclina (ATCC #56851)

<400> SEQUENCE: 44

Met Ala Glu Asp Lys Thr Lys Val Glu Phe Pro Thr Leu Thr Glu Leu
1               5                   10                  15

Lys His Ser Ile Pro Asn Ala Cys Phe Glu Ser Asn Leu Gly Leu Ser
            20                  25                  30

Leu Tyr Tyr Thr Ala Arg Ala Ile Phe Asn Ala Ser Ala Ser Ala Ala
```

-continued

```
        35                  40                  45

Leu Leu Tyr Ala Ala Arg Ser Thr Pro Phe Ile Ala Asp Asn Val Leu
    50                  55                  60

Leu His Ala Leu Val Cys Ala Thr Tyr Ile Tyr Val Gln Gly Val Ile
65                  70                  75                  80

Phe Trp Gly Phe Phe Thr Val Gly His Asp Cys Gly His Ser Ala Phe
                85                  90                  95

Ser Arg Tyr His Ser Val Asn Phe Ile Ile Gly Cys Ile Met His Ser
            100                 105                 110

Ala Ile Leu Thr Pro Phe Glu Ser Trp Arg Val Thr His Arg His His
        115                 120                 125

His Lys Asn Thr Gly Asn Ile Asp Lys Asp Glu Ile Phe Tyr Pro His
    130                 135                 140

Arg Ser Val Lys Asp Leu Gln Asp Val Arg Gln Trp Val Tyr Thr Leu
145                 150                 155                 160

Gly Gly Ala Trp Phe Val Tyr Leu Lys Val Gly Tyr Ala Pro Arg Thr
                165                 170                 175

Met Ser His Phe Asp Pro Trp Asp Pro Leu Leu Leu Arg Arg Ala Ser
            180                 185                 190

Ala Val Ile Val Ser Leu Gly Val Trp Ala Ala Phe Phe Ala Ala Tyr
        195                 200                 205

Ala Tyr Leu Thr Tyr Ser Leu Gly Phe Ala Val Met Gly Leu Tyr Tyr
    210                 215                 220

Tyr Ala Pro Leu Phe Val Phe Ala Ser Phe Leu Val Ile Thr Thr Phe
225                 230                 235                 240

Leu His His Asn Asp Glu Ala Thr Pro Trp Tyr Gly Asp Ser Glu Trp
                245                 250                 255

Thr Tyr Val Lys Gly Asn Leu Ser Ser Val Asp Arg Ser Tyr Gly Ala
            260                 265                 270

Phe Val Asp Asn Leu Ser His His Ile Gly Thr His Gln Val His His
        275                 280                 285

Leu Phe Pro Ile Ile Pro His Tyr Lys Leu Asn Glu Ala Thr Lys His
    290                 295                 300

Phe Ala Ala Ala Tyr Pro His Leu Val Arg Arg Asn Asp Glu Pro Ile
305                 310                 315                 320

Ile Thr Ala Phe Phe Lys Thr Ala His Leu Phe Val Asn Tyr Gly Ala
                325                 330                 335

Val Pro Glu Thr Ala Gln Ile Phe Thr Leu Lys Glu Ser Ala Ala Ala
            340                 345                 350

Ala Lys Ala Lys Ser Asp
        355
```

<210> SEQ ID NO 45
<211> LENGTH: 924
<212> TYPE: DNA
<213> ORGANISM: Yarrowia lipolytica
<220> FEATURE:
<221> NAME/KEY: misc_feature
<223> OTHER INFORMATION: Promoter FBAINm

<400> SEQUENCE: 45

```
aaattgcccc ggagaagacg gccaggccgc ctagatgaca aattcaacaa ctcacagctg     60

actttctgcc attgccacta ggggggggcc tttttatatg gccaagccaa gctctccacg    120

tcggttgggc tgcacccaac aataaatggg tagggttgca ccaacaaagg gatgggatgg    180
```

-continued

```
ggggtagaag atacgaggat aacggggctc aatggcacaa ataagaacga atactgccat    240

taagactcgt gatccagcga ctgacaccat tgcatcatct aagggcctca aaactacctc    300

ggaactgctg cgctgatctg gacaccacag aggttccgag cactttaggt tgcaccaaat    360

gtcccaccag gtgcaggcag aaaacgctgg aacagcgtgt acagtttgtc ttaacaaaaa    420

gtgagggcgc tgaggtcgag cagggtggtg tgacttgtta tagcctttag agctgcgaaa    480

gcgcgtatgg atttggctca tcaggccaga ttgagggtct gtggacacat gtcatgttag    540

tgtacttcaa tcgcccctg gatatagccc cgacaatagg ccgtggcctc attttttttgc    600

cttccgcaca tttccattgc tcggtaccca caccttgctt ctcctgcact tgccaacctt    660

aatactggtt tacattgacc aacatcttac aagcgggggg cttgtctagg gtatatataa    720

acagtggctc tcccaatcgg ttgccagtct cttttttcct ttctttcccc acagattcga    780

aatctaaact acacatcaca gaattccgag ccgtgagtat ccacgacaag atcagtgtcg    840

agacgacgcg ttttgtgtaa tgacacaatc cgaaagtcgc tagcaacaca cactctctac    900

acaaactaac ccagctctgg tacc                                           924
```

<210> SEQ ID NO 46
<211> LENGTH: 5833
<212> TYPE: DNA
<213> ORGANISM: Artificial Sequence
<220> FEATURE:
<223> OTHER INFORMATION: Plasmid pZKUT16

<400> SEQUENCE: 46

```
gtacgaggaa actgtctctg aacagaagaa ggaggacgtc tctgactacg agaactccca     60

gtacaaggag ttcctagtcc cctctcccaa cgagaagctg gccagaggtc tgctcatgct    120

ggccgagctg tcttgcaagg gctctctggc cactggcgag tactccaagc agaccattga    180

gcttgcccga tccgaccccg agtttgtggt tggcttcatt gcccagaacc gacctaaggg    240

cgactctgag gactggctta ttctgacccc cggggtgggt cttgacgaca agggagacgc    300

tctcggacag cagtaccgaa ctgttgagga tgtcatgtct accggaacgg atatcataat    360

tgtcggccga ggtctgtacg gccagaaccg agatcctatt gaggaggcca agcgatacca    420

gaaggctggc tgggaggctt accagaagat taactgttag aggttagact atggatatgt    480

aatttaactg tgtatataga gagcgtgcaa gtatggagcg cttgttcagc ttgtatgatg    540

gtcagacgac ctgtctgatc gagtatgtat gatactgcac aacctgtgta tccgcatgat    600

ctgtccaatg gggcatgttg ttgtgtttct cgatacggag atgctgggta cagtgctaat    660

acgttgaact acttatactt atatgaggct cgaagaaagc tgacttgtgt atgacttaat    720

taatcgagct tggcgtaatc atggtcatag ctgtttcctg tgtgaaattg ttatccgctc    780

acaattccac acaacatacg agccggaagc ataaagtgta aagcctgggg tgcctaatga    840

gtgagctaac tcacattaat tgcgttgcgc tcactgcccg ctttccagtc gggaaacctg    900

tcgtgccagc tgcattaatg aatcggccaa cgcgcgggga gaggcggttt gcgtattggg    960

cgctcttccg cttcctcgct cactgactcg ctgcgctcgg tcgttcggct gcggcgagcg   1020

gtatcagctc actcaaaggc ggtaatacgg ttatccacag aatcagggga taacgcagga   1080

aagaacatgt gagcaaaagg ccagcaaaag gccaggaacc gtaaaaaggc cgcgttgctg   1140

gcgtttttcc ataggctccg cccccctgac gagcatcaca aaaatcgacg ctcaagtcag   1200

aggtggcgaa acccgacagg actataaaga taccaggcgt ttccccctgg aagctccctc   1260

gtgcgctctc ctgttccgac cctgccgctt accggatacc tgtccgcctt tctcccttcg   1320
```

```
ggaagcgtgg cgctttctca tagctcacgc tgtaggtatc tcagttcggt gtaggtcgtt   1380
cgctccaagc tgggctgtgt gcacgaaccc cccgttcagc ccgaccgctg cgccttatcc   1440
ggtaactatc gtcttgagtc caacccggta agacacgact tatcgccact ggcagcagcc   1500
actggtaaca ggattagcag agcgaggtat gtaggcggtg ctacagagtt cttgaagtgg   1560
tggcctaact acggctacac tagaaggaca gtatttggta tctgcgctct gctgaagcca   1620
gttaccttcg gaaaaagagt tggtagctct tgatccggca aacaaaccac cgctggtagc   1680
ggtggttttt ttgtttgcaa gcagcagatt acgcgcagaa aaaaaggatc tcaagaagat   1740
cctttgatct tttctacggg gtctgacgct cagtggaacg aaaactcacg ttaagggatt   1800
ttggtcatga gattatcaaa aaggatcttc acctagatcc ttttaaatta aaaatgaagt   1860
tttaaatcaa tctaaagtat atatgagtaa acttggtctg acagttacca atgcttaatc   1920
agtgaggcac ctatctcagc gatctgtcta tttcgttcat ccatagttgc ctgactcccc   1980
gtcgtgtaga taactacgat acgggagggc ttaccatctg gccccagtgc tgcaatgata   2040
ccgcgagacc cacgctcacc ggctccagat ttatcagcaa taaaccagcc agccggaagg   2100
gccgagcgca gaagtggtcc tgcaacttta tccgcctcca tccagtctat taattgttgc   2160
cgggaagcta gagtaagtag ttcgccagtt aatagtttgc gcaacgttgt tgccattgct   2220
acaggcatcg tggtgtcacg ctcgtcgttt ggtatggctt cattcagctc cggttcccaa   2280
cgatcaaggc gagttacatg atcccccatg ttgtgcaaaa aagcggttag ctccttcggt   2340
cctccgatcg ttgtcagaag taagttggcc gcagtgttat cactcatggt tatggcagca   2400
ctgcataatt ctcttactgt catgccatcc gtaagatgct tttctgtgac tggtgagtac   2460
tcaaccaagt cattctgaga atagtgtatg cggcgaccga gttgctcttg cccggcgtca   2520
atacgggata ataccgcgcc acatagcaga actttaaaag tgctcatcat tggaaaacgt   2580
tcttcggggc gaaaactctc aaggatctta ccgctgttga gatccagttc gatgtaaccc   2640
actcgtgcac ccaactgatc ttcagcatct tttactttca ccagcgtttc tgggtgagca   2700
aaaacaggaa ggcaaaatgc cgcaaaaaag ggaataaggg cgacacggaa atgttgaata   2760
ctcatactct tcctttttca atattattga agcatttatc agggttattg tctcatgagc   2820
ggatacatat ttgaatgtat ttagaaaaat aaacaaatag gggttccgcg cacatttccc   2880
cgaaaagtgc cacctgacgc gccctgtagc ggcgcattaa gcgcggcggg tgtggtggtt   2940
acgcgcagcg tgaccgctac acttgccagc gccctagcgc ccgctccttt cgctttcttc   3000
ccttcctttc tcgccacgtt cgccggcttt ccccgtcaag ctctaaatcg ggggctccct   3060
ttagggttcc gatttagtgc tttacggcac ctcgacccca aaaaacttga ttagggtgat   3120
ggttcacgta gtgggccatc gccctgatag acggtttttc gccctttgac gttggagtcc   3180
acgttcttta atagtggact cttgttccaa actggaacaa cactcaaccc tatctcggtc   3240
tattcttttg atttataagg gattttgccg atttcggcct attggttaaa aaatgagctg   3300
atttaacaaa aatttaacgc gaattttaac aaaatattaa cgcttacaat ttccattcgc   3360
cattcaggct gcgcaactgt tgggaagggc gatcggtgcg ggcctcttcg ctattacgcc   3420
agctggcgaa agggggatgt gctgcaaggc gattaagttg ggtaacgcca gggttttccc   3480
agtcacgacg ttgtaaaacg acggccagtg aattgtaata cgactcacta tagggcgaat   3540
tgggtaccgg gccccccctc gaggtcgacg agtatctgtc tgactcgtca ttgccgcctt   3600
tggagtacga ctccaactat gagtgtgctt ggatcacttt gacgatacat tcttcgttgg   3660
```

-continued

```
aggctgtggg tctgacagct gcgttttcgg cgcggttggc cgacaacaat atcagctgca   3720
acgtcattgc tggctttcat catgatcaca tttttgtcgg caaaggcgac gcccagagag   3780
ccattgacgt tctttctaat ttggaccgat agccgtatag tccagtctat ctataagttc   3840
aactaactcg taactattac cataacatat acttcactgc cccagataag gttccgataa   3900
aaagttctgc agactaaatt tatttcagtc tcctcttcac caccaaaatg ccctcctacg   3960
aagctcgagt gctcaagctc gtggcagcca agaaaaccaa cctgtgtgct tctctggatg   4020
ttaccaccac caaggagctc attgagcttg ccgataaggt cggaccttat gtgtgcatga   4080
tcaaaaccca tatcgacatc attgacgact tcacctacgc cggcactgtg ctcccccctca   4140
aggaacttgc tcttaagcac ggtttcttcc tgttcgagga cagaaagttc gcagatattg   4200
gcaacactgt caagcaccag taccggtgtc accgaatcgc cgagtggtcc gatatcacca   4260
acgcccacgg tgtacccgga accggaatcg atgcagaatt caggagagac cgggttggcg   4320
gcgtatttgt gtcccaaaaa acagccccaa ttgccccaat tgaccccaaa ttgacccagt   4380
agcgggccca accccggcga gagccccctt caccccacat atcaaacctc ccccggttcc   4440
cacacttgcc gttaagggcg tagggtactg cagtctggaa tctacgcttg ttcagacttt   4500
gtactagttt ctttgtctgg ccatccgggt aacccatgcc ggacgcaaaa tagactactg   4560
aaaatttttt tgctttgtgg ttgggacttt agccaagggt ataaaagacc accgtccccg   4620
aattaccttt cctcttcttt tctctctctc cttgtcaact cacacccgaa atcgttaagc   4680
atttccttct gagtataaga atcattcacc atggacatgt ccgtcctgac tctccaagag   4740
tacgagttcg agaagcagtt caacgagaat gaagccatcc aatggatgca ggaaaactgg   4800
aagaaatcct tcctgttttc tgccctctac gctgccttta tctttggtgg acgacatctg   4860
atgaacaagc gagccaagtt tgagctgcga aaacctctcg tgctctggtc cctgaccctc   4920
gctgtcttct ctatcttcgg tgctctgcga actggagcct acatgctcta catcctgatg   4980
accaaaggcc tgaaacagtc tgtttgtgac cagtcctttt acaacggacc cgtctcgaaa   5040
ttctgggctt acgcctttgt gctctccaaa gctcccgaac ttggcgatac catcttcatc   5100
attctgcgaa agcagaaact catcttcctg cactggtatc accacatcac cgtcctcctg   5160
tactcttggt actcctacaa ggacatggtg gctggaggtg gctggttcat gactatgaac   5220
tacggtgtcc acgccgtgat gtactcctac tacgccctcc gagctgccgg tttccgagtc   5280
tctcgaaagt ttgccatgtt catcaccctg tcgcagatca ctcagatgct catgggctgt   5340
gtcattaact acctggtctt caactggatg cagcatgaca atgaccagtg ctactcccac   5400
tttcagaaca tcttctggtc ctctctcatg tacctctcct accttctgct cttctgccat   5460
ttcttctttg aggcctacat tggcaaagtg aagaaagcca ccaaggctga gtaagcggcc   5520
gcaagtgtgg atggggaagt gagtgcccgg ttctgtgtgc acaattggca atccaagatg   5580
gatggattca acacagggat atagcgagct acgtggtggt gcgaggatat agcaacggat   5640
atttatgttt gacacttgag aatgtacgat acaagcactg tccaagtaca atactaaaca   5700
tactgtacat actcatactc gtacccgggc aacggtttca cttgagtgca gtggctagtg   5760
ctcttactcg tacagtgtgc aatactgcgt atcatagtct ttgatgtata tcgtattcat   5820
tcatgttagt tgc                                                      5833
```

<210> SEQ ID NO 47
<211> LENGTH: 804
<212> TYPE: DNA
<213> ORGANISM: Rattus norvegicus

```
<220> FEATURE:
<221> NAME/KEY: misc_feature
<223> OTHER INFORMATION: synthetic C16 elongase (codon-optimized)

<400> SEQUENCE: 47

atggacatgt ccgtcctgac tctccaagag tacgagttcg agaagcagtt caacgagaat     60

gaagccatcc aatggatgca ggaaaactgg aagaaatcct tcctgttttc tgccctctac    120

gctgccttta tctttggtgg acgacatctg atgaacaagc gagccaagtt tgagctgcga    180

aaacctctcg tgctctggtc cctgaccctc gctgtcttct ctatcttcgg tgctctgcga    240

actggagcct acatgctcta catcctgatg accaaaggcc tgaaacagtc tgtttgtgac    300

cagtcctttt acaacggacc cgtctcgaaa ttctgggctt acgcctttgt gctctccaaa    360

gctcccgaac ttggcgatac catcttcatc attctgcgaa agcagaaact catcttcctg    420

cactggtatc accacatcac cgtcctcctg tactcttggt actcctacaa ggacatggtg    480

gctggaggtg gctggttcat gactatgaac tacggtgtcc acgccgtgat gtactcctac    540

tacgccctcc gagctgccgg tttccgagtc tctcgaaagt ttgccatgtt catcaccctg    600

tcgcagatca ctcagatgct catgggctgt gtcattaact acctggtctt caactggatg    660

cagcatgaca atgaccagtg ctactcccac tttcagaaca tcttctggtc ctctctcatg    720

tacctctcct accttctgct cttctgccat ttcttctttg aggcctacat tggcaaagtg    780

aagaaagcca ccaaggctga gtaa                                           804


<210> SEQ ID NO 48
<211> LENGTH: 267
<212> TYPE: PRT
<213> ORGANISM: Rattus norvegicus (GenBank Accession No. AB071986)

<400> SEQUENCE: 48

Met Asn Met Ser Val Leu Thr Leu Gln Glu Tyr Glu Phe Glu Lys Gln
1               5                   10                  15

Phe Asn Glu Asn Glu Ala Ile Gln Trp Met Gln Glu Asn Trp Lys Lys
            20                  25                  30

Ser Phe Leu Phe Ser Ala Leu Tyr Ala Ala Phe Ile Phe Gly Gly Arg
        35                  40                  45

His Leu Met Asn Lys Arg Ala Lys Phe Glu Leu Arg Lys Pro Leu Val
    50                  55                  60

Leu Trp Ser Leu Thr Leu Ala Val Phe Ser Ile Phe Gly Ala Leu Arg
65                  70                  75                  80

Thr Gly Ala Tyr Met Leu Tyr Ile Leu Met Thr Lys Gly Leu Lys Gln
                85                  90                  95

Ser Val Cys Asp Gln Ser Phe Tyr Asn Gly Pro Val Ser Lys Phe Trp
            100                 105                 110

Ala Tyr Ala Phe Val Leu Ser Lys Ala Pro Glu Leu Gly Asp Thr Ile
        115                 120                 125

Phe Ile Ile Leu Arg Lys Gln Lys Leu Ile Phe Leu His Trp Tyr His
    130                 135                 140

His Ile Thr Val Leu Leu Tyr Ser Trp Tyr Ser Tyr Lys Asp Met Val
145                 150                 155                 160

Ala Gly Gly Gly Trp Phe Met Thr Met Asn Tyr Gly Val His Ala Val
                165                 170                 175

Met Tyr Ser Tyr Tyr Ala Leu Arg Ala Ala Gly Phe Arg Val Ser Arg
            180                 185                 190

Lys Phe Ala Met Phe Ile Thr Leu Ser Gln Ile Thr Gln Met Leu Met
```

-continued

```
        195                 200                 205

Gly Cys Val Ile Asn Tyr Leu Val Phe Asn Trp Met Gln His Asp Asn
    210                 215                 220

Asp Gln Cys Tyr Ser His Phe Gln Asn Ile Phe Trp Ser Ser Leu Met
225                 230                 235                 240

Tyr Leu Ser Tyr Leu Leu Leu Phe Cys His Phe Phe Phe Glu Ala Tyr
                245                 250                 255

Ile Gly Lys Val Lys Lys Ala Thr Lys Ala Glu
            260                 265


<210> SEQ ID NO 49
<211> LENGTH: 12663
<212> TYPE: DNA
<213> ORGANISM: Artificial Sequence
<220> FEATURE:
<223> OTHER INFORMATION: Plasmid pKO2UM25E

<400> SEQUENCE: 49

agcttccact ggtcggcgtg gtagtggggc agagtggggt cggtgtgctg caggtaggtg     60

atggccacga gccagtggtt gacccacagg taggggatca ggtagtagag ggtgacggaa    120

gccaggcccc atcggttgat ggagtatgcg atgacggaca tggtgatacc aataccgacg    180

ttagagatcc agatgttgaa ccagtccttc ttctcaaaca gcggggcgtt ggggttgaag    240

tggttgacag cccatttgtt gagcttgggg tacttctgtc cggtaacgta agacagcaga    300

tacagaggcc atccaaacac ctgctgggtg atgaggccgt agagggtcat gaggggagcg    360

tcctcagcaa gctcagacca gtcatgggcg cctcggttct ccataaactc ctttcggtcc    420

ttgggcacaa acaccatatc acgggtgagg tgaccagtgg acttgtggtg catggagtgg    480

gtcagcttcc aggcgtagta agggaccagc atggaggagt gcagaaccca tccggtgacg    540

ttgttgacgg tgttagagtc ggagaaagca gagtggccac actcgtgggc aagaacccac    600

agaccggtgc caaacagacc ctggacaatg gagtacatgg cccaggccac agctcggccg    660

gaagccgagg gaataagagg caggtacgcg taggccatgt aggcaaaaac ggcgataaag    720

aagcaggcgc gccagctgca ttaatgaatc ggccaacgcg cggggagagg cggtttgcgt    780

attgggcgct cttccgcttc ctcgctcact gactcgctgc gctcggtcgt tcggctgcgg    840

cgagcggtat cagctcactc aaaggcggta atacggttat ccacagaatc aggggataac    900

gcaggaaaga acatgtgagc aaaaggccag caaaaggcca ggaaccgtaa aaaggccgcg    960

ttgctggcgt ttttccatag gctccgcccc cctgacgagc atcacaaaaa tcgacgctca   1020

agtcagaggt ggcgaaaccc gacaggacta taaagatacc aggcgtttcc ccctggaagc   1080

tccctcgtgc gctctcctgt tccgaccctg ccgcttaccg gatacctgtc cgcctttctc   1140

ccttcgggaa gcgtggcgct ttctcatagc tcacgctgta ggtatctcag ttcggtgtag   1200

gtcgttcgct ccaagctggg ctgtgtgcac gaaccccccg ttcagcccga ccgctgcgcc   1260

ttatccggta actatcgtct tgagtccaac ccggtaagac acgacttatc gccactggca   1320

gcagccactg gtaacaggat tagcagagcg aggtatgtag gcggtgctac agagttcttg   1380

aagtggtggc ctaactacgg ctacactaga agaacagtat ttggtatctg cgctctgctg   1440

aagccagtta ccttcggaaa aagagttggt agctcttgat ccggcaaaca aaccaccgct   1500

ggtagcggtg gtttttttgt ttgcaagcag cagattacgc gcagaaaaaa aggatctcaa   1560

gaagatcctt tgatcttttc tacggggtct gacgctcagt ggaacgaaaa ctcacgttaa   1620

gggattttgg tcatgagatt atcaaaaagg atcttcacct agatcctttt aaattaaaaa   1680
```

-continued

```
tgaagtttta aatcaatcta aagtatatat gagtaaactt ggtctgacag ttaccaatgc   1740
ttaatcagtg aggcacctat ctcagcgatc tgtctatttc gttcatccat agttgcctga   1800
ctccccgtcg tgtagataac tacgatacgg gagggcttac catctggccc cagtgctgca   1860
atgataccgc gagacccacg ctcaccggct ccagatttat cagcaataaa ccagccagcc   1920
ggaagggccg agcgcagaag tggtcctgca actttatccg cctccatcca gtctattaat   1980
tgttgccggg aagctagagt aagtagttcg ccagttaata gtttgcgcaa cgttgttgcc   2040
attgctacag gcatcgtggt gtcacgctcg tcgtttggta tggcttcatt cagctccggt   2100
tcccaacgat caaggcgagt tacatgatcc cccatgttgt gcaaaaaagc ggttagctcc   2160
ttcggtcctc cgatcgttgt cagaagtaag ttggccgcag tgttatcact catggttatg   2220
gcagcactgc ataattctct tactgtcatg ccatccgtaa gatgcttttc tgtgactggt   2280
gagtactcaa ccaagtcatt ctgagaatag tgtatgcggc gaccgagttg ctcttgcccg   2340
gcgtcaatac gggataatac cgcgccacat agcagaactt taaaagtgct catcattgga   2400
aaacgttctt cggggcgaaa actctcaagg atcttaccgc tgttgagatc cagttcgatg   2460
taacccactc gtgcacccaa ctgatcttca gcatctttta ctttcaccag cgtttctggg   2520
tgagcaaaaa caggaaggca aaatgccgca aaaaagggaa taagggcgac acggaaatgt   2580
tgaatactca tactcttcct ttttcaatat tattgaagca tttatcaggg ttattgtctc   2640
atgagcggat acatatttga atgtatttag aaaaataaac aaataggggt tccgcgcaca   2700
tttccccgaa aagtgccacc tgatgcggtg tgaaataccg cacagatgcg taaggagaaa   2760
ataccgcatc aggaaattgt aagcgttaat attttgttaa aattcgcgtt aaatttttgt   2820
taaatcagct cattttttaa ccaataggcc gaaatcggca aaatccctta taaatcaaaa   2880
gaatagaccg agatagggtt gagtgttgtt ccagtttgga acaagagtcc actattaaag   2940
aacgtggact ccaacgtcaa agggcgaaaa accgtctatc agggcgatgg cccactacgt   3000
gaaccatcac cctaatcaag ttttttgggg tcgaggtgcc gtaaagcact aaatcggaac   3060
cctaaaggga gcccccgatt tagagcttga cggggaaagc cggcgaacgt ggcgagaaag   3120
gaagggaaga aagcgaaagg agcgggcgct agggcgctgg caagtgtagc ggtcacgctg   3180
cgcgtaacca ccacacccgc cgcgcttaat gcgccgctac agggcgcgtc cattcgccat   3240
tcaggctgcg caactgttgg gaagggcgat cggtgcgggc ctcttcgcta ttacgccagc   3300
tggcgaaagg gggatgtgct gcaaggcgat taagttgggt aacgccaggg ttttcccagt   3360
cacgacgttg taaaacgacg gccagtgaat tgtaatacga ctcactatag ggcgaattgg   3420
gcccgacgtc gcatgcttga atctacaagt aggagggttg gagtgattaa gtgaaacttc   3480
tttaacggct ctatgccagt tctattgata tccgaaacat cagtatgaag gtctgataag   3540
ggtgacttct tcccacagat tcgtatcagt acgagtacga gaccggtact tgtaacagta   3600
ttgatactaa agggaaacta caacggttgt cagcgtaatg tgacttcgcc catgaacgca   3660
gacacgcagt gccgagtgcg gtgatatcgc ctactcgtta cgtccatgga ctacacaacc   3720
cctcggcttc gcttggctta gcctcgggct cggtgctgtt cagttaaaac acaatcaaat   3780
aacatttcta ctttttagaa ggcaggccgt caggagcaac tccgactcca ttgacgtttc   3840
taaacatctg aatgccttcc ttaccttcaa caaactggca ggttcgggcg acagtgtaaa   3900
gagacttgat gaagttggtg tcgtcgtgtc ggtagtgctt gcccatgacc ttcttgatct   3960
tctcagtggc gattcgggcg ttgtagaagg gaattcagga gagaccgggt tggcggcgta   4020
```

-continued

```
tttgtgtccc aaaaaacagc cccaattgcc ccaattgacc ccaaattgac ccagtagcgg   4080
gcccaacccc ggcgagagcc cccttcaccc cacatatcaa acctcccccg gttcccacac   4140
ttgccgttaa gggcgtaggg tactgcagtc tggaatctac gcttgttcag actttgtact   4200
agtttctttg tctggccatc cgggtaaccc atgccggacg caaaatagac tactgaaaat   4260
ttttttgctt tgtggttggg actttagcca agggtataaa agaccaccgt ccccgaatta   4320
cctttcctct tcttttctct ctctccttgt caactcacac ccgaaatcgt taagcatttc   4380
cttctgagta taagaatcat tcaccatggt cgctggcaag tccggagctg cagcccacgt   4440
gacccactct tccactctcc ctcgagagta ccacggtgct accaacgact cccgatctga   4500
ggctgccgat gtcaccgtct cgtctatcga cgccgagaag gagatgatta tcaacggacg   4560
agtgtacgac gtctcctcgt tcgtgaagcg acaccctggt ggctccgtca tcaagttcca   4620
gctcggagca gatgcttctg acgcttacaa caacttccac gtccgatcga agaaggctga   4680
caagatgctg tactctcttc cctcccgacc tgccgaggct ggctatgcac aggacgacat   4740
ctctagagac tttgagaagc tgcgactgga actgaaagag gaaggttact tcgagcccaa   4800
tctggtgcac gtgtcctacc gatgtgtcga ggtgcttgcc atgtactggg ctggcgtcca   4860
gctgatctgg tccggatact ggttcctcgg tgccatcgtt gctggaattg ctcaaggtcg   4920
atgcggatgg ctccagcatg aaggcggaca ctactcgctc actggcaaca tcaagattga   4980
ccgacatctc cagatggcca tctatggact gggctgtggt atgtctggct gctactggag   5040
aaaccagcac aacaaacatc acgccactcc tcagaagctc ggaaccgatc ccgacctgca   5100
gaccatgcct ctcgttgcct tccacaagat tgtcggagcc aaggcacgag gcaagggtaa   5160
agcctggctt gcttggcaag ctcccctctt ctttggaggc atcatttgct ccctggtctc   5220
tttcggctgg cagttcgttc tccaccccaa tcatgcactg cgagtgcaca accatctcga   5280
actggcctac atgggtctcc gatacgttct ctggcacctt gcctttggcc atctgggact   5340
cctgtcctct cttcgactgt atgccttcta cgtggctgtc ggtggcacct acatcttcac   5400
caacttcgcc gtctcccata ctcacaagga tgtcgttcct cccaccaagc acatttcgtg   5460
ggctctgtac tctgccaacc acactaccaa ctgttccgac tctcccttttg tcaactggtg   5520
gatggcctac ctcaacttcc agatcgagca ccatctgttc cctccatgc ctcagtacaa   5580
ccaccccaag attgctcctc gagtgcgagc actcttcgag aagcacggag tcgagtacga   5640
cgtccgaccc tatctggaat gctttcgagt gacctacgtc aacctccttg ctgttggcaa   5700
ccctgagcac tcctaccacg agcatactca ctaagcggcc gcaagtgtgg atggggaagt   5760
gagtgcccgg ttctgtgtgc acaattggca atccaagatg gatggattca acacagggat   5820
atagcgagct acgtggtggt gcgaggatat agcaacggat atttatgttt gacacttgag   5880
aatgtacgat acaagcactg tccaagtaca atactaaaca tactgtacat actcatactc   5940
gtacccgggc aacggtttca cttgagtgca gtggctagtg ctcttactcg tacagtgtgc   6000
aatactgcgt atcatagtct ttgatgtata tcgtattcat tcatgtcgac gagtatctgt   6060
ctgactcgtc attgccgcct ttggagtacg actccaacta tgagtgtgct tggatcactt   6120
tgacgataca ttcttcgttg gaggctgtgg gtctgacagc tgcgttttcg gcgcggttgg   6180
ccgacaacaa tatcagctgc aacgtcattg ctggctttca tcatgatcac atttttgtcg   6240
gcaaaggcga cgcccagaga gccattgacg ttctttctaa tttggaccga tagccgtata   6300
gtccagtcta tctataagtt caactaactc gtaactatta ccataacata tacttcactg   6360
ccccagataa ggttccgata aaaagttctg cagactaaat ttatttcagt ctcctcttca   6420
```

-continued

```
ccaccaaaat gccctcctac gaagctcgag ctaacgtcca caagtccgcc tttgccgctc   6480
gagtgctcaa gctcgtggca gccaagaaaa ccaacctgtg tgcttctctg gatgttacca   6540
ccaccaagga gctcattgag cttgccgata aggtcggacc ttatgtgtgc atgatcaaaa   6600
cccatatcga catcattgac gacttcacct acgccggcac tgtgctcccc ctcaaggaac   6660
ttgctcttaa gcacggtttc ttcctgttcg aggacagaaa gttcgcagat attggcaaca   6720
ctgtcaagca ccagtaccgg tgtcaccgaa tcgccgagtg gtccgatatc accaacgccc   6780
acggtgtacc cggaaccgga atcattgctg gcctgcgagc tggtgccgag gaaactgtct   6840
ctgaacagaa gaaggaggac gtctctgact acgagaactc ccagtacaag gagttcctag   6900
tcccctctcc caacgagaag ctggccagag gtctgctcat gctggccgag ctgtcttgca   6960
agggctctct ggccactggc gagtactcca agcagaccat tgagcttgcc cgatccgacc   7020
ccgagtttgt ggttggcttc attgcccaga accgacctaa gggcgactct gaggactggc   7080
ttattctgac cccgggggtg ggtcttgacg acaagggaga cgctctcgga cagcagtacc   7140
gaactgttga ggatgtcatg tctaccggaa cggatatcat aattgtcggc cgaggtctgt   7200
acggccagaa ccgagatcct attgaggagg ccaagcgata ccagaaggct ggctgggagg   7260
cttaccagaa gattaactgt tagaggttag actatggata tgtaatttaa ctgtgtatat   7320
agagagcgtg caagtatgga gcgcttgttc agcttgtatg atggtcagac gacctgtctg   7380
atcgagtatg tatgatactg cacaacctgt gtatccgcat gatctgtcca atggggcatg   7440
ttgttgtgtt tctcgatacg gagatgctgg gtacagtgct aatacgttga actacttata   7500
cttatatgag gctcgaagaa agctgacttg tgtatgactt aattaatttg aatcgaatcg   7560
atgagcctaa aatgaacccg agtatatctc ataaaattct cggtgagagg tctgtgactg   7620
tcagtacaag gtgccttcat tatgccctca accttaccat acctcactga atgtagtgta   7680
cctctaaaaa tgaaatacag tgccaaaagc caaggcactg agctcgtcta acggacttga   7740
tatacaacca attaaaacaa atgaaaagaa atacagttct ttgtatcatt tgtaacaatt   7800
accctgtaca aactaaggta ttgaaatccc acaatattcc caaagtccac ccctttccaa   7860
attgtcatgc ctacaactca tataccaagc actaacctac cgtttaaaca gtgtacgcag   7920
atctactata gaggaacatt taaattgccc cggagaagac ggccaggccg cctagatgac   7980
aaattcaaca actcacagct gactttctgc cattgccact aggggggggc ctttttatat   8040
ggccaagcca agctctccac gtcggttggg ctgcacccaa caataaatgg gtagggttgc   8100
accaacaaag ggatgggatg gggggtagaa gatacgagga taacggggct caatggcaca   8160
aataagaacg aatactgcca ttaagactcg tgatccagcg actgacacca ttgcatcatc   8220
taagggcctc aaaactacct cggaactgct gcgctgatct ggacaccaca gaggttccga   8280
gcactttagg ttgcaccaaa tgtcccacca ggtgcaggca gaaaacgctg gaacagcgtg   8340
tacagtttgt cttaacaaaa agtgagggcg ctgaggtcga gcagggtggt gtgacttgtt   8400
atagccttta gagctgcgaa agcgcgtatg gatttggctc atcaggccag attgagggtc   8460
tgtggacaca tgtcatgtta gtgtacttca atcgcccccct ggatatagcc ccgacaatag   8520
gccgtggcct cattttttttg ccttccgcac atttccattg ctcggtaccc acaccttgct   8580
tctcctgcac ttgccaacct taatactggt ttacattgac caacatctta caagcggggg   8640
gcttgtctag ggtatatata aacagtggct ctcccaatcg gttgccagtc tcttttttcc   8700
tttctttccc cacagattcg aaatctaaac tacacatcac acaatgcctg ttactgacgt   8760
```

-continued

```
ccttaagcga aagtccggtg tcatcgtcgg cgacgatgtc cgagccgtga gtatccacga   8820
caagatcagt gtcgagacga cgcgttttgt gtaatgacac aatccgaaag tcgctagcaa   8880
cacacactct ctacacaaac taacccagct ctccatggca cctcccaaca ctatcgacgc   8940
tggcttgacc cagcgtcata tcaccaccac ggccgcccca acctcggcca agcccgcttt   9000
cgagcgcaac taccagctcc ccgagttcac catcaaggag atccgagagt gcatccctgc   9060
ccactgcttt gagcgctccg gtcttcgtgg tctctgccac gttgccattg atctgacctg   9120
ggcctcgctc ttgttcctgg ctgcaaccca gatcgacaag ttcgagaacc ccttgatccg   9180
ctatctggcc tggcctgcgt actggatcat gcagggcatt gtctgcaccg gcatatgggt   9240
gctggcccac gagtgcggtc accagtcctt ctcgacctcc aagactctca acaacaccgt   9300
cggctggatc ctgcactcga tgctcttggt ccccctaccac tcctggagaa tctcgcactc   9360
gaagcaccac aaggccactg gccacatgac caaggaccag gtctttgttc ccaagacccg   9420
ctcccaggtt ggtttgcctc ccaaggagag cgctgctgct gccgttcaag aggaggacat   9480
gtccgtgcac ctggatgagg aggcccctat tgtgactttg ttctggatgg tgatccagtt   9540
cctgttcgga tggcctgcat acctgatcat gaacgcctct ggtcaggact atggccgctg   9600
gacctcgcac ttccacactt actcgcccat ctttgagccc cgcaacttct tcgacattat   9660
catctcggat ctcggtgtgt tggctgccct cggtgccctg atctacgctt ccatgcagct   9720
gtcgctcttg accgtgacca agtactacat catcccgtac ctgtttgtca acttttggtt   9780
ggtcctgatt actttcttgc agcacaccga ccccaagctg ccccattacc gtgagggtgc   9840
ctggaacttc cagcgtggag ccctctgcac cgttgaccgc tcgtttggca agttcttgga   9900
ccatatgttc cacggcatcg tccataccca tgtggcccat cacttgttct cgcagatgcc   9960
gttctaccat gctgaagaag ctacctacca tctcaagaaa ctgctgggag agtactacgt  10020
ttacgaccca tccccgatcg tcgttgcggt ctggaggtcg ttccgcgagt gccgattcgt  10080
ggaggatcag ggagacgtgg tctttttcaa gaagtaagcg gccgcaagtg tggatgggga  10140
agtgagtgcc cggttctgtg tgcacaattg gcaatccaag atggatggat tcaacacagg  10200
gatatagcga gctacgtggt ggtgcgagga tatagcaacg gatatttatg tttgacactt  10260
gagaatgtac gatacaagca ctgtccaagt acaatactaa acatactgta catactcata  10320
ctcgtacccg ggcaacggtt tcacttgagt gcagtggcta gtgctcttac tcgtacagtg  10380
tgcaatactg cgtatcatag tctttgatgt atatcgtatt cattcatgtt agttgcgtac  10440
gagatcgtca agggtttgtg gccaactggt atttaaatgt agctaacggt agcaggcgaa  10500
ctactggtac atacctcccc cggaatatgt acaggcataa tgcgtatctg tgggacatgt  10560
ggtcgttgcg ccattatgta agcagcgtgt actcctctga ctgtccatat ggtttgctcc  10620
atctcaccct catcgttttc attgttcaca ggcggccaca aaaaaactgt cttctctcct  10680
tctctcttcg ccttagtcta ctcggaccag ttttagttta gcttggcgcc actggataaa  10740
tgagacctca ggccttgtga tgaggaggtc acttatgaag catgttagga ggtgcttgta  10800
tggatagaga agcacccaaa ataataagaa taataataaa acaggggggcg ttgtcatttc  10860
atatcgtgtt ttcaccatca atacacctcc aaacaatgcc cttcatgtgg ccagccccaa  10920
tattgtcctg tagttcaact ctatgcagct cgtatcttat tgagcaagta aaactctgtc  10980
agccgatatt gcccgacccg cgacaagggt caacaaggtg gtgtaaggcc ttcgcagaag  11040
tcaaaactgt gccaaacaaa catctagagt ctctttggtg tttctcgcat atatttwatc  11100
ggctgtctta cgtatttgcg cctcggtacc ggactaattt cggatcatcc ccaatacgct  11160
```

-continued

```
ttttcttcgc agctgtcaac agtgtccatg atctatccac ctaaatgggt catatgaggc  11220

gtataatttc gtggtgctga taataattcc catatatttg acacaaaact tcccccccta  11280

gacatacatc tcacaatctc acttcttgtg cttctgtcac acatctcctc cagctgactt  11340

caactcacac ctctgcccca gttggtctac agcggtataa ggtttctccg catagaggtg  11400

caccactcct cccgatactt gtttgtgtga cttgtgggtc acgacatata tatctacaca  11460

cattgcgcca ccctttggtt cttccagcac aacaaaaaca cgacacgcta accatggagt  11520

ccattgctcc cttcctgccc tccaagatgc ctcaggacct gttcatggac ctcgccagcg  11580

ctatcggtgt ccgagctgct ccctacgtcg atcccctgga ggctgccctg gttgcccagg  11640

ccgagaagta cattcccacc attgtccatc acactcgagg cttcctggtt gccgtggagt  11700

ctcccctggc tcgagagctg cctctgatga accccttcca cgtgctcctg atcgtgctcg  11760

cctacctggt caccgtgttt gtgggtatgc agatcatgaa gaactttgaa cgattcgagg  11820

tcaagacctt ctccctcctg cacaacttct gtctggtctc catctccgcc tacatgtgcg  11880

gtggcatcct gtacgaggct tatcaggcca actatggact gtttgagaac gctgccgatc  11940

acaccttcaa gggtctccct atggctaaga tgatctggct cttctacttc tccaagatca  12000

tggagtttgt cgacaccatg atcatggtcc tcaagaagaa caaccgacag atttcctttc  12060

tgcacgtgta ccaccactct tccatcttca ccatctggtg gctggtcacc ttcgttgctc  12120

ccaacggtga agcctacttc tctgctgccc tgaactcctt catccacgtc atcatgtacg  12180

gctactactt tctgtctgcc ctgggcttca agcaggtgtc gttcatcaag ttctacatca  12240

ctcgatccca gatgacccag ttctgcatga tgtctgtcca gtcttcctgg gacatgtacg  12300

ccatgaaggt ccttggccga cctggatacc ccttcttcat caccgctctg ctctggttct  12360

acatgtggac catgctcggt ctcttctaca acttttaccg aaagaacgcc aagctcgcca  12420

agcaggccaa ggctgacgct gccaaggaga aggccagaaa gctccagtaa gcggccgcca  12480

ccgcggcccg agattccggc ctcttcggcc gccaagcgac ccgggtggac gtctagaggt  12540

acctagcaat taacagatag tttgccggtg ataattctct taacctccca cactcctttg  12600

acataacgat ttatgtaacg aaactgaaat ttgaccagat attgtgtccg cggtggagct  12660

cca                                                                12663


<210> SEQ ID NO 50
<211> LENGTH: 1936
<212> TYPE: DNA
<213> ORGANISM: Yarrowia lipolytica
<220> FEATURE:
<221> NAME/KEY: CDS
<222> LOCATION: (283)..(1539)
<223> OTHER INFORMATION: delta-12 desaturase

<400> SEQUENCE: 50

cgtagttata tacaagaggt agatgcgtgc tggtgttaga ggggctctca ggattaggag     60

gaaaatttga cattggccct caacatataa cctcgggtgt gcctctgttt accctcagct    120

tttgcttgtc cccaagtcag tcacgccagg ccaaaaaggt tggtggattg acagggagaa    180

aaaaaaaagc ctagtgggtt taaactcgag gtaagacatt gaaatatata ccggtcggca    240

tcctgagtcc ctttctcgta ttccaacaga ccgaccatag aa atg gat tcg acc       294
                                               Met Asp Ser Thr
                                               1

acg cag acc aac acc ggc acc ggc aag gtg gcc gtg cag ccc ccc acg      342
Thr Gln Thr Asn Thr Gly Thr Gly Lys Val Ala Val Gln Pro Pro Thr
```

-continued

```
5                   10                  15                  20

gcc ttc att aag ccc att gag aag gtg tcc gag ccc gtc tac gac acc      390
Ala Phe Ile Lys Pro Ile Glu Lys Val Ser Glu Pro Val Tyr Asp Thr
                25                  30                  35

ttt ggc aac gag ttc act cct cca gac tac tct atc aag gat att ctg      438
Phe Gly Asn Glu Phe Thr Pro Pro Asp Tyr Ser Ile Lys Asp Ile Leu
            40                  45                  50

gat gcc att ccc cag gag tgc tac aag cgg tcc tac gtt aag tcc tac      486
Asp Ala Ile Pro Gln Glu Cys Tyr Lys Arg Ser Tyr Val Lys Ser Tyr
        55                  60                  65

tcg tac gtg gcc cga gac tgc ttc ttt atc gcc gtt ttt gcc tac atg      534
Ser Tyr Val Ala Arg Asp Cys Phe Phe Ile Ala Val Phe Ala Tyr Met
    70                  75                  80

gcc tac gcg tac ctg cct ctt att ccc tcg gct tcc ggc cga gct gtg      582
Ala Tyr Ala Tyr Leu Pro Leu Ile Pro Ser Ala Ser Gly Arg Ala Val
85                  90                  95                  100

gcc tgg gcc atg tac tcc att gtc cag ggt ctg ttt ggc acc ggt ctg      630
Ala Trp Ala Met Tyr Ser Ile Val Gln Gly Leu Phe Gly Thr Gly Leu
                105                 110                 115

tgg gtt ctt gcc cac gag tgt ggc cac tct gct ttc tcc gac tct aac      678
Trp Val Leu Ala His Glu Cys Gly His Ser Ala Phe Ser Asp Ser Asn
            120                 125                 130

acc gtc aac aac gtc acc gga tgg gtt ctg cac tcc tcc atg ctg gtc      726
Thr Val Asn Asn Val Thr Gly Trp Val Leu His Ser Ser Met Leu Val
        135                 140                 145

cct tac tac gcc tgg aag ctg acc cac tcc atg cac cac aag tcc act      774
Pro Tyr Tyr Ala Trp Lys Leu Thr His Ser Met His His Lys Ser Thr
    150                 155                 160

ggt cac ctc acc cgt gat atg gtg ttt gtg ccc aag gac cga aag gag      822
Gly His Leu Thr Arg Asp Met Val Phe Val Pro Lys Asp Arg Lys Glu
165                 170                 175                 180

ttt atg gag aac cga ggc gcc cat gac tgg tct gag ctt gct gag gac      870
Phe Met Glu Asn Arg Gly Ala His Asp Trp Ser Glu Leu Ala Glu Asp
                185                 190                 195

gct ccc ctc atg acc ctc tac ggc ctc atc acc cag cag gtg ttt gga      918
Ala Pro Leu Met Thr Leu Tyr Gly Leu Ile Thr Gln Gln Val Phe Gly
            200                 205                 210

tgg cct ctg tat ctg ctg tct tac gtt acc gga cag aag tac ccc aag      966
Trp Pro Leu Tyr Leu Leu Ser Tyr Val Thr Gly Gln Lys Tyr Pro Lys
        215                 220                 225

ctc aac aaa tgg gct gtc aac cac ttc aac ccc aac gcc ccg ctg ttt     1014
Leu Asn Lys Trp Ala Val Asn His Phe Asn Pro Asn Ala Pro Leu Phe
    230                 235                 240

gag aag aag gac tgg ttc aac atc tgg atc tct aac gtc ggt att ggt     1062
Glu Lys Lys Asp Trp Phe Asn Ile Trp Ile Ser Asn Val Gly Ile Gly
245                 250                 255                 260

atc acc atg tcc gtc atc gca tac tcc atc aac cga tgg ggc ctg gct     1110
Ile Thr Met Ser Val Ile Ala Tyr Ser Ile Asn Arg Trp Gly Leu Ala
                265                 270                 275

tcc gtc acc ctc tac tac ctg atc ccc tac ctg tgg gtc aac cac tgg     1158
Ser Val Thr Leu Tyr Tyr Leu Ile Pro Tyr Leu Trp Val Asn His Trp
            280                 285                 290

ctc gtg gcc atc acc tac ctg cag cac acc gac ccc act ctg ccc cac     1206
Leu Val Ala Ile Thr Tyr Leu Gln His Thr Asp Pro Thr Leu Pro His
        295                 300                 305

tac cac gcc gac cag tgg aac ttc acc cga gga gcc gcc gcc acc atc     1254
Tyr His Ala Asp Gln Trp Asn Phe Thr Arg Gly Ala Ala Ala Thr Ile
    310                 315                 320

gac cga gag ttt ggc ttc atc ggc tcc ttc tgc ttc cat gac atc atc     1302
```

-continued

```
Asp Arg Glu Phe Gly Phe Ile Gly Ser Phe Cys Phe His Asp Ile Ile
325                 330                 335                 340

gag acc cac gtt ctg cac cac tac gtg tct cga att ccc ttc tac aac     1350
Glu Thr His Val Leu His His Tyr Val Ser Arg Ile Pro Phe Tyr Asn
                345                 350                 355

gcc cga atc gcc act gag aag atc aag aag gtc atg ggc aag cac tac     1398
Ala Arg Ile Ala Thr Glu Lys Ile Lys Lys Val Met Gly Lys His Tyr
            360                 365                 370

cga cac gac gac acc aac ttc atc aag tct ctt tac act gtc gcc cga     1446
Arg His Asp Asp Thr Asn Phe Ile Lys Ser Leu Tyr Thr Val Ala Arg
        375                 380                 385

acc tgc cag ttt gtt gaa ggt aag gaa ggc att cag atg ttt aga aac     1494
Thr Cys Gln Phe Val Glu Gly Lys Glu Gly Ile Gln Met Phe Arg Asn
    390                 395                 400

gtc aat gga gtc gga gtt gct cct gac ggc ctg cct tct aaa aag         1539
Val Asn Gly Val Gly Val Ala Pro Asp Gly Leu Pro Ser Lys Lys
405                 410                 415

tagagctaga aatgttattt gattgtgttt taactgaaca gcaccgagcc cgaggctaag   1599

ccaagcgaag ccgaggggtt gtgtagtcca tggacgtaac gagtaggcga tatcaccgca   1659

ctcggcactg cgtgtctgcg ttcatgggcg aagtcacatt acgctgacaa ccgttgtagt   1719

ttccctttag tatcaatact gttacaagta ccggtctcgt actcgtactg atacgaatct   1779

gtgggaagaa gtcaccctta tcagaccttc atactgatgt ttcggatatc aatagaactg   1839

gcatagagcc gttaaagaag tttcacttaa tcactccaac cctcctactt gtagattcaa   1899

gcagatcgat aagatggatt tgatggtcag tgctagc                             1936


<210> SEQ ID NO 51
<211> LENGTH: 419
<212> TYPE: PRT
<213> ORGANISM: Yarrowia lipolytica

<400> SEQUENCE: 51

Met Asp Ser Thr Thr Gln Thr Asn Thr Gly Thr Gly Lys Val Ala Val
1               5                   10                  15

Gln Pro Pro Thr Ala Phe Ile Lys Pro Ile Glu Lys Val Ser Glu Pro
            20                  25                  30

Val Tyr Asp Thr Phe Gly Asn Glu Phe Thr Pro Pro Asp Tyr Ser Ile
        35                  40                  45

Lys Asp Ile Leu Asp Ala Ile Pro Gln Glu Cys Tyr Lys Arg Ser Tyr
    50                  55                  60

Val Lys Ser Tyr Ser Tyr Val Ala Arg Asp Cys Phe Phe Ile Ala Val
65                  70                  75                  80

Phe Ala Tyr Met Ala Tyr Ala Tyr Leu Pro Leu Ile Pro Ser Ala Ser
                85                  90                  95

Gly Arg Ala Val Ala Trp Ala Met Tyr Ser Ile Val Gln Gly Leu Phe
            100                 105                 110

Gly Thr Gly Leu Trp Val Leu Ala His Glu Cys Gly His Ser Ala Phe
        115                 120                 125

Ser Asp Ser Asn Thr Val Asn Asn Val Thr Gly Trp Val Leu His Ser
    130                 135                 140

Ser Met Leu Val Pro Tyr Tyr Ala Trp Lys Leu Thr His Ser Met His
145                 150                 155                 160

His Lys Ser Thr Gly His Leu Thr Arg Asp Met Val Phe Val Pro Lys
                165                 170                 175

Asp Arg Lys Glu Phe Met Glu Asn Arg Gly Ala His Asp Trp Ser Glu
```

```
            180                 185                 190

Leu Ala Glu Asp Ala Pro Leu Met Thr Leu Tyr Gly Leu Ile Thr Gln
        195                 200                 205

Gln Val Phe Gly Trp Pro Leu Tyr Leu Leu Ser Tyr Val Thr Gly Gln
    210                 215                 220

Lys Tyr Pro Lys Leu Asn Lys Trp Ala Val Asn His Phe Asn Pro Asn
225                 230                 235                 240

Ala Pro Leu Phe Glu Lys Lys Asp Trp Phe Asn Ile Trp Ile Ser Asn
                245                 250                 255

Val Gly Ile Gly Ile Thr Met Ser Val Ile Ala Tyr Ser Ile Asn Arg
            260                 265                 270

Trp Gly Leu Ala Ser Val Thr Leu Tyr Tyr Leu Ile Pro Tyr Leu Trp
        275                 280                 285

Val Asn His Trp Leu Val Ala Ile Thr Tyr Leu Gln His Thr Asp Pro
    290                 295                 300

Thr Leu Pro His Tyr His Ala Asp Gln Trp Asn Phe Thr Arg Gly Ala
305                 310                 315                 320

Ala Ala Thr Ile Asp Arg Glu Phe Gly Phe Ile Gly Ser Phe Cys Phe
                325                 330                 335

His Asp Ile Ile Glu Thr His Val Leu His His Tyr Val Ser Arg Ile
            340                 345                 350

Pro Phe Tyr Asn Ala Arg Ile Ala Thr Glu Lys Ile Lys Lys Val Met
        355                 360                 365

Gly Lys His Tyr Arg His Asp Asp Thr Asn Phe Ile Lys Ser Leu Tyr
    370                 375                 380

Thr Val Ala Arg Thr Cys Gln Phe Val Glu Gly Lys Glu Gly Ile Gln
385                 390                 395                 400

Met Phe Arg Asn Val Asn Gly Val Gly Val Ala Pro Asp Gly Leu Pro
                405                 410                 415

Ser Lys Lys
```

```
<210> SEQ ID NO 52
<211> LENGTH: 1130
<212> TYPE: DNA
<213> ORGANISM: Yarrowia lipolytica
<220> FEATURE:
<221> NAME/KEY: misc_feature
<223> OTHER INFORMATION: GPAT promoter

<400> SEQUENCE: 52

caacttttct tgtcgacctg agataccgag gttgcgcagg ggatcaactt ttgtgtctca     60

gagggaccca agtgcgtacg gagagtacag tacatactgt agctaacggt agcaggcgaa    120

ctactggtac atacctcccc cggaatatgt acaggcataa tgcgtatctg tgggacatgt    180

ggtcgttgcg ccattatgta agcagcgtgt actcctctga ctgtccatat ggtttgctcc    240

atctcaccct catcgttttc attgttcaca ggcggccaca aaaaaactgt cttctctcct    300

tctctcttcg ccttagtcta ctcggaccag ttttagttta gcttggcgcc actggataaa    360

tgagacctca ggccttgtga tgaggaggtc acttatgaag catgttagga ggtgcttgta    420

tggatagaga agcacccaaa ataataagaa taataataaa acagggggcg ttgtcatttc    480

atatcgtgtt ttcaccatca atacacctcc aaacaatgcc cttcatgtgg ccagccccaa    540

tattgtcctg tagttcaact ctatgcagct cgtatcttat tgagcaagta aaactctgtc    600

agccgatatt gcccgacccg cgacaagggt caacaaggtg gtgtaaggcc ttcgcagaag    660
```

-continued

```
tcaaaactgt gccaaacaaa catctagagt ctctttggtg tttctcgcat atatttaatc    720

ggctgtctta cgtatttggc ctcggtaccg gactaatttc ggatcatccc caatacgctt    780

tttcttcgca gctgtcaaca gtgtccatga tctatccacc taaatgggtc atatgaggcg    840

tataatttcg tggtgctgat aataattccc atatatttga cacaaaactt ccccccctag    900

acatacatct cacaatctca cttcttgtgc ttctgtcaca catctcctcc agctgacttc    960

aactcacacc tctgccccag ttggtctaca gcggtataag gtttctccgc atagaggtgc   1020

accactcctc ccgatacttg tttgtgtgac ttgtgggtca cgacatatat atctacacac   1080

attgcgccac cctttggttc ttccagcaca acaaaaacac gacacgctaa              1130
```

```
<210> SEQ ID NO 53
<211> LENGTH: 1203
<212> TYPE: DNA
<213> ORGANISM: Mortieralla isabellina (GenBank Accession No. AF417245)
<220> FEATURE:
<221> NAME/KEY: CDS
<222> LOCATION: (1)..(1203)
<223> OTHER INFORMATION: delta-12 desaturase

<400> SEQUENCE: 53

atg gca cct ccc aac act atc gat gcc ggc ttg acc cag cgt cat atc       48
Met Ala Pro Pro Asn Thr Ile Asp Ala Gly Leu Thr Gln Arg His Ile
1               5                   10                  15

acc acc acg gcc gcc cca acc tcg gcc aag ccc gct ttc gag cgc aac       96
Thr Thr Thr Ala Ala Pro Thr Ser Ala Lys Pro Ala Phe Glu Arg Asn
            20                  25                  30

tac cag ctc ccc gag ttc act atc aag gag atc cga gag tgc atc cct      144
Tyr Gln Leu Pro Glu Phe Thr Ile Lys Glu Ile Arg Glu Cys Ile Pro
        35                  40                  45

gcc cac tgc ttt gag cgc tcc ggt ctt cgt ggt ctc tgc cac gtt gcc      192
Ala His Cys Phe Glu Arg Ser Gly Leu Arg Gly Leu Cys His Val Ala
    50                  55                  60

att gat ctg acc tgg gcc tcg ctc ttg ttc ctg gct gca acc cag atc      240
Ile Asp Leu Thr Trp Ala Ser Leu Leu Phe Leu Ala Ala Thr Gln Ile
65                  70                  75                  80

gac aag ttc gag aac ccc ttg atc cgc tat ctg gcc tgg cct gcg tac      288
Asp Lys Phe Glu Asn Pro Leu Ile Arg Tyr Leu Ala Trp Pro Ala Tyr
                85                  90                  95

tgg atc atg cag ggc att gtc tgc acc ggc ata tgg gtg ctg gcc cac      336
Trp Ile Met Gln Gly Ile Val Cys Thr Gly Ile Trp Val Leu Ala His
            100                 105                 110

gag tgc ggt cac cag tcc ttc tcg acc tcc aag act ctc aac aac acc      384
Glu Cys Gly His Gln Ser Phe Ser Thr Ser Lys Thr Leu Asn Asn Thr
        115                 120                 125

gtc ggc tgg atc ctg cac tcg atg ctc ttg gtc ccc tac cac tcc tgg      432
Val Gly Trp Ile Leu His Ser Met Leu Leu Val Pro Tyr His Ser Trp
    130                 135                 140

aga atc tcg cac tcg aag cac cac aag gcc act ggc cac atg acc aag      480
Arg Ile Ser His Ser Lys His His Lys Ala Thr Gly His Met Thr Lys
145                 150                 155                 160

gac cag gtc ttt gtt ccc aag acc cgc tcc cag gtt ggt ttg cct ccc      528
Asp Gln Val Phe Val Pro Lys Thr Arg Ser Gln Val Gly Leu Pro Pro
                165                 170                 175

aag gag agc gct gct gct gcc gtt caa gag gag gac atg tcc gtg cac      576
Lys Glu Ser Ala Ala Ala Ala Val Gln Glu Glu Asp Met Ser Val His
            180                 185                 190

ctg gat gag gag gcc cct att gtg act ttg ttc tgg atg gtg atc cag      624
Leu Asp Glu Glu Ala Pro Ile Val Thr Leu Phe Trp Met Val Ile Gln
        195                 200                 205
```

-continued

```
ttc ctg ttc gga tgg cct gca tac ctg atc atg aac gcc tct ggt cag      672
Phe Leu Phe Gly Trp Pro Ala Tyr Leu Ile Met Asn Ala Ser Gly Gln
    210                 215                 220

gac tat ggc cgc tgg acc tcg cac ttc cac act tac tcg ccc atc ttt      720
Asp Tyr Gly Arg Trp Thr Ser His Phe His Thr Tyr Ser Pro Ile Phe
225                 230                 235                 240

gag ccc cgc aac ttc ttc gac att atc atc tcg gat ctc ggt gtg ttg      768
Glu Pro Arg Asn Phe Phe Asp Ile Ile Ile Ser Asp Leu Gly Val Leu
                245                 250                 255

gct gcc ctc ggt gcc ctg atc tac gct tcc atg cag ctg tcg ctc ttg      816
Ala Ala Leu Gly Ala Leu Ile Tyr Ala Ser Met Gln Leu Ser Leu Leu
            260                 265                 270

acc gtg acc aag tac tac atc atc ccg tac ctg ttt gtc aac ttt tgg      864
Thr Val Thr Lys Tyr Tyr Ile Ile Pro Tyr Leu Phe Val Asn Phe Trp
        275                 280                 285

ttg gtc ctg att act ttc ttg cag cac acc gac ccc aag ctg ccc cat      912
Leu Val Leu Ile Thr Phe Leu Gln His Thr Asp Pro Lys Leu Pro His
    290                 295                 300

tac cgt gag ggt gcc tgg aac ttc cag cgt gga gcc ctc tgc acc gtt      960
Tyr Arg Glu Gly Ala Trp Asn Phe Gln Arg Gly Ala Leu Cys Thr Val
305                 310                 315                 320

gac cgc tcg ttt ggc aag ttc ttg gac cat atg ttc cac ggc atc gtc     1008
Asp Arg Ser Phe Gly Lys Phe Leu Asp His Met Phe His Gly Ile Val
                325                 330                 335

cat acc cat gtg gcc cat cac ttg ttc tcg cag atg ccg ttc tac cat     1056
His Thr His Val Ala His His Leu Phe Ser Gln Met Pro Phe Tyr His
            340                 345                 350

gct gaa gaa gct acc tac cat ctc aag aaa ctg ctg gga gag tac tac     1104
Ala Glu Glu Ala Thr Tyr His Leu Lys Lys Leu Leu Gly Glu Tyr Tyr
        355                 360                 365

gtt tac gac cca tcc ccg atc gtc gtt gcg gtc tgg agg tcg ttc cgc     1152
Val Tyr Asp Pro Ser Pro Ile Val Val Ala Val Trp Arg Ser Phe Arg
    370                 375                 380

gag tgc cga ttc gtg gag gat cat gga gac gtg gtc ttt ttc aag aag     1200
Glu Cys Arg Phe Val Glu Asp His Gly Asp Val Val Phe Phe Lys Lys
385                 390                 395                 400

taa                                                                 1203


<210> SEQ ID NO 54
<211> LENGTH: 400
<212> TYPE: PRT
<213> ORGANISM: Mortieralla isabellina (GenBank Accession No. AF417245)

<400> SEQUENCE: 54

Met Ala Pro Pro Asn Thr Ile Asp Ala Gly Leu Thr Gln Arg His Ile
1               5                   10                  15

Thr Thr Thr Ala Ala Pro Thr Ser Ala Lys Pro Ala Phe Glu Arg Asn
            20                  25                  30

Tyr Gln Leu Pro Glu Phe Thr Ile Lys Glu Ile Arg Glu Cys Ile Pro
        35                  40                  45

Ala His Cys Phe Glu Arg Ser Gly Leu Arg Gly Leu Cys His Val Ala
    50                  55                  60

Ile Asp Leu Thr Trp Ala Ser Leu Leu Phe Leu Ala Ala Thr Gln Ile
65                  70                  75                  80

Asp Lys Phe Glu Asn Pro Leu Ile Arg Tyr Leu Ala Trp Pro Ala Tyr
                85                  90                  95

Trp Ile Met Gln Gly Ile Val Cys Thr Gly Ile Trp Val Leu Ala His
            100                 105                 110
```

```
Glu Cys Gly His Gln Ser Phe Ser Thr Ser Lys Thr Leu Asn Asn Thr
        115                 120                 125

Val Gly Trp Ile Leu His Ser Met Leu Leu Val Pro Tyr His Ser Trp
    130                 135                 140

Arg Ile Ser His Ser Lys His His Lys Ala Thr Gly His Met Thr Lys
145                 150                 155                 160

Asp Gln Val Phe Val Pro Lys Thr Arg Ser Gln Val Gly Leu Pro Pro
                165                 170                 175

Lys Glu Ser Ala Ala Ala Ala Val Gln Glu Glu Asp Met Ser Val His
            180                 185                 190

Leu Asp Glu Glu Ala Pro Ile Val Thr Leu Phe Trp Met Val Ile Gln
        195                 200                 205

Phe Leu Phe Gly Trp Pro Ala Tyr Leu Ile Met Asn Ala Ser Gly Gln
    210                 215                 220

Asp Tyr Gly Arg Trp Thr Ser His Phe His Thr Tyr Ser Pro Ile Phe
225                 230                 235                 240

Glu Pro Arg Asn Phe Phe Asp Ile Ile Ile Ser Asp Leu Gly Val Leu
                245                 250                 255

Ala Ala Leu Gly Ala Leu Ile Tyr Ala Ser Met Gln Leu Ser Leu Leu
            260                 265                 270

Thr Val Thr Lys Tyr Tyr Ile Ile Pro Tyr Leu Phe Val Asn Phe Trp
        275                 280                 285

Leu Val Leu Ile Thr Phe Leu Gln His Thr Asp Pro Lys Leu Pro His
    290                 295                 300

Tyr Arg Glu Gly Ala Trp Asn Phe Gln Arg Gly Ala Leu Cys Thr Val
305                 310                 315                 320

Asp Arg Ser Phe Gly Lys Phe Leu Asp His Met Phe His Gly Ile Val
                325                 330                 335

His Thr His Val Ala His His Leu Phe Ser Gln Met Pro Phe Tyr His
            340                 345                 350

Ala Glu Glu Ala Thr Tyr His Leu Lys Lys Leu Leu Gly Glu Tyr Tyr
        355                 360                 365

Val Tyr Asp Pro Ser Pro Ile Val Val Ala Val Trp Arg Ser Phe Arg
    370                 375                 380

Glu Cys Arg Phe Val Glu Asp His Gly Asp Val Val Phe Phe Lys Lys
385                 390                 395                 400
```

<210> SEQ ID NO 55
<211> LENGTH: 1329
<212> TYPE: DNA
<213> ORGANISM: Isochrysis galbana
<220> FEATURE:
<221> NAME/KEY: misc_feature
<223> OTHER INFORMATION: synthetic delta-5 desaturase (codon-optimized)

<400> SEQUENCE: 55

```
atggtcgctg gcaagtccgg agctgcagcc cacgtgaccc actcttccac tctccctcga     60

gagtaccacg gtgctaccaa cgactcccga tctgaggctg ccgatgtcac cgtctcgtct    120

atcgacgccg agaaggagat gattatcaac ggacgagtgt acgacgtctc ctcgttcgtg    180

aagcgacacc ctggtggctc cgtcatcaag ttccagctcg gagcagatgc ttctgacgct    240

tacaacaact tccacgtccg atcgaagaag gctgacaaga tgctgtactc tcttccctcc    300

cgacctgccg aggctggcta tgcacaggac gacatctcta gagactttga gaagctgcga    360

ctggaactga aagaggaagg ttacttcgag cccaatctgg tgcacgtgtc ctaccgatgt    420
```

-continued

```
gtcgaggtgc ttgccatgta ctgggctggc gtccagctga tctggtccgg atactggttc    480
ctcggtgcca tcgttgctgg aattgctcaa ggtcgatgcg gatggctcca gcatgaaggc    540
ggacactact cgctcactgg caacatcaag attgaccgac atctccagat ggccatctat    600
ggactgggct gtggtatgtc tggctgctac tggagaaacc agcacaacaa acatcacgcc    660
actcctcaga agctcggaac cgatcccgac ctgcagacca tgcctctcgt tgccttccac    720
aagattgtcg gagccaaggc acgaggcaag ggtaaagcct ggcttgcttg gcaagctccc    780
ctcttctttg gaggcatcat ttgctccctg gtctctttcg gctggcagtt cgttctccac    840
cccaatcatg cactgcgagt gcacaaccat ctcgaactgg cctacatggg tctccgatac    900
gttctctggc accttgcctt tggccatctg ggactcctgt cctctcttcg actgtatgcc    960
ttctacgtgg ctgtcggtgg cacctacatc ttcaccaact tcgccgtctc ccatactcac   1020
aaggatgtcg ttcctcccac caagcacatt tcgtgggctc tgtactctgc caaccacact   1080
accaactgtt ccgactctcc ctttgtcaac tggtggatgg cctacctcaa cttccagatc   1140
gagcaccatc tgttcccctc catgcctcag tacaaccacc ccaagattgc tcctcgagtg   1200
cgagcactct tcgagaagca cggagtcgag tacgacgtcc gaccctatct ggaatgcttt   1260
cgagtgacct acgtcaacct ccttgctgtt ggcaaccctg agcactccta ccacgagcat   1320
actcactaa                                                            1329
```

```
<210> SEQ ID NO 56
<211> LENGTH: 442
<212> TYPE: PRT
<213> ORGANISM: Isochrysis galbana CCMP1323

<400> SEQUENCE: 56

Met Val Ala Gly Lys Ser Gly Ala Ala Ala His Val Thr His Ser Ser
1               5                   10                  15

Thr Leu Pro Arg Glu Tyr His Gly Ala Thr Asn Asp Ser Arg Ser Glu
            20                  25                  30

Ala Ala Asp Val Thr Val Ser Ser Ile Asp Ala Glu Lys Glu Met Ile
        35                  40                  45

Ile Asn Gly Arg Val Tyr Asp Val Ser Ser Phe Val Lys Arg His Pro
    50                  55                  60

Gly Gly Ser Val Ile Lys Phe Gln Leu Gly Ala Asp Ala Ser Asp Ala
65                  70                  75                  80

Tyr Asn Asn Phe His Val Arg Ser Lys Lys Ala Asp Lys Met Leu Tyr
                85                  90                  95

Ser Leu Pro Ser Arg Pro Ala Glu Ala Gly Tyr Ala Gln Asp Asp Ile
            100                 105                 110

Ser Arg Asp Phe Glu Lys Leu Arg Leu Glu Leu Lys Glu Glu Gly Tyr
        115                 120                 125

Phe Glu Pro Asn Leu Val His Val Ser Tyr Arg Cys Val Glu Val Leu
    130                 135                 140

Ala Met Tyr Trp Ala Gly Val Gln Leu Ile Trp Ser Gly Tyr Trp Phe
145                 150                 155                 160

Leu Gly Ala Ile Val Ala Gly Ile Ala Gln Gly Arg Cys Gly Trp Leu
                165                 170                 175

Gln His Glu Gly Gly His Tyr Ser Leu Thr Gly Asn Ile Lys Ile Asp
            180                 185                 190

Arg His Leu Gln Met Ala Ile Tyr Gly Leu Gly Cys Gly Met Ser Gly
        195                 200                 205
```

-continued

```
Cys Tyr Trp Arg Asn Gln His Asn Lys His His Ala Thr Pro Gln Lys
    210                 215                 220

Leu Gly Thr Asp Pro Asp Leu Gln Thr Met Pro Leu Val Ala Phe His
225                 230                 235                 240

Lys Ile Val Gly Ala Lys Ala Arg Gly Lys Gly Lys Ala Trp Leu Ala
                245                 250                 255

Trp Gln Ala Pro Leu Phe Phe Gly Gly Ile Ile Cys Ser Leu Val Ser
            260                 265                 270

Phe Gly Trp Gln Phe Val Leu His Pro Asn His Ala Leu Arg Val His
        275                 280                 285

Asn His Leu Glu Leu Ala Tyr Met Gly Leu Arg Tyr Val Leu Trp His
    290                 295                 300

Leu Ala Phe Gly His Leu Gly Leu Leu Ser Ser Leu Arg Leu Tyr Ala
305                 310                 315                 320

Phe Tyr Val Ala Val Gly Gly Thr Tyr Ile Phe Thr Asn Phe Ala Val
                325                 330                 335

Ser His Thr His Lys Asp Val Val Pro Pro Thr Lys His Ile Ser Trp
            340                 345                 350

Ala Leu Tyr Ser Ala Asn His Thr Thr Asn Cys Ser Asp Ser Pro Phe
        355                 360                 365

Val Asn Trp Trp Met Ala Tyr Leu Asn Phe Gln Ile Glu His His Leu
    370                 375                 380

Phe Pro Ser Met Pro Gln Tyr Asn His Pro Lys Ile Ala Pro Arg Val
385                 390                 395                 400

Arg Ala Leu Phe Glu Lys His Gly Val Glu Tyr Asp Val Arg Pro Tyr
                405                 410                 415

Leu Glu Cys Phe Arg Val Thr Tyr Val Asn Leu Leu Ala Val Gly Asn
            420                 425                 430

Pro Glu His Ser Tyr His Glu His Thr His
        435                 440
```

<210> SEQ ID NO 57
<211> LENGTH: 6912
<212> TYPE: DNA
<213> ORGANISM: Artificial Sequence
<220> FEATURE:
<223> OTHER INFORMATION: Plasmid pZKUGPI5S

<400> SEQUENCE: 57

```
ggccgcaagt gtggatgggg aagtgagtgc ccggttctgt gtgcacaatt ggcaatccaa     60

gatggatgga ttcaacacag ggatatagcg agctacgtgg tggtgcgagg atatagcaac    120

ggatatttat gtttgacact tgagaatgta cgatacaagc actgtccaag tacaatacta    180

aacatactgt acatactcat actcgtaccc gggcaacggt ttcacttgag tgcagtggct    240

agtgctctta ctcgtacagt gtgcaatact gcgtatcata gtctttgatg tatatcgtat    300

tcattcatgt tagttgcgta cgaggaaact gtctctgaac agaagaagga ggacgtctct    360

gactacgaga actcccagta caaggagttc ctagtcccct ctcccaacga gaagctggcc    420

agaggtctgc tcatgctggc cgagctgtct tgcaagggct ctctggccac tggcgagtac    480

tccaagcaga ccattgagct tgcccgatcc gaccccgagt ttgtggttgg cttcattgcc    540

cagaaccgac ctaagggcga ctctgaggac tggcttattc tgacccccgg ggtgggtctt    600

gacgacaagg gagacgctct cggacagcag taccgaactg ttgaggatgt catgtctacc    660

ggaacggata tcataattgt cggccgaggt ctgtacggcc agaaccgaga tcctattgag    720
```

-continued

```
gaggccaagc gataccagaa ggctggctgg gaggcttacc agaagattaa ctgttagagg    780
ttagactatg gatatgtaat ttaactgtgt atatagagag cgtgcaagta tggagcgctt    840
gttcagcttg tatgatggtc agacgacctg tctgatcgag tatgtatgat actgcacaac    900
ctgtgtatcc gcatgatctg tccaatgggg catgttgttg tgtttctcga tacggagatg    960
ctgggtacag tgctaatacg ttgaactact tatacttata tgaggctcga agaaagctga   1020
cttgtgtatg acttaattaa tcgagcttgg cgtaatcatg gtcatagctg tttcctgtgt   1080
gaaattgtta tccgctcaca attccacaca acatacgagc cggaagcata aagtgtaaag   1140
cctggggtgc ctaatgagtg agctaactca cattaattgc gttgcgctca ctgcccgctt   1200
tccagtcggg aaacctgtcg tgccagctgc attaatgaat cggccaacgc gcggggagag   1260
gcggtttgcg tattgggcgc tcttccgctt cctcgctcac tgactcgctg cgctcggtcg   1320
ttcggctgcg gcgagcggta tcagctcact caaaggcggt aatacggtta tccacagaat   1380
caggggataa cgcaggaaag aacatgtgag caaaaggcca gcaaaaggcc aggaaccgta   1440
aaaaggccgc gttgctggcg tttttccata ggctccgccc ccctgacgag catcacaaaa   1500
atcgacgctc aagtcagagg tggcgaaacc cgacaggact ataaagatac caggcgtttc   1560
cccctggaag ctccctcgtg cgctctcctg ttccgaccct gccgcttacc ggatacctgt   1620
ccgcctttct cccttcggga agcgtggcgc tttctcatag ctcacgctgt aggtatctca   1680
gttcggtgta ggtcgttcgc tccaagctgg gctgtgtgca cgaacccccc gttcagcccg   1740
accgctgcgc cttatccggt aactatcgtc ttgagtccaa cccggtaaga cacgacttat   1800
cgccactggc agcagccact ggtaacagga ttagcagagc gaggtatgta ggcggtgcta   1860
cagagttctt gaagtggtgg cctaactacg gctacactag aaggacagta tttggtatct   1920
gcgctctgct gaagccagtt accttcggaa aaagagttgg tagctcttga tccggcaaac   1980
aaaccaccgc tggtagcggt ggtttttttg tttgcaagca gcagattacg cgcagaaaaa   2040
aaggatctca agaagatcct ttgatctttt ctacggggtc tgacgctcag tggaacgaaa   2100
actcacgtta agggattttg gtcatgagat tatcaaaaag gatcttcacc tagatccttt   2160
taaattaaaa atgaagtttt aaatcaatct aaagtatata tgagtaaact tggtctgaca   2220
gttaccaatg cttaatcagt gaggcaccta tctcagcgat ctgtctattt cgttcatcca   2280
tagttgcctg actccccgtc gtgtagataa ctacgatacg ggagggctta ccatctggcc   2340
ccagtgctgc aatgataccg cgagacccac gctcaccggc tccagattta tcagcaataa   2400
accagccagc cggaagggcc gagcgcagaa gtggtcctgc aactttatcc gcctccatcc   2460
agtctattaa ttgttgccgg gaagctagag taagtagttc gccagttaat agtttgcgca   2520
acgttgttgc cattgctaca ggcatcgtgg tgtcacgctc gtcgtttggt atggcttcat   2580
tcagctccgg ttcccaacga tcaaggcgag ttacatgatc ccccatgttg tgcaaaaaag   2640
cggttagctc cttcggtcct ccgatcgttg tcagaagtaa gttggccgca gtgttatcac   2700
tcatggttat ggcagcactg cataattctc ttactgtcat gccatccgta agatgctttt   2760
ctgtgactgg tgagtactca accaagtcat tctgagaata gtgtatgcgg cgaccgagtt   2820
gctcttgccc ggcgtcaata cgggataata ccgcgccaca tagcagaact ttaaaagtgc   2880
tcatcattgg aaaacgttct tcggggcgaa aactctcaag gatcttaccg ctgttgagat   2940
ccagttcgat gtaacccact cgtgcaccca actgatcttc agcatctttt actttcacca   3000
gcgtttctgg gtgagcaaaa acaggaaggc aaaatgccgc aaaaaaggga ataagggcga   3060
```

-continued

```
cacggaaatg ttgaatactc atactcttcc tttttcaata ttattgaagc atttatcagg   3120
gttattgtct catgagcgga tacatatttg aatgtattta gaaaaataaa caaatagggg   3180
ttccgcgcac atttccccga aaagtgccac ctgacgcgcc ctgtagcggc gcattaagcg   3240
cggcgggtgt ggtggttacg cgcagcgtga ccgctacact tgccagcgcc ctagcgcccg   3300
ctcctttcgc tttcttccct tcctttctcg ccacgttcgc cggctttccc cgtcaagctc   3360
taaatcgggg gctcccttta gggttccgat ttagtgcttt acggcacctc gaccccaaaa   3420
aacttgatta gggtgatggt tcacgtagtg ggccatcgcc ctgatagacg gtttttcgcc   3480
ctttgacgtt ggagtccacg ttctttaata gtggactctt gttccaaact ggaacaacac   3540
tcaaccctat ctcggtctat tcttttgatt tataagggat tttgccgatt tcggcctatt   3600
ggttaaaaaa tgagctgatt taacaaaaat ttaacgcgaa ttttaacaaa atattaacgc   3660
ttacaatttc cattcgccat tcaggctgcg caactgttgg gaagggcgat cggtgcgggc   3720
ctcttcgcta ttacgccagc tggcgaaagg gggatgtgct gcaaggcgat taagttgggt   3780
aacgccaggg ttttcccagt cacgacgttg taaaacgacg gccagtgaat tgtaatacga   3840
ctcactatag ggcgaattgg gtaccgggcc ccccctcgag gtcgacgagt atctgtctga   3900
ctcgtcattg ccgcctttgg agtacgactc caactatgag tgtgcttgga tcactttgac   3960
gatacattct tcgttggagg ctgtgggtct gacagctgcg ttttcggcgc ggttggccga   4020
caacaatatc agctgcaacg tcattgctgg ctttcatcat gatcacattt ttgtcggcaa   4080
aggcgacgcc cagagagcca ttgacgttct ttctaatttg gaccgatagc cgtatagtcc   4140
agtctatcta taagttcaac taactcgtaa ctattaccat aacatatact tcactgcccc   4200
agataaggtt ccgataaaaa gttctgcaga ctaaatttat ttcagtctcc tcttcaccac   4260
caaaatgccc tcctacgaag ctcgagtgct caagctcgtg gcagccaaga aaaccaacct   4320
gtgtgcttct ctggatgtta ccaccaccaa ggagctcatt gagcttgccg ataaggtcgg   4380
accttatgtg tgcatgatca aaacccatat cgacatcatt gacgacttca cctacgccgg   4440
cactgtgctc cccctcaagg aacttgctct taagcacggt ttcttcctgt tcgaggacag   4500
aaagttcgca gatattggca acactgtcaa gcaccagtac cggtgtcacc gaatcgccga   4560
gtggtccgat atcaccaacg cccacggtgt acccggaacc ggaatcgatg cgtatctgtg   4620
ggacatgtgg tcgttgcgcc attatgtaag cagcgtgtac tcctctgact gtccatatgg   4680
tttgctccat ctcaccctca tcgttttcat tgttcacagg cggccacaaa aaaactgtct   4740
tctctccttc tctcttcgcc ttagtctact cggaccagtt ttagtttagc ttggcgccac   4800
tggataaatg agacctcagg ccttgtgatg aggaggtcac ttatgaagca tgttaggagg   4860
tgcttgtatg gatagagaag cacccaaaat aataagaata ataataaaac agggggcgtt   4920
gtcatttcat atcgtgtttt caccatcaat acacctccaa acaatgccct tcatgtggcc   4980
agccccaata ttgtcctgta gttcaactct atgcagctcg tatcttattg agcaagtaaa   5040
actctgtcag ccgatattgc ccgacccgcg acaagggtca acaaggtggt gtaaggcctt   5100
cgcagaagtc aaaactgtgc caaacaaaca tctagagtct ctttggtgtt tctcgcatat   5160
atttwatcgg ctgtcttacg tatttgcgcc tcggtaccgg actaatttcg gatcatcccc   5220
aatacgcttt ttcttcgcag ctgtcaacag tgtccatgat ctatccacct aaatgggtca   5280
tatgaggcgt ataatttcgt ggtgctgata ataattccca tatatttgac acaaaacttc   5340
ccccctaga catacatctc acaatctcac ttcttgtgct tctgtcacac atctcctcca   5400
gctgacttca actcacacct ctgccccagt tggtctacag cggtataagg tttctccgca   5460
```

```
tagaggtgca ccactcctcc cgatacttgt ttgtgtgact tgtgggtcac gacatatata   5520

tctacacaca ttgcgccacc ctttggttct tccagcacaa caaaaacacg acacgctaac   5580

catggtcgct ggcaagtccg gagctgcagc ccacgtgacc cactcttcca ctctccctcg   5640

agagtaccac ggtgctacca acgactcccg atctgaggct gccgatgtca ccgtctcgtc   5700

tatcgacgcc gagaaggaga tgattatcaa cggacgagtg tacgacgtct cctcgttcgt   5760

gaagcgacac cctggtggct ccgtcatcaa gttccagctc ggagcagatg cttctgacgc   5820

ttacaacaac ttccacgtcc gatcgaagaa ggctgacaag atgctgtact ctcttccctc   5880

ccgacctgcc gaggctggct atgcacagga cgacatctct agagactttg agaagctgcg   5940

actggaactg aaagaggaag gttacttcga gcccaatctg gtgcacgtgt cctaccgatg   6000

tgtcgaggtg cttgccatgt actgggctgg cgtccagctg atctggtccg gatactggtt   6060

cctcggtgcc atcgttgctg gaattgctca aggtcgatgc ggatggctcc agcatgaagg   6120

cggacactac tcgctcactg gcaacatcaa gattgaccga catctccaga tggccatcta   6180

tggactgggc tgtggtatgt ctggctgcta ctggagaaac cagcacaaca aacatcacgc   6240

cactcctcag aagctcggaa ccgatcccga cctgcagacc atgcctctcg ttgccttcca   6300

caagattgtc ggagccaagg cacgaggcaa gggtaaagcc tggcttgctt ggcaagctcc   6360

cctcttcttt ggaggcatca tttgctccct ggtctctttc ggctggcagt tcgttctcca   6420

ccccaatcat gcactgcgag tgcacaacca tctcgaactg gcctacatgg gtctccgata   6480

cgttctctgg caccttgcct ttggccatct gggactcctg tcctctcttc gactgtatgc   6540

cttctacgtg gctgtcggtg gcacctacat cttcaccaac ttcgccgtct cccatactca   6600

caaggatgtc gttcctccca ccaagcacat ttcgtgggct ctgtactctg ccaaccacac   6660

taccaactgt tccgactctc cctttgtcaa ctggtggatg gcctacctca acttccagat   6720

cgagcaccat ctgttcccct ccatgcctca gtacaaccac cccaagattg ctcctcgagt   6780

gcgagcactc ttcgagaagc acggagtcga gtacgacgtc cgaccctatc tggaatgctt   6840

tcgagtgacc tacgtcaacc tccttgctgt tggcaaccct gagcactcct accacgagca   6900

tactcactaa gc                                                        6912
```

```
<210> SEQ ID NO 58
<211> LENGTH: 14864
<212> TYPE: DNA
<213> ORGANISM: Artificial Sequence
<220> FEATURE:
<223> OTHER INFORMATION: Plasmid pDMW302T16
<220> FEATURE:
<221> NAME/KEY: misc_feature
<222> LOCATION: (5341)..(5341)
<223> OTHER INFORMATION: n is a, c, g, or t
<220> FEATURE:
<221> NAME/KEY: misc_feature
<222> LOCATION: (5346)..(5349)
<223> OTHER INFORMATION: n is a, c, g, or t

<400> SEQUENCE: 58
```

```
gtacgatagt tagtagacaa caatcagaac atctccctcc ttatataatc acacaggcca     60

gaacgcgcta aactaaagcg ctttggacac tatgttacat tggcattgat tgaactgaaa    120

ccacagtctc cctcgcctga atcgagcaat ggatgttgtc ggaagtcaac ttcactagaa    180

gagcggttct atgccttgtc aagatcatat cataaactca ctctgtatta ccccatctat    240

agaacacttg ttatgaatgg gcggaaacat tccgctatat gcacctttcc acactaatgc    300
```

-continued

```
aaagatgtgc atcttcaacg ggtagtaaga ctggttccga cttccgttgc atggagagca    360
atgacctcga taatgcgaac atcccccaca tatacactct tacacaggcc aatataatct    420
gtgcatttac taaatattta agtctatgca cctgcttgat gaaaagcggc acggatggta    480
tcatctagtt tccgccaatc caagaaccaa ctgtgttggc agtggtgtag cccatggcac    540
acagaccaaa gatgaaaata cagacatcgg cggttcgagc cgtggtgcct cgagcaacac    600
ccttgtaatg caaaagagga gggtaaatgt acaccagagg cacacatgca aacgatccgg    660
tgagagcgac gaaccgatcg agatcgtcgg cacctcccca tgcaacaaag gcggtgacaa    720
acacaaggaa gaaccggaaa atgttcttct gccacttgat ggtagagttg tacttgcctg    780
atcgggtgaa gagaccattc tcgatgattc ggatggcgcg ccagctgcat taatgaatcg    840
gccaacgcgc ggggagaggc ggtttgcgta ttgggcgctc ttccgcttcc tcgctcactg    900
actcgctgcg ctcggtcgtt cggctgcggc gagcggtatc agctcactca aaggcggtaa    960
tacggttatc cacagaatca ggggataacg caggaaagaa catgtgagca aaaggccagc   1020
aaaaggccag gaaccgtaaa aaggccgcgt tgctggcgtt tttccatagg ctccgccccc   1080
ctgacgagca tcacaaaaat cgacgctcaa gtcagaggtg gcgaaacccg acaggactat   1140
aaagatacca ggcgtttccc cctggaagct ccctcgtgcg ctctcctgtt ccgaccctgc   1200
cgcttaccgg atacctgtcc gcctttctcc cttcgggaag cgtggcgctt tctcatagct   1260
cacgctgtag gtatctcagt tcggtgtagg tcgttcgctc caagctgggc tgtgtgcacg   1320
aaccccccgt tcagcccgac cgctgcgcct tatccggtaa ctatcgtctt gagtccaacc   1380
cggtaagaca cgacttatcg ccactggcag cagccactgg taacaggatt agcagagcga   1440
ggtatgtagg cggtgctaca gagttcttga agtggtggcc taactacggc tacactagaa   1500
gaacagtatt tggtatctgc gctctgctga agccagttac cttcggaaaa agagttggta   1560
gctcttgatc cggcaaacaa accaccgctg gtagcggtgg tttttttgtt tgcaagcagc   1620
agattacgcg cagaaaaaaa ggatctcaag aagatccttt gatcttttct acggggtctg   1680
acgctcagtg gaacgaaaac tcacgttaag ggattttggt catgagatta tcaaaaagga   1740
tcttcaccta gatcctttta aattaaaaat gaagttttaa atcaatctaa agtatatatg   1800
agtaaacttg gtctgacagt taccaatgct taatcagtga ggcacctatc tcagcgatct   1860
gtctatttcg ttcatccata gttgcctgac tccccgtcgt gtagataact acgatacggg   1920
agggcttacc atctggcccc agtgctgcaa tgataccgcg agacccacgc tcaccggctc   1980
cagatttatc agcaataaac cagccagccg gaagggccga gcgcagaagt ggtcctgcaa   2040
ctttatccgc ctccatccag tctattaatt gttgccggga agctagagta agtagttcgc   2100
cagttaatag tttgcgcaac gttgttgcca ttgctacagg catcgtggtg tcacgctcgt   2160
cgtttggtat ggcttcattc agctccggtt cccaacgatc aaggcgagtt acatgatccc   2220
ccatgttgtg caaaaaagcg gttagctcct tcggtcctcc gatcgttgtc agaagtaagt   2280
tggccgcagt gttatcactc atggttatgg cagcactgca taattctctt actgtcatgc   2340
catccgtaag atgcttttct gtgactggtg agtactcaac caagtcattc tgagaatagt   2400
gtatgcggcg accgagttgc tcttgcccgg cgtcaatacg ggataatacc gcgccacata   2460
gcagaacttt aaaagtgctc atcattggaa aacgttcttc ggggcgaaaa ctctcaagga   2520
tcttaccgct gttgagatcc agttcgatgt aacccactcg tgcacccaac tgatcttcag   2580
catcttttac tttcaccagc gtttctgggt gagcaaaaac aggaaggcaa aatgccgcaa   2640
aaaagggaat aagggcgaca cggaaatgtt gaatactcat actcttcctt tttcaatatt   2700
```

```
attgaagcat ttatcagggt tattgtctca tgagcggata catatttgaa tgtatttaga   2760
aaaataaaca aataggggtt ccgcgcacat ttccccgaaa agtgccacct gatgcggtgt   2820
gaaataccgc acagatgcgt aaggagaaaa taccgcatca ggaaattgta agcgttaata   2880
ttttgttaaa attcgcgtta aatttttgtt aaatcagctc attttttaac caataggccg   2940
aaatcggcaa aatcccttat aaatcaaaag aatagaccga gatagggttg agtgttgttc   3000
cagtttggaa caagagtcca ctattaaaga acgtggactc caacgtcaaa gggcgaaaaa   3060
ccgtctatca gggcgatggc ccactacgtg aaccatcacc ctaatcaagt tttttggggt   3120
cgaggtgccg taaagcacta aatcggaacc ctaaagggag cccccgattt agagcttgac   3180
ggggaaagcc ggcgaacgtg gcgagaaagg aagggaagaa agcgaaagga gcgggcgcta   3240
gggcgctggc aagtgtagcg gtcacgctgc gcgtaaccac cacacccgcc gcgcttaatg   3300
cgccgctaca gggcgcgtcc attcgccatt caggctgcgc aactgttggg aagggcgatc   3360
ggtgcgggcc tcttcgctat tacgccagct ggcgaaaggg ggatgtgctg caaggcgatt   3420
aagttgggta acgccagggt tttcccagtc acgacgttgt aaaacgacgg ccagtgaatt   3480
gtaatacgac tcactatagg gcgaattggg cccgacgtcg catgcttaga agtgaggatt   3540
acaagaagcc tctggatatc aatgatgaac gtactcagcg gctggtcaag catttcgacc   3600
gtcgaatcga cgaggtgttc acctttgaca agcgagggtt cccaattgat cacgttctcg   3660
agttgttcaa atcttctctc aacatctctc tgcatgaact atctctgttg acgaacgtgt   3720
cacccactgt tcctcgaacg cccttctccg agtttggtct gaacatcttc gatctcaaac   3780
tgacccccgc agtgatcaat agtgccatgc cactgccgat gcggtgcgaa catccctgga   3840
gggattctcg gagctctaca caatgcagat tctgtcgtcg agtactctct accttgctcg   3900
aatgacttat tgtgctacta ctgcactcat gcttcgatca tgtgccctac tgcaccccaa   3960
atttggtgat ctgattgaga cagagtaccc tcttcagctg attcagaaga tcatcagcaa   4020
catgaatgat gtggttgacc aggcaggctg ttgtagtcac gtccttcact tcaagttcat   4080
tcttcatctg cttctgtttt actttgacag gcaaatgaag acatggtacg acttgatgga   4140
ggccaagaac gccatttcac cccgagacac cgaagtgcct gaaatcctgg ctgcccccat   4200
tgataacatc ggaaactacg gtattccgga aagtgtatat agaacctttc cccagcttgt   4260
gtctgtggat atggatggtg taatcccctt aattaaaagg cgttgaaaca gaatgagcca   4320
gacagcaagg acaaggtggc caacagcaag gagtccaaaa agccctctat tgacgagatc   4380
cacgatgtta ttgctcatga ggtttccgag ctcgatgctg ggaagaagaa gtgatttgta   4440
tataagaaat aaatgagata tagtaaagga gtgcaagaga atggcaaggt ggtcaaattc   4500
tatattactt gcagtcactg gttcctcgtt gacatgaatg aagttaccgt tggcatagct   4560
gatttaatat ataactgtcc aactaactct cacctagata taacccatgt gtgtgtttcc   4620
aatcatcaat gcggccgcgc ctacttaagc aacgggcttg ataacagcgg ggggggtgcc   4680
cacgttgttg cggttgcgga agaacagaac acccttacca gcaccctcgg caccagcgct   4740
gggctcaacc cactggcaca tacgcgcact gcggtacatg gcgcggatga agccacgagg   4800
accatcctgg acatcagccc ggtagtgctt gcccatgatg ggcttaatgg cctcggtggc   4860
ctcgtccgcg ttgtagaagg ggatgctgct gacgtagtgg tggaggacat gagtctcgat   4920
gatgccgtgg agaaggtggc ggccgatgaa gcccatctca cggtcaatgg tagcagcggc   4980
accacggacg aagttccact cgtcgttggt gtagtgggga agggtagggt cggtgtgctg   5040
```

-continued

```
gaggaaggtg atggcaacga gccagtggtt aacccagagg tagggaacaa agtaccagat   5100
ggccatgttg tagaaaccga acttctgaac gaggaagtac agagcagtgg ccatcagacc   5160
gataccaata tcgctgagga cgatgagctt agcgtcactg ttctcgtaca gagggctgcg   5220
gggatcgaag tggttaacac caccgccgag gccgttatgc ttgcccttgc cgcgaccctc   5280
acgctggcgc tcgtggtagt tgtggccggt aacattggtg atgaggtagt tgggccagcc   5340
nacgannnnc tcagtaagat gagcgagctc gtgggtcatc tttccgagac gagtagcctg   5400
ctgctcgcgg gttcggggaa cgaagaccat gtcacgctcc atgttgccag tggccttgtg   5460
gtgctttcgg tgggagattt gccagctgaa gtaggggaca aggagggaag agtgaagaac   5520
ccagccagta atgtcgttga tgatgcgaga atcggagaaa gcaccgtgac cgcactcatg   5580
ggcaataacc cagagaccag taccgaaaag accctgaaga acggtgtaca cggcccacag   5640
accagcgcgg gcgggggtgg aggggatata ttcgggggtc acaaagttgt accagatgct   5700
gaaagtggta gtcaggagga caatgtcgcg gaggatataa ccgtatccct tgagagcgga   5760
gcgcttgaag cagtgcttag ggatggcatt gtagatgtcc ttgatggtaa agtcgggaac   5820
ctcgaactgg ttgccgtagg tgtcgagcat gacaccatac tcggacttgg gcttggcgat   5880
atcaacctcg gacatggacg agagcgatgt ggaagaggcc gagtggcggg gagagtctga   5940
aggagagacg gcggcagact cagaatccgt cacagtagtt gaggtgacgg tgcgtctaag   6000
cgcagggttc tgcttgggca gagccgaagt ggacgccatg gtgaatgatt cttatactca   6060
gaaggaaatg cttaacgatt tcgggtgtga gttgacaagg agagagagaa aagaagagga   6120
aaggtaattc ggggacggtg gtcttttata cccttggcta aagtcccaac cacaaagcaa   6180
aaaaattttc agtagtctat tttgcgtccg gcatgggtta cccggatggc cagacaaaga   6240
aactagtaca aagtctgaac aagcgtagat tccagactgc agtaccctac gcccttaacg   6300
gcaagtgtgg gaaccggggg aggtttgata tgtggggtga agggggctct cgccggggtt   6360
gggcccgcta ctgggtcaat ttggggtcaa ttggggcaat tggggctgtt ttttgggaca   6420
caaatacgcc gccaacccgg tctctcctga attctctctc ttgagctttt ccataacaag   6480
ttcttctgcc tccaggaagt ccatgggtgg tttgatcatg gttttggtgt agtggtagtg   6540
cagtggtggt attgtgactg gggatgtagt tgagaataag tcatacacaa gtcagctttc   6600
ttcgagcctc atataagtat aagtagttca acgtattagc actgtaccca gcatctccgt   6660
atcgagaaac acaacaacat gccccattgg acagatcatg cggatacaca ggttgtgcag   6720
tatcatacat actcgatcag acaggtcgtc tgaccatcat acaagctgaa caagcgctcc   6780
atacttgcac gctctctata tacacagtta aattacatat ccatagtcta acctctaaca   6840
gttaatcttc tggtaagcct cccagccagc cttctggtat cgcttggcct cctcaatagg   6900
atctcggttc tggccgtaca gacctcggcc gacaattatg atatccgttc cggtagacat   6960
gacatcctca acagttcggt actgctgtcc gagagcgtct cccttgtcgt caagacccac   7020
cccgggggtc agaataagcc agtcctcaga gtcgccctta ggtcggttct gggcaatgaa   7080
gccaaccaca aactcggggt cggatcgggc aagctcaatg gtctgcttgg agtactcgcc   7140
agtggccaga gagcccttgc aagacagctc ggccagcatg agcagacctc tggccagctt   7200
ctcgttggga gaggggacta ggaactcctt gtactgggag ttctcgtagt cagagacgtc   7260
ctccttcttc tgttcagaga cagtttcctc ggcaccagct cgcaggccag caatgattcc   7320
ggttccgggt acaccgtggg cgttggtgat atcggaccac tcggcgattc ggtgacaccg   7380
gtactggtgc ttgacagtgt tgccaatatc tgcgaacttt ctgtcctcga acaggaagaa   7440
```

-continued

```
accgtgctta agagcaagtt ccttgagggg gagcacagtg ccggcgtagg tgaagtcgtc   7500
aatgatgtcg atatgggttt tgatcatgca cacataaggt ccgaccttat cggcaagctc   7560
aatgagctcc ttggtggtgg taacatccag agaagcacac aggttggttt tcttggctgc   7620
cacgagcttg agcactcgag cggcaaaggc ggacttgtgg acgttagctc gagcttcgta   7680
ggagggcatt ttggtggtga agaggagact gaaataaatt tagtctgcag aactttttat   7740
cggaacctta tctggggcag tgaagtatat gttatggtaa tagttacgag ttagttgaac   7800
ttatagatag actggactat acggctatcg gtccaaatta gaaagaacgt caatggctct   7860
ctgggcgtcg cctttgccga caaaaatgtg atcatgatga aagccagcaa tgacgttgca   7920
gctgatattg ttgtcggcca accgcgccga aaacgcagct gtcagaccca cagcctccaa   7980
cgaagaatgt atcgtcaaag tgatccaagc acactcatag ttggagtcgt actccaaagg   8040
cggcaatgac gagtcagaca gatactcgtc gactcatcga tcgaggaaga ggacaagcgg   8100
ctgcttctta agtttgtgac atcagtatcc aaggcaccat tgcaaggatt caaggctttg   8160
aacccgtcat ttgccattcg taacgctggt agacaggttg atcggttccc tacggcctcc   8220
acctgtgtca atcttctcaa gctgcctgac tatcaggaca ttgatcaact tcggaagaaa   8280
cttttgtatg ccattcgatc acatgctggt ttcgatttgt cttagaggaa cgcatataca   8340
gtaatcatag agaataaacg atattcattt attaaagtag atagttgagg tagaagttgt   8400
aaagagtgat aaatagcggc cgcttactgg agctttctgg ccttctcctt ggcagcgtca   8460
gccttggcct gcttggcgag cttggcgttc tttcggtaaa agttgtagaa gagaccgagc   8520
atggtccaca tgtagaacca gagcagagcg gtgatgaaga aggggtatcc aggtcggcca   8580
aggaccttca tggcgtacat gtcccaggaa gactggacag acatcatgca gaactgggtc   8640
atctgggatc gagtgatgta gaacttgatg aacgacacct gcttgaagcc cagggcagac   8700
agaaagtagt agccgtacat gatgacgtgg atgaaggagt tcagggcagc agagaagtag   8760
gcttcaccgt tgggagcaac gaaggtgacc agccaccaga tggtgaagat ggaagagtgg   8820
tggtacacgt gcagaaagga aatctgtcgg ttgttcttct tgaggaccat gatcatggtg   8880
tcgacaaact ccatgatctt ggagaagtag aagagccaga tcatcttagc catagggaga   8940
cccttgaagg tgtgatcggc agcgttctca aacagtccat agttggcctg ataagcctcg   9000
tacaggatgc caccgcacat gtaggcggag atggagacca gacagaagtt gtgcaggagg   9060
gagaaggtct tgacctcgaa tcgttcaaag ttcttcatga tctgcatacc cacaaacacg   9120
gtgaccaggt aggcgagcac gatcaggagc acgtggaagg ggttcatcag aggcagctct   9180
cgagccaggg gagactccac ggcaaccagg aagcctcgag tgtgatggac aatggtggga   9240
atgtacttct cggcctgggc aaccagggca gcctccaggg gatcgacgta gggagcagct   9300
cggacaccga tagcgctggc gaggtccatg aacaggtcct gaggcatctt ggagggcagg   9360
aagggagcaa tggactccat gggcaggacc tgtgttagta cattgtcggg gagtcatcaa   9420
ttggttcgac aggttgtcga ctgttagtat gagctcaatt gggctctggt gggtcgatga   9480
cacttgtcat ctgtttctgt tgggtcatgt ttccatcacc ttctatggta ctcacaattc   9540
gtccgattcg cccgaatccg ttaataccga ctttgatggc catgttgatg tgtgtttaat   9600
tcaagaatga atatagagaa gagaagaaga aaaaagattc aattgagccg gcgatgcaga   9660
cccttatata aatgttgcct tggacagacg gagcaagccc gcccaaacct acgttcggta   9720
taatatgtta agctttttaa cacaaaggtt tggcttgggg taacctgatg tggtgcaaaa   9780
```

-continued

```
gaccgggcgt tggcgagcca ttgcgcgggc gaatggggcc gtgactcgtc tcaaattcga   9840
gggcgtgcct caattcgtgc cccgtggct ttttcccgcc gtttccgccc cgtttgcacc   9900
actgcagccg cttctttggt tcggacacct tgctgcgagc taggtgcctt gtgctactta   9960
aaaagtggcc tcccaacacc aacatgacat gagtgcgtgg gccaagacac gttggcgggg  10020
tcgcagtcgg ctcaatggcc cggaaaaaac gctgctggag ctggttcgga cgcagtccgc  10080
cgcggcgtat ggatatccgc aaggttccat agcgccattg ccctccgtcg gcgtctatcc  10140
cgcaacctct aaatagagcg ggaatataac ccaagcttct ttttttttcct ttaacacgca  10200
caccccccaac tatcatgttg ctgctgctgt ttgactctac tctgtggagg ggtgctccca  10260
cccaacccaa cctacaggtg gatccggcgc tgtgattggc tgataagtct cctatccgga  10320
ctaattctga ccaatgggac atgcgcgcag gacccaaatg ccgcaattac gtaaccccaa  10380
cgaaatgcct acccctcttt ggagcccagc ggccccaaat ccccccaagc agcccggttc  10440
taccggcttc catctccaag cacaagcagc ccggttctac cggcttccat ctccaagcac  10500
ccctttctcc acaccccaca aaaagacccg tgcaggacat cctactgcgt gtttaaacac  10560
cactaaaacc ccacaaaata tatcttaccg aatatacaga tctactatag aggaacaatt  10620
gccccggaga agacggccag gccgcctaga tgacaaattc aacaactcac agctgacttt  10680
ctgccattgc cactaggggg gggccttttt atatggccaa gccaagctct ccacgtcggt  10740
tgggctgcac ccaacaataa atgggtaggg ttgcaccaac aaagggatgg gatggggggt  10800
agaagatacg aggataacgg ggctcaatgg cacaaataag aacgaatact gccattaaga  10860
ctcgtgatcc agcgactgac accattgcat catctaaggg cctcaaaact acctcggaac  10920
tgctgcgctg atctggacac cacagaggtt ccgagcactt taggttgcac caaatgtccc  10980
accaggtgca ggcagaaaac gctggaacag cgtgtacagt ttgtcttaac aaaaagtgag  11040
ggcgctgagg tcgagcaggg tggtgtgact tgttatagcc tttagagctg cgaaagcgcg  11100
tatggatttg gctcatcagg ccagattgag ggtctgtgga cacatgtcat gttagtgtac  11160
ttcaatcgcc ccctggatat agccccgaca ataggccgtg gcctcatttt tttgccttcc  11220
gcacatttcc attgctcggt acccacacct tgcttctcct gcacttgcca accttaatac  11280
tggtttacat tgaccaacat cttacaagcg gggggcttgt ctagggtata tataaacagt  11340
ggctctccca atcggttgcc agtctctttt ttcctttctt tcccccacaga ttcgaaatct  11400
aaactacaca tcacacaatg cctgttactg acgtccttaa gcgaaagtcc ggtgtcatcg  11460
tcggcgacga tgtccgagcc gtgagtatcc acgacaagat cagtgtcgag acgacgcgtt  11520
ttgtgtaatg acacaatccg aaagtcgcta gcaacacaca ctctctacac aaactaaccc  11580
agctctccat ggctgccgct ccctctgtgc gaacctttac ccgagccgag gttctgaacg  11640
ctgaggctct gaacgagggc aagaaggacg ctgaggctcc cttcctgatg atcatcgaca  11700
acaaggtgta cgacgtccga gagttcgtcc ctgaccatcc tggaggctcc gtgattctca  11760
cccacgttgg caaggacggc accgacgtct ttgacacctt tcatcccgag gctgcttggg  11820
agactctcgc caacttctac gttggagaca ttgacgagtc cgaccgagac atcaagaacg  11880
atgactttgc cgctgaggtc cgaaagctgc gaaccctgtt ccagtctctc ggctactacg  11940
actcctctaa ggcctactac gccttcaagg tctccttcaa cctctgcatc tggggactgt  12000
ccaccgtcat tgtggccaag tggggtcaga cctccaccct cgccaacgtg ctctctgctg  12060
ccctgctcgg cctgttctgg cagcagtgcg gatggctggc tcacgacttt ctgcaccacc  12120
aggtcttcca ggaccgattc tggggtgatc tcttcggagc cttcctggga ggtgtctgcc  12180
```

-continued

```
agggcttctc ctcttcctgg tggaaggaca agcacaacac tcaccatgcc gctcccaacg  12240
tgcatggcga ggatcctgac attgacaccc accctctcct gacctggtcc gagcacgctc  12300
tggagatgtt ctccgacgtc cccgatgagg agctgacccg aatgtggtct cgattcatgg  12360
tcctgaacca gacctggttc tacttcccca ttctctcctt cgctcgactg tcttggtgcc  12420
tccagtccat tctctttgtg ctgcccaacg gtcaggctca caagccctcc ggagctcgag  12480
tgcccatctc cctggtcgag cagctgtccc tcgccatgca ctggacctgg tacctcgcta  12540
ccatgttcct gttcatcaag gatcctgtca acatgctcgt gtacttcctg gtgtctcagg  12600
ctgtgtgcgg aaacctgctc gccatcgtgt tctccctcaa ccacaacggt atgcctgtga  12660
tctccaagga ggaggctgtc gacatggatt tctttaccaa gcagatcatc actggtcgag  12720
atgtccatcc tggactgttc gccaactggt tcaccggtgg cctgaactac cagatcgagc  12780
atcacctgtt cccttccatg cctcgacaca acttctccaa gatccagcct gccgtcgaga  12840
ccctgtgcaa gaagtacaac gtccgatacc acaccactgg tatgatcgag ggaactgccg  12900
aggtcttctc ccgactgaac gaggtctcca aggccacctc caagatgggc aaggctcagt  12960
aagcggccgc atgagaagat aaatatataa atacattgag atattaaatg cgctagatta  13020
gagagcctca tactgctcgg agagaagcca agacgagtac tcaaagggga ttacaccatc  13080
catatccaca gacacaagct ggggaaaggt tctatataca ctttccggaa taccgtagtt  13140
tccgatgtta tcaatggggg cagccaggat ttcaggcact tcggtgtctc ggggtgaaat  13200
ggcgttcttg gcctccatca agtcgtacca tgtcttcatt tgcctgtcaa agtaaaacag  13260
aagcagatga agaatgaact tgaagtgaag gaatttaaac gacggaattc ctgcagccca  13320
tctgcagaat tcaggagaga ccgggttggc ggcgtatttg tgtcccaaaa aacagcccca  13380
attgccccaa ttgaccccaa attgacccag tagcgggccc aaccccggcg agagcccccct  13440
tcaccccaca tatcaaacct cccccggttc ccacacttgc cgttaagggc gtagggtact  13500
gcagtctgga atctacgctt gttcagactt tgtactagtt tctttgtctg gccatccggg  13560
taacccatgc cggacgcaaa atagactact gaaaattttt ttgctttgtg gttgggactt  13620
tagccaaggg tataaaagac caccgtcccc gaattacctt tcctcttctt ttctctctct  13680
ccttgtcaac tcacacccga aatcgttaag catttccttc tgagtataag aatcattcac  13740
catggacatg tccgtcctga ctctccaaga gtacgagttc gagaagcagt tcaacgagaa  13800
tgaagccatc caatggatgc aggaaaactg gaagaaatcc ttcctgtttt ctgccctcta  13860
cgctgccttt atctttggtg gacgacatct gatgaacaag cgagccaagt ttgagctgcg  13920
aaaacctctc gtgctctggt ccctgaccct cgctgtcttc tctatcttcg gtgctctgcg  13980
aactggagcc tacatgctct acatcctgat gaccaaaggc ctgaaacagt ctgtttgtga  14040
ccagtccttt tacaacggac ccgtctcgaa attctgggct tacgcctttg tgctctccaa  14100
agctcccgaa cttggcgata ccatcttcat cattctgcga aagcagaaac tcatcttcct  14160
gcactggtat caccacatca ccgtcctcct gtactcttgg tactcctaca aggacatggt  14220
ggctggaggt ggctggttca tgactatgaa ctacggtgtc cacgccgtga tgtactccta  14280
ctacgccctc cgagctgccg gtttccgagt ctctcgaaag tttgccatgt tcatcaccct  14340
gtcgcagatc actcagatgc tcatgggctg tgtcattaac tacctggtct tcaactggat  14400
gcagcatgac aatgaccagt gctactccca ctttcagaac atcttctggt cctctctcat  14460
gtacctctcc taccttctgc tcttctgcca tttcttcttt gaggcctaca ttggcaaagt  14520
```

```
gaagaaagcc accaaggctg agtaagcggc cgcaagtgtg gatggggaag tgagtgcccg  14580

gttctgtgtg cacaattggc aatccaagat ggatggattc aacacaggga tatagcgagc  14640

tacgtggtgg tgcgaggata tagcaacgga tatttatgtt tgacacttga gaatgtacga  14700

tacaagcact gtccaagtac aatactaaac atactgtaca tactcatact cgtacccggg  14760

caacggtttc acttgagtgc agtggctagt gctcttactc gtacagtgtg caatactgcg  14820

tatcatagtc tttgatgtat atcgtattca ttcatgttag ttgc                  14864
```

<210> SEQ ID NO 59
<211> LENGTH: 1174
<212> TYPE: DNA
<213> ORGANISM: Yarrowia lipolytica
<220> FEATURE:
<221> NAME/KEY: misc_feature
<223> OTHER INFORMATION: Promoter GPDIN

<400> SEQUENCE: 59

```
aaacacgcag taggatgtcc tgcacgggtc tttttgtggg gtgtggagaa aggggtgctt    60

ggagatggaa gccggtagaa ccgggctgct tgtgcttgga gatggaagcc ggtagaaccg   120

ggctgcttgg ggggatttgg ggccgctggg ctccaaagag gggtaggcat ttcgttgggg   180

ttacgtaatt gcggcatttg ggtcctgcgc gcatgtccca ttggtcagaa ttagtccgga   240

taggagactt atcagccaat cacagcgccg gatccacctg taggttgggt tgggtgggag   300

cacccctcca cagagtagag tcaaacagca gcagcaacat gatagttggg ggtgtgcgtg   360

ttaaaggaaa aaaaagaagc ttgggttata ttcccgctct atttagaggt tgcgggatag   420

acgccgacgg agggcaatgg cgctatggaa ccttgcggat atccatacgc cgcggcggac   480

tgcgtccgaa ccagctccag cagcgttttt tccgggccat tgagccgact gcgaccccgc   540

caacgtgtct tggcccacgc actcatgtca tgttggtgtt gggaggccac tttttaagta   600

gcacaaggca cctagctcgc agcaaggtgt ccgaaccaaa gaagcggctg cagtggtgca   660

aacggggcgg aaacggcggg aaaaagccac gggggcacga attgaggcac gccctcgaat   720

ttgagacgag tcacggcccc attcgcccgc gcaatggctc gccaacgccc ggtcttttgc   780

accacatcag gttaccccaa gccaaacctt tgtgttaaaa agcttaacat attataccga   840

acgtaggttt gggcgggctt gctccgtctg tccaaggcaa catttatata agggtctgca   900

tcgccggctc aattgaatct tttttcttct tctcttctct atattcattc ttgaattaaa   960

cacacatcaa catggccatc aaagtcggta ttaacggatt cggcgaatc ggacgaattg  1020

tgagtaccat agaaggtgat ggaaacatga cccaacagaa acagatgaca agtgtcatcg  1080

acccaccaga gcccaattga gctcatacta acagtcgaca acctgtcgaa ccaattgatg  1140

actccccgac aatgtactaa cacaggtcct gccc                             1174
```

<210> SEQ ID NO 60
<211> LENGTH: 6540
<212> TYPE: DNA
<213> ORGANISM: Artificial Sequence
<220> FEATURE:
<223> OTHER INFORMATION: Plasmid pZKUGPE1S

<400> SEQUENCE: 60

```
ggccgcaagt gtggatgggg aagtgagtgc ccggttctgt gtgcacaatt ggcaatccaa    60

gatggatgga ttcaacacag ggatatagcg agctacgtgg tggtgcgagg atatagcaac   120

ggatatttat gtttgacact tgagaatgta cgatacaagc actgtccaag tacaatacta   180
```

-continued

```
aacatactgt acatactcat actcgtaccc gggcaacggt ttcacttgag tgcagtggct    240
agtgctctta ctcgtacagt gtgcaatact gcgtatcata gtctttgatg tatatcgtat    300
tcattcatgt tagttgcgta cgaggaaact gtctctgaac agaagaagga ggacgtctct    360
gactacgaga actcccagta caaggagttc ctagtcccct ctcccaacga gaagctggcc    420
agaggtctgc tcatgctggc cgagctgtct tgcaagggct ctctggccac tggcgagtac    480
tccaagcaga ccattgagct tgcccgatcc gaccccgagt ttgtggttgg cttcattgcc    540
cagaaccgac ctaagggcga ctctgaggac tggcttattc tgacccccgg ggtgggtctt    600
gacgacaagg gagacgctct cggacagcag taccgaactg ttgaggatgt catgtctacc    660
ggaacggata tcataattgt cggccgaggt ctgtacggcc agaaccgaga tcctattgag    720
gaggccaagc gataccagaa ggctggctgg gaggcttacc agaagattaa ctgttagagg    780
ttagactatg gatatgtaat ttaactgtgt atatagagag cgtgcaagta tggagcgctt    840
gttcagcttg tatgatggtc agacgacctg tctgatcgag tatgtatgat actgcacaac    900
ctgtgtatcc gcatgatctg tccaatgggg catgttgttg tgtttctcga tacggagatg    960
ctgggtacag tgctaatacg ttgaactact tatacttata tgaggctcga agaaagctga   1020
cttgtgtatg acttaattaa tcgagcttgg cgtaatcatg gtcatagctg tttcctgtgt   1080
gaaattgtta tccgctcaca attccacaca acatacgagc cggaagcata aagtgtaaag   1140
cctggggtgc ctaatgagtg agctaactca cattaattgc gttgcgctca ctgcccgctt   1200
tccagtcggg aaacctgtcg tgccagctgc attaatgaat cggccaacgc gcggggagag   1260
gcggtttgcg tattgggcgc tcttccgctt cctcgctcac tgactcgctg cgctcggtcg   1320
ttcggctgcg gcgagcggta tcagctcact caaaggcggt aatacggtta tccacagaat   1380
caggggataa cgcaggaaag aacatgtgag caaaaggcca gcaaaaggcc aggaaccgta   1440
aaaaggccgc gttgctggcg tttttccata ggctccgccc ccctgacgag catcacaaaa   1500
atcgacgctc aagtcagagg tggcgaaacc cgacaggact ataaagatac caggcgtttc   1560
cccctggaag ctccctcgtg cgctctcctg ttccgaccct gccgcttacc ggatacctgt   1620
ccgcctttct cccttcggga agcgtggcgc tttctcatag ctcacgctgt aggtatctca   1680
gttcggtgta ggtcgttcgc tccaagctgg gctgtgtgca cgaacccccc gttcagcccg   1740
accgctgcgc cttatccggt aactatcgtc ttgagtccaa cccggtaaga cacgacttat   1800
cgccactggc agcagccact ggtaacagga ttagcagagc gaggtatgta ggcggtgcta   1860
cagagttctt gaagtggtgg cctaactacg gctacactag aaggacagta tttggtatct   1920
gcgctctgct gaagccagtt accttcggaa aaagagttgg tagctcttga tccggcaaac   1980
aaaccaccgc tggtagcggt ggtttttttg tttgcaagca gcagattacg cgcagaaaaa   2040
aaggatctca agaagatcct ttgatctttt ctacggggtc tgacgctcag tggaacgaaa   2100
actcacgtta agggattttg gtcatgagat tatcaaaaag gatcttcacc tagatccttt   2160
taaattaaaa atgaagtttt aaatcaatct aaagtatata tgagtaaact tggtctgaca   2220
gttaccaatg cttaatcagt gaggcaccta tctcagcgat ctgtctattt cgttcatcca   2280
tagttgcctg actccccgtc gtgtagataa ctacgatacg ggagggctta ccatctggcc   2340
ccagtgctgc aatgataccg cgagacccac gctcaccggc tccagattta tcagcaataa   2400
accagccagc cggaagggcc gagcgcagaa gtggtcctgc aactttatcc gcctccatcc   2460
agtctattaa ttgttgccgg gaagctagag taagtagttc gccagttaat agtttgcgca   2520
acgttgttgc cattgctaca ggcatcgtgg tgtcacgctc gtcgtttggt atggcttcat   2580
```

-continued

```
tcagctccgg ttcccaacga tcaaggcgag ttacatgatc ccccatgttg tgcaaaaaag   2640
cggttagctc cttcggtcct ccgatcgttg tcagaagtaa gttggccgca gtgttatcac   2700
tcatggttat ggcagcactg cataattctc ttactgtcat gccatccgta agatgctttt   2760
ctgtgactgg tgagtactca accaagtcat tctgagaata gtgtatgcgg cgaccgagtt   2820
gctcttgccc ggcgtcaata cgggataata ccgcgccaca tagcagaact ttaaaagtgc   2880
tcatcattgg aaaacgttct tcggggcgaa aactctcaag gatcttaccg ctgttgagat   2940
ccagttcgat gtaacccact cgtgcaccca actgatcttc agcatctttt actttcacca   3000
gcgtttctgg gtgagcaaaa acaggaaggc aaaatgccgc aaaaaaggga ataagggcga   3060
cacggaaatg ttgaatactc atactcttcc tttttcaata ttattgaagc atttatcagg   3120
gttattgtct catgagcgga tacatatttg aatgtattta gaaaaataaa caaatagggg   3180
ttccgcgcac atttccccga aaagtgccac ctgacgcgcc ctgtagcggc gcattaagcg   3240
cggcgggtgt ggtggttacg cgcagcgtga ccgctacact tgccagcgcc ctagcgcccg   3300
ctcctttcgc tttcttccct tcctttctcg ccacgttcgc cggctttccc cgtcaagctc   3360
taaatcgggg gctcccttta gggttccgat ttagtgcttt acggcacctc gaccccaaaa   3420
aacttgatta gggtgatggt tcacgtagtg ggccatcgcc ctgatagacg gtttttcgcc   3480
ctttgacgtt ggagtccacg ttctttaata gtggactctt gttccaaact ggaacaacac   3540
tcaaccctat ctcggtctat tcttttgatt tataagggat tttgccgatt tcggcctatt   3600
ggttaaaaaa tgagctgatt taacaaaaat ttaacgcgaa ttttaacaaa atattaacgc   3660
ttacaatttc cattcgccat tcaggctgcg caactgttgg gaagggcgat cggtgcgggc   3720
ctcttcgcta ttacgccagc tggcgaaagg gggatgtgct gcaaggcgat taagttgggt   3780
aacgccaggg ttttcccagt cacgacgttg taaaacgacg gccagtgaat tgtaatacga   3840
ctcactatag ggcgaattgg gtaccgggcc ccccctcgag gtcgacgagt atctgtctga   3900
ctcgtcattg ccgcctttgg agtacgactc caactatgag tgtgcttgga tcactttgac   3960
gatacattct tcgttggagg ctgtgggtct gacagctgcg ttttcggcgc ggttggccga   4020
caacaatatc agctgcaacg tcattgctgg ctttcatcat gatcacattt ttgtcggcaa   4080
aggcgacgcc cagagagcca ttgacgttct ttctaatttg gaccgatagc cgtatagtcc   4140
agtctatcta taagttcaac taactcgtaa ctattaccat aacatatact tcactgcccc   4200
agataaggtt ccgataaaaa gttctgcaga ctaaatttat ttcagtctcc tcttcaccac   4260
caaaatgccc tcctacgaag ctcgagtgct caagctcgtg gcagccaaga aaaccaacct   4320
gtgtgcttct ctggatgtta ccaccaccaa ggagctcatt gagcttgccg ataaggtcgg   4380
accttatgtg tgcatgatca aaacccatat cgacatcatt gacgacttca cctacgccgg   4440
cactgtgctc cccctcaagg aacttgctct taagcacggt ttcttcctgt tcgaggacag   4500
aaagttcgca gatattggca acactgtcaa gcaccagtac cggtgtcacc gaatcgccga   4560
gtggtccgat atcaccaacg cccacggtgt acccggaacc ggaatcgatg cgtatctgtg   4620
ggacatgtgg tcgttgcgcc attatgtaag cagcgtgtac tcctctgact gtccatatgg   4680
tttgctccat ctcaccctca tcgttttcat tgttcacagg cggccacaaa aaaactgtct   4740
tctctccttc tctcttcgcc ttagtctact cggaccagtt ttagtttagc ttggcgccac   4800
tggataaatg agacctcagg ccttgtgatg aggaggtcac ttatgaagca tgttaggagg   4860
tgcttgtatg gatagagaag cacccaaaat aataagaata ataataaaac agggggcgtt   4920
```

-continued

```
gtcatttcat atcgtgtttt caccatcaat acacctccaa acaatgccct tcatgtggcc   4980
agccccaata ttgtcctgta gttcaactct atgcagctcg tatcttattg agcaagtaaa   5040
actctgtcag ccgatattgc ccgacccgcg acaagggtca acaaggtggt gtaaggcctt   5100
cgcagaagtc aaaactgtgc caaacaaaca tctagagtct ctttggtgtt tctcgcatat   5160
atttwatcgg ctgtcttacg tatttgcgcc tcggtaccgg actaatttcg gatcatcccc   5220
aatacgcttt ttcttcgcag ctgtcaacag tgtccatgat ctatccacct aaatgggtca   5280
tatgaggcgt ataatttcgt ggtgctgata ataattccca tatatttgac acaaaacttc   5340
ccccccctaga catacatctc acaatctcac ttcttgtgct tctgtcacac atctcctcca   5400
gctgacttca actcacacct ctgccccagt tggtctacag cggtataagg tttctccgca   5460
tagaggtgca ccactcctcc cgatacttgt ttgtgtgact tgtgggtcac gacatatata   5520
tctacacaca ttgcgccacc ctttggttct tccagcacaa caaaaacacg acacgctaac   5580
catggagtcc attgctccct tcctgccctc caagatgcct caggacctgt tcatggacct   5640
cgccagcgct atcggtgtcc gagctgctcc ctacgtcgat cccctggagg ctgccctggt   5700
tgcccaggcc gagaagtaca ttcccaccat tgtccatcac actcgaggct tcctggttgc   5760
cgtggagtct cccctggctc gagagctgcc tctgatgaac cccttccacg tgctcctgat   5820
cgtgctcgcc tacctggtca ccgtgtttgt gggtatgcag atcatgaaga actttgaacg   5880
attcgaggtc aagaccttct ccctcctgca caacttctgt ctggtctcca tctccgccta   5940
catgtgcggt ggcatcctgt acgaggctta tcaggccaac tatggactgt ttgagaacgc   6000
tgccgatcac accttcaagg gtctccctat ggctaagatg atctggctct tctacttctc   6060
caagatcatg gagtttgtcg acaccatgat catggtcctc aagaagaaca accgacagat   6120
ttcctttctg cacgtgtacc accactcttc catcttcacc atctggtggc tggtcacctt   6180
cgttgctccc aacggtgaag cctacttctc tgctgccctg aactccttca tccacgtcat   6240
catgtacggc tactactttc tgtctgccct gggcttcaag caggtgtcgt tcatcaagtt   6300
ctacatcact cgatcccaga tgacccagtt ctgcatgatg tctgtccagt cttcctggga   6360
catgtacgcc atgaaggtcc ttggccgacc tggatacccc ttcttcatca ccgctctgct   6420
ctggttctac atgtggacca tgctcggtct cttctacaac ttttaccgaa agaacgccaa   6480
gctcgccaag caggccaagg ctgacgctgc caaggagaag gccagaaagc tccagtaagc   6540
```

```
<210> SEQ ID NO 61
<211> LENGTH: 7323
<212> TYPE: DNA
<213> ORGANISM: Artificial Sequence
<220> FEATURE:
<223> OTHER INFORMATION: Plasmid pZUF-MOD-1

<400> SEQUENCE: 61
```

```
gtacgagccg gaagcataaa gtgtaaagcc tggggtgcct aatgagtgag ctaactcaca     60
ttaattgcgt tgcgctcact gcccgctttc cagtcgggaa acctgtcgtg ccagctgcat    120
taatgaatcg gccaacgcgc ggggagaggc ggtttgcgta ttgggcgctc ttccgcttcc    180
tcgctcactg actcgctgcg ctcggtcgtt cggctgcggc gagcggtatc agctcactca    240
aaggcggtaa tacggttatc cacagaatca ggggataacg caggaaagaa catgtgagca    300
aaaggccagc aaaaggccag gaaccgtaaa aaggccgcgt tgctggcgtt tttccatagg    360
ctccgccccc ctgacgagca tcacaaaaat cgacgctcaa gtcagaggtg gcgaaacccg    420
acaggactat aaagatacca ggcgtttccc cctggaagct ccctcgtgcg ctctcctgtt    480
```

-continued

```
ccgaccctgc cgcttaccgg atacctgtcc gcctttctcc cttcgggaag cgtggcgctt    540
tctcatagct cacgctgtag gtatctcagt tcggtgtagg tcgttcgctc caagctgggc    600
tgtgtgcacg aaccccccgt tcagcccgac cgctgcgcct tatccggtaa ctatcgtctt    660
gagtccaacc cggtaagaca cgacttatcg ccactggcag cagccactgg taacaggatt    720
agcagagcga ggtatgtagg cggtgctaca gagttcttga agtggtggcc taactacggc    780
tacactagaa ggacagtatt tggtatctgc gctctgctga agccagttac cttcggaaaa    840
agagttggta gctcttgatc cggcaaacaa accaccgctg gtagcggtgg tttttttgtt    900
tgcaagcagc agattacgcg cagaaaaaaa ggatctcaag aagatccttt gatcttttct    960
acggggtctg acgctcagtg gaacgaaaac tcacgttaag ggattttggt catgagatta   1020
tcaaaaagga tcttcaccta gatcctttta aattaaaaat gaagttttaa atcaatctaa   1080
agtatatatg agtaaacttg gtctgacagt taccaatgct taatcagtga ggcacctatc   1140
tcagcgatct gtctatttcg ttcatccata gttgcctgac tccccgtcgt gtagataact   1200
acgatacggg agggcttacc atctggcccc agtgctgcaa tgataccgcg agacccacgc   1260
tcaccggctc cagatttatc agcaataaac cagccagccg gaagggccga gcgcagaagt   1320
ggtcctgcaa ctttatccgc ctccatccag tctattaatt gttgccggga agctagagta   1380
agtagttcgc cagttaatag tttgcgcaac gttgttgcca ttgctacagg catcgtggtg   1440
tcacgctcgt cgtttggtat ggcttcattc agctccggtt cccaacgatc aaggcgagtt   1500
acatgatccc ccatgttgtg caaaaaagcg gttagctcct tcggtcctcc gatcgttgtc   1560
agaagtaagt tggccgcagt gttatcactc atggttatgg cagcactgca taattctctt   1620
actgtcatgc catccgtaag atgcttttct gtgactggtg agtactcaac caagtcattc   1680
tgagaatagt gtatgcggcg accgagttgc tcttgcccgg cgtcaatacg ggataatacc   1740
gcgccacata gcagaacttt aaaagtgctc atcattggaa aacgttcttc ggggcgaaaa   1800
ctctcaagga tcttaccgct gttgagatcc agttcgatgt aacccactcg tgcacccaac   1860
tgatcttcag catcttttac tttcaccagc gtttctgggt gagcaaaaac aggaaggcaa   1920
aatgccgcaa aaaagggaat aagggcgaca cggaaatgtt gaatactcat actcttcctt   1980
tttcaatatt attgaagcat ttatcagggt tattgtctca tgagcggata catatttgaa   2040
tgtatttaga aaaataaaca aataggggtt ccgcgcacat ttccccgaaa agtgccacct   2100
gacgcgccct gtagcggcgc attaagcgcg gcgggtgtgg tggttacgcg cagcgtgacc   2160
gctacacttg ccagcgccct agcgcccgct cctttcgctt tcttcccttc ctttctcgcc   2220
acgttcgccg gctttccccg tcaagctcta aatcgggggc tccctttagg gttccgattt   2280
agtgctttac ggcacctcga ccccaaaaaa cttgattagg gtgatggttc acgtagtggg   2340
ccatcgccct gatagacggt ttttcgccct ttgacgttgg agtccacgtt ctttaatagt   2400
ggactcttgt tccaaactgg aacaacactc aaccctatct cggtctattc ttttgattta   2460
taagggattt tgccgatttc ggcctattgg ttaaaaaatg agctgattta acaaaaattt   2520
aacgcgaatt ttaacaaaat attaacgctt acaatttcca ttcgccattc aggctgcgca   2580
actgttggga agggcgatcg gtgcgggcct cttcgctatt acgccagctg gcgaaagggg   2640
gatgtgctgc aaggcgatta agttgggtaa cgccagggtt ttcccagtca cgacgttgta   2700
aaacgacggc cagtgaattg taatacgact cactataggg cgaattgggt accgggcccc   2760
ccctcgaggt cgatggtgtc gataagcttg atatcgaatt catgtcacac aaaccgatct   2820
```

-continued

```
tcgcctcaag gaaacctaat tctacatccg agagactgcc gagatccagt ctacactgat   2880
taattttcgg gccaataatt taaaaaaatc gtgttatata atattatatg tattatatat   2940
atacatcatg atgatactga cagtcatgtc ccattgctaa atagacagac tccatctgcc   3000
gcctccaact gatgttctca atatttaagg ggtcatctcg cattgtttaa taataaacag   3060
actccatcta ccgcctccaa atgatgttct caaaatatat tgtatgaact tatttttatt   3120
acttagtatt attagacaac ttacttgctt tatgaaaaac acttcctatt taggaaacaa   3180
tttataatgg cagttcgttc atttaacaat ttatgtagaa taaatgttat aaatgcgtat   3240
gggaaatctt aaatatggat agcataaatg atatctgcat tgcctaattc gaaatcaaca   3300
gcaacgaaaa aaatcccttg tacaacataa atagtcatcg agaaatatca actatcaaag   3360
aacagctatt cacacgttac tattgagatt attattggac gagaatcaca cactcaactg   3420
tctttctctc ttctagaaat acaggtacaa gtatgtacta ttctcattgt tcatacttct   3480
agtcatttca tcccacatat tccttggatt tctctccaat gaatgacatt ctatcttgca   3540
aattcaacaa ttataataag atataccaaa gtagcggtat agtggcaatc aaaaagcttc   3600
tctggtgtgc ttctcgtatt tatttttatt ctaatgatcc attaaaggta tatatttatt   3660
tcttgttata taatcctttt gtttattaca tgggctggat acataaaggt attttgattt   3720
aatttttttgc ttaaattcaa tccccccctcg ttcagtgtca actgtaatgg taggaaatta   3780
ccatactttt gaagaagcaa aaaaaatgaa agaaaaaaaa aatcgtattt ccaggttaga   3840
cgttccgcag aatctagaat gcggtatgcg gtacattgtt cttcgaacgt aaaagttgcg   3900
ctccctgaga tattgtacat ttttgctttt acaagtacaa gtacatcgta caactatgta   3960
ctactgttga tgcatccaca acagtttgtt ttgttttttt ttgttttttt tttttctaat   4020
gattcattac cgctatgtat acctacttgt acttgtagta agccgggtta ttggcgttca   4080
attaatcata gacttatgaa tctgcacggt gtgcgctgcg agttactttt agcttatgca   4140
tgctacttgg gtgtaatatt gggatctgtt cggaaatcaa cggatgctca atcgatttcg   4200
acagtaatta attaagtcat acacaagtca gctttcttcg agcctcatat aagtataagt   4260
agttcaacgt attagcactg tacccagcat ctccgtatcg agaaacacaa caacatgccc   4320
cattggacag atcatgcgga tacacaggtt gtgcagtatc atacatactc gatcagacag   4380
gtcgtctgac catcatacaa gctgaacaag cgctccatac ttgcacgctc tctatataca   4440
cagttaaatt acatatccat agtctaacct ctaacagtta atcttctggt aagcctccca   4500
gccagccttc tggtatcgct tggcctcctc aataggatct cggttctggc cgtacagacc   4560
tcggccgaca attatgatat ccgttccggt agacatgaca tcctcaacag ttcggtactg   4620
ctgtccgaga gcgtctccct tgtcgtcaag acccaccccg gggtcagaa taagccagtc   4680
ctcagagtcg cccttaggtc ggttctgggc aatgaagcca accacaaact cggggtcgga   4740
tcgggcaagc tcaatggtct gcttggagta ctcgccagtg gccagagagc ccttgcaaga   4800
cagctcggcc agcatgagca gacctctggc cagcttctcg ttgggagagg ggactaggaa   4860
ctccttgtac tgggagttct cgtagtcaga gacgtcctcc ttcttctgtt cagagacagt   4920
ttcctcggca ccagctcgca ggccagcaat gattccggtt ccgggtacac cgtgggcgtt   4980
ggtgatatcg gaccactcgg cgattcggtg acaccggtac tggtgcttga cagtgttgcc   5040
aatatctgcg aactttctgt cctcgaacag gaagaaaccg tgcttaagag caagttcctt   5100
gagggggagc acagtgccgg cgtaggtgaa gtcgtcaatg atgtcgatat gggttttgat   5160
catgcacaca taaggtccga ccttatcggc aagctcaatg agctccttgg tggtggtaac   5220
```

-continued

```
atccagagaa gcacacaggt tggttttctt ggctgccacg agcttgagca ctcgagcggc   5280
aaaggcggac ttgtggacgt tagctcgagc ttcgtaggag ggcattttgg tggtgaagag   5340
gagactgaaa taaatttagt ctgcagaact ttttatcgga accttatctg ggcagtgaa    5400
gtatatgtta tggtaatagt tacgagttag ttgaacttat agatagactg gactatacgg   5460
ctatcggtcc aaattagaaa gaacgtcaat ggctctctgg gcgtcgcctt tgccgacaaa   5520
aatgtgatca tgatgaaagc cagcaatgac gttgcagctg atattgttgt cggccaaccg   5580
cgccgaaaac gcagctgtca gacccacagc ctccaacgaa gaatgtatcg tcaaagtgat   5640
ccaagcacac tcatagttgg agtcgtactc caaaggcggc aatgacgagt cagacagata   5700
ctcgtcgact caggcgacga cggaattcct gcagcccatc tgcagaattc aggagagacc   5760
gggttggcgg cgtatttgtg tcccaaaaaa cagccccaat tgccccggag aagacggcca   5820
ggccgcctag atgacaaatt caacaactca cagctgactt tctgccattg ccactagggg   5880
ggggcctttt tatatggcca agccaagctc tccacgtcgg ttgggctgca cccaacaata   5940
aatgggtagg gttgcaccaa caaagggatg ggatgggggg tagaagatac gaggataacg   6000
gggctcaatg gcacaaataa gaacgaatac tgccattaag actcgtgatc cagcgactga   6060
caccattgca tcatctaagg gcctcaaaac tacctcggaa ctgctgcgct gatctggaca   6120
ccacagaggt tccgagcact ttaggttgca ccaaatgtcc caccaggtgc aggcagaaaa   6180
cgctggaaca gcgtgtacag tttgtcttaa caaaaagtga gggcgctgag gtcgagcagg   6240
gtggtgtgac ttgttatagc ctttagagct gcgaaagcgc gtatggattt ggctcatcag   6300
gccagattga gggtctgtgg acacatgtca tgttagtgta cttcaatcgc cccctggata   6360
tagccccgac aataggccgt ggcctcattt ttttgccttc cgcacatttc cattgctcgg   6420
tacccacacc ttgcttctcc tgcacttgcc aaccttaata ctggtttaca ttgaccaaca   6480
tcttacaagc ggggggcttg tctagggtat atataaacag tggctctccc aatcggttgc   6540
cagtctcttt tttcctttct ttccccacag attcgaaatc taaactacac atcacacaat   6600
gcctgttact gacgtcctta agcgaaagtc cggtgtcatc gtcggcgacg atgtccgagc   6660
cgtgagtatc cacgacaaga tcagtgtcga gacgacgcgt tttgtgtaat gacacaatcc   6720
gaaagtcgct agcaacacac actctctaca caaactaacc cagctctcca tggatccagg   6780
cctgttaacg gccattacgg cctgcaggat ccgaaaaaac ctcccacacc tcccccctgaa  6840
cctgaaacat aaaatgaatg caattgttgt tgttaacttg tttattgcag cttataatgg   6900
ttacaaataa agcaatagca tcacaaattt cacaaataaa gcattttttt cactgcattc   6960
tagttgtggt ttgtccaaac tcatcaatgt atcttatcat gtctgcggcc gcaagtgtgg   7020
atggggaagt gagtgcccgg ttctgtgtgc acaattggca atccaagatg gatggattca   7080
acacagggat atagcgagct acgtggtggt gcgaggatat agcaacggat atttatgttt   7140
gacacttgag aatgtacgat acaagcactg tccaagtaca atactaaaca tactgtacat   7200
actcatactc gtacccgggc aacggtttca cttgagtgca gtggctagtg ctcttactcg   7260
tacagtgtgc aatactgcgt atcatagtct ttgatgtata tcgtattcat tcatgttagt   7320
tgc                                                                 7323
```

<210> SEQ ID NO 62
<211> LENGTH: 28
<212> TYPE: DNA
<213> ORGANISM: Artificial Sequence
<220> FEATURE:

<223> OTHER INFORMATION: Primer PZUF-mod1

<400> SEQUENCE: 62
gatcccatgg atccaggcct gttaacgg 28

<210> SEQ ID NO 63
<211> LENGTH: 32
<212> TYPE: DNA
<213> ORGANISM: Artificial Sequence
<220> FEATURE:
<223> OTHER INFORMATION: Primer PZUF-mod2

<400> SEQUENCE: 63
gatcgcggcc gcagacatga taagatacat tg 32

<210> SEQ ID NO 64
<211> LENGTH: 253
<212> TYPE: DNA
<213> ORGANISM: Artificial Sequence
<220> FEATURE:
<223> OTHER INFORMATION: 253 bp "stuffer" DNA fragment for construction of pZUF-MOD-1

<400> SEQUENCE: 64
gatcccatgg atccaggcct gttaacggcc attacggcct gcaggatccg aaaaaacctc 60
ccacacctcc ccctgaacct gaaacataaa atgaatgcaa ttgttgttgt taacttgttt 120
attgcagctt ataatggtta caaataaagc aatagcatca caaatttcac aaataaagca 180
tttttttcac tgcattctag ttgtggtttg tccaaactca tcaatgtatc ttatcatgtc 240
tgcggccgcg atc 253

<210> SEQ ID NO 65
<211> LENGTH: 8165
<212> TYPE: DNA
<213> ORGANISM: Artificial Sequence
<220> FEATURE:
<223> OTHER INFORMATION: Plasmid pZUF17

<400> SEQUENCE: 65
gtacgagccg gaagcataaa gtgtaaagcc tggggtgcct aatgagtgag ctaactcaca 60
ttaattgcgt tgcgctcact gcccgctttc cagtcgggaa acctgtcgtg ccagctgcat 120
taatgaatcg gccaacgcgc ggggagaggc ggtttgcgta ttgggcgctc ttccgcttcc 180
tcgctcactg actcgctgcg ctcggtcgtt cggctgcggc gagcggtatc agctcactca 240
aaggcggtaa tacggttatc cacagaatca ggggataacg caggaaagaa catgtgagca 300
aaaggccagc aaaaggccag gaaccgtaaa aaggccgcgt tgctggcgtt tttccatagg 360
ctccgccccc ctgacgagca tcacaaaaat cgacgctcaa gtcagaggtg gcgaaacccg 420
acaggactat aaagatacca ggcgtttccc cctggaagct ccctcgtgcg ctctcctgtt 480
ccgaccctgc cgcttaccgg atacctgtcc gcctttctcc cttcgggaag cgtggcgctt 540
tctcatagct cacgctgtag gtatctcagt tcggtgtagg tcgttcgctc caagctgggc 600
tgtgtgcacg aaccccccgt tcagcccgac cgctgcgcct tatccggtaa ctatcgtctt 660
gagtccaacc cggtaagaca cgacttatcg ccactggcag cagccactgg taacaggatt 720
agcagagcga ggtatgtagg cggtgctaca gagttcttga agtggtggcc taactacggc 780
tacactagaa ggacagtatt tggtatctgc gctctgctga agccagttac cttcggaaaa 840
agagttggta gctcttgatc cggcaaacaa accaccgctg gtagcggtgg tttttttgtt 900

-continued

```
tgcaagcagc agattacgcg cagaaaaaaa ggatctcaag aagatccttt gatcttttct    960

acggggtctg acgctcagtg gaacgaaaac tcacgttaag ggattttggt catgagatta   1020

tcaaaaagga tcttcaccta gatcctttta aattaaaaat gaagttttaa atcaatctaa   1080

agtatatatg agtaaacttg gtctgacagt taccaatgct taatcagtga ggcacctatc   1140

tcagcgatct gtctatttcg ttcatccata gttgcctgac tccccgtcgt gtagataact   1200

acgatacggg agggcttacc atctggcccc agtgctgcaa tgataccgcg agacccacgc   1260

tcaccggctc cagatttatc agcaataaac cagccagccg gaagggccga gcgcagaagt   1320

ggtcctgcaa ctttatccgc ctccatccag tctattaatt gttgccggga agctagagta   1380

agtagttcgc cagttaatag tttgcgcaac gttgttgcca ttgctacagg catcgtggtg   1440

tcacgctcgt cgtttggtat ggcttcattc agctccggtt cccaacgatc aaggcgagtt   1500

acatgatccc ccatgttgtg caaaaaagcg gttagctcct tcggtcctcc gatcgttgtc   1560

agaagtaagt tggccgcagt gttatcactc atggttatgg cagcactgca taattctctt   1620

actgtcatgc catccgtaag atgcttttct gtgactggtg agtactcaac caagtcattc   1680

tgagaatagt gtatgcggcg accgagttgc tcttgcccgg cgtcaatacg ggataatacc   1740

gcgccacata gcagaacttt aaaagtgctc atcattggaa aacgttcttc ggggcgaaaa   1800

ctctcaagga tcttaccgct gttgagatcc agttcgatgt aacccactcg tgcacccaac   1860

tgatcttcag catcttttac tttcaccagc gtttctgggt gagcaaaaac aggaaggcaa   1920

aatgccgcaa aaaagggaat aagggcgaca cggaaatgtt gaatactcat actcttcctt   1980

tttcaatatt attgaagcat ttatcagggt tattgtctca tgagcggata catatttgaa   2040

tgtatttaga aaaataaaca aataggggtt ccgcgcacat ttccccgaaa agtgccacct   2100

gacgcgccct gtagcggcgc attaagcgcg gcgggtgtgg tggttacgcg cagcgtgacc   2160

gctacacttg ccagcgccct agcgcccgct cctttcgctt tcttcccttc ctttctcgcc   2220

acgttcgccg gctttccccg tcaagctcta aatcgggggc tccctttagg gttccgattt   2280

agtgctttac ggcacctcga ccccaaaaaa cttgattagg gtgatggttc acgtagtggg   2340

ccatcgccct gatagacggt ttttcgccct ttgacgttgg agtccacgtt ctttaatagt   2400

ggactcttgt tccaaactgg aacaacactc aaccctatct cggtctattc ttttgattta   2460

taagggattt tgccgatttc ggcctattgg ttaaaaaatg agctgattta acaaaaattt   2520

aacgcgaatt ttaacaaaat attaacgctt acaatttcca ttcgccattc aggctgcgca   2580

actgttggga agggcgatcg gtgcgggcct cttcgctatt acgccagctg gcgaaagggg   2640

gatgtgctgc aaggcgatta agttgggtaa cgccagggtt ttcccagtca cgacgttgta   2700

aaacgacggc cagtgaattg taatacgact cactataggg cgaattgggt accgggcccc   2760

ccctcgaggt cgatggtgtc gataagcttg atatcgaatt catgtcacac aaaccgatct   2820

tcgcctcaag gaaacctaat tctacatccg agagactgcc gagatccagt ctacactgat   2880

taattttcgg gccaataatt taaaaaaatc gtgttatata atattatatg tattatatat   2940

atacatcatg atgatactga cagtcatgtc ccattgctaa atagacagac tccatctgcc   3000

gcctccaact gatgttctca atatttaagg ggtcatctcg cattgtttaa taataaacag   3060

actccatcta ccgcctccaa atgatgttct caaaatatat tgtatgaact tatttttatt   3120

acttagtatt attagacaac ttacttgctt tatgaaaaac acttcctatt taggaaacaa   3180

tttataatgg cagttcgttc atttaacaat ttatgtagaa taaatgttat aaatgcgtat   3240

gggaaatctt aaatatggat agcataaatg atatctgcat tgcctaattc gaaatcaaca   3300
```

-continued

```
gcaacgaaaa aaatcccttg tacaacataa atagtcatcg agaaatatca actatcaaag   3360
aacagctatt cacacgttac tattgagatt attattggac gagaatcaca cactcaactg   3420
tctttctctc ttctagaaat acaggtacaa gtatgtacta ttctcattgt tcatacttct   3480
agtcatttca tcccacatat tccttggatt tctctccaat gaatgacatt ctatcttgca   3540
aattcaacaa ttataataag atataccaaa gtagcggtat agtggcaatc aaaaagcttc   3600
tctggtgtgc ttctcgtatt tatttttatt ctaatgatcc attaaaggta tatatttatt   3660
tcttgttata taatcctttt gtttattaca tgggctggat acataaaggt attttgattt   3720
aatttttttgc ttaaattcaa tccccccctcg ttcagtgtca actgtaatgg taggaaatta   3780
ccatactttt gaagaagcaa aaaaaatgaa agaaaaaaaa aatcgtattt ccaggttaga   3840
cgttccgcag aatctagaat gcggtatgcg gtacattgtt cttcgaacgt aaaagttgcg   3900
ctccctgaga tattgtacat ttttgctttt acaagtacaa gtacatcgta caactatgta   3960
ctactgttga tgcatccaca acagtttgtt ttgttttttt ttgttttttt tttttctaat   4020
gattcattac cgctatgtat acctacttgt acttgtagta agccgggtta ttggcgttca   4080
attaatcata gacttatgaa tctgcacggt gtgcgctgcg agttactttt agcttatgca   4140
tgctacttgg gtgtaatatt gggatctgtt cggaaatcaa cggatgctca atcgatttcg   4200
acagtaatta attaagtcat acacaagtca gctttcttcg agcctcatat aagtataagt   4260
agttcaacgt attagcactg tacccagcat ctccgtatcg agaaacacaa caacatgccc   4320
cattggacag atcatgcgga tacacaggtt gtgcagtatc atacatactc gatcagacag   4380
gtcgtctgac catcatacaa gctgaacaag cgctccatac ttgcacgctc tctatataca   4440
cagttaaatt acatatccat agtctaacct ctaacagtta atcttctggt aagcctccca   4500
gccagccttc tggtatcgct tggcctcctc aataggatct cggttctggc cgtacagacc   4560
tcggccgaca attatgatat ccgttccggt agacatgaca tcctcaacag ttcggtactg   4620
ctgtccgaga gcgtctccct tgtcgtcaag acccaccccg ggggtcagaa taagccagtc   4680
ctcagagtcg cccttaggtc ggttctgggc aatgaagcca accacaaact cggggtcgga   4740
tcgggcaagc tcaatggtct gcttggagta ctcgccagtg gccagagagc ccttgcaaga   4800
cagctcggcc agcatgagca gacctctggc cagcttctcg ttgggagagg ggactaggaa   4860
ctccttgtac tgggagttct cgtagtcaga gacgtcctcc ttcttctgtt cagagacagt   4920
ttcctcggca ccagctcgca ggccagcaat gattccggtt ccgggtacac cgtgggcgtt   4980
ggtgatatcg gaccactcgg cgattcggtg acaccggtac tggtgcttga cagtgttgcc   5040
aatatctgcg aactttctgt cctcgaacag gaagaaaccg tgcttaagag caagttcctt   5100
gagggggagc acagtgccgg cgtaggtgaa gtcgtcaatg atgtcgatat gggttttgat   5160
catgcacaca taaggtccga ccttatcggc aagctcaatg agctccttgg tggtggtaac   5220
atccagagaa gcacacaggt tggttttctt ggctgccacg agcttgagca ctcgagcggc   5280
aaaggcggac ttgtggacgt tagctcgagc ttcgtaggag ggcattttgg tggtgaagag   5340
gagactgaaa taaatttagt ctgcagaact ttttatcgga accttatctg ggcagtgaa   5400
gtatatgtta tggtaatagt tacgagttag ttgaacttat agatagactg gactatacgg   5460
ctatcggtcc aaattagaaa gaacgtcaat ggctctctgg gcgtcgcctt tgccgacaaa   5520
aatgtgatca tgatgaaagc cagcaatgac gttgcagctg atattgttgt cggccaaccg   5580
cgccgaaaac gcagctgtca gacccacagc ctccaacgaa gaatgtatcg tcaaagtgat   5640
```

-continued

```
ccaagcacac tcatagttgg agtcgtactc caaaggcggc aatgacgagt cagacagata   5700
ctcgtcgact caggcgacga cggaattcct gcagcccatc tgcagaattc aggagagacc   5760
gggttggcgg cgtatttgtg tcccaaaaaa cagccccaat tgccccggag aagacggcca   5820
ggccgcctag atgacaaatt caacaactca cagctgactt tctgccattg ccactagggg   5880
ggggcctttt tatatggcca agccaagctc tccacgtcgg ttgggctgca cccaacaata   5940
aatgggtagg gttgcaccaa caaagggatg ggatgggggg tagaagatac gaggataacg   6000
gggctcaatg gcacaaataa gaacgaatac tgccattaag actcgtgatc cagcgactga   6060
caccattgca tcatctaagg gcctcaaaac tacctcggaa ctgctgcgct gatctggaca   6120
ccacagaggt tccgagcact ttaggttgca ccaaatgtcc caccaggtgc aggcagaaaa   6180
cgctggaaca gcgtgtacag tttgtcttaa caaaaagtga gggcgctgag gtcgagcagg   6240
gtggtgtgac ttgttatagc ctttagagct gcgaaagcgc gtatggattt ggctcatcag   6300
gccagattga gggtctgtgg acacatgtca tgttagtgta cttcaatcgc cccctggata   6360
tagccccgac aataggccgt ggcctcattt ttttgccttc cgcacatttc cattgctcgg   6420
tacccacacc ttgcttctcc tgcacttgcc aaccttaata ctggtttaca ttgaccaaca   6480
tcttacaagc ggggggcttg tctagggtat atataaacag tggctctccc aatcggttgc   6540
cagtctcttt tttcctttct ttccccacag attcgaaatc taaactacac atcacacaat   6600
gcctgttact gacgtcctta agcgaaagtc cggtgtcatc gtcggcgacg atgtccgagc   6660
cgtgagtatc cacgacaaga tcagtgtcga gacgacgcgt tttgtgtaat gacacaatcc   6720
gaaagtcgct agcaacacac actctctaca caaactaacc cagctctcca tggctgagga   6780
taagaccaag gtcgagttcc ctaccctgac tgagctgaag cactctatcc ctaacgcttg   6840
ctttgagtcc aacctcggac tctcgctcta ctacactgcc cgagcgatct tcaacgcatc   6900
tgcctctgct gctctgctct acgctgcccg atctactccc ttcattgccg ataacgttct   6960
gctccacgct ctggtttgcg ccacctacat ctacgtgcag ggtgtcatct tctggggttt   7020
ctttaccgtc ggtcacgact gtggtcactc tgccttctcc cgataccact ccgtcaactt   7080
catcattggc tgcatcatgc actctgccat tctgactccc ttcgagtcct ggcgagtgac   7140
ccaccgacac catcacaaga acactggcaa cattgataag gacgagatct tctaccctca   7200
tcggtccgtc aaggacctcc aggacgtgcg acaatgggtc tacaccctcg gaggtgcttg   7260
gtttgtctac ctgaaggtcg gatatgctcc tcgaaccatg tcccactttg accccctgga   7320
ccctctcctg cttcgacgag cctccgctgt catcgtgtcc ctcggagtct gggctgcctt   7380
cttcgctgcc tacgcctacc tcacatactc gctcggcttt gccgtcatgg gcctctacta   7440
ctatgctcct ctctttgtct ttgcttcgtt cctcgtcatt actaccttct tgcatcacaa   7500
cgacgaagct actccctggt acggtgactc ggagtggacc tacgtcaagg gcaacctgag   7560
ctccgtcgac cgatcgtacg gagctttcgt ggacaacctg tctcaccaca ttggcaccca   7620
ccaggtccat cacttgttcc ctatcattcc ccactacaag ctcaacgaag ccaccaagca   7680
ctttgctgcc gcttaccctc acctcgtgag acgtaacgac gagcccatca ttactgcctt   7740
cttcaagacc gctcacctct ttgtcaacta cggagctgtg cccgagactg ctcagatttt   7800
caccctcaaa gagtctgccg ctgcagccaa ggccaagagc gactaagcgg ccgcaagtgt   7860
ggatggggaa gtgagtgccc ggttctgtgt gcacaattgg caatccaaga tggatggatt   7920
caacacaggg atatagcgag ctacgtggtg gtgcgaggat atagcaacgg atatttatgt   7980
ttgacacttg agaatgtacg atacaagcac tgtccaagta caatactaaa catactgtac   8040
```

```
atactcatac tcgtacccgg gcaacggttt cacttgagtg cagtggctag tgctcttact   8100

cgtacagtgt gcaatactgc gtatcatagt ctttgatgta tatcgtattc attcatgtta   8160

gttgc                                                               8165


<210> SEQ ID NO 66
<211> LENGTH: 32
<212> TYPE: DNA
<213> ORGANISM: Artificial Sequence
<220> FEATURE:
<223> OTHER INFORMATION: Primer mgpat-cdna-5

<400> SEQUENCE: 66

gatcggatcc tcagatctac gactttgtgt cg                                   32


<210> SEQ ID NO 67
<211> LENGTH: 33
<212> TYPE: DNA
<213> ORGANISM: Artificial Sequence
<220> FEATURE:
<223> OTHER INFORMATION: Primer MGPAT-cDNA-R

<400> SEQUENCE: 67

gatcgcggcc gcctaaatgt cttttgactt ggc                                  33


<210> SEQ ID NO 68
<211> LENGTH: 9239
<212> TYPE: DNA
<213> ORGANISM: Artificial Sequence
<220> FEATURE:
<223> OTHER INFORMATION: Plasmid pMGPAT-17
<220> FEATURE:
<221> NAME/KEY: misc_feature
<222> LOCATION: (1510)..(1510)
<223> OTHER INFORMATION: n is a, c, g, or t
<220> FEATURE:
<221> NAME/KEY: misc_feature
<222> LOCATION: (1577)..(1577)
<223> OTHER INFORMATION: n is a, c, g, or t
<220> FEATURE:
<221> NAME/KEY: misc_feature
<222> LOCATION: (1584)..(1584)
<223> OTHER INFORMATION: n is a, c, g, or t
<220> FEATURE:
<221> NAME/KEY: misc_feature
<222> LOCATION: (1712)..(1712)
<223> OTHER INFORMATION: n is a, c, g, or t
<220> FEATURE:
<221> NAME/KEY: misc_feature
<222> LOCATION: (1729)..(1729)
<223> OTHER INFORMATION: n is a, c, g, or t
<220> FEATURE:
<221> NAME/KEY: misc_feature
<222> LOCATION: (1759)..(1759)
<223> OTHER INFORMATION: n is a, c, g, or t
<220> FEATURE:
<221> NAME/KEY: misc_feature
<222> LOCATION: (1820)..(1820)
<223> OTHER INFORMATION: n is a, c, g, or t
<220> FEATURE:
<221> NAME/KEY: misc_feature
<222> LOCATION: (1822)..(1822)
<223> OTHER INFORMATION: n is a, c, g, or t
<220> FEATURE:
<221> NAME/KEY: misc_feature
<222> LOCATION: (1831)..(1831)
<223> OTHER INFORMATION: n is a, c, g, or t
<220> FEATURE:
<221> NAME/KEY: misc_feature
<222> LOCATION: (1841)..(1841)
<223> OTHER INFORMATION: n is a, c, g, or t
<220> FEATURE:
```

<221> NAME/KEY: misc_feature
<222> LOCATION: (1913)..(1913)
<223> OTHER INFORMATION: n is a, c, g, or t
<220> FEATURE:
<221> NAME/KEY: misc_feature
<222> LOCATION: (1941)..(1941)
<223> OTHER INFORMATION: n is a, c, g, or t
<220> FEATURE:
<221> NAME/KEY: misc_feature
<222> LOCATION: (2033)..(2033)
<223> OTHER INFORMATION: n is a, c, g, or t
<220> FEATURE:
<221> NAME/KEY: misc_feature
<222> LOCATION: (2130)..(2130)
<223> OTHER INFORMATION: n is a, c, g, or t

<400> SEQUENCE: 68

```
ccatggatcc tcagatctac gactttgtgt cgttcttctt cactatcctg ctcgacatct     60

tcttcaggga gattcgtccc agaggcgcac acaagattcc acaaaaaggc cccgtgatct    120

ttgtcgccgc tcctcatgcc aatcagtttg tcgatcctct cgtcttgatg cgagagtgcg    180

gccgcagagt ctcattcctt gcagccaaaa agtccatgga ccgccggtgg attggtgcaa    240

tggcacgctc gatgaatgcg attcctgttg agcgcccccca ggaccttgct aaagccggct    300

cgggaatcat caaacttctg gatcgttatg gcgaccctct tcgggtcacc ggtgtcggca    360

ctaaattcac aaaggagctg cttgtgggcg accagatctc ccttccaaag gacgtcggtg    420

tcycagctgt gggcgagatc atatctgata ccgagctgat tgtcaagaag gaattcaaag    480

agctcaaggc ccttgagttg ctgaccagtg ctgaaggaac caagtacaaa tgcctacccc    540

atatggacca gacgaacgtc tacaaaactg tctttgagcg ccttaacgca ggacattgcg    600

ttggcatttt ccccgaggga ggctcccacg atcgtgctga aatgctgcca ttgaaagctg    660

gagtcaccat catggccctg ggcgcattag ccgccaaccc ttccttggat ctcaagattg    720

tcacctgcgg cctcaactac tttcacccgc atcgcttccg ctcgcgtgca gtagtcgagt    780

ttggcgagcc attgacggtt tcgcctgagc tggtcgaaat gtacaagcga ggcggggcgg    840

aaaagcgaga ggcttgcgga aaactgctcg acacgatcta tgaagctctc cgcggtgtca    900

ctctcaacgc gcctgattac gagacattga tggtcattca agcggcccgt cgcctttaca    960

agcctactca tcgcaagctg cagatctcgc aggtcgttga gttgaaccgt aggttcgtcg   1020

caggatacat gcacttcaag gacaatccaa aagtcattga agccaaggat aaagtcatgc   1080

attacaacac tcagctgcgg taccatggat tgcgggatca ccaagtgaat attcgcacca   1140

ccaggaagca cgctatcggc atgctcatct ctcggctgat ccagatgatc tttttgagtt   1200

gtctggcgct acctggaacy ctgatgaatc ttccggtcgc cattgtcgct cgtgtcatca   1260

gcaacaaaaa ggccaaagag gcgctggctg cctcgacagt caaaattgct ggaagggacg   1320

tcttggctac gtggaagttg ctggtcgctc taggattgat gcctgttctg tacttcacgt   1380

actccgtcat ggtcttcatc tattgcagcc gcttcgacct atcgttcaag tcgcgtcttt   1440

tggttgcttg ggcagcatgg gcgcttattc cttttgtaac ctacgcaagc atccgctttg   1500

gtgaagttgn tatcgatatc ttcaagtcta ttcgcccatt gttcctgtcc atcatcccgg   1560

gcgaggagag cacgatnaac gacntgcgca aggcgcgcgc agaacttcaa aagaccatca   1620

ccaatctcat caatgagcta gcgccgcaga tatatcccga ctttgattca aagcgcatcc   1680

tcgatccatc ccctgcagat cgtcccagcc gntcagcatc aggcaccanc cttgcacaga   1740

cgattttcaa cacggctgnt cagcccttga accaatggct aggcaaggat ggccgctttg   1800

aatgggagcg taccgaggan tntgatgcag ntgacgtgtt nttctttttg gacccagcga   1860
```

-continued

```
gaggaattat ggggcggtct agggcgtcgt cttggggagg tggagcattt acncctgctg   1920
ttgatgggtc gcgatcccgg natcggagca ggacaagcag cttcacgtcg ggccagatcc   1980
agctgggcga gggcttcaaa ctcgaggcac tgacggagct gccgcgggac aanccttttg   2040
cagaagtgac caggcggttg agtgtgagcc gaatgcagag atatgggctg gagggtatga   2100
cgcgctcgga tacggatgaa aacgaaggcn ccgccaagtc aaaagacatt taggcggccg   2160
caagtgtgga tggggaagtg agtgcccggt tctgtgtgca caattggcaa tccaagatgg   2220
atggattcaa cacagggata tagcgagcta cgtggtggtg cgaggatata gcaacggata   2280
tttatgtttg acacttgaga atgtacgata caagcactgt ccaagtacaa tactaaacat   2340
actgtacata ctcatactcg tacccgggca acggtttcac ttgagtgcag tggctagtgc   2400
tcttactcgt acagtgtgca atactgcgta tcatagtctt tgatgtatat cgtattcatt   2460
catgttagtt gcgtacgagc cggaagcata aagtgtaaag cctggggtgc ctaatgagtg   2520
agctaactca cattaattgc gttgcgctca ctgcccgctt tccagtcggg aaacctgtcg   2580
tgccagctgc attaatgaat cggccaacgc gcggggagag gcggtttgcg tattgggcgc   2640
tcttccgctt cctcgctcac tgactcgctg cgctcggtcg ttcggctgcg gcgagcggta   2700
tcagctcact caaaggcggt aatacggtta tccacagaat caggggataa cgcaggaaag   2760
aacatgtgag caaaaggcca gcaaaaggcc aggaaccgta aaaaggccgc gttgctggcg   2820
tttttccata ggctccgccc ccctgacgag catcacaaaa atcgacgctc aagtcagagg   2880
tggcgaaacc cgacaggact ataaagatac caggcgtttc cccctggaag ctccctcgtg   2940
cgctctcctg ttccgaccct gccgcttacc ggatacctgt ccgcctttct cccttcggga   3000
agcgtggcgc tttctcatag ctcacgctgt aggtatctca gttcggtgta ggtcgttcgc   3060
tccaagctgg gctgtgtgca cgaacccccc gttcagcccg accgctgcgc cttatccggt   3120
aactatcgtc ttgagtccaa cccggtaaga cacgacttat cgccactggc agcagccact   3180
ggtaacagga ttagcagagc gaggtatgta ggcggtgcta cagagttctt gaagtggtgg   3240
cctaactacg gctacactag aaggacagta tttggtatct gcgctctgct gaagccagtt   3300
accttcggaa aaagagttgg tagctcttga tccggcaaac aaaccaccgc tggtagcggt   3360
ggtttttttg tttgcaagca gcagattacg cgcagaaaaa aaggatctca agaagatcct   3420
ttgatctttt ctacggggtc tgacgctcag tggaacgaaa actcacgtta agggattttg   3480
gtcatgagat tatcaaaaag gatcttcacc tagatccttt taaattaaaa atgaagtttt   3540
aaatcaatct aaagtatata tgagtaaact tggtctgaca gttaccaatg cttaatcagt   3600
gaggcaccta tctcagcgat ctgtctattt cgttcatcca tagttgcctg actccccgtc   3660
gtgtagataa ctacgatacg ggagggctta ccatctggcc ccagtgctgc aatgataccg   3720
cgagacccac gctcaccggc tccagattta tcagcaataa accagccagc cggaagggcc   3780
gagcgcagaa gtggtcctgc aactttatcc gcctccatcc agtctattaa ttgttgccgg   3840
gaagctagag taagtagttc gccagttaat agtttgcgca acgttgttgc cattgctaca   3900
ggcatcgtgg tgtcacgctc gtcgtttggt atggcttcat tcagctccgg ttcccaacga   3960
tcaaggcgag ttacatgatc ccccatgttg tgcaaaaaag cggttagctc cttcggtcct   4020
ccgatcgttg tcagaagtaa gttggccgca gtgttatcac tcatggttat ggcagcactg   4080
cataattctc ttactgtcat gccatccgta agatgctttt ctgtgactgg tgagtactca   4140
accaagtcat tctgagaata gtgtatgcgg cgaccgagtt gctcttgccc ggcgtcaata   4200
```

-continued

```
cgggataata ccgcgccaca tagcagaact ttaaaagtgc tcatcattgg aaaacgttct   4260
tcggggcgaa aactctcaag gatcttaccg ctgttgagat ccagttcgat gtaacccact   4320
cgtgcaccca actgatcttc agcatctttt actttcacca gcgtttctgg gtgagcaaaa   4380
acaggaaggc aaaatgccgc aaaaaaggga ataagggcga cacggaaatg ttgaatactc   4440
atactcttcc tttttcaata ttattgaagc atttatcagg gttattgtct catgagcgga   4500
tacatatttg aatgtattta gaaaaataaa caaatagggg ttccgcgcac atttccccga   4560
aaagtgccac ctgacgcgcc ctgtagcggc gcattaagcg cggcgggtgt ggtggttacg   4620
cgcagcgtga ccgctacact tgccagcgcc ctagcgcccg ctcctttcgc tttcttccct   4680
tcctttctcg ccacgttcgc cggctttccc cgtcaagctc taaatcgggg gctcccttta   4740
gggttccgat ttagtgcttt acggcacctc gaccccaaaa aacttgatta gggtgatggt   4800
tcacgtagtg ggccatcgcc ctgatagacg gtttttcgcc ctttgacgtt ggagtccacg   4860
ttctttaata gtggactctt gttccaaact ggaacaacac tcaaccctat ctcggtctat   4920
tcttttgatt tataagggat tttgccgatt tcggcctatt ggttaaaaaa tgagctgatt   4980
taacaaaaat ttaacgcgaa ttttaacaaa atattaacgc ttacaatttc cattcgccat   5040
tcaggctgcg caactgttgg gaagggcgat cggtgcgggc ctcttcgcta ttacgccagc   5100
tggcgaaagg gggatgtgct gcaaggcgat taagttgggt aacgccaggg ttttcccagt   5160
cacgacgttg taaaacgacg gccagtgaat tgtaatacga ctcactatag ggcgaattgg   5220
gtaccgggcc ccccctcgag gtcgatggtg tcgataagct tgatatcgaa ttcatgtcac   5280
acaaaccgat cttcgcctca aggaaaccta attctacatc cgagagactg ccgagatcca   5340
gtctacactg attaatttc gggccaataa tttaaaaaaa tcgtgttata taatattata   5400
tgtattatat atatacatca tgatgatact gacagtcatg tcccattgct aaatagacag   5460
actccatctg ccgcctccaa ctgatgttct caatatttaa ggggtcatct cgcattgttt   5520
aataataaac agactccatc taccgcctcc aaatgatgtt ctcaaaatat attgtatgaa   5580
cttattttta ttacttagta ttattagaca acttacttgc tttatgaaaa acacttccta   5640
tttaggaaac aatttataat ggcagttcgt tcatttaaca atttatgtag aataaatgtt   5700
ataaatgcgt atgggaaatc ttaaatatgg atagcataaa tgatatctgc attgcctaat   5760
tcgaaatcaa cagcaacgaa aaaaatccct tgtacaacat aaatagtcat cgagaaatat   5820
caactatcaa agaacagcta ttcacacgtt actattgaga ttattattgg acgagaatca   5880
cacactcaac tgtctttctc tcttctagaa atacaggtac aagtatgtac tattctcatt   5940
gttcatactt ctagtcattt catcccacat attccttgga tttctctcca atgaatgaca   6000
ttctatcttg caaattcaac aattataata agatatacca aagtagcggt atagtggcaa   6060
tcaaaaagct tctctggtgt gcttctcgta tttattttta ttctaatgat ccattaaagg   6120
tatatattta tttcttgtta tataatcctt ttgtttatta catgggctgg atacataaag   6180
gtattttgat ttaatttttt gcttaaattc aatccccccct cgttcagtgt caactgtaat   6240
ggtaggaaat taccatactt ttgaagaagc aaaaaaaatg aaagaaaaaa aaaatcgtat   6300
ttccaggtta gacgttccgc agaatctaga atgcggtatg cggtacattg ttcttcgaac   6360
gtaaaagttg cgctccctga gatattgtac atttttgctt ttacaagtac aagtacatcg   6420
tacaactatg tactactgtt gatgcatcca caacagtttg ttttgttttt ttttgttttt   6480
tttttttcta atgattcatt accgctatgt atacctactt gtacttgtag taagccgggt   6540
tattggcgtt caattaatca tagacttatg aatctgcacg gtgtgcgctg cgagttactt   6600
```

-continued

```
ttagcttatg catgctactt gggtgtaata ttgggatctg ttcggaaatc aacggatgct   6660
caatcgattt cgacagtaat taattaagtc atacacaagt cagctttctt cgagcctcat   6720
ataagtataa gtagttcaac gtattagcac tgtacccagc atctccgtat cgagaaacac   6780
aacaacatgc cccattggac agatcatgcg gatacacagg ttgtgcagta tcatacatac   6840
tcgatcagac aggtcgtctg accatcatac aagctgaaca agcgctccat acttgcacgc   6900
tctctatata cacagttaaa ttacatatcc atagtctaac ctctaacagt taatcttctg   6960
gtaagcctcc cagccagcct tctggtatcg cttggcctcc tcaataggat ctcggttctg   7020
gccgtacaga cctcggccga caattatgat atccgttccg gtagacatga catcctcaac   7080
agttcggtac tgctgtccga gagcgtctcc cttgtcgtca agacccaccc cgggggtcag   7140
aataagccag tcctcagagt cgcccttagg tcggttctgg gcaatgaagc caaccacaaa   7200
ctcggggtcg gatcgggcaa gctcaatggt ctgcttggag tactcgccag tggccagaga   7260
gcccttgcaa gacagctcgg ccagcatgag cagacctctg gccagcttct cgttgggaga   7320
ggggactagg aactccttgt actgggagtt ctcgtagtca gagacgtcct ccttcttctg   7380
ttcagagaca gtttcctcgg caccagctcg caggccagca atgattccgg ttccgggtac   7440
accgtgggcg ttggtgatat cggaccactc ggcgattcgg tgacaccggt actggtgctt   7500
gacagtgttg ccaatatctg cgaactttct gtcctcgaac aggaagaaac cgtgcttaag   7560
agcaagttcc ttgaggggga gcacagtgcc ggcgtaggtg aagtcgtcaa tgatgtcgat   7620
atgggttttg atcatgcaca cataaggtcc gaccttatcg gcaagctcaa tgagctcctt   7680
ggtggtggta acatccagag aagcacacag gttggttttc ttggctgcca cgagcttgag   7740
cactcgagcg gcaaaggcgg acttgtggac gttagctcga gcttcgtagg agggcatttt   7800
ggtggtgaag aggagactga aataaattta gtctgcagaa ctttttatcg gaaccttatc   7860
tggggcagtg aagtatatgt tatggtaata gttacgagtt agttgaactt atagatagac   7920
tggactatac ggctatcggt ccaaattaga aagaacgtca atggctctct gggcgtcgcc   7980
tttgccgaca aaaatgtgat catgatgaaa gccagcaatg acgttgcagc tgatattgtt   8040
gtcggccaac cgcgccgaaa acgcagctgt cagacccaca gcctccaacg aagaatgtat   8100
cgtcaaagtg atccaagcac actcatagtt ggagtcgtac tccaaaggcg gcaatgacga   8160
gtcagacaga tactcgtcga ctcaggcgac gacggaattc ctgcagccca tctgcagaat   8220
tcaggagaga ccgggttggc ggcgtatttg tgtcccaaaa aacagcccca attgccccgg   8280
agaagacggc caggccgcct agatgacaaa ttcaacaact cacagctgac tttctgccat   8340
tgccactagg ggggggcctt tttatatggc caagccaagc tctccacgtc ggttgggctg   8400
cacccaacaa taaatgggta gggttgcacc aacaaaggga tgggatgggg ggtagaagat   8460
acgaggataa cggggctcaa tggcacaaat aagaacgaat actgccatta agactcgtga   8520
tccagcgact gacaccattg catcatctaa gggcctcaaa actacctcgg aactgctgcg   8580
ctgatctgga caccacagag gttccgagca ctttaggttg caccaaatgt cccaccaggt   8640
gcaggcagaa aacgctggaa cagcgtgtac agtttgtctt aacaaaaagt gagggcgctg   8700
aggtcgagca gggtggtgtg acttgttata gcctttagag ctgcgaaagc gcgtatggat   8760
ttggctcatc aggccagatt gagggtctgt ggacacatgt catgttagtg tacttcaatc   8820
gcccccctgga tatagccccg acaataggcc gtggcctcat ttttttgcct tccgcacatt   8880
tccattgctc ggtacccaca ccttgcttct cctgcacttg ccaaccttaa tactggttta   8940
```

-continued

```
cattgaccaa catcttacaa gcggggggct tgtctagggt atatataaac agtggctctc   9000

ccaatcggtt gccagtctct tttttccttt ctttccccac agattcgaaa tctaaactac   9060

acatcacaca atgcctgtta ctgacgtcct taagcgaaag tccggtgtca tcgtcggcga   9120

cgatgtccga gccgtgagta tccacgacaa gatcagtgtc gagacgacgc gttttgtgta   9180

atgacacaat ccgaaagtcg ctagcaacac acactctcta cacaaactaa cccagctct    9239
```

MORTIERELLA ALPINA GLYCEROL-3-PHOSPHATE O-ACYLTRANSFERASE FOR ALTERATION OF POLYUNSATURATED FATTY ACIDS AND OIL CONTENT IN OLEAGINOUS ORGANISMS

This application claims the benefit of U.S. Patent Application No. 60/624,812, filed Nov. 4, 2004.

FIELD OF THE INVENTION

This invention is in the field of biotechnology. More specifically, this invention pertains to the identification of a nucleic acid fragment isolated from *Mortierella alpina* encoding a glycerol-3-phosphate o-acyltransferase (GPAT). This enzyme is useful for altering the quantity of oil in oleaginous organisms, such as oleaginous bacteria, yeast, algae and fungi.

BACKGROUND OF THE INVENTION

The present invention is in support of the development of an oleaginous yeast that accumulates oils enriched in long-chain ω-3 and/or ω-6 polyunsaturated fatty acids ("PUFAs"; e.g., 18:3, 18:4, 20:3, 20:4, 20:5, 22:6 fatty acids). Toward this end, the natural abilities of oleaginous yeast (mostly limited to 18:2 fatty acid production) have been enhanced by advances in genetic engineering, leading to the production of 20:4 (arachidonic acid or "ARA"), 20:5 (eicosapentaenoic acid or "EPA") and 22:6 (docosahexaenoic acid or "DHA") PUFAs in transformant *Yarrowia lipolytica.* These ω-3 and ω-6 fatty acids were produced by introducing and expressing heterologous genes encoding the ω-3/ω-6 biosynthetic pathway in the oleaginous host (see W2004/101757 and co-pending U.S. Patent Application No. 60/624,812). However, in addition to developing techniques to introduce the appropriate fatty acid desaturases and elongases into these particular host organisms, it is also necessary to increase the transfer of PUFAs into storage lipid pools following their synthesis.

As is well known in the art, the process of triacylglycerol (TAG) biosynthesis (wherein newly synthesized PUFAs are transferred into a host organism's storage lipid pools) requires the catalytic activity of various acyltransferases as most free fatty acids become esterified to coenzyme A (CoA) to yield acyl-CoAs. Specifically, a series of four reactions occur in the endoplasmic reticulum of the cell to form TAGs, as shown in the Table below.

TABLE 1

General Reactions Of de Novo Triacylglycerol Biosynthesis

| Reaction | Enzyme |
|---|---|
| sn-Glycerol-3-Phosphate → Lysophosphatidic Acid (1-acyl-sn-glycerol 3-phosphate or "LPA") | Glycerol-3-phosphate acyltransferase (GPAT); [E.C. 2.3.1.15]; esterifies 1st acyl-CoA to sn-1 position of sn-glycerol 3-phosphate |
| LPA → Phosphatidic Acid (1,2-diacylglycerol phosphate or "PA") | Lysophosphatidic acid acyltransferase (LPAAT) [E.C. 2.3.1.51]; esterifies 2nd acyl-CoA to sn-2 position of LPA |
| PA → 1,2-Diacylglycerol ("DAG") | Phosphatidic acid phosphatase [E.C. 3.1.3.4] removes a phosphate from PA |
| DAG → Triacylglycerol ("TAG") | Diacylglycerol acyltransferase (DGAT) [E.C. 2.3.1.20]; transfers acyl-CoA to the sn-3 position of DAG Or Phospholipid:diacylglycerol acyltransferase (PDAT) [E.C.2.3.1.158]; transfers fatty acyl-group from sn-2 position of phosphatidylcholine to sn-3 position of DAG |

In addition to those acyltransferases above, acyl-CoA:cholesterol acyltransferases (ACATs), lecithin:cholesterol acyltransferases (LCATs) and lysophosphatidylcholine acyltransferases (LPCATs) are also intimately involved in the biosynthesis of TAGs. The role of each of these acyltransferases in regulating lipid acyl composition is largely mediated through their individual substrate specificities.

This application is concerned primarily with the first step in the synthesis of TAG (wherein glycerol-3-phosphate is converted to LPA), thereby limiting the acyltransferase(s) of primary importance to GPAT (also referred to as glycerol-3-phosphate o-acyltransferase in the literature). GPAT activity is found in all species including bacteria, fungi, plants and animals. In mammals, it is found to varying degrees in many tissues including liver, adipose, heart, lung, kidney, adrenal, muscle, lactating mammary, intestinal mucosa, brain and in many mammalian cultured cell lines (Bell, R. M., et al., In: The Enzymes, (Boyer, P. D., ed.) v. 16, pp. 87–112, Academic NY (1983)). There are two known isoforms of GPAT activity in mammals: one which isolates with the mitochondria, preferentially uses saturated fatty acyl-CoAs and whose major acylation end product is primarily LPA; and, one which isolates with the microsomal endoplasmic reticulum (ER) fraction, uses saturated and unsaturated fatty acyl-CoAs equally well and whose major acylation product is PA (Hill, J. O., et al. *Science* 280:1371–1374 (1998); Dircks, L., Sul, H. S., *Lipid Res.* 38:461–479 (1999)). Similarly, the plant cell contains three types of GPAT, which are located in the chloroplasts, mitochondria and cytoplasm, respectively. The enzyme in chloroplasts is soluble and uses acyl-(acyl-carrier protein) as the acyl donor, whereas the enzymes in the mitochondria and the cytoplasm are bound to membranes and use acyl-CoA as the acyl donor. The distinct fatty-acyl preferences of these various GPAT isoforms is thought to be responsible for the observed predominance of saturated (versus unsaturated) fatty acids in the sn-1 position. GPAT is also potentially a rate-limiting reaction, and thus should be considered an important and controlling enzyme early in the pathway of de novo synthesis of TAGs and phospholipids.

Despite the clear importance of GPAT in glycerophospholipid biosynthesis, characterization of different GPAT isoforms has been difficult and sequence information (either nucleotide or protein) of GPAT genes is limited. It is predicted that a GPAT from a microorganism that naturally produces long-chain PUFAs (e.g., *Mortierella, Pythium, Cyclotella, Nitzschia, Crypthecodinium* and *Thraustochytrium,* producing e.g., ARA, EPA and/or DHA) would incorporate long-chain PUFAs with increased efficiency, relative to a GPAT that does not naturally interact with long-chain PUFAs. The only known disclosure providing genes encoding GPATs from these types of organisms is that of WO 2004/087902 (describing GPATs in the moss, *Physcomitrella patens*). The microsomal GPAT of *Mortierella ramanniana* var. *angulispora* was recently purified to homogeneity and its acyl-CoA specificity was characterized (Mishra, S., *Biochem. J.* 355(10):315–322 (2001))]; however, the protein was not sequenced. Thus, there is a need for the identification and isolation of a gene encoding GPAT from an organism such as those suggested above, to permit its use in the production and accumulation of long-chain PUFAs in the storage lipid pools (i.e., TAG fraction) of transformant oleaginous yeast.

Surprisingly, the Applicants have isolated a novel GPAT gene from the filamentous fungus *Mortierella alpina.* It is expected that the gene of the present invention ("GPAT") will be useful to enable one to modify the transfer of long-chain free fatty acids (e.g., ω-3 and/or ω-6 fatty acids) into the TAG pool in oleaginous yeast.

SUMMARY OF THE INVENTION

The invention relates to the discovery of a gene encoding a glycerol-3-phosphate o-acyltransferase from *Mortierella.* This gene and encoded enzyme are useful in manipulating the production of commercially useful oils in microorganisms, and particularly in oleaginous yeast. Accordingly the invention provides an isolated nucleic acid molecule encoding a glycerol-3-phosphate o-acyltransferase, selected from the group consisting of:

(a) an isolated nucleic acid molecule encoding the amino acid sequence as set forth in SEQ ID NO:2;

(b) an isolated nucleic acid molecule that hybridizes with (a) under the following hybridization conditions: 0.1×SSC, 0.1% SDS, 65° C. and washed with 2×SSC, 0.1% SDS followed by 0.1×SSC, 0.1% SDS; or, (c) an isolated nucleic acid molecule that is completely complementary to (a) or (b).

Similarly the invention provides a polypeptide encoded by the isolated nucleic acid molecule of the invention as well as genetic chimera of these molecules and host cells comprising the same.

In one preferred embodiment the invention provides a method of producing triacylglycerols in a transformed host cell comprising:

(a) providing a transformed host cell comprising:

(i) at least one gene encoding a glycerol-3-phosphate o-acyltransferase having the amino acid sequence as set forth in SEQ ID NO:2; and, (ii) a source of fatty acids;

(b) growing the cell of step (a) under conditions whereby the at least one gene encoding a glycerol-3-phosphate o-acyltransferase is expressed, resulting in the transfer of the fatty acids to triacylglycerol; and, (c) optionally recovering the triacylglycerol of step (b).

In one embodiment the source of fatty acids is ω-3 or ω-6 fatty acids and in an other embodiment the host cells contain a disruption in the native glycerol-3-phosphate o-acyltransferase gene.

BRIEF DESCRIPTION OF THE DRAWINGS AND SEQUENCE DESCRIPTIONS

FIG. 1 graphically represents the relationship between SEQ ID NOs:1, 2, 6, 9, 13, 20, 21, 22, 23, 24 and 25, each of which relates to glycerol-3-phosphate o-acyltransferase (GPAT) in *Mortierella alpina.*

Figure 2:
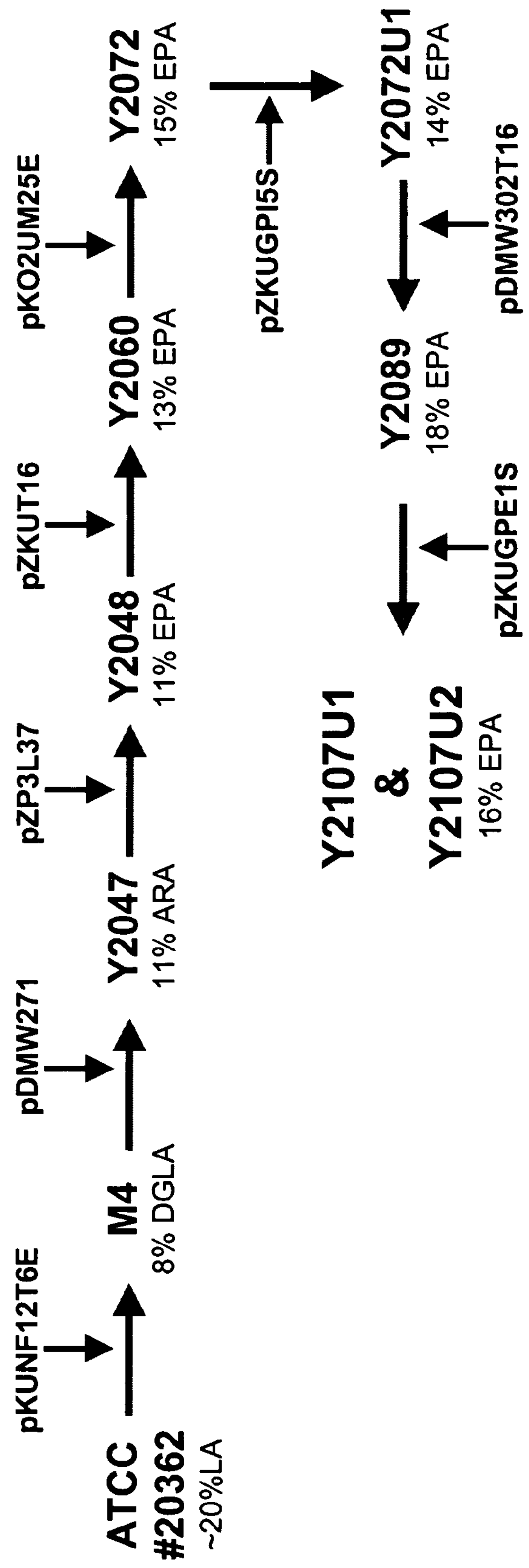

FIG. 2 diagrams the development of *Yarrowia lipolytica* strains Y2107U1 and Y2107U2, producing up to 16% EPA in the total lipid fraction.

Figure 3:
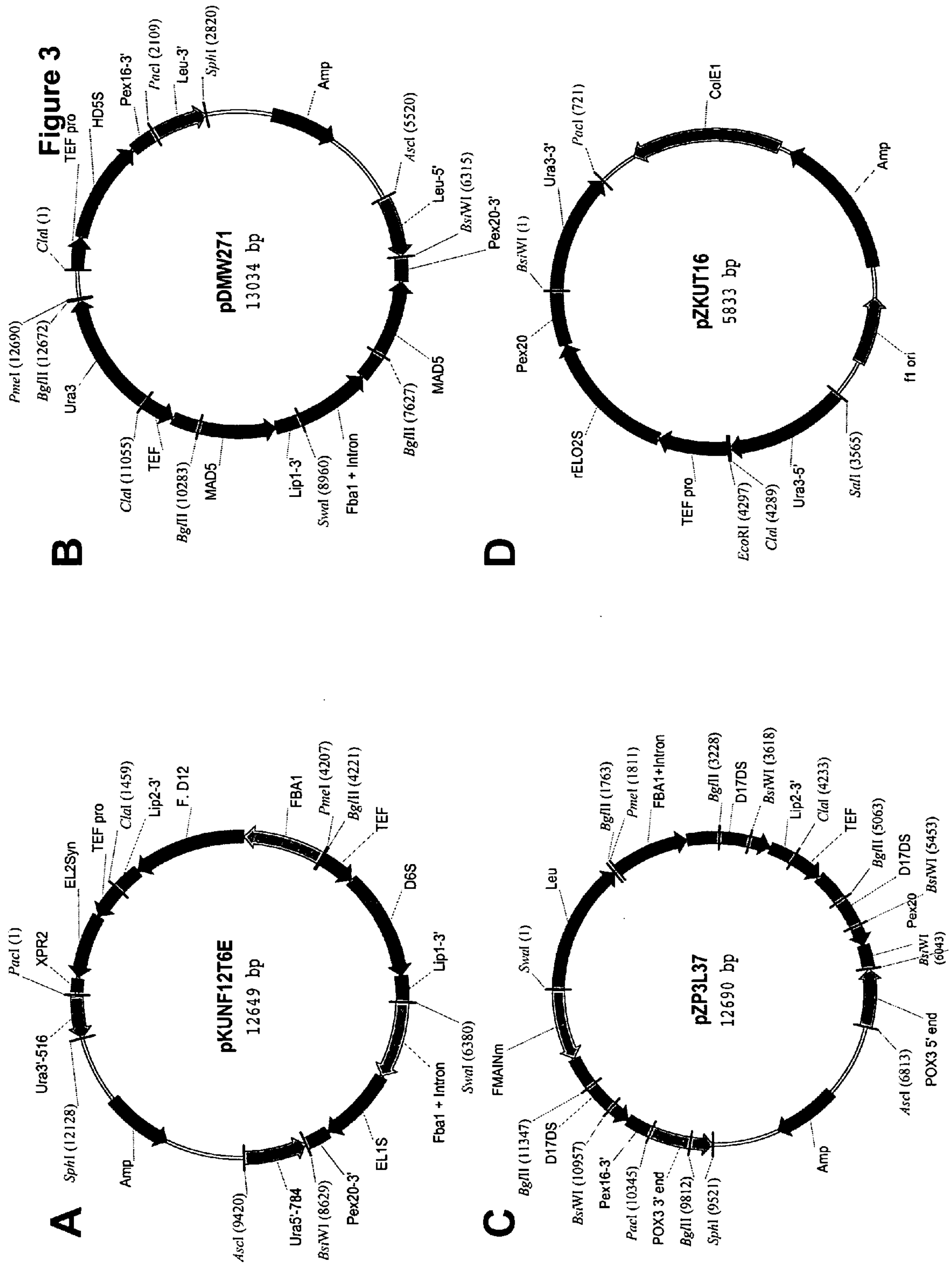

FIG. 3 provides plasmid maps for the following: (A) pKUNF12T6E; (B) pDMW271; (C) pZP3L37; and (D) pZKUT16.

FIG. 4 provides plasmid maps for the following: (A) pKO2UM25E; (B) pZKUGPI5S; (C) pDMW302T16; and (D) pZKUGPE1S.

FIG. 5 provides plasmid maps for the following: (A) pZUF17; (B) pZUF-Mod-1; and (C) pMGPAT-17.

Figure 6:
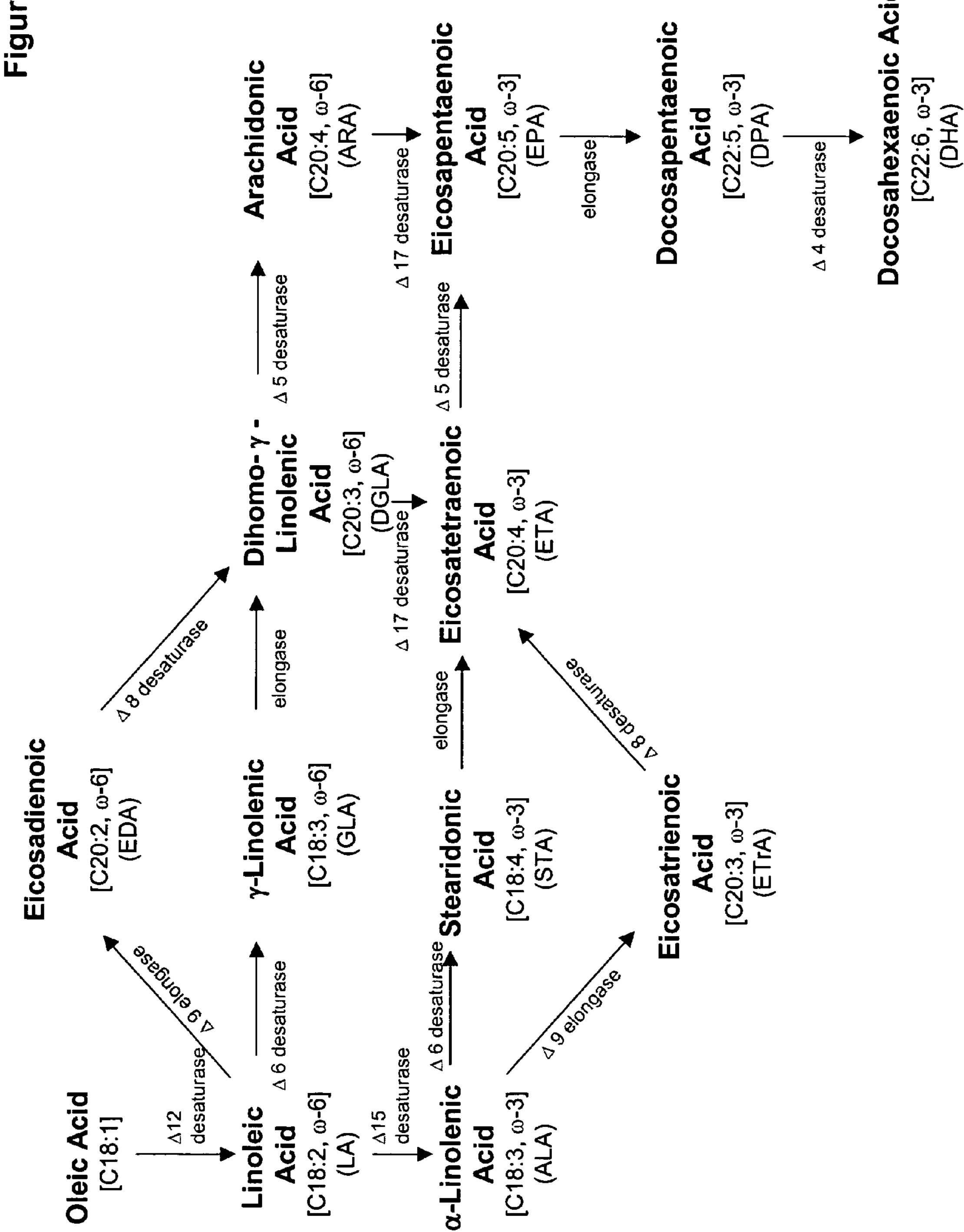

FIG. 6 illustrates the ω-3 and ω-6 fatty acid biosynthetic pathways.

The invention can be more fully understood from the following detailed description and the accompanying sequence descriptions, which form a part of this application.

The following sequences comply with 37 C.F.R. §1.821–1.825 ("Requirements for Patent Applications Containing Nucleotide Sequences and/or Amino Acid Sequence Disclosures—the Sequence Rules") and are consistent with World Intellectual Property Organization (WIPO) Standard ST.25 (1998) and the sequence listing requirements of the EPO and PCT (Rules 5.2 and 49.5(a-bis), and Section 208 and Annex C of the Administrative Instructions). The symbols and format used for nucleotide and amino acid sequence data comply with the rules set forth in 37 C.F.R. §1.822.

SEQ ID NOs:1, 2, 6, 9, 13, 20–25, 27–36, 38–41, 43–45, 47, 48, 50–56 and 59 are ORFs encoding genes or proteins (or portions thereof), as identified in Table 2.

TABLE 2

Summary Of Gene And Protein SEQ ID Numbers

| Description and Abbreviation | Nucleic acid SEQ ID NO. | Protein SEQ ID NO. |
|---|---|---|
| *Mortierella alpina* glycerol-3-phosphate o-acyltransferase (GPAT)-coding region | 1 (2151 bp) | 2 (716 AA) |
| *Mortierella alpina* GPAT-partial cDNA sequence | 6 (1212 bp) | — |
| *Mortierella alpina* GPAT-genomic fragment comprising −1050 bp to +2886 bp region | 9 (3936 bp) | — |
| *Mortierella alpina* GPAT-3' cDNA sequence obtained by genome walking | 13 (965 bp) | — |
| *Mortierella alpina* GPAT-5' sequence obtained by genome walking | 20 (1908 bp) | — |
| *Mortierella alpina* GPAT-internal sequence obtained by genome walking | 21 (967 bp) | — |
| *Mortierella alpina* GPAT-intron #1 | 22 (275 bp) | — |
| *Mortierella alpina* GPAT-intron #2 | 23 (255 bp) | — |
| *Mortierella alpina* GPAT-intron #3 | 24 (83 bp) | — |
| *Mortierella alpina* GPAT-intron #4 | 25 (99 bp) | — |
| *Yarrowia lipolytica* FBAIN promoter | 27 (973 bp) | — |
| Synthetic $C_{18/20}$ elongase gene derived from *Mortierella alpina*, codon-optimized for expression in *Yarrowia lipolytica* | 28 (957 bp) | 29 (318 AA) |
| Synthetic Δ6 desaturase, derived from *Mortierella alpina*, codon-optimized for expression in *Yarrowia lipolytica* | 30 (1374 bp) | 31 (457 AA) |
| *Yarrowia lipolytica* FBA promoter | 32 (1001 bp) | — |
| *Fusarium moniliforme* Δ12 desaturase | 33 (1434 bp) | 34 (477 AA) |
| Synthetic $C_{18/20}$ elongase gene derived from *Thraustochytrium aureum*, codon-optimized for expression in *Yarrowia lipolytica* | 35 (819 bp) | 36 (272 AA) |
| *Mortierella alpina* Δ5 desaturase | 38 (1341 bp) | 39 (446 AA) |
| Synthetic Δ5 desaturase derived from *Homo sapiens*, codon-optimized for expression in *Yarrowia lipolytica* | 40 (1335 bp) | 41 (444 AA) |
| Synthetic Δ17 desaturase gene derived from *Saprolegnia diclina*, codon-optimized for expression in *Yarrowia lipolytica* | 43 (1077 bp) | 44 (358 AA) |
| *Yarrowia lipolytica* FBAINm promoter | 45 (924 bp) | — |
| Synthetic $C_{16/18}$ elongase gene derived from *Rattus norvegicus*, codon-optimized for expression in *Yarrowia lipolytica* | 47 (804 bp) | 48 (267 AA) |

TABLE 2-continued

Summary Of Gene And Protein SEQ ID Numbers

| Description and Abbreviation | Nucleic acid SEQ ID NO. | Protein SEQ ID NO. |
|---|---|---|
| *Yarrowia lipolytica* Δ12 desaturase | 50 (1936 bp) | 51 (419 AA) |
| *Yarrowia lipolytica* GPAT promoter | 52 (1130 bp) | — |
| *Mortierella isabellina* Δ12 desaturase | 53 (1203 bp) | 54 (400 AA) |
| Synthetic Δ5 desaturase derived from *Isochrysis galbana*, codon-optimized for expression in *Yarrowia lipolytica* | 55 (1329 bp) | 56 (442 AA) |
| *Yarrowia lipolytica* GPDIN promoter | 59 (1174 bp) | — |

SEQ ID NOs:26, 37, 42, 46, 49, 57, 58, 60, 61, 65 and 68 are plasmids as identified in Table 3.

TABLE 3

Summary of Plasmid SEQ ID Numbers

| Plasmid | Corresponding FIG. | SEQ ID NO |
|---|---|---|
| pKUNF12T6E | 3A | 26 (12,649 bp) |
| pDMW271 | 3B | 37 (13,034 bp) |
| pZP3L37 | 3C | 42 (12,690 bp) |
| pZKUT16 | 3D | 46 (5,833 bp) |
| pKO2UM25E | 4A | 49 (12,663 bp) |
| pZKUGPI5S | 4B | 57 (6,912 bp) |
| pDMW302T16 | 4C | 58 (14,864 bp) |
| pZKUGPE1S | 4D | 60 (6,540 bp) |
| pZUF-MOD-1 | 5B | 61 (7,323 bp) |
| pZUF17 | 5A | 65 (8,165 bp) |
| pMGPAT-17 | 5C | 68 (9,239 bp) |

SEQ ID NOs:3–5 correspond to BD-Clontech Creator Smart® cDNA library kit primers SMART IV oligonucleotide, CDSIII/3' PCR primer and 5'-PCR primer.

SEQ ID NOs:7 and 8 correspond to primers MGPAT-N1 and MGPAT-NR5, respectively, used for degenerate PCR to amplify the *M. alpina* GPAT.

SEQ ID NOs:10, 11 and 12 correspond to primers MGPAT-5N1, MGPAT-5N2 and MGPAT-5N3, respectively, used for amplification of the 3'-end of GPAT.

SEQ ID NOs:14 and 15 correspond to the Genome Walker adaptor used to isolate a 5' genomic GPAT fragment by genome-walking.

SEQ ID NOs:16–19 correspond to the PCR primers used in genome-walking: MGPAT-5-1A, Adaptor-1 (AP1), MGPAT-3N1 and Nested Adaptor Primer 2 (AP2), respectively.

SEQ ID NOs:62 and 63 correspond to primers pzuf-mod1 and pzuf-mod2, respectively, used for creating "control" plasmid pZUF-MOD-1.

SEQ ID NO:64 corresponds to a 253 bp "stuffer" DNA fragment for construction of pZUF-MOD-1.

SEQ ID NOs:65 and 66 correspond to primers mgpat-cdna-5 and mgpat-cdna-R, respectively, used for amplifying the *M. alpina* GPAT.

DETAILED DESCRIPTION OF THE INVENTION

All patents, patent applications, and publications cited herein are incorporated by reference in their entirety. This specifically includes, but is not limited to, the following Applicants' Assignee's copending applications: U.S. patent application Ser. No. 10/840,478 (filed May 6, 2004), U.S. patent application Ser. No. 10/840,579 (filed May 6, 2004), U.S. patent application Ser. No. 10/869,630 (filed Jun. 16, 2004), U.S. patent application Ser. No. 10/987,548 (filed Nov. 12, 2004), U.S. patent application Ser. No. 11/225,354 (filed Sep. 13, 2005), U.S. Patent Application No. 60/624,812 (filed Nov. 4, 2004), U.S. patent application Ser. No. 11/183,664 (filed Jul. 18, 2005) and U.S. patent application Ser. No. 11/185,301 (filed Jul. 20, 2005).

In accordance with the subject invention, Applicants have isolated a *Mortierella alpina* gene encoding a glycerol-3-phosphate o-acyltransferase (GPAT) useful for transferring fatty acids into storage triacylglycerols (TAGs). This gene may be useful in altering the quantity of long-chain polyunsaturated fatty acids (PUFAs) produced in oleaginous yeast.

The importance of PUFAs are undisputed. For example, certain PUFAs are important biological components of healthy cells and are recognized as "essential" fatty acids that cannot be synthesized de novo in mammals and instead must be obtained either in the diet or derived by further desaturation and elongation of linoleic acid (LA) or α-linolenic acid (ALA). Additionally, a high intake of long-chain ω-3 PUFAs produces cardiovascular protective effects (Dyerberg, J. et al., *Amer. J. Clin Nutr.* 28:958–966 (1975); Dyerberg, J. et al., *Lancet* 2(8081):117–119 (Jul. 15, 1978); Shimokawa, H., *World Rev Nutr Diet,* 88:100–108 (2001); von Schacky, C., and Dyerberg, J., *World Rev Nutr Diet,* 88:90–99 (2001)). Numerous other studies document wide-ranging health benefits conferred by administration of ω-3 and/or ω-6 fatty acids against a variety of symptoms and diseases (e.g., asthma, psoriasis, eczema, diabetes, cancer).

As such, the subject invention finds many applications. PUFAs, or derivatives thereof, accumulated by the methodology disclosed herein can be used as dietary substitutes, or supplements, particularly infant formulas, for patients undergoing intravenous feeding or for preventing or treating malnutrition. Alternatively, the purified PUFAs (or derivatives thereof) may be incorporated into cooking oils, fats or margarines formulated so that in normal use the recipient would receive the desired amount for dietary supplementation. The PUFAs may also be incorporated into infant formulas, nutritional supplements or other food products and may find use as anti-inflammatory or cholesterol lowering agents. Optionally, the compositions may be used for pharmaceutical use (human or veterinary). In this case, the PUFAs are generally administered orally but can be administered by any route by which they may be successfully absorbed, e.g., parenterally (e.g., subcutaneously, intramuscularly or intravenously), rectally, vaginally or topically (e.g., as a skin ointment or lotion).

Supplementation of humans or animals with PUFAs produced by recombinant means can result in increased levels of the added PUFAs, as well as their metabolic progeny. For example, treatment with ARA can result not only in increased levels of ARA, but also downstream products of ARA such as prostaglandins. Complex regulatory mechanisms can make it desirable to combine various PUFAs, or add different conjugates of PUFAs, in order to prevent, control or overcome such mechanisms to achieve the desired levels of specific PUFAs in an individual.

Definitions

In this disclosure, a number of terms and abbreviations are used. The following definitions are provided.

"Open reading frame" is abbreviated ORF.

"Polymerase chain reaction" is abbreviated PCR.

"American Type Culture Collection" is abbreviated ATCC.

"Polyunsaturated fatty acid(s)" is abbreviated PUFA(s).

"Glycerol-3-phosphate o-acyltransferase" is abbreviated GPAT.

"Triacylglycerols" are abbreviated TAGs.

"Co-enzyme A" is abbreviated CoA.

The term "fatty acids" refers to long-chain aliphatic acids (alkanoic acids) of varying chain length, from about $C_{12}$ to $C_{22}$ (although both longer and shorter chain length acids are known). The predominant chain lengths are between $C_{16}$ and $C_{22}$. The structure of a fatty acid is represented by a simple notation system of "X:Y", where X is the total number of carbon (C) atoms in the particular fatty acid and Y is the number of double bonds. Additional details concerning the differentiation between "saturated fatty acids" versus "unsaturated fatty acids", "monounsaturated fatty acids" versus "polyunsaturated fatty acids" (or "PUFAs"), and "ω-6 fatty acids" ω-6 or n-6) versus "ω-3 fatty acids" ω-3 or n-3) are provided in WO2004/101757.

Nomenclature used to describe PUFAs in the present disclosure is shown below in Table 4. In the column titled "Shorthand Notation", the omega-reference system is used to indicate the number of carbons, the number of double bonds and the position of the double bond closest to the omega carbon, counting from the omega carbon (which is numbered 1 for this purpose). The remainder of the Table summarizes the common names of ω-3 and ω-6 fatty acids, the abbreviations that will be used throughout the specification and each compounds' chemical name.

TABLE 4

Nomenclature Of Polyunsaturated Fatty Acids

| Common Name | Abbreviation | Chemical Name | Shorthand Notation |
|---|---|---|---|
| Linoleic | LA | cis-9,12-octadecadienoic | 18:2 ω-6 |
| γ-Linoleic | GLA | cis-6,9,12-octadecatrienoic | 18:3 ω-6 |
| Eicosadienoic | EDA | cis-11,14-eicosadienoic | 20:2 ω-6 |
| Dihomo-γ-Linoleic | DGLA | cis-8,11,14-eicosatrienoic | 20:3 ω-6 |
| Arachidonic | ARA | cis-5,8,11,14-eicosatetraenoic | 20:4 ω-6 |
| α-Linolenic | ALA | cis-9,12,15-octadecatrienoic | 18:3 ω-3 |
| Stearidonic | STA | cis-6,9,12,15-octadecatetraenoic | 18:4 ω-3 |
| Eicosatrienoic | ETrA | cis-11,14,17-eicosatrienoic | 20:3 ω-3 |
| Eicosatetraenoic | ETA | cis-8,11,14,17-eicosatetraenoic | 20:4 ω-3 |
| Eicosapentaenoic | EPA | cis-5,8,11,14,17-eicosapentaenoic | 20:5 ω-3 |
| Docosapentaenoic | DPA | cis-7,10,13,16,19-docosapentaenoic | 22:5 ω-3 |
| Docosa-hexaenoic | DHA | cis-4,7,10,13,16,19-docosahexaenoic | 22:6 ω-3 |

"Microbial oils" or "single cell oils" are those oils naturally produced by microorganisms (e.g., algae, oleaginous yeast and filamentous fungi) during their lifespan. The term "oil" refers to a lipid substance that is liquid at 25° C. and usually polyunsaturated. In contrast, the term "fat" refers to a lipid substance that is solid at 25° C. and usually saturated. "Lipid bodies" refer to lipid droplets that usually are bounded by specific proteins and a monolayer of phospholipid. These organelles are sites where most organisms transporustore neutral lipids. Lipid bodies are thought to arise from microdomains of the endoplasmic reticulum that contain TAG-biosynthesis enzymes; and, their synthesis and size appear to be controlled by specific protein components.

"Neutral lipids" refer to those lipids commonly found in cells in lipid bodies as storage fats and oils and are so called because at cellular pH, the lipids bear no charged groups. Generally, they are completely non-polar with no affinity for water. Neutral lipids generally refer to mono-, di-, and/or triesters of glycerol with fatty acids, also called monoacylglycerol, diacylglycerol or TAG, respectively (or collectively, acylglycerols). A hydolysis reaction must occur to release free fatty acids from acylglycerols.

The terms "triacylglycerol", "oil" and "TAGs" refer to neutral lipids composed of three fatty acyl residues esterified to a glycerol molecule (and such terms will be used interchangeably throughout the present disclosure herein). Such oils can contain long-chain PUFAs, as well as shorter saturated and unsaturated fatty acids and longer chain saturated fatty acids. Thus, "oil biosynthesis" generically refers to the synthesis of TAGs in the cell.

The term "GPAT" refers to a glycerol-3-phosphate o-acyltransferase enzyme (EC 2.3.1.15). This enzyme is responsible for the transfer of an acyl-CoA group onto sn-glycerol 3-phosphate to produce CoA and 1-acyl-sn-glycerol 3-phosphate (lysophosphatidic acid or "LPA"). The terminology used herein does not differentiate between different isoforms of the GPAT enzyme (i.e., GPAT may preferentially be located within the mitochondria, endoplasmic reticulum or chloroplast). The coding region of a representative GPAT gene, isolated from *Mortierella alpina,* is provided herein as SEQ ID NO:1; the corresponding GPAT protein sequence is provided as SEQ ID NO:2.

The term "PUFA biosynthetic pathway enzyme" refers to any of the following enzymes (and genes which encode said enzymes) associated with the biosynthesis of a PUFA, including: a Δ4 desaturase, a Δ5 desaturase, a Δ6 desaturase, a Δ12 desaturase, a Δ15 desaturase, a Δ17 desaturase, a Δ9 desaturase, a Δ8 desaturase, a $C_{14/16}$elongase, a $C_{16/18}$ elongase, a $C_{18/20}$ elongase, a Δ9 elongase and/or a $C_{20/22}$ elongase.

The term "ω-3/ω-6 fatty acid biosynthetic pathway" refers to a set of genes which, when expressed under the appropriate conditions encode enzymes that catalyze the production of either or both ω-3 and ω-6 fatty acids. Typically the genes involved in the ω-3/ω-6 fatty acid biosynthetic pathway encode some or all of the following enzymes: Δ12 desaturase, Δ6 desaturase, a $C_{18/20}$ elongase, a $C_{20/22}$ elongase, Δ5 desaturase, Δ17 desaturase, Δ15 desaturase, Δ9 desaturase, Δ8 desaturase, a Δ9 elongase and Δ4 desaturase. A representative pathway is illustrated in FIG. 6, providing for the conversion of oleic acid through various intermediates to DHA, which demonstrates how both ω-3 and ω-6 fatty acids may be produced from a common source. The pathway is naturally divided into two portions where one portion will generate ω-3 fatty acids and the other portion, only ω-6 fatty acids. That portion that only generates ω-3 fatty acids will be referred to herein as the ω-3 fatty acid biosynthetic pathway, whereas that portion that generates only ω-6 fatty acids will be referred to herein as the ω-6 fatty acid biosynthetic pathway.

The term "functional" as used herein in context with the ω-3/ω-6 fatty acid biosynthetic pathway means that some (or all) of the genes in the pathway express active enzymes, resulting in in vivo catalysis or substrate conversion. It should be understood that "ω-3/ω-6 fatty acid biosynthetic pathway" or "functional ω-3/ω-6 fatty acid biosynthetic pathway" does not imply that all the genes listed in the above paragraph are required, as a number of fatty acid products will only require the expression of a subset of the genes of this pathway.

The term "desaturase" refers to a polypeptide that can desaturate, i.e., introduce a double bond, in one or more fatty acids to produce a mono- or polyunsaturated fatty acid. Despite use of the omega-reference system throughout the specification in reference to specific fatty acids, it is more convenient to indicate the activity of a desaturase by counting from the carboxyl end of the substrate using the delta-system. Of particular interest herein are: Δ12 desaturases that desaturate a fatty acid between the $12^{th}$ and $13^{th}$ carbon atoms numbered from the carboxyl-terminal end of the molecule and that catalyze the conversion of oleic acid to LA; Δ15 desaturases that catalyze the conversion of LA to ALA; Δ17 desaturases that catalyze the conversion of ARA to EPA and/or DGLA to ETA; Δ6 desaturases that catalyze the conversion of LA to GLA and/or ALA to STA; Δ5 desaturases that catalyze the conversion of DGLA to ARA and/or ETA to EPA; Δ4 desaturases that catalyze the conversion of DPA to DHA; Δ8 desaturases that catalyze the conversion of EDA to DGLA and/or ETrA to ETA; and Δ9 desaturases that catalyze the conversion of palmitate to palmitoleic acid (16:1) and/or stearate to oleic acid (18:1).

The term "fatty acid elongase" or "elongase" refers to a polypeptide that can elongate a fatty acid carbon chain to produce an acid that is 2 carbons longer than the fatty acid substrate that the elongase acts upon. This process of elongation occurs in a multi-step mechanism in association with fatty acid synthase, whereby CoA is the acyl carrier (Lassner et al., *The Plant Cell* 8:281–292 (1996)). Briefly, malonyl-CoA is condensed with a long-chain acyl-CoA to yield $CO_2$ and a β-ketoacyl-CoA (where the acyl moiety has been elongated by two carbon atoms). Subsequent reactions include reduction to β-hydroxyacyl-CoA, dehydration to an enoyl-CoA and a second reduction to yield the elongated acyl-CoA. Examples of reactions catalyzed by fatty acid elongases are the conversion of GLA to DGLA, STA to ETA, and EPA to DPA. In general, the substrate selectivity of elongases is somewhat broad but segregated by both chain length and the degree of unsaturation. Accordingly, elongases can have different specificities. For example, a $C_{14/16}$ elongase will prefer a $C_{14}$ substrate, a $C_{16/18}$ elongase will prefer a $C_{16}$ substrate, a $C_{18/20}$ elongase will prefer a $C_{18}$ substrate and a $C_{20/22}$ elongase will prefer a $C_{20}$ substrate. In like manner, a Δ9 elongase is able to catalyze the conversion of LA and ALA to EDA and ETrA, respectively.

The term "oleaginous" refers to those organisms that tend to store their energy source in the form of lipid (Weete, In: Fungal Lipid Biochemistry, $2^{nd}$ Ed., Plenum, 1980). Generally, the cellular oil content of these microorganisms follows a sigmoid curve, wherein the concentration of lipid increases until it reaches a maximum at the late logarithmic or early stationary growth phase and then gradually decreases during the late stationary and death phases (Yongmanitchai and Ward, *Appl. Environ. Microbiol.* 57:419–25 (1991)).

The term "oleaginous yeast" refers to those microorganisms classified as yeasts that can make oil. Generally, the cellular oil or triacylglycerol content of oleaginous microorganisms follows a sigmoid curve, wherein the concentration of lipid increases until it reaches a maximum at the late logarithmic or early stationary growth phase and then gradually decreases during the late stationary and death phases (Yongmanitchai and Ward, *Appl. Environ. Microbiol.* 57:419–25 (1991)). It is not uncommon for oleaginous microorganisms to accumulate in excess of about 25% of their dry cell weight as oil. Examples of oleaginous yeast include, but are no means limited to, the following genera: *Yarrowia, Candida, Rhodotorula, Rhodosporidium, Cryptococcus, Trichosporon* and *Lipomyces.*

The term "fermentable carbon substrate" means a carbon source that a microorganism will metabolize to derive energy. Typical carbon sources of the invention include, but are not limited to: monosaccharides, oligosaccharides, polysaccharides, alkanes, fatty acids, esters of fatty acids, monoglycerides, diglycerides, triglycerides, carbon dioxide, methanol, formaldehyde, formate and carbon-containing amines.

As used herein, the terms "isolated nucleic acid fragment" or "isolated nucleic acid molecule" will be used interchangeably and will mean a polymer of RNA or DNA that is single- or double-stranded, optionally containing synthetic, non-natural or altered nucleotide bases. An isolated nucleic acid fragment in the form of a polymer of DNA may be comprised of one or more segments of cDNA, genomic DNA or synthetic DNA.

A nucleic acid molecule is "hybridizable" to another nucleic acid molecule, such as a cDNA, genomic DNA, or RNA molecule, when a single-stranded form of the nucleic acid molecule can anneal to the other nucleic acid molecule under the appropriate conditions of temperature and solution ionic strength. Hybridization and washing conditions are well known and exemplified in Sambrook, J., Fritsch, E. F. and Maniatis, T. *Molecular Cloning: A Laboratory Manual,* $2^{nd}$ ed., Cold Spring Harbor Laboratory: Cold Spring Harbor, N.Y. (1989), particularly Chapter 11 and Table 11.1 therein (entirely incorporated herein by reference). The conditions of temperature and ionic strength determine the "stringency" of the hybridization. Stringency conditions can be adjusted to screen for moderately similar fragments (such as homologous sequences from distantly related organisms), to highly similar fragments (such as genes that duplicate functional enzymes from closely related organisms). Post-hybridization washes determine stringency conditions. One set of preferred conditions uses a series of washes starting with 6×SSC, 0.5% SDS at room temperature for 15 min, then repeated with 2×SSC, 0.5% SDS at 45° C. for 30 min, and then repeated twice with 0.2×SSC, 0.5% SDS at 50° C. for 30 min. A more preferred set of stringent conditions uses higher temperatures in which the washes are identical to those above except for the temperature of the final two 30 min washes in 0.2×SSC, 0.5% SDS was increased to 60° C. Another preferred set of highly stringent conditions uses two final washes in 0.1×SSC, 0.1% SDS at 65° C. An additional set of stringent conditions include hybridization at 0.1×SSC, 0.1% SDS, 65° C. and washed with 2×SSC, 0.1% SDS followed by 0.1×SSC, 0.1% SDS, for example.

Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of Tm for hybrids of nucleic acids having those sequences. The relative stability (corresponding to higher Tm) of nucleic acid hybridizations decreases in the following order: RNA:RNA, DNA:RNA, DNA:DNA. For hybrids of greater than 100 nucleotides in length, equations for calculating Tm have been derived (see Sambrook et al., supra, 9.50–9.51). For hybridizations with shorter nucleic acids, i.e., oligonucleotides, the position of mismatches becomes more important, and the length of the oligonucleotide determines its specificity (see Sambrook et al., supra, 11.7–11.8). In one embodiment the length for a hybridizable nucleic acid is at least about 10 nucleotides. Preferably a minimum length for a hybridizable nucleic acid is at least about 15 nucleotides; more preferably at least about 20 nucleotides; and most preferably the length is at least about 30 nucleotides. Furthermore, the skilled artisan will recognize that the temperature and wash solution salt concentration may be adjusted as necessary according to factors such as length of the probe.

A "substantial portion" of an amino acid or nucleotide sequence is that portion comprising enough of the amino acid sequence of a polypeptide or the nucleotide sequence of a gene to putatively identify that polypeptide or gene, either by manual evaluation of the sequence by one skilled in the art, or by computer-automated sequence comparison and identification using algorithms such as BLAST (Basic Local Alignment Search Tool; Altschul, S. F., et al., *J. Mol. Biol.* 215:403–410 (1993)). In general, a sequence of ten or more contiguous amino acids or thirty or more nucleotides is necessary in order to putatively identify a polypeptide or nucleic acid sequence as homologous to a known protein or gene. Moreover, with respect to nucleotide sequences, gene specific oligonucleotide probes comprising 20–30 contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12–15 bases may be used as amplification primers in PCR in order to obtain a particular nucleic acid fragment comprising the primers. Accordingly, a "substantial portion" of a nucleotide sequence comprises enough of the sequence to specifically identify and/or isolate a nucleic acid fragment comprising the sequence. The instant specification teaches partial or complete amino acid and nucleotide sequences encoding one or more particular microbial proteins. The skilled artisan, having the benefit of the sequences as reported herein, may now use all or a substantial portion of the disclosed sequences for purposes known to those skilled in this art. Accordingly, the instant invention comprises the complete sequences as reported in the accompanying Sequence Listing, as well as substantial portions of those sequences as defined above.

The term "complementary" is used to describe the relationship between nucleotide bases that are capable of hybridizing to one another. For example, with respect to DNA, adenosine is complementary to thymine and cytosine is complementary to guanine. Accordingly, the instant invention also includes isolated nucleic acid fragments that are complementary to the complete sequences as reported in the accompanying Sequence Listing, as well as those substantially similar nucleic acid sequences.

The term "percent identity", as known in the art, is a relationship between two or more polypeptide sequences or two or more polynucleotide sequences, as determined by comparing the sequences. In the art, "identity" also means the degree of sequence relatedness between polypeptide or polynucleotide sequences, as the case may be, as determined by the match between strings of such sequences. "Identity" and "similarity" can be readily calculated by known methods, including but not limited to those described in: 1.) *Computational Molecular Biology* (Lesk, A. M., Ed.) Oxford University: NY (1988); 2.) *Biocomputing: Informatics and Genome Projects* (Smith, D. W., Ed.) Academic: NY (1993); 3.) *Computer Analysis of Sequence Data. Part I* (Griffin, A. M., and Griffin, H. G., Eds.) Humania: NJ (1994); 4.) *Sequence Analysis in Molecular Biology* (von Heinje, G., Ed.) Academic (1987); and 5.) *Sequence Analysis Primer* (Gribskov, M. and Devereux, J., Eds.) Stockton: NY (1991). Preferred methods to determine identity are designed to give the best match between the sequences tested. Methods to determine identity and similarity are codified in publicly available computer programs. Sequence alignments and percent identity calculations may be performed using the Megalign program of the LASERGENE bioinformatics computing suite (DNASTAR Inc., Madison, Wis.). Multiple alignment of the sequences is performed using the Clustal method of alignment (Higgins and Sharp, *CABIOS.* 5:151–153 (1989)) with default parameters (GAP PENALTY=10, GAP LENGTH PENALTY=10). Default parameters for pairwise alignments using the Clustal method are: KTUPLE 1, GAP PENALTY=3, WINDOW=5 and DIAGONALS SAVED=5.

Suitable nucleic acid fragments (isolated polynucleotides of the present invention) encode polypeptides that are at least about 70% identical, preferably at least about 75% identical, and more preferably at least about 80% identical to the amino acid sequences reported herein. Preferred nucleic acid fragments encode amino acid sequences that are about 85% identical to the amino acid sequences reported herein. More preferred nucleic acid fragments encode amino acid sequences that are at least about 90% identical to the amino acid sequences reported herein. Most preferred are nucleic acid fragments that encode amino acid sequences that are at least about 95% identical to the amino acid sequences reported herein. Suitable nucleic acid fragments not only have the above homologies but typically encode a polypeptide having at least 50 amino acids, preferably at least 100 amino acids, more preferably at least 150 amino acids, still more preferably at least 200 amino acids, and most preferably at least 250 amino acids.

The term "sequence analysis software" refers to any computer algorithm or software program that is useful for the analysis of nucleotide or amino acid sequences. "Sequence analysis software" may be commercially available or independently developed. Typical sequence analysis software will include, but is not limited to: 1.) the GCG suite of programs (Wisconsin Package Version 9.0, Genetics Computer Group (GCG), Madison, Wis.); 2.) BLASTP, BLASTN, BLASTX (Altschul et al., *J. Mol. Biol.* 215: 403–410 (1990)); 3.) DNASTAR (DNASTAR, Inc. Madison, Wis.); 4.) Sequencher (Gene Codes Corporation, Ann Arbor, Mich.); and 5.) the FASTA program incorporating the Smith-Waterman algorithm (W. R. Pearson, *Comput. Methods Genome Res.,* [Proc. Int. Symp.] (1994), Meeting Date 1992, 111–20. Suhai, Sandor, Ed. Plenum: New York, N.Y.). Within the context of this application it will be understood that where sequence analysis software is used for analysis, that the results of the analysis will be based on the "default values" of the program referenced, unless otherwise specified. As used herein "default values" will mean any set of values or parameters that originally load with the software when first initialized.

"Codon degeneracy" refers to the nature in the genetic code permitting variation of the nucleotide sequence without affecting the amino acid sequence of an encoded polypeptide. The skilled artisan is well aware of the "codon-bias" exhibited by a specific host cell in usage of nucleotide codons to specify a given amino acid. Therefore, when synthesizing a gene for improved expression in a host cell, it is desirable to design the gene such that its frequency of codon usage approaches the frequency of preferred codon usage of the host cell.

The term "codon-optimized", as it refers to genes or coding regions of nucleic acid molecules, refers to modification of codons such that the altered codons reflect the typical codon usage of the host organism without altering the polypeptide for which the DNA codes.

"Chemically synthesized", as related to a sequence of DNA, means that the component nucleotides were assembled in vitro. Manual chemical synthesis of DNA may be accomplished using well-established procedures; or, automated chemical synthesis can be performed using one of a number of commercially available machines. "Synthetic genes" can be assembled from oligonucleotide building blocks that are chemically synthesized using procedures known to those skilled in the art. These building blocks are ligated and annealed to form gene segments that are then enzymatically assembled to construct the entire gene. Accordingly, the genes can be tailored for optimal gene expression based on optimization of nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell, where sequence information is available.

"Gene" refers to a nucleic acid fragment that expresses a specific protein, and that may refer to the coding region alone or may include regulatory sequences preceding (5' non-coding sequences) and following (3' non-coding sequences) the coding sequence. "Native gene" refers to a gene as found in nature with its own regulatory sequences. "Chimeric gene" refers to any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene that is introduced into the host organism by gene transfer. Foreign genes can comprise native genes inserted into a non-native organism, native genes introduced into a new location within the native host, or chimeric genes. A "transgene" is a gene that has been introduced into the genome by a transformation procedure. A "codon-optimized gene" is a gene having its frequency of codon usage designed to mimic the frequency of preferred codon usage of the host cell.

"Coding sequence" refers to a DNA sequence that codes for a specific amino acid sequence. "Suitable regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, polyadenylation recognition sequences, RNA processing sites, effector binding sites and stem-loop structures.

"Promoter" refers to a DNA sequence capable of controlling the expression of a coding sequence or functional RNA. In general, a coding sequence is located 3' to a promoter sequence. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental or physiological conditions. Promoters that cause a gene to be expressed in most cell types at most times are commonly referred to as "constitutive promoters". It is further recognized that since in most cases the exact boundaries of regulatory sequences have not been completely defined, DNA fragments of different lengths may have identical promoter activity.

The term "3' non-coding sequences" or "transcription terminator" refers to DNA sequences located downstream of a coding sequence. This includes polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The 3' region can influence the transcription, RNA processing or stability, or translation of the associated coding sequence.

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from post-transcriptional processing of the primary transcript and is referred to as the mature RNA. "Messenger RNA" or "mRNA" refers to the RNA that is without introns and that can be translated into protein by the cell. "cDNA" refers to a double-stranded DNA that is complementary to, and derived from, mRNA. "Sense" RNA refers to RNA transcript that includes the mRNA and so can be translated into protein by the cell. "Antisense RNA" refers to a RNA transcript that is complementary to all or part of a target primary transcript or mRNA and that blocks the expression of a target gene (U.S. Pat. No. 5,107,065; WO 99/28508). The complementarity of an antisense RNA may be with any part of the specific gene transcript, i.e., at the 5' non-coding sequence, 3' non-coding sequence, or the coding sequence. "Functional RNA" refers to antisense RNA, ribozyme RNA, or other RNA that is not translated and yet has an effect on cellular processes.

The term "operably linked" refers to the association of nucleic acid sequences on a single nucleic acid fragment so that the function of one is affected by the other. For example, a promoter is operably linked with a coding sequence when it is capable of affecting the expression of that coding sequence (i.e., the coding sequence is under the transcriptional control of the promoter). Coding sequences can be operably linked to regulatory sequences in sense or antisense orientation.

The term "expression", as used herein, refers to the transcription and stable accumulation of sense (mRNA) or antisense RNA derived from the nucleic acid fragment(s) of the invention. Expression may also refer to translation of mRNA into a polypeptide.

"Transformation" refers to the transfer of a nucleic acid molecule into a host organism, resulting in genetically stable inheritance. The nucleic acid molecule may be a plasmid that replicates autonomously, for example; or, it may integrate into the genome of the host organism. Host organisms containing the transformed nucleic acid fragments are referred to as "transgenic" or "recombinant" or "transformed" organisms.

The terms "plasmid", "vector" and "cassette" refer to an extra chromosomal element often carrying genes that are not part of the central metabolism of the cell, and usually in the form of circular double-stranded DNA fragments. Such elements may be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell. "Expression cassette" refers to a specific vector containing a foreign gene(s) and having elements in addition to the foreign gene(s) that allow for enhanced expression of that gene in a foreign host.

The term "homologous recombination" refers to the exchange of DNA fragments between two DNA molecules (during cross over). The fragments that are exchanged are flanked by sites of identical nucleotide sequences between the two DNA molecules (i.e., "regions of homology").

The term "regions of homology" refer to stretches of nucleotide sequence on nucleic acid fragments that participate in homologous recombination that have homology to each other. Effective homologous recombination will generally take place where these regions of homology are at least about 10 bp in length where at least about 50 bp in length is preferred. Typically fragments that are intended for recombination contain at least two regions of homology where targeted gene disruption or replacement is desired.

Standard recombinant DNA and molecular cloning techniques used herein are well known in the art and are described by Sambrook, J., Fritsch, E. F. and Maniatis, T., *Molecular Cloning: A Laboratory Manual,* $2^{nd}$ ed., Cold Spring Harbor Laboratory: Cold Spring Harbor, N.Y. (1989) (hereinafter "Maniatis"); by Silhavy, T. J., Bennan, M. L. and Enquist, L. W., *Experiments with Gene Fusions,* Cold Spring Harbor Laboratory: Cold Spring Harbor, N.Y. (1984); and by Ausubel, F. M. et al., *Current Protocols in Molecular Biology,* published by Greene Publishing Assoc. and Wiley-Interscience (1987).

Microbial Biosynthesis of Fatty Acids and Triacylglycerols

The process of de novo synthesis of palmitate (16:0) in oleaginous microorganisms is described in U.S. Ser. No. 10/840,579. This fatty acid is the precursor of longer-chain saturated and unsaturated fatty acid derivates, which are formed through the action of elongases and desaturases. For example, palmitate is converted to stearic acid by a $C_{16/18}$ fatty acid elongase; palmitate and stearate (as CoA and/or ACP esters) are converted to their unsaturated derivatives, palmitoleic (16:1) and oleic (18:1) acids, respectively, by the action of a Δ9 desaturase.

TAGs (the primary storage unit for fatty acids) are formed by a series of reactions. First, one molecule of acyl-CoA is esterified to glycerol-3-phosphate via GPAT to produce lysophosphatidic acid (LPA) (and CoA as a by-product). Secondly, LPAAT catalyzes a reaction whereby LPA is converted to 2-diacylglycerol phosphate (commonly identified as phosphatidic acid (PA)) (and CoA as a by-product) by the esterification of a second molecule of acyl-CoA. Third, phosphatidic acid phosphatase is responsible for the removal of a phosphate group from phosphatidic acid to yield 1,2-diacylglycerol (DAG). And finally, a third fatty acid is added to the sn-3 position of DAG by a DAG acyltransferase (e.g., PDAT, DGAT1 or DGAT2) to form TAG.

A wide spectrum of fatty acids can be incorporated into TAGs, including saturated and unsaturated fatty acids and short-chain and long-chain fatty acids. Some non-limiting examples of fatty acids that can be incorporated into TAGs by acyltransferases (e.g., DGAT2) include: capric (10:0), lauric (12:0), myristic (14:0), palmitic (16:0), palmitoleic (16:1), stearic (18:0), oleic (18:1), vaccenic (18:1), LA (18:2), eleostearic (18:3), GLA (18:3), ALA (18:3), STA (18:4), arachidic (20:0), EDA (20:2), DGLA (20:3), ETrA (20:3), ARA (20:4), ETA (20:4), EPA (20:5), behenic (22:0), DPA (22:5), DHA (22:6), lignoceric (24:0), nervonic (24:1), cerotic (26:0), and montanic (28:0) fatty acids. In preferred embodiments of the present invention, incorporation of PUFAs into TAG is most desirable.

Biosynthesis of Omega-3 and Omega-6 Polyunsaturated Fatty Acids

The metabolic process that converts LA to GLA, DGLA and ARA (the ω-6 pathway) and ALA to STA, ETA, EPA, DPA and DHA (the ω-3 pathway) involves elongation of the carbon chain through the addition of two-carbon units and desaturation of the molecule through the addition of double bonds (FIG. 6). This requires a series of desaturation and elongation enzymes. Specifically, oleic acid is converted to LA (18:2), the first of the ω-6 fatty acids, by the action of a Δ12 desaturase. Subsequent ω-6 fatty acids are produced as follows: 1.) LA is converted to GLA by the activity of a Δ6 desaturase; 2.) GLA is converted to DGLA by the action of an elongase; and 3.) DGLA is converted to ARA by the action of a Δ5 desaturase. In like manner, linoleic acid (LA) is converted to ALA, the first of the ω-3 fatty acids, by the action of a Δ15 desaturase. Subsequent ω-3 fatty acids are produced in a series of steps similar to that for the ω-6 fatty acids. Specifically, 1.) ALA is converted to STA by the activity of a Δ6 desaturase; 2.) STA is converted to ETA by the activity of an elongase; and 3.) ETA is converted to EPA by the activity of a Δ5 desaturase. Alternatively, ETA and EPA can be produced from DGLA and ARA, respectively, by the activity of a Δ17 desaturase. EPA can be further converted to DHA by the activity of an elongase and a Δ4 desaturase.

In alternate embodiments, a Δ9 elongase is able to catalyze the conversion of LA and ALA to eicosadienoic acid (EDA; C20:2) and eicosatrienoic acid (ETrA; C20:3), respectively. A Δ8 desaturase then converts these products to DGLA and ETA, respectively.

Many microorganisms, including algae, bacteria, molds, fungi and yeast can synthesize PUFAs and omega fatty acids in the ordinary course of cellular metabolism. Alternatively, if the host organism of choice does not natively produce the desired PUFAs (or possess the desired lipid profile), one skilled in the art will be familiar with the considerations and techniques necessary to introduce an expression cassette encoding appropriate enzymes for PUFA biosynthesis into the host organism of choice. For these purposes, a variety of desaturase and elongase genes involved in PUFA production have been identified through genetic means and the DNA sequences of some of these genes are publicly available (e.g., see U.S. Ser. No. 10/840,579 for a review of available genes in GenBank and/or the patent literature and considerations for choosing a specific polypeptide having desaturase or elongase activity). And, although not elaborated in detail herein, numerous teachings are provided in the literature wherein various organisms are engineered to produce specific PUFAs; some illustrative references are provided as follows, although these should not be construed as limiting: WO 98/46763; WO 98/46764; WO 98/46765; WO 99/64616; WO 02/077213; WO 03/093482; WO 04/057001; WO 04/090123; WO 04/087902; WO 04/101757; U.S. Pat. Nos. 6,140,486; 6,459,018; 6,136,574; U.S. 03/0172399; U.S. 04/0172682; U.S. 04/098762; U.S. 04/0111763; U.S. 04/0053379; U.S. 04/0049805; U.S. 04/0237139; U.S. 04/0172682; Beaudoin F. et al., *PNAS USA,* 97(12):6421–6426 (2000); Dyer, J. M. et al., *Appl. Envi. Microbiol.,* 59:224–230 (2002); Domergue, F. et al. *Eur. J.*

*Biochem.* 269:4105–4113 (2002); Qi, B. et al., *Nature Biotech.* 22:739–745 (2004); and Abbadi et al., *The Plant Cell,* 16:2734–2748 (2004)).

Briefly, however, a variety of ω-3/ω-6 PUFA products can be produced (prior to their transfer to TAGs), depending on the fatty acid substrate and the particular genes of the ω-3/ω-6 fatty acid biosynthetic pathway that are present in (or transformed into) the host cell. As such, production of the desired fatty acid product can occur directly (wherein the fatty acid substrate is converted directly into the desired fatty acid product without any intermediate steps or pathway intermediates) or indirectly (wherein multiple genes encoding the ω-3/ω-6 biosynthetic pathway may be used in combination, such that a series of reactions occur to produce a desired PUFA). Specifically, for example, it may be desirable to transform an oleaginous yeast with an expression cassette comprising a A6 desaturase, a $C_{18/20}$ elongase, a Δ5 desaturase and a Δ17 desaturase for the overproduction of EPA. As is well known to one skilled in the art, various other combinations of the following enzymatic activities may be useful to express in an oleaginous organism: a Δ15 desaturase, a Δ4 desaturase, a Δ5 desaturase, a Δ6 desaturase, Δ12 desaturase, a Δ9 desaturase, a Δ8 desaturase, a Δ12 desaturase, a Δ9 elongase, a $C_{14/16}$ elongase, a $C_{16/18}$ elongase, a $C_{18/20}$ elongase and/or a $C_{20/22}$ elongase (see FIG. 6). The particular genes included within a particular expression cassette will depend on the oleaginous organism (and its PUFA profile and/or desaturase/elongase profile), the availability of substrate and the desired end product(s).

Sequence Identification of *Mortierella alpina* GPAT

In the present invention, a gene encoding GPAT has been isolated from *Mortierella alpina. M. alpina* is an organism that naturally accumulates fatty acids having chain lengths equal to or greater than $C_{20}$ in its TAG fraction, thus indicating that the GPAT is likely to have the desired substrate specificity that would favor incorporation of long-chain PUFAs into TAGs.

Comparison of the GPAT nucleotide base and deduced amino acid sequences to public databases, using a BLAST algorithm (Altschul, S. F., et al., *Nucleic Acids Res.* 25:3389–3402 (1997)), reveals that the most similar known sequences are about 47% identical to the amino acid sequence of GPAT reported herein over a length of 716 amino acids. Preferred amino acid fragments are at least about 70%–80% identical to the sequences herein, where those sequences that are 85%–90% identical are particularly suitable and those sequences that are about 95% identical are most preferred. Similarly, preferred GPAT encoding nucleic acid sequences corresponding to the instant ORF are those encoding active proteins and which are at least about 70%–80% identical to the nucleic acid sequences encoding GPAT reported herein, where those sequences that are 85%–90% identical are particularly suitable and those sequences that are about 95% identical are most preferred.

Isolation of Homologs

GPAT nucleic acid fragments of the instant invention may be used to isolate genes encoding homologous proteins from the same or other microbial species. Isolation of homologous genes using sequence-dependent protocols is well known in the art. Examples of sequence-dependent protocols include, but are not limited to: 1.) methods of nucleic acid hybridization; 2.) methods of DNA and RNA amplification, as exemplified by various uses of nucleic acid amplification technologies [e.g., polymerase chain reaction (PCR), Mullis et al., U.S. Pat. No. 4,683,202; ligase chain reaction (LCR), Tabor, S. et al., *Proc. Acad. Sci. USA* 82:1074 (1985); or strand displacement amplification (SDA), Walker, et al., *Proc. Natl. Acad. Sci. U.S.A.,* 89:392 (1992)]; and 3.) methods of library construction and screening by complementation.

For example, genes encoding similar proteins or polypeptides to the GPAT described herein could be isolated directly by using all or a portion of the instant nucleic acid fragments as DNA hybridization probes to screen libraries from any desired yeast or fungus using methodology well known to those skilled in the art. Specific oligonucleotide probes based upon the instant nucleic acid sequences can be designed and synthesized by methods known in the art (Maniatis, supra). Moreover, the entire sequences can be used directly to synthesize DNA probes by methods known to the skilled artisan (e.g., random primers DNA labeling, nick translation or end-labeling techniques), or RNA probes using available in vitro transcription systems. In addition, specific primers can be designed and used to amplify a part of (or full-length of) the instant sequences. The resulting amplification products can be labeled directly during amplification reactions or labeled after amplification reactions, and used as probes to isolate full-length DNA fragments under conditions of appropriate stringency.

Typically, in PCR-type amplification techniques, the primers have different sequences and are not complementary to each other. Depending on the desired test conditions, the sequences of the primers should be designed to provide for both efficient and faithful replication of the target nucleic acid. Methods of PCR primer design are common and well known in the art (Thein and Wallace, "The use of oligonucleotides as specific hybridization probes in the Diagnosis of Genetic Disorders", in *Human Genetic Diseases: A Practical Approach,* K. E. Davis Ed., (1986) pp 33–50, IRL: Herndon, Va.; and Rychlik, W., In *Methods in Molecular Biology*, White, B. A. Ed., (1993) Vol. 15, pp 31–39, PCR Protocols: Current Methods and Applications. Humania: Totowa, N.J.).

Generally two short segments of the instant sequences may be used in PCR protocols to amplify longer nucleic acid fragments encoding homologous genes from DNA or RNA. PCR may also be performed on a library of cloned nucleic acid fragments wherein the sequence of one primer is derived from the instant nucleic acid fragments, and the sequence of the other primer takes advantage of the presence of the polyadenylic acid tracts to the 3' end of the mRNA precursor encoding microbial genes.

Alternatively, the second primer sequence may be based upon sequences derived from the cloning vector. For example, the skilled artisan can follow the RACE protocol (Frohman et al., *PNAS USA* 85:8998 (1988)) to generate cDNAs by using PCR to amplify copies of the region between a single point in the transcript and the 3' or 5' end. Primers oriented in the 3' and 5' directions can be designed from the instant sequences. Using commercially available 3' RACE or 5' RACE systems (BRL, Gaithersburg, Md.), specific 3' or 5' cDNA fragments can be isolated (Ohara et al., *PNAS USA* 86:5673 (1989); Loh et al., *Science* 243:217 (1989)).

Alternatively, the instant GPAT sequences may be employed as hybridization reagents for the identification of homologs. The basic components of a nucleic acid hybridization test include a probe, a sample suspected of containing the gene or gene fragment of interest, and a specific hybridization method. Probes of the present invention are typically single-stranded nucleic acid sequences that are complementary to the nucleic acid sequences to be detected. Probes are "hybridizable" to the nucleic acid sequence to be detected. The probe length can vary from 5 bases to tens of thousands of bases, and will depend upon the specific test to be done. Typically a probe length of about 15 bases to about 30 bases is suitable. Only part of the probe molecule need be complementary to the nucleic acid sequence to be detected. In addition, the complementarity between the probe and the target sequence need not be perfect. Hybridization does occur between imperfectly complementary molecules with the result that a certain fraction of the bases in the hybridized region are not paired with the proper complementary base.

Hybridization methods are well defined. Typically the probe and sample must be mixed under conditions that will permit nucleic acid hybridization. This involves contacting the probe and sample in the presence of an inorganic or organic salt under the proper concentration and temperature conditions. The probe and sample nucleic acids must be in contact for a long enough time that any possible hybridization between the probe and sample nucleic acid may occur. The concentration of probe or target in the mixture will determine the time necessary for hybridization to occur. The higher the probe or target concentration, the shorter the hybridization incubation time needed. Optionally, a chaotropic agent may be added. The chaotropic agent stabilizes nucleic acids by inhibiting nuclease activity. Furthermore, the chaotropic agent allows sensitive and stringent hybridization of short oligonucleotide probes at room temperature (Van Ness and Chen, *Nucl. Acids Res.* 19:5143–5151 (1991)). Suitable chaotropic agents include guanidinium chloride, guanidinium thiocyanate, sodium thiocyanate, lithium tetrachloroacetate, sodium perchlorate, rubidium tetrachloroacetate, potassium iodide and cesium trifluoroacetate, among others. Typically, the chaotropic agent will be present at a final concentration of about 3 M. If desired, one can add formamide to the hybridization mixture, typically 30–50% (v/v).

Various hybridization solutions can be employed. Typically, these comprise from about 20 to 60% volume, preferably 30%, of a polar organic solvent. A common hybridization solution employs about 30–50% v/v formamide, about 0.15 to 1 M sodium chloride, about 0.05 to 0.1 M buffers (e.g., sodium citrate, Tris-HCl, PIPES or HEPES (pH range about 6–9)), about 0.05 to 0.2% detergent (e.g., sodium dodecylsulfate), or between 0.5–20 mM EDTA, FICOLL (Pharmacia Inc.) (about 300–500 kdal), polyvinylpyrrolidone (about 250–500 kdal) and serum albumin. Also included in the typical hybridization solution will be unlabeled carrier nucleic acids from about 0.1 to 5 mg/mL, fragmented nucleic DNA (e.g., calf thymus or salmon sperm DNA, or yeast RNA), and optionally from about 0.5 to 2% wt/vol glycine. Other additives may also be included, such as volume exclusion agents that include a variety of polar water-soluble or swellable agents (e.g., polyethylene glycol), anionic polymers (e.g., polyacrylate or polymethylacrylate) and anionic saccharidic polymers (e.g., dextran sulfate).

Nucleic acid hybridization is adaptable to a variety of assay formats. One of the most suitable is the sandwich assay format. The sandwich assay is particularly adaptable to hybridization under non-denaturing conditions. A primary component of a sandwich-type assay is a solid support. The solid support has adsorbed to it or covalently coupled to it immobilized nucleic acid probe that is unlabeled and complementary to one portion of the sequence.

Availability of the instant nucleotide and deduced amino acid sequences facilitates immunological screening of DNA expression libraries. Synthetic peptides representing portions of the instant amino acid sequences may be synthesized. These peptides can be used to immunize animals to produce polyclonal or monoclonal antibodies with specificity for peptides or proteins comprising the amino acid sequences. These antibodies can then be used to screen DNA expression libraries to isolate full-length DNA clones of interest (Lerner, R. A. *Adv. Immunol.* 36:1 (1984); Maniatis, supra).

Gene Optimization for Improved Heterologous Expression

It may be desirable to modify the expression of the instant GPAT and/or ω-3/ω-6 biosynthetic pathway enzymes to achieve optimal conversion efficiency of each, according to the specific TAG composition of interest. As such, a variety of techniques can be utilized to improve/optimize the expression of a polypeptide of interest in an alternative host. Two such techniques include codon-optimization and mutagenesis of the gene.

Codon Optimization

As will be appreciated by one skilled in the art, it is frequently useful to modify a portion of the codons encoding a particular polypeptide that is to be expressed in a foreign host, such that the modified polypeptide uses codons that are preferred by the alternate host. Use of host-preferred codons can substantially enhance the expression of the foreign gene encoding the polypeptide.

In general, host-preferred codons can be determined within a particular host species of interest by examining codon usage in proteins (preferably those expressed in the largest amount) and determining which codons are used with highest frequency. Thus, the coding sequence for a specific polypeptide of interest can be synthesized in whole or in part using the codons preferred in the host species. All (or portions) of the DNA also can be synthesized to remove any destabilizing sequences or regions of secondary structure that would be present in the transcribed mRNA. All (or portions) of the DNA also can be synthesized to alter the base composition to one more preferable in the desired host cell.

Thus, for example, it may be desirable to modify a portion of the codons encoding the GPAT polypeptide, to enhance the expression of the gene in *Yarrowia lipolytica*. The codon usage profile and the consensus sequence around the 'ATG' translation initiation codon for this particular organism are taught in WO 2004/101753; likewise, a method for rapid synthesis of genes optimized for expression in *Y. lipolytica* is also provided.

Mutagenesis

Methods for synthesizing sequences and bringing sequences together are well established in the literature. For example, in vitro mutagenesis and selection, site-directed mutagenesis, error prone PCR (Melnikov et al., *Nucleic Acids Research,* 27(4):1056–1062 (Feb. 15, 1999)), "gene shuffling" or other means can be employed to obtain mutations of naturally occurring GPAT genes. This would permit production of a GPAT polypeptide having activity in vivo with more desirable physical and kinetic parameters for function in the host cell (e.g., a longer half-life or a higher rate of synthesis of TAGs from fatty acids).

If desired, the regions of a GPAT polypeptide important for enzymatic activity can be determined through routine mutagenesis, expression of the resulting mutant polypeptides and determination of their activities. Mutants may include deletions, insertions and point mutations, or combinations thereof. A typical functional analysis begins with deletion mutagenesis to determine the N- and C-terminal limits of the protein necessary for function, and then internal deletions, insertions or point mutants are made to further determine regions necessary for function. Other techniques such as cassette mutagenesis or total synthesis also can be used. Deletion mutagenesis is accomplished, for example, by using exonucleases to sequentially remove the 5' or 3' coding regions. Kits are available for such techniques. After deletion, the coding region is completed by ligating oligonucleotides containing start or stop codons to the deleted coding region after the 5' or 3' deletion, respectively. Alternatively, oligonucleotides encoding start or stop codons are inserted into the coding region by a variety of methods including site-directed mutagenesis, mutagenic PCR or by ligation onto DNA digested at existing restriction sites. Internal deletions can similarly be made through a variety of methods including the use of existing restriction sites in the DNA, by use of mutagenic primers via site-directed mutagenesis or mutagenic PCR. Insertions are made through methods such as linker-scanning mutagenesis, site-directed mutagenesis or mutagenic PCR. Point mutations are made through techniques such as site-directed mutagenesis or mutagenic PCR.

Chemical mutagenesis also can be used for identifying regions of a GPAT polypeptide important for activity. A mutated construct is expressed, and the ability of the resulting altered protein to function as desired is assayed. Such structure-function analysis can determine which regions may be deleted, which regions tolerate insertions, and which point mutations allow the mutant protein to function in substantially the same way as the native GPAT.

All such mutant proteins and nucleotide sequences encoding them that are derived from the GPAT described herein are within the scope of the present invention.

Metabolic Engineering to Up-Regulate Genes and Biosynthetic Pathways Affecting Fatty Acid Synthesis and Oil Accumulation in Oleaginous Yeast Methods useful for manipulating biochemical pathways are well known to those skilled in the art. It is expected that introduction of chimeric genes encoding the GPAT described herein, under the control of the appropriate promoters, will result in increased transfer of fatty acids (and preferentially long-chain PUFAs) to storage TAGs. As such, the present invention encompasses a method for increasing the TAG content in a host cell comprising expressing the GPAT enzyme of the present invention in a transformed host cell producing a fatty acid, such that the fatty acid is transferred to the TAG pool.

Additional copies of GPAT genes may be introduced into the host to increase the transfer of fatty acids to the TAG fraction. Expression of the genes also can be increased at the transcriptional level through the use of a stronger promoter (either regulated or constitutive) to cause increased expression, by removing/deleting destabilizing sequences from either the mRNA or the encoded protein, or by adding stabilizing sequences to the mRNA (U.S. Pat. No. 4,910,141). Yet another approach to increase expression of heterologous genes is to increase the translational efficiency of the encoded mRNAs by replacement of codons in the native gene with those for optimal gene expression in the selected host.

In one specific embodiment, the present invention encompasses a method of increasing the ω-3 and/or ω-6 fatty acid content of TAGs in an oleaginous yeast, since it is possible to introduce an expression cassette encoding each of the enzymes necessary for ω-3 and/or ω-6 fatty acid biosynthesis into the organism (since naturally produced PUFAs in these organisms are limited to 18:2 (i.e., LA), and less commonly 18:3 (i.e., ALA) fatty acids). Thus, the method comprises:

a) providing a transformed oleaginous yeast host cell possessing at least one gene encoding at least one enzyme of the ω-3/ω-6 fatty acid biosynthetic pathway and the GPAT of the present invention;
b) growing the yeast cells of step (a) in the presence of a fermentable carbon substrate, whereby the gene(s) of the ω-3/ω-6 fatty acid biosynthetic pathway and GPAT are expressed, whereby a ω-3 and/or ω-6 fatty acid is produced, and whereby the ω-3 and/or ω-6 fatty acid is transferred to TAGs.

Within the context of the present invention, it may be useful to modulate the expression of the TAG biosynthetic pathway by any one of the methods described above. For example, the present invention provides a gene encoding a key enzyme in the fatty acid biosynthetic pathway leading to the storage of TAGs. This gene encodes the GPAT enzyme. It will be particularly useful to express this gene in oleaginous yeast to maximize production and accumulation of TAGs using various means for metabolic engineering of the host organism. In preferred embodiments, modification of the expression levels of this gene in combination with expression of ω-3/ω-6 biosynthetic genes can be utilized to maximize production and accumulation of preferred PUFAs in the TAG pool.

Metabolic Engineering to Down-Regulate Undesirable Genes and Biosynthetic Pathways Affecting Fatty Acid Synthesis and Oil Accumulation in Oleaqinous Yeast In some embodiments, it may be useful to disrupt or inactivate a host organism's native GPAT, based on the complete sequences described herein, the complement of those complete sequences, substantial portions of those sequences, codon-optimized acyltransferases derived therefrom, and those sequences that are substantially homologous thereto. In an alternate embodiment, a transformant host organism comprising a disruption or inactivation of its native GPAT may then be advantageously transformed to express a heterologous GPAT (e.g., if the heterologous GPAT has different substrate specificity than the native GPAT).

For gene disruption, a foreign DNA fragment (typically a selectable marker gene) is inserted into the structural gene to be disrupted in order to interrupt its coding sequence and thereby functionally inactivate the gene. Transformation of the disruption cassette into the host cell results in replacement of the functional native gene by homologous recombination with the non-functional disrupted gene (see, for example: Hamilton et al., *J. Bacteriol.* 171:4617–4622 (1989); Balbas et al., *Gene* 136:211–213 (1993); Gueldener et al., *Nucleic Acids Res.* 24:2519–2524 (1996); and Smith et al., *Methods Mol. Cell. Biol.* 5:270–277(1996)).

Antisense technology is another method of down-regulating genes when the sequence of the target gene is known. To accomplish this, a nucleic acid segment from the desired gene is cloned and operably linked to a promoter such that the anti-sense strand of RNA will be transcribed. This construct is then introduced into the host cell and the antisense strand of RNA is produced. Antisense RNA inhibits gene expression by preventing the accumulation of mRNA that encodes the protein of interest. The person skilled in the art will know that special considerations are associated with the use of antisense technologies in order to reduce expression of particular genes. For example, the proper level of expression of antisense genes may require the use of different chimeric genes utilizing different regulatory elements known to the skilled artisan.

Although targeted gene disruption and antisense technology offer effective means of down-regulating genes where the sequence is known, other less specific methodologies have been developed that are not sequence-based (e.g., mutagenesis via UV radiation/chemical agents or use of transposable elements/transposons; see WO 04/101757).

As described in U.S. Patent Application No. 60/624812, the Applicants have discovered that expression of heterologous acyltransferases in conjunction with knockouts of the corresponding native *Yarrowia lipolytica* acyltransferase can significantly increase the overall long-chain ω-3 PUFAs that are produced in transformant *Y. lipolytica* host cells engineered for PUFA biosynthesis. This manipulation is thought to reduce substrate competition between the native and heterologous acyltransferase; and, when the heterologous acyltransferase has specificity for those fatty acids that are 18:3 and greater (in comparison to the native enzymes that may not efficiently catalyze reactions with longer chain fatty acids since naturally produced PUFAs in *Y. lipolytica* are limited to 18:2 fatty acids), more efficient acyltransferase reactions are likely enabled within the transformant host. Thus, within the context of the present invention, it may be useful to disrupt or inactivate a host organism's native GPAT (e.g., the *Y. lipolytica* GPAT) that does not have specificity for long-chain PUFAs (e.g., 20:0, 22:0) or that has difficulty efficiently synthesizing TAGs comprising fatty acids that are 18:3 and greater in length (e.g., EPA). Then, the heterologous (or "foreign") GPAT of the present invention (i.e. SEQ ID NO:2) could be expressed to enable increased accumulation of long-chain PUFAs in the organism's TAG fraction, since substrate competition between the native and heterologous acyltransferase would be reduced. One skilled in the art would readily be able to apply the teachings herein toward the advantageous manipulation of GPAT enzymes and homologs in other oleaginous organisms.

In conjunction with this approach, or alternatively, it may be necessary to disrupt genes and pathways that diminish the existing fatty acid pool and/or that hydrolyze TAGs to regulate (and/or maximize) TAG accumulation.

Expression Systems, Cassettes and Vectors

The gene and gene product of the instant sequences described herein may be produced in microbial host cells, particularly in the cells of oleaginous yeast (e.g., *Yarrowia lipolytica*). Expression in recombinant microbial hosts may be useful for the transfer of various fatty acids to TAGs.

Microbial expression systems and expression vectors containing regulatory sequences that direct high level expression of foreign proteins are well known to those skilled in the art. Any of these could be used to construct chimeric genes for production of the gene products of the instant GPAT sequences. These chimeric genes could then be introduced into appropriate microorganisms via transformation to provide high level expression of the encoded enzymes.

Vectors or DNA cassettes useful for the transformation of suitable host cells are well known in the art. The specific choice of sequences present in the construct is dependent upon the desired expression products (supra), the nature of the host cell and the proposed means of separating transformed cells versus non-transformed cells. Typically, however, the vector or cassette contains sequences directing transcription and translation of the relevant gene(s), a selectable marker and sequences allowing autonomous replication or chromosomal integration. Suitable vectors comprise a region 5' of the gene that controls transcriptional initiation and a region 3' of the DNA fragment that controls transcriptional termination. It is most preferred when both control regions are derived from genes from the transformed host cell, although it is to be understood that such control regions need not be derived from the genes native to the specific species chosen as a production host.

Initiation control regions or promoters which are useful to drive expression of the instant ORF in the desired host cell are numerous and familiar to those skilled in the art. Virtually any promoter capable of directing expression of this gene in the selected host cell is suitable for the present invention. Expression in a host cell can be accomplished in a transient or stable fashion. Transient expression can be accomplished by inducing the activity of a regulatable promoter operably linked to the gene of interest. Stable expression can be achieved by the use of a constitutive promoter operably linked to the gene of interest. As an example, when the host cell is yeast, transcriptional and translational regions functional in yeast cells are provided, particularly from the host species. The transcriptional initiation regulatory regions can be obtained, for example, from: 1.) genes in the glycolytic pathway, such as alcohol dehydrogenase, glyceraldehyde-3-phosphate-dehydrogenase (WO 2005/003310; co-pending U.S. patent application Ser. No. 11/11/183664), phosphoglycerate mutase (WO 2005/003310), fructose-bisphosphate aldolase (WO 2005/049805), phosphoglucose-isomerase, phosphoglycerate kinase, glycerol-3-phosphate O-acyltransferase (see U.S. Patent Application No. 60/610,060), etc.; or, 2.) regulatable genes such as acid phosphatase, lactase, metallothionein, glucoamylase, the translation elongation factor EF1-α (TEF) protein (U.S. Pat. No. 6,265,185), ribosomal protein S7 (U.S. Pat. No. 6,265,185), ammonium transporter proteins (co-pending U.S. patent application Ser. No. 11/185,301), etc. Any one of a number of regulatory sequences can be used, depending upon whether constitutive or induced transcription is desired, the efficiency of the promoter in expressing the ORF of interest, the ease of construction and the like.

Nucleotide sequences surrounding the translational initiation codon 'ATG' have been found to affect expression in yeast cells. If the desired polypeptide is poorly expressed in yeast, the nucleotide sequences of exogenous genes can be modified to include an efficient yeast translation initiation sequence to obtain optimal gene expression. For expression in yeast, this can be done by site-directed mutagenesis of an inefficiently expressed gene by fusing it in-frame to an endogenous yeast gene, preferably a highly expressed gene. Alternatively, one can determine the consensus translation initiation sequence in the host and engineer this sequence into heterologous genes for their optimal expression in the host of interest (see, e.g., WO 2004/101753 for specific teachings applicable for *Yarrowia lipolytica*).

The termination region can be derived from the 3' region of the gene from which the initiation region was obtained or from a different gene. A large number of termination regions are known and function satisfactorily in a variety of hosts (when utilized both in the same and different genera and species from where they were derived). The termination region usually is selected more as a matter of convenience rather than because of any particular property. Preferably, the termination region is derived from a yeast gene, particularly *Saccharomyces, Schizosaccharomyces, Candida, Yarrowia* or *Kluyveromyces.* The 3'-regions of mammalian genes encoding γ-interferon and α-2 interferon are also known to function in yeast. Termination control regions may also be derived from various genes native to the preferred hosts. Optionally, a termination site may be unnecessary; however, it is most preferred if included.

As one of skill in the art is aware, merely inserting a gene into a cloning vector does not ensure that it will be successfully expressed at the level needed. In response to the need for a high expression rate, many specialized expression vectors have been created by manipulating a number of different genetic elements that control aspects of transcription, translation, protein stability, oxygen limitation and secretion from the host cell. More specifically, some of the molecular features that have been manipulated to control gene expression include: 1.) the nature of the relevant transcriptional promoter and terminator sequences; 2.) the number of copies of the cloned gene and whether the gene is plasmid-borne or integrated into the genome of the host cell; 3.) the final cellular location of the synthesized foreign protein; 4.) the efficiency of translation in the host organism; 5.) the intrinsic stability of the cloned gene protein within the host cell; and 6.) the codon usage within the cloned gene, such that its frequency approaches the frequency of preferred codon usage of the host cell. Each of these types of modifications are encompassed in the present invention, as means to further optimize expression of the GPAT enzyme described herein.

Preferred Microbial Hosts for Recombinant Expression of GPAT

Host cells for expression of the instant GPAT gene and nucleic acid fragments may include microbial hosts that grow on a variety of feedstocks, including simple or complex carbohydrates, organic acids and alcohols and/or hydrocarbons over a wide range of temperature and pH values. Although the gene described in the instant invention has been isolated for expression in an oleaginous yeast, and in particular *Yarrowia lipolytica,* it is contemplated that because transcription, translation and the protein biosynthetic apparatus is highly conserved, any bacteria, yeast, algae and/or filamentous fungus will be a suitable host for expression of the present nucleic acid fragments.

Preferred microbial hosts are oleaginous organisms, such as oleaginous yeast. These oleaginous organisms are naturally capable of oil synthesis and accumulation, wherein the total oil content can comprise greater than about 25% of the cellular dry weight, more preferably greater than about 30% of the cellular dry weight and most preferably greater than about 40% of the cellular dry weight. Additionally, there is basis for the use of these organisms for the production of PUFAs, as seen in WO 2004/101757 and co-pending U.S. Patent Application No. 60/624,812.

Genera typically identified as oleaginous yeast include, but are not limited to: *Yarrowia, Candida, Rhodotorula, Rhodosporidium, Cryptococcus, Trichosporon* and *Lipomyces*. More specifically, illustrative oil-synthesizing yeast include: *Rhodosporidium toruloides, Lipomyces starkeyii, L. lipoferus, Candida revkaufi, C. pulcherrima, C. tropicalis, C. utilis, Trichosporon pullans, T. cutaneum, Rhodotorula glutinus, R. graminis* and *Yarrowia lipolytica* (formerly classified as *Candida lipolytica*).

Most preferred is the oleaginous yeast *Yarrowia lipolytica;* and, in a further embodiment, most preferred are the *Y. lipolytica* strains designated as ATCC #20362, ATCC #8862, ATCC #18944, ATCC #76982, ATCC #90812 and/or LGAM S(7)1 (Papanikolaou S., and Aggelis G., *Bioresour. Technol.* 82(1):43–9 (2002)).

Transformation of Microbial Hosts

Once the DNA encoding a polypeptide suitable for expression in an oleaginous yeast has been obtained, it is placed in a plasmid vector capable of autonomous replication in a host cell or it is directly integrated into the genome of the host cell. Integration of expression cassettes can occur randomly within the host genome or can be targeted through the use of constructs containing regions of homology with the host genome sufficient to target recombination within the host locus. Where constructs are targeted to an endogenous locus, all or some of the transcriptional and translational regulatory regions can be provided by the endogenous locus.

Where two or more genes are expressed from separate replicating vectors, it is desirable that each vector has a different means of selection and should lack homology to the other construct(s) to maintain stable expression and prevent reassortment of elements among constructs. Judicious choice of regulatory regions, selection means and method of propagation of the introduced construct(s) can be experimentally determined so that all introduced genes are expressed at the necessary levels to provide for synthesis of the desired products.

Constructs comprising the gene of interest may be introduced into a host cell by any standard technique. These techniques include transformation (e.g., lithium acetate transformation [*Methods in Enzymology,* 194:186–187 (1991)]), protoplast fusion, biolistic impact, electroporation, microinjection, or any other method that introduces the gene of interest into the host cell. More specific teachings applicable for oleaginous yeast (i.e., *Yarrowia lipolytica*) include U.S. Pat. No. 4,880,741 and U.S. Pat. No. 5,071,764 and Chen, D. C. et al. (*Appl Microbiol Biotechnol.* 48(2): 232–235-(1997)).

For convenience, a host cell that has been manipulated by any method to take up a DNA sequence (e.g., an expression cassette) will be referred to as "transformed" or "recombinant" herein. The transformed host will have at least one copy of the expression construct and may have two or more, depending upon whether the gene is integrated into the genome, amplified or is present on an extrachromosomal element having multiple copy numbers. The transformed host cell can be identified by various selection techniques, as described in U.S. Ser. No. 10/869,630.

Following transformation, substrates suitable for the gene products of the instant sequence (and optionally other PUFA enzymes that are expressed within the host cell), may be produced by the host either naturally or transgenically, or they may be provided exogenously.

Fermentation Processes for Triacylglycerol Biosynthesis and Accumulation

The transformed microbial host cell is grown under conditions that optimize activity of fatty acid biosynthetic genes, acyltransferase genes and the GPAT of the invention herein. This leads to production of the greatest and the most economical yield of fatty acids, which can in turn be transferred to TAGs for storage. In general, media conditions that may be optimized include the type and amount of carbon source, the type and amount of nitrogen source, the carbon-to-nitrogen ratio, the oxygen level, growth temperature, pH, length of the biomass production phase, length of the oil accumulation phase and the time of cell harvest. Microorganisms of interest, such as oleaginous yeast, are grown in complex media (e.g., yeast extract-peptone-dextrose broth (YPD)) or a defined minimal media that lacks a component necessary for growth and thereby forces selection of the desired expression cassettes (e.g., Yeast Nitrogen Base (DIFCO Laboratories, Detroit, Mich.)).

Fermentation media in the present invention must contain a suitable carbon source. Suitable carbon sources may include, but are not limited to: monosaccharides (e.g., glucose, fructose), disaccharides (e.g., lactose, sucrose), oligosaccharides, polysaccharides (e.g., starch, cellulose or mixtures thereof), sugar alcohols (e.g., glycerol) or mixtures from renewable feedstocks (e.g., cheese whey permeate, cornsteep liquor, sugar beet molasses, barley malt). Additionally, carbon sources may include alkanes, fatty acids, esters of fatty acids, monoglycerides, diglycerides, triglycerides, phospholipids and various commercial sources of fatty acids including vegetable oils (e.g., soybean oil) and animal fats. Additionally, the carbon substrate may include one-carbon substrates (e.g., carbon dioxide, methanol, formaldehyde, formate, carbon-containing amines) for which metabolic conversion into key biochemical intermediates has been demonstrated. Hence it is contemplated that the source of carbon utilized in the present invention may encompass a wide variety of carbon-containing substrates and will only be limited by the choice of the host organism. Although all of the above mentioned carbon substrates and mixtures thereof are expected to be suitable in the present invention, preferred carbon substrates are sugars and/or fatty acids. Most preferred is glucose and/or fatty acids containing between 10–22 carbons.

Nitrogen may be supplied from an inorganic (e.g., $(NH_4)_2SO_4$) or organic (e.g., urea, glutamate) source. In addition to appropriate carbon and nitrogen sources, the fermentation media must also contain suitable minerals, salts, cofactors, buffers, vitamins and other components known to those skilled in the art suitable for the growth of the microorganism and promotion of the enzymatic pathways necessary for fatty acid production. Particular attention is given to several metal ions (e.g., $Mn^{+2}$, $Co^{+2}$, $Zn^{+2}$, $Mg^{+2}$) that promote synthesis of lipids and PUFAs (Nakahara, T. et al., *Ind. Appl. Single Cell Oils,* D. J. Kyle and R. Colin, eds. pp 61–97 (1992)).

Preferred growth media in the present invention are common commercially prepared media, such as Yeast Nitrogen Base (DIFCO Laboratories, Detroit, Mich.). Other defined or synthetic growth media may also be used and the appropriate medium for growth of the particular microorganism will be known by one skilled in the art of microbiology or fermentation science. A suitable pH range for the fermentation is typically between about pH 4.0 to pH 8.0, wherein pH 5.5 to pH 7.0 is preferred as the range for the initial growth conditions. The fermentation may be conducted under aerobic or anaerobic conditions, wherein microaerobic conditions are preferred.

Typically, accumulation of high levels of fatty acids and TAGs in oleaginous yeast cells requires a two-stage process, since the metabolic state must be "balanced" between growth and synthesis/storage of fats. Thus, most preferably, a two-stage fermentation process is necessary for the production of oils in oleaginous yeast. This approach is described in U.S. Ser. No. 10/840,579, as are various suitable fermentation process designs (i.e., batch, fed-batch and continuous) and considerations during growth.

Purification of Fatty Acids

Fatty acids, including PUFAs, may be found in the host microorganism as free fatty acids or in esterified forms such as acylglycerols, phospholipids, sulfolipids or glycolipids, and may be extracted from the host cell through a variety of means well-known in the art. One review of extraction techniques, quality analysis and acceptability standards for yeast lipids is that of Z. Jacobs (*Crtical Reviews in Biotechnology* 12(5/6):463–491 (1992)). A brief review of downstream processing is also available by A. Singh and O. Ward (*Adv. Appl. Microbiol.* 45:271–312 (1997)).

In general, means for the purification of fatty acids (including PUFAs) may include extraction with organic solvents, sonication, supercritical fluid extraction (e.g., using carbon dioxide), saponification and physical means such as presses, or combinations thereof. One is referred to the teachings of WO 2004/101757 for additional details.

DESCRIPTION OF PREFERRED EMBODIMENTS

The Applicants' ultimate goal is the development of an oleaginous yeast that accumulates TAGs enriched in ω-3 and/or ω-6 PUFAs. In support of this goal, acyltransferases must be identified that function efficiently in oleaginous yeast to enable synthesis and high accumulation of preferred TAGs in these hosts. Specifically, modification of the expression levels of these acyltransferases will enable increased transfer of fatty acids (and particularly, PUFAs having chain lengths equal to or greater than $C_{20}$) to TAGs. Thus, identification of efficient acyltransferases is necessary for the manipulation of the amount of ω-3/ω-6 PUFAs incorporated into the TAG fraction produced in transformant host cells.

In the present invention, Applicants have isolated and cloned a gene from *Mortierella alpina* that encodes GPAT. Based on the ability of the native organism to synthesize ARA at concentrations greater than 50% of the total fatty acids (TFAs), it was expected that GPAT would have excellent efficiency synthesizing TAGs comprising long-chain fatty acids. Furthermore, the Applicants hypothesized that the *M. alpina* GPAT would be useful for expression in various microbial hosts, and particularly for over-expression in oleaginous yeast whose native GPAT may not have the substrate specificity necessary to enable efficient incorporation of PUFAs having chain lengths equal to or greater than $C_{20}$ into the TAG fraction. To test this, the *M. alpina* GPAT was over-expressed in an engineered strain of *Yarrowia lipolytica* producing about 16% EPA. Additional benefits may result, since expression of the GPAT of the instant invention may also be placed under the control of strong constitutive or regulated promoters that do not have the regulatory constraints of the native gene.

EXAMPLES

The present invention is further defined in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions.

General Methods

Standard recombinant DNA and molecular cloning techniques used in the Examples are well known in the art and are described by: 1.) Sambrook, J., Fritsch, E. F. and Maniatis, T. *Molecular Cloning: A Laboratory Manual;* Cold Spring Harbor Laboratory: Cold Spring Harbor, N.Y. (1989) (Maniatis); 2.) T. J. Silhavy, M. L. Bennan, and L. W. Enquist, Experiments with Gene Fusions; Cold Spring Harbor Laboratory: Cold Spring Harbor, N.Y. (1984); and 3.)

Ausubel, F. M. et al., Current Protocols in Molecular Biology, published by Greene Publishing Assoc. and Wiley-Interscience (1987).

Materials and methods suitable for the maintenance and growth of microbial cultures are well known in the art. Techniques suitable for use in the following Examples may be found as set out in *Manual of Methods for General Bacteriology* (Phillipp Gerhardt, R. G. E. Murray, Ralph N. Costilow, Eugene W. Nester, Willis A. Wood, Noel R. Krieg and G. Briggs Phillips, Eds), American Society for Microbiology: Washington, D.C. (1994)); or by Thomas D. Brock in *Biotechnology: A Textbook of Industrial Microbiology,* $2^{nd}$ ed., Sinauer Associates: Sunderland, Mass. (1989). All reagents, restriction enzymes and materials used for the growth and maintenance of microbial cells were obtained from Aldrich Chemicals (Milwaukee, Wis.), DIFCO Laboratories (Detroit, Mich.), GIBCO/BRL (Gaithersburg, Md.) or Sigma Chemical Company (St. Louis, Mo.), unless otherwise specified.

*E. coli* TOP1 0 cells were obtained from Invitrogen (Carlsbad, Calif.). *E. coli* (XL1-Blue) competent cells were purchased from the Stratagene Company (San Diego, Calif.). *E. coli* strains were typically grown at 37° C. on Luria Bertani (LB) plates.

General molecular cloning was performed according to standard methods (Sambrook et al., supra). Oligonucleotides were synthesized by Sigma-Genosys (Spring, Tex.). PCR products were cloned into Promega's pGEM-T-easy vector (Madison, Wis.).

DNA sequence was generated on an ABI Automatic sequencer using dye terminator technology (U.S. Pat. No. 5,366,860; EP 272,007) using a combination of vector and insert-specific primers. Sequence editing was performed in Sequencher (Gene Codes Corporation, Ann Arbor, Mich.). All sequences represent coverage at least two times in both directions. Comparisons of genetic sequences were accomplished using DNASTAR software (DNASTAR, Inc., (Madison, Wis.).

The meaning of abbreviations is as follows: "sec" means second(s), "min" means minute(s), "h" means hour(s), "d" means day(s), "µl" means microliter(s), "mL" means milliliter(s), "L" means liter(s), "µM" means micromolar, "mM" means millimolar, "M" means molar, "mmol" means millimole(s), "µmole" mean micromole(s), "g" means gram(s), "µg" means microgram(s), "ng" means nanogram(s), "U" means unit(s), "bp" means base pair(s) and "kB" means kilobase(s).

Transformation and Cultivation of *Yarrowia lipolytica*

*Y. lipolytica* strain ATCC #20362 was purchased from the American Type Culture Collection (Rockville, Md.). *Y. lipolytica* strains were usually grown at 28° C. on YPD agar (1% yeast extract, 2% bactopeptone, 2% glucose, 2% agar).

Transformation of *Y. lipolytica* was performed according to the method of Chen, D. C. et al. (*Appl. Microbiol Biotechnol.* 48(2):232–235 (1997)), unless otherwise noted. Briefly, *Yarrowia* was streaked onto a YPD plate and grown at 30° C. for approximately 18 hr. Several large loopfuls of cells were scraped from the plate and resuspended in 1 mL of transformation buffer containing: 2.25 mL of 50% PEG, average MW 3350; 0.125 mL of 2 M Li acetate, pH 6.0; 0.125 mL of 2 M DTT; and 50 µg sheared salmon sperm DNA. Then, approximately 500 ng of linearized plasmid DNA was incubated in 100 µl of resuspended cells, and maintained at 39° C. for 1 hr with vortex mixing at 15 min intervals. The cells were plated onto selection media plates and maintained at 30° C. for 2 to 3 days.

For selection of transformants, minimal medium ("MM") was generally used; the composition of MM is as follows: 0.17% yeast nitrogen base (DIFCO Laboratories, Detroit, Mich.) without ammonium sulfate or amino acids, 2% glucose, 0.1% proline, pH 6.1). Supplements of leucine and/or uracil were added as appropriate to a final concentration of 0.01% (thereby producing "MMLe" and "MMU" selection media, each prepared with 20 g/L agar).

Alternatively, transformants were selected on 5-fluoroorotic acid ("FOA"; also 5-fluorouracil-6-carboxylic acid monohydrate) selection media, comprising: 0.17% yeast nitrogen base (DIFCO Laboratories, Detroit, Mich.) without ammonium sulfate or amino acids, 2% glucose, 0.1% proline, 75 mg/L uracil, 75 mg/L uridine, 900 mg/L FOA (Zymo Research Corp., Orange, Calif.) and 20 g/L agar.

Finally, for the "two-stage growth conditions" designed to promote conditions of oleaginy, High Glucose Media ("HGM") was prepared as follows: 14 g/L $KH_2PO_4$, 4 g/L $K_2HPO_4$, 2 g/L $MgSO_4 \cdot 7H_2O$, 80 g/L glucose (pH 6.5).

Fatty Acid Analysis of *Yarrowia lipolytica*

For fatty acid analysis, cells were collected by centrifugation and lipids were extracted as described in Bligh, E. G. & Dyer, W. J. (*Can. J. Biochem. Physiol.* 37:911–917 (1959)). Fatty acid methyl esters were prepared by transesterification of the lipid extract with sodium methoxide (Roughan, G., and Nishida I. *Arch Biochem Biophys.* 276 (1):38–46 (1990)) and subsequently analyzed with a Hewlett-Packard 6890 GC fitted with a 30-m×0.25 mm (i.d.) HP-INNOWAX (Hewlett-Packard) column. The oven temperature was from 170° C. (25 min hold) to 185° C. at 3.5° C./min.

For direct base transesterification, *Yarrowia* culture (3 mL) was harvested, washed once in distilled water, and dried under vacuum in a Speed-Vac for 5–10 min. Sodium methoxide (100 µl of 1%) was added to the sample, and then the sample was vortexed and rocked for 20 min. After adding 3 drops of 1 M NaCl and 400 µl hexane, the sample was vortexed and spun. The upper layer was removed and analyzed by GC as described above.

Example 1

Preparation of *Mortierella alpina* Genomic DNA and cDNA

The present Example describes the preparation of genomic DNA and cDNA from *Mortierella alpina* (ATCC #16266).

Preparation of Genomic DNA from *Mortierella alpina*

Genomic DNA was isolated from Mortierella alpina (ATCC #16266) using a QiaPrep Spin Miniprep Kit (Qiagen, Catalog #627106). Cells grown on a YPD agar plate (2% Bacto-yeast extract, 3% Bactor-peptone, 2% glucose, 2.5% bacto-agar) were scraped off and resuspended in 1.2 mL of kit buffer P1. The resuspended cells were placed in two 2.0 mL screw cap tubes, each containing 0.6 mL glass beads (0.5 mm diameter). The cells were homogenized at the HOMOGENIZE setting on a Biospec (Bartlesville, Okla.) mini bead beater for 2 min. The tubes were then centrifuged at 14,000 rpm in an Eppendorf microfuge for 2 min. The supernatant (0.75 mL) was transferred to three 1.5 mL microfuge tubes. Equal volumes of kit buffer P2 were added to each tube. After mixing the tubes by inversion three times, 0.35 mL of buffer N3 was added to each tube. The contents of each tube were again mixed by inversion for a total of five times. The mixture was centrifuged at 14,000 rpm in an Eppendorf microfuge for 5 min. The supernatant from each tube was transferred individually into 3 separate kit spin columns. The columns were then subjected to the following steps: centrifugation (1 min at 14,000 rpm), wash once with buffer PE, centrifugation (1 min at 14,000 rpm), and then a final centrifugation (1 min at 14,000 rpm). Buffer EB (50 μl) was added to each column and let stand for 1 min. The genomic DNA was then eluted by centrifugation at 14,000 rpm for 1 min.

Preparation of cDNA from *Mortierella alpina* cDNA of *Mortierella alpina* was prepared using the BD-Clontech Creator Smart® cDNA library kit (Mississauga, ON, Canada), according to the manufacturer's protocol. Specifically, *M. alpina* strain ATCC #16266 was grown in 60 mL YPD medium for 3 days at 23° C. Cells were pelleted by centrifugation at 3750 rpm in a Beckman GH3.8 rotor for 10 min and resuspended in 6×0.6 mL Trizole reagent (Invitrogen). Resuspended cells were transferred to six 2 mL screw cap tubes each containing 0.6 mL of 0.5 mm glass beads. The cells were homogenized at the HOMOGENIZE setting on a Biospec mini bead beater for 2 min. The tubes were briefly spun to settle the beads. Liquid was transferred to 4 fresh 1.5 mL microfuge tubes and 0.2 mL chloroform:isoamyl alcohol (24:1) was added to each tube. The tubes were shaken by hand for 1 min and let stand for 3 min. The tubes were then spun at 14,000 rpm for 10 min at 4° C. The upper layer was transferred to 4 new tubes. Isopropyl alcohol (0.5 mL) was added to each tube. Tubes were incubated at room temperature for 15 min, followed by centrifugation at 14,000 rpm and 4° C. for 10 min. The pellets were washed with 1 mL each of 75% ethanol, made with RNase free water and air-dried. The total RNA sample was then redissolved in 500 μl of water, and the amount of RNA was measured by A260 nm using a 1:50 diluted RNA sample. A total of 3.14 mg RNA was obtained.

This total RNA sample was further purified with the Qiagen RNeasy total RNA Midi kit following the manufacturer's protocol. Thus, the total RNA sample was diluted to 2 mL and mixed with 8 mL of buffer RLT with 80 μl of P-mercaptoethanol and 5.6 mL 100% ethanol. The sample was divided into 4 portions and loaded onto 4 RNeasy midid columns. The columns were then centrifuged for 5 min at 4500×g. To wash the columns, 2 mL of buffer RPE was loaded and the columns centrifuged for 2 min at 4500×g. The washing step was repeated once, except that the centrifugation time was extended to 5 min. Total RNA was eluted by applying 250 μl of RNase free water to each column, waiting for 1 min and centrifuging at 4500×g for 3 min.

PolyA(+)RNA was then isolated from the above total RNA sample, following the protocol of Amersham Biosciences' mRNA Purification Kit. Briefly, 2 oligo-dT-cellulose columns were used. The columns were washed twice with 1 mL each of high salt buffer. The total RNA sample from the previous step was diluted to 2 mL total volume and adjusted to 10 mM Tris/HCl, pH 8.0, 1 mM EDTA. The sample was heated at 65° C. for 5 min, then placed on ice. Sample buffer (0.4 mL) was added and the sample was then loaded onto the two oligo-dT-cellulose columns under gravity feed. The columns were centrifuged at 350×g for 2 min, washed 2× with 0.25 mL each of high salt buffer, each time followed by centrifugation at 350×g for 2 min. The columns were further washed 3 times with low salt buffer, following the same centrifugation routine. Poly(A)+RNA was eluted by washing the column 4 times with 0.25 mL each of elution buffer preheated to 65° C., followed by the same centrifugation procedure. The entire purification process was repeated once. Purified poly(A)+RNA was obtained with a concentration of 30.4 ng/μl.

cDNA was generated, using the LD-PCR method specified by BD-Clontech and 0.1 μg of polyA(+) RNA sample. Specifically, for 1st strand cDNA synthesis, 3 μl of the poly(A)+RNA sample was mixed with 1 μl of SMART IV oligo nucleotide (SEQ ID NO:3) and 1 μl of CDSIII/3' PCR primer (SEQ ID NO:4). The mixture was heated at 72° C. for 2 min and cooled on ice for 2 min. To the tube was added the following: 2 μl first strand buffer, 1 μl 20 mM DTT, 1 μl 10 mM dNTP mix and 1 μl Powerscript reverse transcriptase. The mixture was incubated at 42° C. for 1 hr and cooled on ice.

The 1st strand cDNA synthesis mixture was used as template for the PCR reaction. Specifically, the reaction mixture contained the following: 2 μl of the 1st strand cDNA mixture, 2 μl 5'-PCR primer (SEQ ID NO:5), 2 μl CDSIII/3'-PCR primer (SEQ ID NO:4), 80 μl water, 10 μl 10× Advantage 2 PCR buffer, 2 μl 50× dNTP mix and 2 μl 50× Advantage 2 polymerase mix. The thermocycler conditions were set for 95° C. for 20 sec, followed by 20 cycles of 95° C. for 5 sec and 68° C. for 6 min on a GenAmp 9600 instrument. PCR product was quantitated by agarose gel electrophoresis and ethidium bromide staining.

Example 2

Cloning of a Partial Putative GPAT Sequence from *Mortierella alpina*

By PCR Using Degenerate PCR Primers

The present Example describes the identification of a cDNA fragment (SEQ ID NO:6) encoding a 3' portion of the *M. alpina* GPAT (provided herein as SEQ ID NOs:1 and 2) by degenerate PCR using *M. alpina* cDNA as template (from Example 1).

Based on sequences of GPAT from *Aspergillus nidulans* (GenBank Accession No. EAA62242) and *Neurospora crassa* (GenBank Accession No. XP_325840), the following primers were designed for degenerate PCR:

```
MGPAT-N1    (SEQ ID NO:7)  CCNCAYGCNAAYCARTTYGT

MGPAT-NR5   (SEQ ID NO:8)  TTCCANGTNGCCATNTCRTC

[Note: The nucleic acid degeneracy code used for
SEQ ID NOs:7 and 8 was as follows: R = A/G;
Y = C/T; and N = A/C/T/G.]
```

PCR amplification was carried out in a Perkin Elmer GeneAmp 9600 PCR machine using TaKaRa ExTaq premix Taq polymerase (TaKaRa Bio Inc., Otsu, Shiga, Japan). Amplification was carried out as follows: 30 cycles of denaturation at 94° C. for 30 sec, annealing at 55° C. for 30 sec and elongation at 72° C. for 90 sec, followed by a final elongation cycle at 72° C. for 7 min.

A fragment of ~1.2 kB was obtained (SEQ ID NO:6). This fragment was purified with a Qiagen QiaQuick PCR purification kit, cloned into the TOPO® cloning vector pCR2.1-TOPO (Invitrogen), and sequenced. The resultant sequence, when translated, had homology to known GPATs, based on BLAST program analysis (Basic Local Alignment Search Tool; Altschul, S. F., et al., *J. Mol. Biol.* 215:403–410 (1993); infra).

Example 3

Isolation of the Full-Length GPAT Sequence from *Mortierella alpina*

Based on the sequence of the 1212 bp cDNA fragment, the 5' and 3' end regions of the *M. alpina* GPAT were cloned by PCR amplification and genome walking techniques. This enabled assembly of a contig, corresponding to the −1050 bp to +2885 bp region of the *M. alpina* GPAT (SEQ ID NO:9). This contig included the entire coding region of GPAT and four introns (SEQ ID NOs:22, 23, 24 and 25).

PCR Amplification of the 3'-End of GPAT ORF

The *M. alpina* cDNA sample described in Example 1 (1 μl) was used as a template for amplification of the 3'-end of the GPAT. Primers MGPAT-5N1 (SEQ ID NO:10) and CDSIII/3' (SEQ ID NO:4) were used as primers. PCR amplification was carried out in a Perkin Elmer GeneAmp 9600 PCR machine using TaKaRa ExTaq premix Taq polymerase (TaKaRa Bio Inc., Otsu, Shiga, Japan). Amplification was carried out as follows: 30 cycles of denaturation at 94° C. for 30 sec, annealing at 55° C. for 30 sec and elongation at 72° C. for 120 sec, followed by a final elongation cycle at 72° C. for 7 min.

The PCR product was diluted 1:10, and 1 μl of diluted PCR product was used as template for the second round of amplification, using MGPAT-5N2 (SEQ ID NO:11) and CDSIII/3' as primers. The conditions were exactly the same as described above. The second round PCR product was again diluted 1:10 and 1 μl of the diluted PCR product used as template for a third round of PCR, using MGPAT-5N3 (SEQ ID NO:12) and CDSIII/3' as primers. The PCR conditions were again the same.

A ~1 kB fragment was generated in the third round of PCR. This fragment was purified with a Qiagen PCR purification kit and cloned into pCR2.1-TOPO vector for sequence analysis. Results from sequence analysis showed that this 965 bp fragment (SEQ ID NO:13) corresponded with the 3'-end of the GPAT gene.

Genome Walking to Isolate the 5'-End of the *M. alpina* GPAT

A Clontech Universal GenomeWalker™ kit was used to obtain a piece of genomic DNA corresponding to the 5'-end region of the *M. alpina* GPAT. Briefly, 2.5 μg each of *M. alpina* genomic DNA was digested with DraI, EcoRV, PvuII or StuI individually, the digested DNA samples were purified using Qiagen Qiaquick PCR purification kits and eluted with 30 μl each of kit buffer EB, and the purified samples were then ligated with Genome Walker adaptor (SEQ ID NOs:14 [top strand] and 15 [bottom strand]), as shown below:

```
5'-GTAATACGACTCACTATAGGGCACGCGTGGTCGACGGCCCGGGCTGGT-3'

                                      3'-H2N-CCCGACCA-5'
```

Each ligation reaction mixture contained 1.9 μl of 25 μM Genome Walker adaptor, 1.6 μl 10× ligation buffer, 0.5 μl T4 DNA ligase and 4 μl of one of the purified digested genomic DNA samples. The reaction mixtures were incubated at 16° C. overnight. The reaction was terminated by incubation at 70° C. for 5 min. Then, 72 μl of 10 mM Tris HCl, 1 mM EDTA, pH 7.4 buffer was added to each ligation reaction mix.

Four separate PCR reactions were performed, each using one of the four ligation mixtures as template. The PCR reaction mixtures contained 1 μl of ligation mixture, 0.5 μl of 20 μM MGPAT-5-1A (SEQ ID NO:16), 1 μl of 10 μM kit primer AP1 (SEQ ID NO:17), 22.5 μl water, and 25 μl ExTaq premix Taq 2×PCR solution (TaKaRa). The PCR reactions were carried out for 32 cycles using the following conditions: denaturation at 94° C. for 30 sec, annealing at 55° C. for 30 sec, and elongation at 72° C. for 180 sec. A final elongation cycle at 72° C. for 7 min was carried out, followed by reaction termination at 4° C.

The products of each PCR reaction were diluted 1:50 individually and used as templates for a second round of PCR. Each reaction mixture contained 1 μl of one of the diluted PCR product as template, 0.5 μl of 20 μM MGPAT-3N1 (SEQ ID NO:18), 21 μl of 10 μM kit primer AP2 (SEQ ID NO:19), 22.5 μl water and 25 μl of ExTaq premix Taq 2×PCR solution (TaKaRa). PCR reactions were carried out for 32 cycles using the same thermocycler conditions described above.

A DNA fragment was obtained from the second round of PCR. This fragment was purified and cloned into pCR2.1-TOPO and sequenced. Sequence analysis showed that the 1908 bp fragment (SEQ ID NO:20) was the 5'-end of the *M. alpina* GPAT gene.

Similarly, a 966 bp fragment (SEQ ID NO:21) was obtained by two rounds of genome walking as described above, except using primer MGPAT-5N1 as the gene specific primer for the first round of PCR and primer MGPAT-5N2 as the gene specific primer for the second round. This fragment was also purified, cloned into pCR2.1-TOPO and sequenced. Sequence analysis showed that it contained a portion of the GPAT gene; however, the fragment was not long enough to extend to either end of the gene. Comparison with the 3' cDNA sequence (SEQ ID NO:13) showed that the last 171 bp of the ORF was not included.

Assembly of the Full-Length GPAT Sequence from *Mortierella alpina*

A 3935 bp sequence (SEQ ID NO:9) containing the complete GPAT gene (comprising a region extending 1050 bases upstream of the GPAT translation initiation 'ATG' codon and extending 22 bases beyond the GPAT termination codon) was assembled from the sequences of the original partial cDNA fragment (SEQ ID NO:6), the 3' cDNA fragment (SEQ ID NO:13), the internal genomic fragment (SEQ ID NO:21), and the 5' genomic fragment (SEQ ID NO:20) described above (graphically illustrated in FIG. 1). Included in this region is the 2151 bp GPAT ORF. The complete nucleotide sequence of the *M. alpina* GPAT ORF from 'ATG' to the stop codon 'TAG' is provided as SEQ ID NO:1 (corresponding to bases 1050 to 2863 of SEQ ID NO:9, excluding the four introns (i.e., intron 1 [SEQ ID NO:22], corresponding to bases 1195 to 1469 of SEQ ID NO:9; intron 2 [SEQ ID NO:23], corresponding to bases 1585 to 1839 of SEQ ID NO:9; intron 3 [SEQ ID NO:24], corresponding to bases 2795 to 2877 of SEQ ID NO:9 and intron 4 [SEQ ID NO:25], corresponding to bases 2940 to 3038 of SEQ ID NO:9). The translated amino acid sequence (SEQ ID NO:2) showed homology with a number of fungal, plant and animal GPATs.

More specifically, identity of the sequence was determined by conducting BLAST (Basic Local Alignment Search Tool; Altschul, S. F., et al., *J. Mol. Biol.* 215:403–410 (1993)) searches for similarity to sequences contained in the BLAST "nr" database (comprising all non-redundant GenBank CDS translations, sequences derived from the 3-dimensional structure Brookhaven Protein Data Bank, the SWISS-PROT protein sequence database, EMBL and DDBJ databases). The sequence was analyzed for similarity to all publicly available DNA sequences contained in the "nr" database using the BLASTN algorithm provided by the National Center for Biotechnology Information (NCBI). The DNA sequence was translated in all reading frames and compared for similarity to all publicly available protein sequences contained in the "nr" database, using the BLASTX algorithm (Gish, W. and States, D. J. *Nature Genetics* 3:266–272 (1993)) provided by the NCBI. The results of the BLAST comparison summarizing the sequence to which SEQ ID NO:2 has the most similarity are reported according to the % identity, % similarity, and Expectation value. "% Identity" is defined as the percentage of amino acids that are identical between the two proteins. % Similarity" is defined as the percentage of amino acids that are identical or conserved between the two proteins. Expectation value" estimates the statistical significance of the match, specifying the number of matches, with a given score, that are expected in a search of a database of this size absolutely by chance.

Thus, the amino acid fragment described herein as SEQ ID NO:2 had 47% identity and 65% similarity with the protein sequence of the putative GPAT of Ustilago maydis (GenBank Accession No. EAK84237), with an expectation value of 1e-152; additionally, SEQ ID NO:2 had 47% identity and 62% similarity with the GPAT of *Aspergillus fumigatus* (GenBank Accession No. EAL20089), with an expectation value of 1e-142.

Example 4

Generation of EPA-Producing *Y. lipolytica* ATCC #20362 Strain Y2107U1

The present Example describes the construction of strain Y2107U1, derived from *Yarrowia lipolytica* ATCC #20362, capable of producing significant concentrations of EPA relative to the total lipids (FIG. 2). The affect of *M. alpina* GPAT gene over-expression was examined in this EPA producing strain based on analysis of TAG content, as described in Example 5 (infra).

The development of strain Y2107U1 (producing 16% EPA and possessing a Ura-phenotype) herein required the construction of strain M4 (producing 8% DGLA), strain Y2047 (producing 11% ARA), strain Y2048 (producing 11% EPA), strain Y2060 (producing 13% EPA), strain Y2072 (producing 15% EPA), strain Y2072U1 (producing 14% EPA) and Y2089 (producing 18% EPA).

Generation of M4 Strain to Produce About 8% DGLA of Total Lipids

Construct pKUNF12T6E (FIG. 3A; SEQ ID NO:26) was generated to integrate four chimeric genes (comprising a Δ12 desaturase, a Δ6 desaturase and two $C_{18/20}$ elongases) into the Ura3 loci of wild type *Yarrowia* strain ATCC #20362, to thereby enable production of DGLA. The pKUNF12T6E plasmid contained the following components:

TABLE 5

Description of Plasmid pKUNF12T6E (SEQ ID NO:26)

| RE Sites And Nucleotides Within SEQ ID NO:26 | Description Of Fragment And Chimeric Gene Components |
|---|---|
| AscI/BsiWI (9420-8629) | 784 bp 5' part of *Yarrowia* Ura3 gene (GenBank Accession No. AJ306421) |
| SphI/PacI (12128-1) | 516 bp 3' part of *Yarrowia* Ura3 gene (GenBank Accession No. AJ306421) |
| SwaI/BsiWI (6380-8629) | FBAIN::EL1S:Pex20, comprising:<br>FBAIN: FBAIN promoter (SEQ ID NO:27)<br>EL1S: codon-optimized elongase 1 gene (SEQ ID NO:28), derived from *Mortierella alpina* (GenBank Accession No. AX464731)<br>Pex20: Pex20 terminator sequence from *Yarrowia* Pex20 gene (GenBank Accession No. AF054613) |
| BglII/SwaI (4221-6380) | TEF::Δ6S::Lip1, comprising:<br>TEF: TEF promoter (GenBank Accession No. AF054508)<br>Δ6S: codon-optimized Δ6 desaturase gene (SEQ ID NO:30), derived from *Mortierella alpina* (GenBank Accession No. AF465281)<br>Lip1: Lip1 terminator sequence from *Yarrowia* Lip1 gene (GenBank Accession No. Z50020) |
| PmeI/ClaI (4207-1459) | FBA::F.Δ12::Lip2, comprising:<br>FBA: FBA promoter (SEQ ID NO:32)<br>F.Δ12: *Fusarium moniliforme* Δ12 desaturase gene (SEQ ID NO:33)<br>Lip2: Lip2 terminator sequence from *Yarrowia* Lip2 gene (GenBank Accession No. AJ012632) |
| ClaI/PacI (1459-1) | TEF::EL2S::XPR, comprising:<br>TEF: TEF promoter (GenBank Accession No. AF054508)<br>EL2S: codon-optimized elongase gene (SEQ ID NO:35), derived from *Thraustochytrium aureum* (U.S. Pat. No. 6,677,145)<br>XPR: ~100 bp of the 3' region of the *Yarrowia* Xpr gene (GenBank Accession No. M17741) |

The pKUNF12T6E plasmid was digested with AscI/SphI, and then used for transformation of wild type *Y. lipolytica* ATCC #20362 according to the General Methods. The transformant cells were plated onto FOA selection media plates and maintained at 30° C. for 2 to 3 days. The FOA resistant colonies were picked and streaked onto MM and MMU selection plates. The colonies that could grow on MMU plates but not on MM plates were selected as Ura-strains. Single colonies of Ura-strains were then inoculated into liquid MMU at 30° C. and shaken at 250 rpm/min for 2 days. The cells were collected by centrifugation, lipids were extracted, and fatty acid methyl esters were prepared by trans-esterification, and subsequently analyzed with a Hewlett-Packard 6890 GC.

GC analyses showed the presence of DGLA in the transformants containing the 4 chimeric genes of pKUNF12T6E, but not in the wild type *Yarrowia* control strain. Most of the selected 32 Ura-strains produced about 6% DGLA of total lipids. There were 2 strains (i.e., strains M4 and 13-8) that produced about 8% DGLA of total lipids.

Generation of Strain Y2047 to Produce About 11% ARA of Total Lipids

Construct pDMW271 (FIG. 3B; SEQ ID NO:37) was generated to integrate three Δ5 chimeric genes into the Leu2 gene of *Yarrowia* strain M4. Plasmid pDMW271 contained the following components, as described in Table 6:

TABLE 6

Description of Plasmid pDMW271 (SEQ ID NO:37)

| RE Sites And Nucleotides Within SEQ ID NO:37 | Description Of Fragment And Chimeric Gene Components |
|---|---|
| AscI/BsiWI (5520-6315) | 788 bp 5' part of *Yarrowia* Leu2 gene (GenBank Accession No. AF260230) |
| SphI/PacI (2820-2109) | 703 bp 3' part of *Yarrowia* Leu2 gene (GenBank Accession No. AF260230) |
| SwaI/BsiWI (8960-6315) | FBAIN::MAΔ5::Pex20, comprising: FBAIN: FBAIN Promoter (SEQ ID NO:27) MAΔ5: *Mortierella alpina* Δ5 desaturase gene (SEQ ID NO:38) (GenBank Accession No. AF067654) Pex20: Pex20 terminator sequence of *Yarrowia* Pex20 gene (GenBank Accession No. AF054613) |
| SwaI/ClaI (8960-11055) | TEF::MAΔ5::Lip1, comprising: TEF: TEF promoter (GenBank Accession No. AF054508) MAΔ5: as described for FBAIN::MAΔ5::Pex20 (supra) Lip1: Lip1 terminator sequence of *Yarrowia* Lip1 gene (GenBank Accession No. Z50020) |
| PmeI/ClaI (12690-11055) | *Yarrowia* Ura3 gene (GenBank Accession No. AJ306421) |
| ClaI/PacI (1-2109) | TEF::HΔ5S::Pex16, comprising: TEF: TEF promoter (GenBank Accession No. AF054508) HΔ5S: codon-optimized Δ5 desaturase gene (SEQ ID NO:40), derived from *Homo sapiens* (GenBank Accession No. NP_037534) Pex16: Pex16 terminator sequence of *Yarrowia* Pex16 gene (GenBank Accession No. U75433) |

Plasmid pDMW271 was digested with AscI/SphI, and then used to transform strain M4 according to the General Methods. Following transformation, the cells were plated onto MMLe plates and maintained at 30° C. for 2 to 3 days. The individual colonies grown on MMLe plates were picked and streaked onto MM and MMLe plates. Those colonies that could grow on MMLe plates but not on MM plates were selected as Leu2$^-$ strains. Single colonies of Leu2$^-$ strains were then inoculated into liquid MMLe media at 30° C. and shaken at 250 rpm/min for 2 days. The cells were collected by centrifugation, lipids were extracted, and fatty acid methyl esters were prepared by trans-esterification, and subsequently analyzed with a Hewlett-Packard 6890 GC.

GC analyses showed the presence of ARA in pDMW271 transformants, but not in the parental M4 strain. Specifically, of the 48 selected Leu2$^-$ transformants with pDMW271, there were 35 strains that produced less than 5% ARA of total lipids, 12 strains that produced 6–8% ARA, and 1 strain that produced about 11% ARA of total lipids in the engineered *Yarrowia*. The strain that produced 11% ARA was named "Y2047".

Generation of Y2048 Strain to Produce About 11% EPA of Total Lipids

Construct pZP3L37 (FIG. 3C; SEQ ID NO:42) was created to integrate three synthetic Δ17 desaturase chimeric genes into the acyl-CoA oxidase 3 gene of strain Y2047. The plasmid pZP3L37 contained the following components:

TABLE 7

Description of Plasmid pZP3L37 (SEQ ID NO:42)

| RE Sites And Nucleotides Within SEQ ID NO:42 | Description Of Fragment And Chimeric Gene Components |
|---|---|
| AscI/BsiWI (6813-6043) | 763 bp 5' part of *Yarrowia* Pox3 gene (GenBank Accession No. AJ001301) |
| SphI/PacI (9521-10345) | 818 bp 3' part of *Yarrowia* Pox3 gene (GenBank Accession No. AJ001301) |
| ClaI/BsiWI (4233-6043) | TEF::Δ17S::Pex20, comprising: TEF: TEF promoter (GenBank Accession No. AF054508) Δ17S: codon-optimized Δ17 desaturase gene (SEQ ID NO:43), derived from *S. diclina* (US 2003/0196217 A1) Pex20: Pex20 terminator sequence of *Yarrowia* Pex20 gene (GenBank Accession No. AF054613) |
| ClaI/PmeI (4233-1811) | FBAIN::Δ17S::Lip2, comprising: FBAIN: FBAIN promoter (SEQ ID NO:27) Δ17S: SEQ ID NO:43 (supra) Lip2: Lip2 terminator sequence of *Yarrowia* Lip2 gene (GenBank Accession No. AJ012632) |
| PmeI/SwaI (1811-1) | *Yarrowia* Leu2 gene (GenBank Accession No. AF260230) |
| PacI/SwaI (10345-1) | FBAINm::Δ17S::Pex16, comprising: FBAINm: FBAINm promoter (SEQ ID NO:45) Δ17S: SEQ ID NO:43 (supra) Pex16: Pex16 terminator sequence of *Yarrowia* Pex16 gene (GenBank Accession No. U75433) |

Plasmid pZP3L37 was digested with AscI/SphI, and then used to transform strain Y2047 according to the General Methods. Following transformation, the cells were plated onto MM plates and maintained at 30° C. for 2 to 3 days. A total of 96 transformants grown on the MM plates were picked and re-streaked onto fresh MM plates. Once grown, these strains were individually inoculated into liquid MM at 30° C. and shaken at 250 rpm/min for 2 days. The cells were collected by centrifugation, lipids were extracted, and fatty acid methyl esters were prepared by trans-esterification, and subsequently analyzed with a Hewlett-Packard 6890 GC.

GC analyses showed the presence of EPA in most of the transformants with pZP3L37, but not in the parental strain (i.e., Y2047). Among the 96 selected transformants with pZP3L37, there were 20 strains that produced less than 2% EPA, 23 strains that produced 2–3% EPA, 5 strains that produced 3–4% EPA, and 2 strains (i.e., strain #71 and strain #94) that produced about 6% EPA of total lipids in the engineered Yarrowia.

Strain #71 (which produced 6% EPA) was further analyzed by culturing it as follows ("two-stage growth conditions"). First, cells were grown in triplicate in liquid MM at 30° C. with shaking at 250 rpm/min for 48 hrs. The cells were collected by centrifugation and the liquid supernatant was extracted. The pelleted cells were resuspended in HGM and grown for 72 hrs at 30° C. with shaking at 250 rpm/min. The cells were again collected by centrifugation and the liquid supernatant was extracted.

GC analyses showed that strain #71 produced about 11% EPA of total lipids. The strain was designated as "Y2048".

Generation of Y2060 Strain to Produce About 13% EPA of Total Lipids With Ura-Phenotype In order to disrupt the Ura3 gene in strain Y2048, construct pZKUT16 (FIG. 3D; SEQ ID NO:46) was created to integrate a TEF::rELO2S::Pex20 chimeric gene into the Ura3 gene of strain Y2048. rELO2S is a codon-optimized rELO gene encoding a rat hepatic enzyme that elongates 16:0 to 18:0 (i.e., a $C_{16/18}$ elongase). Plasmid pZKUT16 contained the following components:

TABLE 8

Description Of Plasmid pZKUT16 (SEQ ID NO:46)

| RE Sites And Nucleotides Within SEQ ID NO:46 | Description Of Fragment And Chimeric Gene Components |
|---|---|
| BsiWI/PacI (1-721) | 721 bp 5' part of *Yarrowia* Ura3 gene (GenBank Accession No. AJ306421) |
| SalI/ClaI (3565-4289) | 724 bp 3' part of *Yarrowia* Ura3 gene (GenBank Accession No. AJ306421) |
| ClaI/BsiWI (4289-1) | TEF::rELO2S::Pex20, comprising:<br>TEF: TEF Promoter (GenBank Accession No. AF054508)<br>rELO2S: codon-optimized rELO2 elongase gene (SEQ ID NO:47), derived from rat (GenBank Accession No. AB071986)<br>Pex20 terminator sequence of *Yarrowia* Pex20 gene (GenBank Accession No. AF054613) |

Specifically, plasmid pZKUT16 was digested with SalI/PacI, and then used to transform strain Y2048 according to the General Methods. Following transformation, cells were plated onto MM+5-FOA selection plates and maintained at 30° C. for 2 to 3 days.

A total of 40 transformants grown on MM+5-FOA plates were picked and re-streaked onto MM plates and MM+5-FOA plates, separately. Those strains that could grow on MM+5-FOA plates, but not on MM plates, were selected as Ura-strains. Each of these 40 Ura-strains were individually inoculated into liquid MMU and grown at 30° C. with shaking at 250 rpm/min for 2 days. The cells were collected by centrifugation, lipids were extracted, and fatty acid methyl esters were prepared by trans-esterification, and subsequently analyzed with a Hewlett-Packard 6890 GC.

GC analyses showed that there were 14 strains that produced less than 5% EPA, 9 strains that produced 5–5.9% EPA, 15 strains that produced 6–6.9% EPA, and 7 strains that produced 7–8% EPA of total lipids after two day growth in MMU media. The strains that produced 7–8% EPA were further analyzed using two-stage growth conditions (i.e., 48 hrs MM+96 hrs in HGM). GC analyses showed that all these strains produced more than 10% EPA; and, one of them produced about 13% EPA of the total lipids. That strain was designated as strain "Y2060".

Generation of Y2072 Strain to Produce About 15% EPA of Total Lipids

Construct pKO2UM25E (FIG. 4A; SEQ ID NO:49) was used to integrate a cluster of three chimeric genes (comprising a $C_{18/20}$ elongase, a Δ12 desaturase and a Δ5 desaturase) and a Ura3 gene into the native *Yarrowia* Δ12 desaturase gene site of strain Y2060. Plasmid pKO2UM25E contained the following components:

TABLE 9

Description of Plasmid pKO2UM25E (SEQ ID NO:49)

| RE Sites And Nucleotides Within SEQ ID NO:49 | Description Of Fragment And Chimeric Gene Components |
|---|---|
| HindIII/AscI (1-728) | 728 bp 5' part of *Yarrowia* Δ12 desaturase gene (SEQ ID NO:50) |
| SphI/EcoRI 3436-3992) | 556 bp 3' part of *Yarrowia* Δ12 desaturase gene (SEQ ID NO:50) |
| BsiWI/HindIII (10437-1) | GPAT::EL1S::XPR, comprising:<br>GPAT: GPAT promoter (SEQ ID NO:52)<br>EL1S: codon-optimized elongase 1 gene (SEQ ID NO:28), derived from *Mortierella alpina* (GenBank Accession No. AX464731)<br>XPR: ~100 bp of the 3' region of the *Yarrowia* Xpr gene (GenBank Accession No. M17741) |
| BglII/BsiWI (7920-10437) | FBAIN::M.Δ12.Pex20, comprising:<br>FBAIN: FBAIN promoter (SEQ ID NO:27)<br>M.Δ12: *Mortierella isabellina* Δ12 desaturase gene (GenBank Accession No. AF417245; SEQ ID NO:53)<br>Pex20: Pex20 terminator sequence of *Yarrowia* Pex20 gene (GenBank Accession No. AF054613) |
| SalI/PacI (6046-7544) | *Yarrowia* Ura3 gene (Gene Bank Accession No. AJ306421) |
| EcoRI/SalI (3992-6046) | TEF::I.Δ5S::Pex20, comprising:<br>TEF: TEF Promoter (GenBank Accession No. AF054508)<br>I.Δ5S: codon-optimized Δ5 desaturase gene (SEQ ID NO:55), derived from *Isochrysis galbana* (WO 2002/081668)<br>Pex20: Pex20 terminator sequence of *Yarrowia* Pex20 gene (GenBank Accession No. AF054613) |

Plasmid pKO2UM25E was digested with SphI/AscI, and then used to transform Y2060 according to the General Methods. Following transformation, cells were plated onto MM plates and maintained at 30° C. for 2 to 3 days.

A total of 63 transformants grown on MM plates were picked and re-streaked onto fresh MM plates. Once grown, these strains were individually inoculated into liquid MM at 30° C. and cultured with shaking at 250 rpm/min for 2 days. The cells were collected by centrifugation, lipids were extracted, and fatty acid methyl esters were prepared by trans-esterification, and subsequently analyzed with a Hewlett-Packard 6890 GC.

GC analyses showed the presence of EPA in almost all transformants with pKO2UM25E after one-day growth in MM media. Among the 63 selected transformants, there were 26 strains that produced 6–8.9% EPA and 46 strains that produced more than 9% EPA. The strains that produced more than 9% EPA were selected for further analysis using two-stage growth conditions (i.e., 48 hrs MM+96 hrs HGM). GC analyses showed that 45 out of the 46 selected strains produced 11–14.5% EPA while culture #2 produced 15.1% EPA of total lipids after the two-stage growth. This strain (i.e., #2) was designated as strain "Y2072".

Generation of Y2072U1 Strain to Produce About 14% EPA of Total Lipids With Ura-Phenotype The construct pZKUGPI5S (FIG. 4B; SEQ ID NO:57) was created to integrate a GPAT::I.Δ5S::Pex20 chimeric gene into the Ura3 gene of Y2072 strain. More specifically, plasmid pZKUGPI5S contained the following components:

TABLE 10

Description of Plasmid pZKUGPI5S (SEQ ID NO:57)

| RE Sites And Nucleotides Within SEQ ID NO:57 | Description Of Fragment And Chimeric Gene Components |
|---|---|
| BsiWI/PacI (318-1038) | 721 bp 5' part of *Yarrowia* Ura3 gene (GenBank Accession No. AJ306421) |
| SalI/ClaI (3882-4606) | 724 bp 3' part of *Yarrowia* Ura3 gene (GenBank Accession No. AJ306421) |
| ClaI/BsiWI (4606-318) | GPAT::I.Δ5S::Pex20, comprising:<br>GPAT: GPAT promoter (SEQ ID NO:52)<br>I.Δ5S: codon-optimized Δ5 desaturase gene (SEQ ID NO:55), derived from *Isochrysis galbana* (WO 2002/081668)<br>Pex20: Pex20 terminator sequence of *Yarrowia* Pex20 gene (GenBank Accession No. AF054613) |

Plasmid pZKUGPI5S was digested with SalI/PacI, and then used to transform strain Y2072 according to the General Methods. Following transformation, cells were plated onto MM+5-FOA selection plates and 15 maintained at 30° C. for 3 to 4 days.

A total of 24 transformants grown on MM+5-FOA plates were picked and re-streaked onto MM plates and MM+5-FOA plates, separately. Those strains that could grow on MM+5-FOA plates, but not on MM plates, were selected as Ura-strains. Each of these 24 Ura-strains were individually inoculated into liquid MMU and grown at 30° C. with shaking at 250 rpm/min for 2 days. The cells were collected by centrifugation, lipids were extracted, and fatty acid methyl esters were prepared by trans-esterification, and subsequently analyzed with a Hewlett-Packard 6890 GC.

GC analyses showed that there were 8 strains that produced 7.3–8.9% EPA, 14 strains that produced 9–9.9% EPA, 1 strain that produced 10.5% EPA (i.e., #1) and 1 strain that produced 10.7% EPA (i.e., #23) of total lipids after two day growth in MMU. Strains #1 and #23 were further analyzed using the two-stage growth conditions (i.e., 48 hrs MM+96 hrs HGM). GC analyses showed that these two strains produced about 14% EPA of total lipids after the two-stage growth. Strain #1 was designated as strain "Y2072U1".

Generation of Y2089 Strain to Produce About 18% EPA of Total Lipids

Construct pDMW302T16 (FIG. 4C; SEQ ID NO:58) was created to integrate a cluster of four chimeric genes (comprising a $C_{16/18}$ elongase, a $C_{18/20}$ elongase, a Δ6 desaturase and a Δ12 desaturase) and a Ura3 gene into the *Yarrowia* lipase1 gene site of Y2072U1 strain. Plasmid pDMW302T16 contained the following components:

TABLE 11

Description of Plasmid pDMW302T16 (SEQ ID NO: 58)

| RE Sites And Nucleotides Within SEQ ID NO: 58 | Description Of Fragment And Chimeric Gene Components |
|---|---|
| BsiWI/AscI (1–817) | 817 bp 5' part of *Yarrowia* lipase1 gene (GenBank Accession No. Z50020) |
| SphI/PacI 3525–4294 | 769 bp 3' part of *Yarrowia* lipase1 gene (GenBank Accession No. Z50020) |
| EcoRI/BsiWI (13328–1) | TEF::rELO2S::Pex20: as described for pZKUT16 (supra) |
| BglII/EcoRI (10599–13306) | FBAIN::D6S::Lip1, comprising:<br>FBAIN: FBAIN promoter (SEQ ID NO: 27)<br>Δ65: codon-optimized Δ6 desaturase gene (SEQ ID NO: 30), derived from *Mortierella alpina* (GenBank Accession No. AF465281)<br>Lip1: Lip1 terminator sequence from *Yarrowia* Lip1 gene (GenBank Accession No. Z50020) |
| ClaI/PmeI (8078–10555) | GPDIN::EL1S::Lip2, comprising:<br>GPDIN: GPDIN promoter (SEQ ID NO: 59)<br>EL1S: codon-optimized elongase 1 gene (SEQ ID NO: 28), derived from *Mortierella alpina* (GenBank Accession No. AX464731)<br>Lip2: Lip2 terminator of *Yarrowia* lipase2 gene (GenBank Accession No. AJ012632) |
| EcoRI/ClaI (6450–8078) | *Yarrowia* Ura 3 gene (Gene Bank Accession No. AJ306421) |
| PacI/EcoRI (4294–6450) | TEF::F.Δ12::Pex16, comprising:<br>TEF: TEF Promoter (GenBank Accession No. AF054508)<br>F.Δ12: *Fusarium moniliforme* Δ12 desaturase gene (SEQ ID NO: 33)<br>Pex16: Pex16 terminator of *Yarrowia* Pex16 gene (GenBank Accession No. U75433) |

Plasmid pDMW302T16 was digested with SphI/AscI, and then used to transform strain Y2072U1 according to the General Methods. Following transformation, cells were plated onto MM plates and maintained at 30° C. for 3 to 4 days.

A total of 48 transformants grown on MM plates were picked and re-streaked onto fresh MM plates. Once grown, these strains were individually inoculated into liquid MM and grown at 30° C. with shaking at 250 rpm/min for 2 days. The cells were collected by centrifugation, lipids were extracted, and fatty acid methyl esters were prepared by trans-esterification, and subsequently analyzed with a Hewlett-Packard 6890 GC.

GC analyses showed that EPA was produced in almost all transformants of Y2072U1 with pDMW302T16 after two-day growth in MM media. Among the 48 selected transformants, there were 27 strains that produced less than 10% EPA, 14 strains that produced 10–12.9% EPA and 5 strains that produced 13–13.9% EPA. Strain #34 (that produced 13.9% EPA) was selected for further analysis using the two-stage growth procedure (i.e., 48 hrs MM+96 hrs in HGM). GC analyses showed that strain #34 produced about 18% EPA of total lipids. Strain #34 was designated as strain "Y2089".

Generation of Y2107U1 Strain to Produce About 16% EPA of Total Lipids with Ura-Phenotype Construct pZKUGPE1S (FIG. 4D; SEQ ID NO:60) was created to integrate a GPAT::EL1S::Pex20 chimeric gene into the Ura3 gene of strain Y2089. More specifically, plasmid pZKUGPE1S contained the following components:

TABLE 12

| Description of Plasmid pZKUGPE1S (SEQ ID NO: 60) | |
|---|---|
| RE Sites And Nucleotides Within SEQ ID NO: 60 | Description Of Fragment And Chimeric Gene Components |
| BsiWI/PacI (318–1038) | 721 bp 5' part of *Yarrowia* Ura3 gene (GenBank Accession No. AJ306421) |
| SalI/ClaI (3882–4606) | 724 bp 3' part of *Yarrowia* Ura3 gene (GenBank Accession No. AJ306421) |
| ClaI/BsiWI (4606–318) | GPAT::E1S::Pex20, comprising: GPAT: GPAT promoter (SEQ ID NO: 52) EL1S: codon-optimized elongase 1 gene (SEQ ID NO: 28), derived from *Mortierella alpina* (GenBank Accession No. AX464731) Pex20: Pex20 terminator sequence of *Yarrowia* Pex20 gene (GenBank Accession No. AF054613) |

Plasmid pZKUGPE1S was digested with PstI/PacI, and then used to transform strain Y2089 according to the General Methods. Following transformation, cells were plated onto MM+5-FOA selection plates and maintained at 30° C. for 3 to 4 days.

A total of 8 transformants grown on MM+5-FOA plates were picked and re-streaked onto MM plates and MM+5-FOA plates, separately. Those strains that could grow on MM+5-FOA plates, but not on MM plates, were selected as Ura-strains. Each of these 8 Ura-strains were individually inoculated into liquid MMU and grown at 30° C. with shaking at 250 rpm/min for 2 days. The cells were collected by centrifugation, lipids were extracted, and fatty acid methyl esters were prepared by trans-esterification, and subsequently analyzed with a Hewlett-Packard 6890 GC.

GC analyses showed that there were 6 strains that produced 6.6–8.7% EPA and 2 strains that produced 9.4–10% EPA (#4 and #5) of total lipids after two day growth in MMU. Strains #4 and #5 were further analyzed using the two-stage growth conditions (i.e., 48 hrs MM+96 hrs HGM). GC analyses showed that these two strains produced about 16% EPA of total lipids after the two-stage growth. Strain #4 was designated as strain "Y2107U1" and strain #5 was designated as strain "Y2107U2".

Example 5

Heterologous Expression of the *Mortierella alpina* GPAT in *Yarrowia lipolytica*

The present Example describes the over-expression of the *M. alpina* GPAT ORF in a chimeric gene under the control of a *Yarrowia lipolytica* promoter in *Y. lipolytica* strain Y2107U1, and the effect of the over-expression as determined by an analysis of TAG content.

Construction of Vector pZUF-MOD-1

Vector pZUF-MOD-1 (SEQ ID NO:61) was prepared as follows. First, primers pzuf-mod1 (SEQ ID NO:62) and pzuf-mod2 (SEQ ID NO:63) were used to amplify a 253 bp "stuffer" DNA fragment (SEQ ID NO:64) using PDNR-LIB (ClonTech, Palo Alto, Calif.) as template. The amplified fragment was purified with a Qiagen QiaQuick PCR purification kit, digested with NcoI and NotI using standard conditions, and then purified again with a QiaQuick PCR purification kit. This fragment was ligated into similarly digested NcoI-/NotI-cut pZUF17 vector (SEQ ID NO:65; FIG. 5A) and the resulting ligation mixture was used to transform *E. coli* Top10 cells (Invitrogen). Plasmid DNA was purified from 4 resulting colonies using a Qiagen QiaPrep Spin Miniprep kit. The purified plasmids were digested with NcoI and NotI to confirm the presence of the ~250 bp fragment. The resulting plasmid was named "pZUF-MOD-1" (SEQ ID NO:61; FIG. 5B).

Construction of Plasmid DMGPAT-17, Comprising a FBAIN::MGPAT::PEX20-3' Chimeric Gene The *M. alpina* GPAT ORF was cloned as follows. Primers MGPAT-cDNA-5 and MGPAT-cDNA-R (SEQ ID NOs:66 and 67) were used to amplify the GPAT ORF from the cDNA of *M. alpina* (Example 1) by PCR. The reaction mixture contained 1 μl of the cDNA, 1 μl each of the primers, 22 μl water and 25 μl ExTaq premix 2×Taq PCR solution (TaKaRa Bio Inc., Otsu, Shiga, 520-2193, Japan). Amplification was carried out as follows: initial denaturation at 94° C. for 150 sec, followed by 30 cycles of denaturation at 94° C. for 30 sec, annealing at 55° C. for 30 sec and elongation at 72° C. for 120 sec. A final elongation cycle at 72° C. for 10 min was carried out, followed by reaction termination at 4° C. An ~2.2 kB DNA fragment was obtained from the PCR reaction. It was purified using a Qiagen PCR purification kit according to the manufacturer's protocol.

The purified PCR product was digested with BamHI and EcoRI, and a ~470 bp fragment was isolated by gel agarose electrophoresis and purified using Qiagen gel purification kit. Separately, the PCR product was also cut with EcoRI and NotI, and a 1.69 kB fragment isolated and purified as above. The two fragments were ligated into BamHI and NotI cut pZUF-MOD-1 vector (SEQ ID NO:61; FIG. 5B), such that the gene was under the control of the *Y. lipolytica* FBAIN promoter and the PEX20-3' terminator region in the auto-replicating vector for expression in *Y. lipolytica*. Correct transformants were confirmed by restriction analysis of miniprep DNA and the resultant plasmid was designated as "pMGPAT-17" (SEQ ID NO:68; FIG. 5C).

Analysis of Lipid Content in Transformant *Y. lipolytica* Strain Y2107U1 Over-Expressing *M. alpina* GPAT

*Y. lipolytica* strain Y2107U1 (from Example 4, producing 16% EPA of total lipids) was transformed with plasmid pMGPAT-17 and plasmid pZUF-MOD-1 (control), respectively, according to the General Methods. Transformants were grown for 2 days in synthetic MM supplemented with amino acids, followed by 4 days in HGM. The fatty acid profile of two transformants containing pZUF-MOD-1 and four transformants containing pMGPAT-17, are shown below in the Table, based on GC analysis (as described in the General Methods). Fatty acids are identified as 18:0, 18:1 (oleic acid), 18:2 (LA), GLA, DGLA, ARA, ETA and EPA; and the composition of each is presented as a % of the total fatty acids.

TABLE 13

Lipid Content In *Yarrowia* Strain Y2107U1 Engineered To Over-Express *M. alpina* GPAT

| Strain | Total Fatty Acids | | | | | | | |
|---|---|---|---|---|---|---|---|---|
| | 18:0 | 18:1 | 18:2 | GLA | DGLA | ARA | ETA | EPA |
| Y2107U1 + pZUF-MOD-1 #1 | 2.8 | 22.7 | 9.8 | 28.5 | 2.7 | 1.7 | 0.4 | 17.4 |
| Y2107U1 + pZUF-MOD-1 #2 | 2.5 | 23.4 | 10.3 | 28.7 | 2.5 | 1.5 | 0.3 | 16.8 |
| Y2107U1 + pMGPAT-17 #1 | 3.2 | 14.8 | 11.7 | 29.8 | 5.6 | 2.0 | 0.3 | 18.4 |
| Y2107U1 + pMGPAT-17 #2 | 2.9 | 16.3 | 11.7 | 28.3 | 6.1 | 1.8 | 0.4 | 16.9 |
| Y2107U1 + pMGPAT-17 #3 | 2.1 | 14.3 | 10.8 | 27.5 | 7.2 | 1.4 | 0.4 | 17.4 |
| Y2107U1 + pMGPAT-17 #4 | 2.7 | 15.7 | 11.5 | 29.1 | 6.3 | 1.7 | 0.4 | 17.3 |

As demonstrated above, expression of the *M. alpina* GPAT from pMGPAT-17 increased the DGLA concentration from ~2.5% in the "control" strains to 6.5%. The level of 18:1 decreased from ~23% to ~16%. An additional increase in DGLA (or any other downstream PUFAs) would be expected, if the native *Yarrowia lipolytica* GPAT was knocked-out in a transformant strain expressing pMGPAT-17.

What is claimed is:

1. An isolated nucleic acid molecule selected from the group consisting of:

(a) an isolated nucleic acid molecule encoding a glycerol-3-phosphate o-acyltransferase, having the amino acid sequence as set forth in SEQ ID NO:2;

(b) an isolated nucleic acid molecule encoding a glycerol-3-phosphate o-acyltransferase, that hybridizes with (a) under the following hybridization conditions; 0.1×SSC, 0.1% SDS, 65° C. and washed with 2×SSC, 0.1% SDS followed by 0.1×SSC, 0.1% SDS; or, an isolated nucleic acid molecule that is completely complementary to the full length of (a) or (b).

2. The isolated nucleic acid molecule of claim 1 as set forth in SEQ ID NO:1.

3. An isolated nucleic acid molecule comprising a first nucleotide sequence encoding a glycerol-3-phosphate o-acyltransferase of at least 716 amino acids that has at least 95% identity based on the BLAST method of alignment when compared to a polypeptide having the sequence as set forth in SEQ ID NO:2;

or a second nucleotide sequence comprising the complement of the first nucleotide sequence.

4. A chimeric gene comprising the isolated nucleic acid molecule of claim 1 operably linked to suitable regulatory sequences.

5. A transformed host cell comprising the chimeric gene of claim 4, wherein the transformed host cell is selected from the group consisting of algae, bacteria, fungi and yeasts.

6. The transformed host cell of claim 5, wherein the yeast is an oleaginous yeast.

7. The transformed host cell of claim 6, wherein the oleaginous yeast cell is selected from the group consisting of: *Yarrowia, Candida, Rhodotorula, Rhodosporidium, Cryptococcus, Trichosporon* and *Lipomyces*.

8. The transformed host cell of claim 7, wherein to host cell is *Yarrowia lipolytica*.

* * * * *

UNITED STATES PATENT AND TRADEMARK OFFICE

CERTIFICATE OF CORRECTION

PATENT NO. : 7,192,762 B2
APPLICATION NO. : 11/254173
DATED : March 20, 2007
INVENTOR(S) : Daniel Joseph Macool and Xue Zhixiong It is certified that error appears in the above-identified patent and that said Letters Patent is hereby corrected as shown below:

Col. 216, line 30: "to" should read --the--

Signed and Sealed this

Eighth Day of May, 2007

JON W. DUDAS
*Director of the United States Patent and Trademark Office*